(12) United States Patent
Suva et al.

(10) Patent No.: US 12,171,783 B2
(45) Date of Patent: Dec. 24, 2024

(54) METHODS AND COMPOSITIONS FOR TARGETING DEVELOPMENTAL AND ONCOGENIC PROGRAMS IN H3K27M GLIOMAS

(71) Applicants: The Broad Institute, Inc., Cambridge, MA (US); Massachusetts Institute of Technology, Cambridge, MA (US); The General Hospital Corporation, Boston, MA (US); Dana-Farber Cancer Institute, Inc., Boston, MA (US)

(72) Inventors: Mario Suva, Boston, MA (US); Bradley Bernstein, Boston, MA (US); Aviv Regev, Cambridge, MA (US); Mariella Filbin, Boston, MA (US); Itay Tirosh, Cambridge, MA (US); Volker Hovestadt, Boston, MA (US)

(73) Assignees: The Broad Institute, Inc., Cambridge, MA (US); Massachusetts Institute of Technology, Cambridge, MA (US); The General Hospital Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 97 days.

(21) Appl. No.: 16/763,705

(22) PCT Filed: Nov. 13, 2018

(86) PCT No.: PCT/US2018/060799
§ 371 (c)(1),
(2) Date: May 13, 2020

(87) PCT Pub. No.: WO2019/094955
PCT Pub. Date: May 16, 2019

(65) Prior Publication Data
US 2020/0384022 A1 Dec. 10, 2020

Related U.S. Application Data

(60) Provisional application No. 62/586,093, filed on Nov. 14, 2017, provisional application No. 62/585,468, filed on Nov. 13, 2017.

(51) Int. Cl.
| | | |
|---|---|---|
| A61K 35/17 | (2015.01) | |
| A61K 31/519 | (2006.01) | |
| A61K 38/50 | (2006.01) | |
| A61P 35/00 | (2006.01) | |
| C07K 16/28 | (2006.01) | |
| C07K 16/30 | (2006.01) | |

(52) U.S. Cl.
CPC ............ *A61K 35/17* (2013.01); *A61K 31/519* (2013.01); *A61K 38/50* (2013.01); *A61P 35/00* (2018.01); *C07K 16/2863* (2013.01); *C07K 16/3053* (2013.01); *C07K 2317/31* (2013.01)

(58) Field of Classification Search
CPC ...... A61K 35/17; A61K 31/519; A61K 38/50; A61K 47/6865; A61P 35/00; C07K 16/2863; C07K 16/3053; C07K 2317/31
See application file for complete search history.

(56) References Cited

U.S. PATENT DOCUMENTS

| | | |
|---|---|---|
| 4,816,567 A | 3/1989 | Cabilly et al. |
| 5,270,163 A | 12/1993 | Gold et al. |
| 5,686,281 A | 11/1997 | Roberts |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,479,626 B1 | 11/2002 | Kim et al. |

(Continued)

FOREIGN PATENT DOCUMENTS

| | | |
|---|---|---|
| EP | 2 764 103 A2 | 8/2014 |
| EP | 2 771 468 A1 | 9/2014 |

(Continued)

OTHER PUBLICATIONS

Kumar, et al., Oncotarget, May 2017 (Year: 2017).*
St. Jude Clinical Trial; ClinicalTrials.gov Identifier: NCT01393912; First Posted Jul. 13, 2011 (Year: 2011).*
Hashizume, et al., Nature Medicine 2014 20, 1394-1396 (Year: 2014).*
Jin, et al., Nature Medicine 2017 23, 1352-1361 (Year: 2017).*
Zhou, et al., Antibody Therapeutics 2022 5:311 (Year: 2022).*
Choi, et al., ACS Nano 2023 17(9):8153 (Year: 2023).*
Huang, et al., J. Med. Chem. 2022 65:5317 (Year: 2022).*

(Continued)

*Primary Examiner* — Karen A. Canella
*Assistant Examiner* — Sydney Van Druff
(74) *Attorney, Agent, or Firm* — Foley & Lardner LLP; Sunit Talapatra

(57) ABSTRACT

The subject matter disclosed herein is generally directed to compositions and methods for treating diffuse gliomas with histone H3 lysine27-to-methionine mutations (H3K27M-gliomas). Disclosed herein are gene signatures specific for tumor cell types and compositions for treatment of H3K27M gliomas. In one embodiment, PRC1 is targeted in a treatment regimen for H3K27M-gliomas.

11 Claims, 34 Drawing Sheets

Specification includes a Sequence Listing.

(56) References Cited

U.S. PATENT DOCUMENTS

| | | |
|---|---|---|
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 10,815,730 B2 | 10/2020 | Liu et al. |
| 2004/0171156 A1 | 9/2004 | Hartley et al. |
| 2004/0224402 A1 | 11/2004 | Bonyhadi et al. |
| 2010/0104509 A1 | 4/2010 | King et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0023497 A1 | 1/2014 | Giglio et al. |
| 2014/0107039 A1 | 4/2014 | Allis et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0232883 A1 | 8/2015 | Dahlman et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2017/0047193 A1 | 2/2017 | Jiang et al. |
| 2017/0105997 A1 | 4/2017 | Creasy et al. |
| 2017/0211142 A1 | 7/2017 | Smargon et al. |
| 2017/0283504 A1 | 10/2017 | Wiltzius et al. |
| 2018/0085444 A1 | 3/2018 | Morgan et al. |

FOREIGN PATENT DOCUMENTS

| | | |
|---|---|---|
| EP | 2 784 162 A1 | 10/2014 |
| EP | 2 771 468 B1 | 2/2015 |
| EP | 2 784 162 B1 | 4/2015 |
| EP | 2 764 103 B1 | 8/2015 |
| EP | 3 009 511 A2 | 4/2016 |
| WO | 92/15322 A1 | 9/1992 |
| WO | 96/40281 A2 | 12/1996 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |

(56) References Cited

FOREIGN PATENT DOCUMENTS

| | | |
|---|---|---|
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/028682 A1 | 2/2016 |
| WO | 2016/049258 A2 | 3/2016 |
| WO | 2016/069591 A2 | 5/2016 |
| WO | 2016/070061 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/106244 A1 | 6/2016 |
| WO | 2016/161516 A1 | 10/2016 |
| WO | 2016/191756 A1 | 12/2016 |
| WO | 2016/196388 A1 | 12/2016 |
| WO | 2016/205749 A1 | 12/2016 |
| WO | 2016/205759 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/070605 A1 | 4/2017 |
| WO | 2017075537 A1 | 5/2017 |
| WO | 2017/211900 A1 | 12/2017 |
| WO | 2017/219027 A1 | 12/2017 |
| WO | 2018/005873 A1 | 1/2018 |
| WO | 2018/028647 A1 | 2/2018 |
| WO | 2018/035250 A1 | 2/2018 |
| WO | 2018/170333 A1 | 9/2018 |
| WO | 2018/191553 A1 | 10/2018 |
| WO | 2019/005866 A1 | 1/2019 |
| WO | 2019/089803 A1 | 5/2019 |
| WO | 2019/094955 A1 | 5/2019 |
| WO | 2019/113499 A1 | 6/2019 |
| WO | 2020/006049 A1 | 1/2020 |

OTHER PUBLICATIONS

Filbin, et al., "Developmental and Oncogenic Programs in H3K27M Gliomas Dissected by Single-Cell RNA-seq", Science, vol. 360, No. 6386, 2018, 331-335.
Gargiulo, et al., "In Vivo RNAi Screen for BMI1 Targets Identified TGF-B/BMP-ER Stress Pathwasys Key Regulators of Neural-and Malignant Glioma-Stem Cell Homeostasis", Cancer Cell, 23, May 13, 2013, pp. 660-676.
Jordaan, et al., "CSPG4: A Target for Selective Delivery of Human Cytolytic Fusion Proteins and TRAIL", Biomedicines, vol. 5, No. 3, 2017, pp. 1-17.
Nishida, et al., "Preclinical Activity of the Novel B-Cell-Specific Moloney Murine Leukemia Virus Integration site 1 Inhibitor PTC-209 in Acute Myeloid Leukemia: Implications for Leukemia Therapy", Cancer Science, vo. 106, No. 12, 2015, pp. 1705-1713.
Sturm, et al., "Pediatric and Adult Glioblastoma: Multiform (epi)genomic Culprits Emerge", Nat Rev Cancer, 14(2), Feb. 2014, pp. 92-107.
The Broad Institute, Inc., et al., "Notification of Transmittal of the International Search Report and the Written Opinion of the International Searching Authority, or the Declarationcationnsmittal", PCT/US2018/060799, Feb. 7, 2019, 14 pages.
Wang, et al., "Pharmacological Inhibition of BMi1 by PTC-209 Impaired Tumor Growth in Head Neck Squamous Cell Carcinoma", Cancer Cell Int, vol. 17, No. 107, 2017, pp. 1-14.
The Broad Institute, Inc., International Preliminary Report on Patentability issued in International Application No. PCT/US2018/060799, mailed on May 28, 2020, 10 pages.
Ben-Porath et al., "An Embryonic Stem Cell-Like Gene Expression Signature in Poorly Differentiated Aggressive Human Tumors", Nature Genetics, vol. 40, No. 5, May 2008, 20 pages.
Cordero et al., "Histone H3.3K27M Represses p16 to Accelerate Gliomagenesis in a Murine Model of DIPG", Molecular Cancer Research, vol. 15, No. 9, May 18, 2017, 1243-1254.
De Vries et al., "Prolonged Ezh2 Depletion in Glioblastoma Causes a Robust Switch in Cell Fate Resulting in Tumor Progression", Cell Reports, vol. 10, No. 3, Jan. 20, 2015, 383-397.
Flavahan et al., "Insulator Dysfunction and Oncogene Activation in IDH Mutant Gliomas", Nature, vol. 529, Jan. 7, 2016, 16 pages.
Funato et al., "Use of Human Embryonic Stem Cells to Model Pediatric Gliomas With H3.3K27M Histone Mutation", Science, vol. 346, No. 6216, Dec. 19, 2014, 10 pages.
Godlewski et al., "Targeting of the Bmi-1 oncogene/stem Cell Renewal Factor by microRNA-128 Inhibits Glioma Proliferation and Self-Renewal", Cancer Research, vol. 68, No. 22, Nov. 15, 2008, 9125-9130.
Herz et al., "Histone H3 Lysine-To-Methionine Mutants as a Paradigm to Study Chromatin Signaling", Science, vol. 345, No. 6200, Aug. 29, 2014, 13 pages.
Johnson et al., "Rational Development and Characterization of Humanized anti-EGFR Variant III Chimeric Antigen Receptor T Cells for Glioblastoma", Science Translational Medicine, vol. 7, No. 275, Feb. 18, 2015, 14 pages.
Kreso et al., "Evolution of the Cancer Stem Cell Model", Cell Stem Cell, vol. 14, No. 3, Mar. 6, 2014, 275-291.
Lathia et al., "Cancer Stem Cells in Glioblastoma", Genes and Development, vol. 29, No. 12, Jun. 15, 2015, 1203-1217.
Lewis et al., "Inhibition of PRC2 Activity by a Gain-Of-Function H3 Mutation Found in Pediatric Glioblastoma", Science, vol. 340, No. 6134, May 17, 2013, 10 pages.
Mohammad et al., "EZH2 is a Potential Therapeutic Target for H3K27M-mutant Pediatric Gliomas", Nature Medicine, vol. 23, No. 4, Feb. 2017, 12 pages.
Nagaraja et al., "Transcriptional Dependencies in Diffuse Intrinsic Pontine Glioma", Cancer Cell—Cell Press, vol. 31, No. 5, May 8, 2017, 635-652.
Suva et al., "EZH2 is Essential for Glioblastoma Cancer Stem Cell Maintenance", Cancer Research, vol. 69, No. 24, Nov. 24, 2009, 9211-9218.
Suva et al., "Epigenetic Reprogramming in Cancer", Science, vol. 339, No. 6127, Mar. 29, 2013, 1567-1570.
Suva et al., "Reconstructing and Reprogramming the Tumor-Propagating Potential of Glioblastoma Stem-Like Cells", Cell, vol. 157, No. 3, Apr. 24, 2014, 25 pages.

(56) References Cited

OTHER PUBLICATIONS

Abudayyeh et al., C2c2 is a single-component programmable RNA-guided RNA targeting CRISPR effector, Science, Aug. 5, 2016, vol. 353, No. 6299 (23 pages).

Ackloo et al., "Chemical probes targeting epigenetic proteins: Applications beyond oncology," Epigenetics, 2017, vol. 12, No. 5 (pp. 378-400).

Agathanggelou et al., "Expression of immune regulatory molecules in Epstein-Barr virus-associated nasopharyngeal carcinomas with prominent lymphoid stroma. Evidence for a functional interaction between epithelial tumor cells and infiltrating lymphoid cells," American Journal of Pathology, Oct. 1995, vol. 147, No. 4 (pp. 1152-1160).

Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).

Altman et al., "Phenotypic Analysis of Antigen-specific T Lymphocytes," Science, Oct. 4, 1996, vol. 274, No. 5284 (pp. 94-96).

Andersen et al., "Parallel detection of antigen-specific T cell responses by combinatorial encoding of MHC multimers," Nature Protocols, 2012, vol. 7 (pp. 891-902).

Baba et al., "Highly Enhanced Expression of CD70 on Human T-Lymphotropic Virus Type 1-Carrying T-Cell Lines and Adult T-Cell Leukemia Cells," Journal of Virology, Apr. 2008, vol. 82, No. 8 (pp. 3843-3852).

Bartel et al., "MicroRNAs: Genomics, Biogenesis, Mechanism, and Function," Cell, Jan. 23, 2004, vol. 116, No. 2 (pp. 281-297).

Bartunek et al., Avian stem cell factor (SCF): production and characterization of the recombinant His-tagged SCF of chicken and its neutralizing antibody, Cytokine, Jan. 1996, vol. 8, Issue 1 (pp. 14-20).

Berdeja et al., "Durable Clinical Responses in Heavily Pretreated Patients with Relapsed/Refractory Multiple Myeloma: Updated Results from a Multicenter Study of bb2121 Anti-Bema CAR T Cell Therapy," Blood 2017, vol. 130 (pp. 740).

Besser et al., "Clinical responses in a phase II study using adoptive transfer of short-term cultured tumor infiltration lymphocytes in metastatic melanoma patients," Clinical Cancer Research, May 1, 2010, vol. 16, No. 9 (pp. 2646-2655).

Binz et al., "Engineering novel binding proteins from nonimmunoglobulin domains," Nature Biotechnology, 2005, vol. 23 (pp. 1257-1268).

Boch et al., "Breaking the Code Of DNA Binding Specificity Of T AL-Type III Effectors," Science, Dec. 11, 2009 vol. 326, No. 5959 (pp. 1509-1512).

Bondeson et al., "Targeted Protein Degradation by Small Molecules," Annual Review of Pharmacology and Toxicology, Jan. 6, 2017, vol. 57 (pp. 107-123).

Boni et al., "Adoptive transfer of allogeneic tumor-specific T cells mediates effective regression of large tumors across major histocompatibility barriers," Blood, Dec. 1, 2008, vol. 112, No. 12 (pp. 4746-4754).

Bramsen et al., "Development of Therapeutic-Grade Small Interfering RNAs by Chemical Engineering," Frontiers in Genetics, Aug. 20, 2012, vol. 3, Article 154 (pp. 1-22).

Brinkman et al., "Easy quantitative assessment of genome editing by sequence trace decomposition," Nucleic Acids Research, 2014, vol. 42, No. 22 e168 (pp. 1-8).

Budde et al., "Combining a CD20 Chimeric Antigen Receptor and an Inducible Caspase 9 Suicide Switch to Improve the Efficacy and Safety of T Cell Adoptive Immunotherapy for Lymphoma," PLoS One, 2013, vol. 8, No. 12, e82742 (10 pages).

Canver et al., "BCL11A enhancer dissection by Cas9-mediated in situ saturating mutagenesis," Nature, vol. 527, 2015 (pp. 192-197) [including Supplementary Material].

Carlson et al., "Identification of Amino Acids in the Glutamate Receptor, GluR3, Important for Antibody-binding and Receptor-specific Activation," The Journal of Biological Chemistry, Apr. 25, 1997, vol. 272, No. 17 (pp. 11295-11301).

Carr et al., "Genome Engineering," Nature Biotechnology, Dec. 2009, vol. 27, No. 12 (pp. 1151-1162).

Cermak et al., "Efficient Design and Assembly of Custom Talen and Other Tal Effector-Based Constructs for DNA Targeting", Nucleic Acids Research, 2011, vol. 39, No. 12 (pp. 1-11).

Chahlavi et al., "Glioblastomas Induce T-Lymphocyte Death by Two Distinct Pathways Involving Gangliosides and CD70," Cancer Research, Jun. 15, 2005, vol. 65, No. 12 (pp. 5428-5438).

Chan et al., "The histone H3.3K27M mutation m pediatric glioma reprograms H3K27 methylation and gene expression," Genes & development, 2013, vol. 27 (pp. 985-990).

Chen et al., "Dynamic Imaging of Genomic Loci in Living Human Cells by an Optimized CRISPR/Cas System," Cell, 2013, vol. 155 (pp. 1479-1491).

Chen et al., "Genome-wide CRISPR Screen in a Mouse Model of Tumor Growth and Metastasis," Cell, 2015 vol. 160 (pp. 1-15).

Chen et al., Effects of Interleukin-1a, Interleukin-1 Receptor Antagonist, and Neutralizing Antibody on Proinflammatory Cytokine Expression by Human Squamous Cell Carcinoma Lines, Cancer Research, Aug. 15, 1998, vol. 58, No. 16 (pp. 3668-3678).

Chu et al., "Efficient Generation of Rosa26 Knock-in Mice using Crispr/Cas9 in C57bl/6 Zygotes," BMC Biotechnology, Jan. 16, 2016, vol. 16, No. 4 (15 pages).

Chung et al., "Polycistronic RNA polymerase II expression vectors for RNA interference based on BIC/miR-155," Nucleic Acids Research, 2006, vol. 34, No. 7 (14 pages).

Cibulskis et al. "Sensitive Detection of Somatic Point Mutations in Impure and Heterogeneous Cancer Samples," Nature Biotechnology, 2013, vol. 31, No. 3 (pp. 213-219).

Cibulskis et al., "ContEst: estimating cross-contamination of human samples in next-generation sequencing data," Bioinformatics, 2011, vol. 27, No. 18 (pp. 2601-2602).

Clackson et al., "Making antibody fragments using phage display libraries," Nature, Aug. 1991, vol. 352 (pp. 624-628).

Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].

Cooper et al., "T-cell clones can be rendered specific for CD19: toward the selective augmentation of the graft-versus-B-lineage leukemia effect," Blood, Feb. 15, 2003, vol. 101, No. 4 (pp. 1637-1644).

Costello et al., "Discovery and characterization of artifactual mutations in deep coverage targeted capture sequencing data due to oxidative DNA damage during sample preparation," Nucleic Acids Research, 2013, vol. 41, No. 6 (pp. 1-12).

Cox et al., "RNA editing with CRISPR-Cas13," Science, Nov. 24, 2017, vol. 358, No. 6366 (pp. 1019-1027).

Dellinger et al., "Streamlined process for the chemical synthesis of RNA using 2'-O-thionocarbamate-protected nucleoside phosphoramidites in the solid phase," Journal of the American Chemical Society, Aug. 3, 2011. vol. 133, No. 30 (pp. 11540-11556).

Deng et al., "An Agonist Murine Monoclonal Antibody to the Human c-Mpl Receptor Stimulates Megakaryocytopoiesis," Blood, Sep. 1998, vol. 92, No. 6 (pp. 1981-1988).

Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).

Di Croce et al., "Transcriptional regulation by Polycomb group proteins," Nature Structural & Molecular Biology, 2013, vol. 20 (1147-1155).

Di Stasi et al., "Inducible apoptosis as a safety switch for adoptive cell therapy," Clinical Trial, New England Journal of Medicine, Nov. 3, 2011, vol. 365, No. 18 (pp. 1673-1683).

Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].

Doyon et al., "Enhancing zinc-finger-nuclease activity with improved obligate heterodimeric architectures," Nature Methods, Jan. 2011, vol. 8, No. 1 (pp. 74-79).

(56) References Cited

OTHER PUBLICATIONS

Dudley et al., "Adoptive Cell Transfer Therapy Following Non-Myeloablative but Lymphodepleting Chemotherapy for the Treatment of Patients with Refractory Metastatic Melanoma," Journal of Clinical Oncology, Apr. 1, 2005, vol. 23, No. 10 (pp. 2346-2357).
Dudley et al., "Cancer regression and autoimmunity in patients after clonal repopulation with antitumor lymphocytes," Science, 2002, vol. 298, No. 5594 (pp. 850-854).
East-Seletsky et al., "Two distinct RNase activities of CRISPR-C2c2 enable guide-RNA processing and RNA detection," Nature, Oct. 13, 2016, vol. 538, No. 7624 (pp. 270-273).
Ellington et al., "In vitro selection of RNA molecules that bind specific ligands," Nature, 1990, vol. 346, No. 6287 (pp. 818-822).
Eyquem et al., "Targeting a CAR to the TRAC Locus with CRISPR/Cas9 Enhances Tumour Rejection," Nature, Mar. 2, 2017, vol. 543, No. 7643 (pp. 113-117).
Fisher et al., "A scalable, fully automated process for construction of sequence-ready human exome targeted capture libraries," Genome biology, 2011, vol. 12-R1 (pp. 1-15).
Francis et al., "Chromatin compaction by a polycomb group protein complex," Science, 2004, vol. 306 (pp. 1574-1577).
Friedman et al., "Effective Targeting of Multiple BCMA-Expressing Hematological Malignancies by Anti-BCMA CART Cells," Human Gene Therapy, May 2018, vol. 29, No. 5 (pp. 585-601).
Gao et al., "Engineered Cpf1 Enzymes with Altered PAM Specificities," Nature Biotechnology, Aug. 2017, vol. 35, No. 8 (pp. 789-792).
Gaudelli et al., "Programmable base editing of A-T to G-C in genomic DNA without DNA cleavage," Nature, Nov. 23, 2017, vol. 551, No. 7681 (pp. 464-471).
Gebauer and Skerra, "Engineered protein scaffolds as next-generation antibody therapeutics," Current Opinion in Chemical Biology, Jun. 2009, vol. 13, No. 3 (pp. 245-255).
Genbank identifier NM_006139 *Homos sapiens* CD28 molecule (CD28), transcript variant1, mRNA (6 pages).
Georgiadis et al., "Long Terminal Repeat CRISPR-CAR-Coupled 'Universal' T Cells Mediate Potent Anti-leukemic Effects," Molecular Therapy, May 2, 2018 vol. 26, No. 5 (pp. 1215-1227).
Gill et al., "Biopharmaceutical drug discovery using novel protein scaffolds," Current Opinion in Biotechnology, 2006, vol. 17, No. 6 (653-658).
Gnirke et al., "Solution hybrid selection with ultra-long oligonucleotides for massively parallel targeted sequencing," Nature Biotechnology, Feb. 2009, vol. 27, No. 2 (pp. 182-189).
Greco et al., "Improving the safety of cell therapy with the TK-suicide gene," Frontiers in Pharmacology, May 5, 2015, vol. 6, No. 95 (13 pages).
Gruber et al., "The Vienna RNA Websuite," Nucleic Acids Research, Apr. 19, 2008, vol. 36 (pp. W70-W74).
Harper et al., "Inhibition of anchorage-independent growth of human melanoma cells by a monoclonal antibody to a chondroitin sulfate proteoglycan," Journal of the National Cancer Institute, Aug. 1, 1983, vol. 71, No. 2 (pp. 259-263).
Harrington et al., "Programmed DNA destruction by miniature CRISPR-Cas14 enzymes," Science, Nov. 16, 2018 vol. 362, No. 6416 (pp. 839-842).
Harrop et al., "Antibodies to TR2 (Herpesvirus Entry Mediator), a New Member of the TNF Receptor Superfamily, Block T Cell Proliferation, Expression of Activation Markers, and Production of Cytokines," Journal of Immunology, 1998, vol. 161, No. 4 (pp. 1786-1794).
Helbig et al., "A single weekly dose of imatinib is sufficient to induce and maintain remission of chronic eosinophilic leukaemia in FIP1L1-PDGFRA-expressing patients," British Journal of Haematology, Apr. 2008 vol. 141, No. 2 (pp. 200-204).
Hendel et al., "Chemically modified guide RNAs enhance CRISPR-Cas genome editing in human primary cells," Nature Biotechnology Sep. 2015, vol. 33, No. 9 (pp. 985-989).

Hicke et al., "Escort aptamers: a delivery service for diagnosis and therapy," The Journal of Clinical Investigation, Oct. 2000, vol. 106, No. 8 (pp. 923-928).
Hinrichs et al., "Exploiting the curative potential of adoptive T-cell therapy for cancer," Immunological Reviews, Jan. 2014, vol. 257, No. 1 (pp. 56-71).
Horwell et al., "The 'peptoid' approach to the design of non-peptide, small molecule agonists and antagonists of neuropeptides," Trends in Biotechnology, Apr. 1995, vol. 13, No. 4 (pp. 132-134).
Houot et al., "T-cell-based immunotherapy: adoptive cell transfer and checkpoint inhibition," Cancer Immunology Research, 2015, vol. 3, No. 10 (pp. 1115-1122).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases", Nature Biotechnology, Sep. 2013, vol. 31, No. 9 (pp. 827-832).
Hughes et al., "Transfer of a TCR gene derived from a patient with a marked antitumor response conveys highly active T-cell effector functions," Human Gene Therapy, Apr. 2005, vol. 16, No. 4 (pp. 457-472).
Hunter et al., "High Levels of Soluble Immunoregulatory Receptors in Patients with Waldenstro M's Macroglobulinemia," Blood, Nov. 16, 2004, vol. 104, No. 11 (2 pages).
Irving et al., "Engineering Chimeric Antigen Receptor T-Cells for Racing in Solid Tumors: Don't Forget the Fuel," Frontiers in Immunology, Apr. 3, 2017, vol. 8, Article 267 (19 pages).
Ismail et al., "A Small Molecule Inhibitor of Polycomb Repressive Complex 1 Inhibits Ubiquitin Signaling at DNA Double-strand Breaks," Journal of Biological Chemistry, Sep. 13, 2013, vol. 288, No. 37 (pp. 26944-26954).
Jensen et al., "Design and Implementation of Adoptive Therapy with Chimeric Antigen Receptor-Modified T Cells," Immunological Reviews, Jan. 2014, vol. 257, No. 1 (32 pages).
Jiang et al., "RNA-guided editing of bacterial genomes using CRISPR-Cas systems," Nature Biotechnology, Mar. 2013, vol. 31 [30 pages, including supplementary information] (pp. 233-239).
Jin et al., "CD70, a novel target of CAR T-cell therapy for gliomas," Neuro-Oncology Jan. 10, 2018, vol. 20, No. 1 (pp. 55-65).
Johnson et al., "Gene therapy with human and mouse T-cell receptors mediates cancer regression and targets normal tissues expressing cognate antigen," Blood, Jul. 2009, vol. 114, No. 3 (pp. 535-546).
Jones et al., "Pediatric high-grade glioma: biologically and clinically in need of new thinking," Neuro-oncology, 2017, vol. 19, No. 2 (pp. 153-161).
Junker et al., "CD70: a new tumor specific biomarker for renal cell carcinoma," The Journal of Urology, Jun. 2005, vol. 173, No. 6 (pp. 2150-2153).
Kalos et al., "T Cells with Chimeric Antigen Receptors Have Potent Antitumor Effects and Can Establish Memory in Patients with Advanced Leukemia," Science Translational Medicine, Aug. 10, 2011, vol. 3, No. 95 (12 pages).
Kamta et al. "Advancing Cancer Therapy with Present and Emerging Immuno-Oncology Approaches," Frontiers in Oncology, Apr. 18, 2017, vol. 7, No. 64 (15 pages).
Kantarjian et al., "Nilotinib in imatinib-resistant CML and Philadelphia chromosome-positive ALL," New England Journal of Medicine, Jun. 15, 2006, vol. 354, No. 24 (pp. 2542-2451).
Keefe et al., "Aptamers as therapeutics," Nature Reviews, Jul. 2010, vol. 9 (pp. 537-550).
Kelley et al., "Versatility of chemically synthesized guide RNAs for CRISPR-Cas9 genome editing," Journal of Biotechnology, Sep. 2016, vol. 233, 10 (pp. 74-83).
Kent, "Blat—The BLAST-Like Alignment Tool," Genome Research, 2002, vol. 12 (pp. 656-664).
Kim et al., "Chimeric restriction endonuclease," Proceedings of the National Academy of Sciences, USA, Biochemistry, Feb. 1994, vol. 91 (pp. 883-887).
Kim et al., "Hybrid restriction enzymes: Zinc finger fusions to Fok I cleavage domain," Proceedings of the National Academy of Science, USA, Feb. 1996, vol. 93, No. 3 (pp. 1156-1160).

(56) References Cited

OTHER PUBLICATIONS

Kim et al., "Highly efficient RNA-guided genome editing in human cells via delivery of purified Cas9 ribonucleoproteins," Genome Research, Jun. 2014, vol. 24, No. 6 (pp. 1012-1019).
Kleinstiver et al., "Engineered CRISPR-Cas9 nucleases with altered PAM specificities," Nature, Jul. 23, 2015, vol. 523, No. 7561 (pp. 481-485).
Kochenderfer et al., "Construction and Pre-clinical Evaluation of Anti-CD19 Chimeric Antigen Receptor," Journal of Immunotherapy, Sep. 2009, vol. 32, No. 7 (pp. 689-702).
Kohler et al., "Continuous cultures of fused cells secreting antibody of predefined specificity," Nature, 1975, vol. 256 (pp. 495-497).
Kolmar, "Alternative binding proteins: biological activity and therapeutic potential of cystine-knot miniproteins," The FEBS Journal, 2008, 275 (pp. 2684-2690).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Kooreman et al., "Autologous iPSC-Based Vaccines Elicit Anti-tumor Responses In Vivo," Cell Stem Cell, Apr. 5, 2018, vol. 22, No. 4 (pp. 501-513).
Kreso et al., "Self-renewal as a therapeutic target in human colorectal cancer," Nature Medicine, 2014, vol. 20 (pp. 1-10).
La Manno et al., "Molecular Diversity of Midbrain Development in Mouse, Human, and Stem Cells," Cell, Oct. 6, 2016, vol. 167 (pp. 566-580).
Lagos-Quintana et al., "Identification of Novel Genes Coding for Small Expressed RNAs," Science, Oct. 26, 2001, vol. 294 (pp. 853-858).
Lagos-Quintana et al., "Identification of tissue-specific microRNAs from mouse," Current Biology, Apr. 30, 2002, vol. 12, (pp. 735-739).
Lagos-Quintana et al., "New microRNAs from mouse and human," RNA, 2003, vol. 9 (pp. 175-179).
Lai et al., "Modular PROTAC Design for the Degradation of Oncogenic BCR-ABL," Angewandte Chemie International Edition [Engl] Jan. 11, 2016, vol. 55, No. 2 (pp. 807-810).
Lamb et al., "The Connectivity Map: Using Gene-Expression Signatures to Connect Small Molecules, Genes, and Disease," Science, Sep. 29, 2006, vol. 313, Issue 5795 (pp. 1929-1935).
Lamb, "The Connectivity Map: A New Tool for Biomedical Research," Nature Reviews, Cancer, Jan. 2007, vol. 7, No. 1 (pp. 54-60).
Lau et al., "An abundant class of tiny RNAs with probable regulatory roles in Caenorhabditis elegans," Science, Oct. 26, 2001, vol. 294 (pp. 858-862).
Lawrence et al., "Discovery and saturation analysis of cancer genes across 21 tumour types," Nature, Jan. 23, 2014, vol. 505, No. 7484 (pp. 495-501).
Le Mercier et al., "Beyond CTLA-4 and PD-1, the generation Z of negative checkpoint regulators," Frontiers in Immunology, Aug. 21, 2015, vol. 6, Article 418 (15 pages).
Lebel et al., "Diffusion tensor imaging of white matter tract evolution over the lifespan," Neuroimage, Mar. 2012, vol. 60, No. 1 (pp. 340-352).
Lee et al., "An Extensive Class of Small RNAs in Caenorhabditis elegans," Science, Oct. 26, 2001, vol. 294 (pp. 862-864).
Lee et al., "Synthetically modified guide RNA and donor DNA are a versatile platform for CRISPR-Cas9 engineering," Elife, May 2, 2017, vol. 6 e25312 (17 pages).
Legut et al., "CRISPR-mediated TCR replacement generates superior anticancer transgenic T cells," Blood, 2018, vol. 131, No. 3 (pp. 311-322).
Levine et al., "The core of the polycomb repressive complex is compositionally and functionally conserved in flies and humans," Molecular and Cellular Biology, Sep. 2002, vol. 22, No. 17 (pp. 6070-6078).
Levy-Nissenbaum et al., Nanotechnology and aptamers: applications in drug delivery, Trends in Biotechnology, Aug. 2008, vol. 26, No. 8 (pp. 442-449).
Li et al., "Adoptive cell therapy with CD4+ T helper 1 cells and CD8+ cytotoxic T cells enhances complete rejection of an established tumour, leading to generation of endogenous memory responses to non-targeted tumour epitopes," Clinical Translational Immunology, Oct. 20, 2017, vol. 6, No. 10 e160 (10 pages).
Li et al., "Engineering CRISPR-Cpf1 crRNAs and mRNAs to maximize genome editing efficiency," Nature Biomedical Engineering, May 2017, vol. 1, No. 5 (21 pages).
Li et al., "Fast and accurate short read alignment with Burrows-Wheeler transform," Bioinformatics, 2009, vol. 25, No. 14 (pp. 1754-1760).
Li et al., "RSEM: accurate transcript quantification from RNA-Seq data with or without a reference genome," BMC Bioinformatics, 2011, vol. 12 No. 323 (16 pages).
Liau et al., "Adaptive Chromatin Remodeling Drives Glioblastoma Stem Cell Plasticity and Drug Tolerance," Cell Stem Cell, Feb. 2, 2017, vol. 20, No. 2 (pp. 233-246).
Liautard et al., "Specific Inhibition of IL-6 Signalling with Monoclonal Antibodies Against the gp130 Receptor," Cytokine, Apr. 1997, vol. 9, No. 4 (pp. 223-241).
Lim et al., "The microRNAs of Caenorhabditis elegans," Genes & Development, Apr. 15, 2003, vol. 17, No. 8 (pp. 991-1008).
Lim et al., "Vertebrate microRNA genes," Science, Mar. 7, 2003, vol. 299, No. 5612 (p. 1540).
Liu et al., "Mosaic analysis with double markers reveals tumor cell of origin in glioma," Cell, Jul. 22, 2011, vol. 146, No. 2 (pp. 209-221).
Lu et al., "Demethylation of the Same Promoter Sequence Increases CD70 Expression in Lupus T Cells and T Cells Treated with Lupus-Inducing Drugs," The Journal of Immunology, May 15, 2005, vol. 174, No. 10 (pp. 6212-6219).
Maher et al., "Human T-lymphocyte cytotoxicity and proliferation directed by a single chimeric TCRzeta /CD28 receptor," Nature Biotechnology, Jan. 2002, vol. 20, No. 1 (pp. 70-75).
Marks et al., "By-passing immunization. Human antibodies from V-gene libraries displayed on phage," Journal of Molecular Biology, 1991, vol. 222, No. 3 (pp. 581-597).
Marques et al., "Oligodendrocyte heterogeneity in the mouse juvenile and adult central nervous system," Science, Jun. 10, 2016, vol. 352, No. 6291 (pp. 1326-1329).
Martin-Orozco et al., "T helper 17 cells promote cytotoxic T cell activation in tumor immunity," Immunity, Nov. 20, 2009, vol. 31, No. 5 (pp. 787-798).
Matsuda et al., "Controlled expression of transgenes introduced by in vivo electroporation," Proceedings of the National Academy of Sciences, Jan. 16, 2007, vol. 104, No. 3 (pp. 1027-1032).
Maus et al., "Adoptive immunotherapy for cancer or viruses," Annual Review of Immunology, 2014, vol. 32 (pp. 189-225).
McKenna et al., "The Genome Analysis Toolkit: A MapReduce framework for analyzing next-generation DNA sequencing data," Genome Research, 2010, vol. 20 (pp. 1297-1303).
Mettananda et al., "Editing an alpha-globin enhancer in primary human hematopoietic stem cells as a treatment for beta-thalassemia," Nature Communications, Sep. 4, 2017, vol. 8, No. 1 (11 pages).
Miyamoto et al., "Rapid and orthogonal logic gating with a gibberellin-induced dimerization system," Nature Chemical Biology, 2012, vol. 8, No. 5 (pp. 465-470).
Monje et al., "Hedgehog-responsive candidate cell of origin for diffuse intrinsic pontine glioma," Proceedings of the National Academy of Sciences, USA Mar. 15, 2011, vol. 108 (pp. 4453-4458).
Morgan et al., "Cancer Regression in Patients After Transfer of Genetically Engineered Lymphocytes," Science, Oct. 6, 2006, vol. 314, No. 5796 (pp. 126-129).
Morocz et al., "Brain edema development after MRI-guided focused ultrasound treatment," Journal of Magnetic Resonance Imaging, Jan.-Feb. 1998, vol. 8, No. 1 (pp. 136-142).
Moscou et al., "A Simple Cipher Governs DNA Recognition by TAL Effectors", Science, Dec. 11, 2009, vol. 326 (p. 1501).

(56) References Cited

OTHER PUBLICATIONS

Mouhieddine et al., "Immunotherapy in Multiple Myeloma: The Era of CAR T Cell Therapy," Hematologist, Apr. 2018, vol. 15, issue 3 (8 pages).
Moussatov et al., "A Possible Approach To The Treatment of Polycystic Ovarian Syndrome Using Focused Ultrasound," Ultrasonics, 1998, vol. 36, No. 8 (pp. 893-900).
Muller et al., "Single-cell sequencing maps gene expression to mutational phylogenies m PDGF- and EGF-driven gliomas," Molecular Systems Biology, 2016, vol. 12, No. 889 (pp. 1-17).
Muller et al., "VEGF and the Fab fragment of a humanized neutralizing antibody: crystal structure of the complex at 2.4 A resolution and mutational analysis of the interface," Structure, 1998, vol. 6, No. 9 (pp. 1153-1167).
Muranski et al., "Tumor-specific Th17-polarized cells eradicate large established melanoma," Blood, Jul. 15, 2008, vol. 112, No. 2 (pp. 362-373).
Nakamura et al., "Codon usage tabulated from the international DNA sequence databases: status for the year 2000," Nucleic Acids Research, 2000, vol. 28, No. 1 (p. 292).
Nicholson et al., "Construction and characterisation of a functional CD19 specific single chain Fv fragment for immunotherapy of B lineage leukaemia and lymphoma," Molecular Immunology, Nov.-Dec. 1997, vol. 34, Nos. 16-17 (pp. 1157-1165).
Nikbakht et al., "Spatial and temporal homogeneity of driver mutations in diffuse intrinsic pontine glioma," Nature Communications, 2016, vol. 7, No. 11185 (pp. 1-8)).
Nishimasu et al., "Crystal Structure of Cas9 in Complex with Guide RNA and Target DNA," Cell, Feb. 27, 2014, vol. 156 (pp. 935-949).
Nishimasu et al., "Crystal Structure of *Staphylococcus aureus* Cas9", Cell, 2015, vol. 162 (pp. 1113-1126) [with Supplemental Information].
Nixon et al., "Engineered protein inhibitors of proteases," Current Opinion in Drug Discovery & Development, Mar. 1, 2006, vol. 9, No. 2 (pp. 261-268).
Nowak et al., "Survey and Summary—Guide RNA engineering for versatile Cas9 functionality," Nucleic Acids Research, Oct. 12, 2016, vol. 44, No. 20 (pp. 9555-9564).
Nygren, "Alternative binding proteins: Affibody binding proteins developed from a small three-helix bundle scaffold," The FEBS Journal, 2008, vol. 275 (pp. 2668-2676).
Paige et al., "RNA mimics of green fluorescent protein," Science, Jul. 29, 2011, vol. 333, No. 6042 (pp. 642-646).
Paix et al., "High Efficiency, Homology-Directed Genome Editing in Caenorhabditis elegans Using CRISPR-Cas9 Ribonucleoprotein Complexes," Genetics, Sep. 2015, vol. 201 (pp. 47-54).
Park et al., "CD70 as a target for chimeric antigen receptor T cells in head and neck squamous cell carcinoma," Oral Oncology Mar. 2018, vol. 78 (pp. 145-150).
Parker et al., "Scheme for ranking potential HLA-A2 binding peptides based on independent binding of individual peptide side-chains," The Journal of Immunology, Jan. 1, 1994, vol. 152, No. 1 (pp. 163-175).
Parnas et al., "A Genome-Wide CRISPR Screen in Primary Immune Cells to Dissect Regulatory Networks," 2015, vol. 162 (pp. 675-686) [with Supplementary Information].
Patel et al., "Single-cell RNA-seq highlights intratumoral heterogeneity in primary glioblastoma," Science, Jun. 20, 2014, vol. 344, No. 6190 (pp. 1396-1401).
Picelli et al. "Full-length RNA-seq from single cells using Smart-seq2," Nature Protocols, Jan. 2014, vol. 9, No. 1 (pp. 171-181).
Pitard et al., "Production and characterization of monoclonal antibodies against the leukemia inhibitory factor low affinity receptor, gp190," Journal of Immunological Methods, 1997, vol. 205 pp. (177-190).
Platt et al., "CRISPR-Cas9 Knockin Mice for Genome Editing and Cancer Modeling," Cell, 2014, vol. 159 (pp. 440-455).
Poirot et al., "Multiplex genome edited T-cell manufacturing platform for 'off-the-shelf' adoptive T-cell immunotherapies," Cancer Research, Sep. 15, 2015, vol. 75, No. 18 (pp. 3853-3864).

Prat et al., "Agonistic monoclonal antibodies against the Met receptor dissect the biological responses to HGF," Journal of Cell Science, 1998, vol. 111 (pp. 237-247).
Qasim et al., "Molecular remission of infant B-ALL after infusion of universal TALEN gene-edited CAR T cells," Cancer, Science Translational Medicine, Jan. 25, 2017, vol. 9 (pp. 1-8).
Qi et al., "HEDD: the human epigenetic drug database," Database, 2016 (pp. 1-10).
Rahdar et al., "Synthetic CRISPR RNA-Cas9-guided genome editing in human cells," Proceedings of the American Academy of Sciences, U.S.A. Nov. 16, 2015 (pp. E7110-E7117).
Rajasagi et al., "Systematic Identification of Personal Tumor-specific Neoantigens in Chronic Lymphocytic Leukemia," Blood, Jun. 2, 2014, vol. 124, No. 3 (pp. 453-462).
Ramanan et al., "CRISPR-Cas9 cleavage of viral DNA efficiently suppresses hepatitis B virus," Nature/Scientific Reports, Jun. 2015 (9 pages).
Ramos et al., "An inducible caspase 9 suicide gene to improve the safety of mesenchymal stromal cell therapies," Stem Cells, Jun. 2010, vol. 28, No. 6 (pp. 1107-1115).
Ramos et al., "Oncotator: cancer variant annotation tool," Human Mutation, Apr. 15, vol. 36, No. 4 (pp. E2423-E2429).
Ran et al., "Double Nicking by RNA-guided CRISPR Cas9 for enhanced genome editing specificity", Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Ran et al., "In vivo genome editing using *Staphylococcus aureus* Cas9," Nature, vol. 520, 2015, (pp. 186-191). [Includes Supplemental information, 12 pages].
Ren et al., "Multiplex Genome Editing to Generate Universal CAR T Cells Resistant to PD1 Inhibition." Clinical Cancer Research, May 1, 2017, vol. 23, No. 9 (pp. 2255-2266).
Restifo et al., "Adoptive Immunotherapy for Cancer: Harnessing the T Cell Response", Nature Reviews Immunology, Mar. 22, 2012, vol. 12, No. 4 (pp. 269-281).
Rivera et al., "CSPG4 as a target of antibody-based immunotherapy for malignant mesothelioma," Clinical Cancer Research, Oct. 1, 2012, vol. 18, No. 19 (pp. 5352-5363).
Rosenberg et al., "Adoptive cell transfer as personalized immunotherapy for human cancer," Cancer Immunology and Immunotherapy, Apr. 2015, vol. 348, Issue 6230 (pp. 62-69).
Sadelain et al., "Eliminating Cells Gone Astray," New England Journal of Medicine, Nov. 3, 2011, vol. 365, No. 18 (pp. 1735-1737).
Scaringe et al., "Advanced 5'-silyl-2'-orthoester approach to RNA oligonucleotide synthesis," Methods in Enzymology, 2000, vol. 317 (pp. 3-18).
Scaringe et al., "Novel RNA Synthesis Method Using 5'0-Silyl-2'-O-orthoester Protecting Groups," Journal of the American Chemical Society, 1998, vol. 120, No. 45 (pp. 11820-11821).
Schindler et al., "Structural mechanism for STI-571 inhibition of abelson tyrosine kinase," Science, Sep. 15, 2000, vol. 289, No. 5486 (pp. 1938-1942).
Schwartzentruber et al., "Driver mutations in histone H3.3 and chromatin remodelling genes in paediatric glioblastoma," Nature, 2012, vol. 482 (pp. 226-231).
Shah et al., "Discovery of imatinib-responsive FIP1L1-PDGFRA mutation during refractory acute myeloid leukemia transformation of chronic myelomonocytic leukemia," Journal of Hematology & Oncology, 2014, vol. 7. No. 26 (5 pages).
Shalem et al., "Genome-Scale CRISPR-Cas9 Knockout Screening in Human Cells," Science, Jan. 3, 2014, vol. 343 (pp. 84-87).
Shalem et al., "High-throughput functional genomics using CRISPR-Cas9" Nature Review Genetics, 2015, vol. 16, No. 5 (pp. 299-311).
Shao et al.,"Stabilization of chromatin structure by PRC1, a Polycomb complex," Cell, Jul. 9, 1999, vol. 98 (pp. 37-46).
Sharma et al., "Antisense oligonucleotides: modifications and clinical trials," Medical Chemistry Journal, 2014, 5 (pp. 1454-1471).
Shmakov et al., "Discovery and Functional Characterization of Diverse Class 2 CRISPR-Cas Systems," Molecular Cell, Nov. 1, 2015, vol. 60, No. 3 (pp. 385-397).

(56) References Cited

OTHER PUBLICATIONS

Silverman et al., "Multivalent avimer proteins evolved by exon shuffling of a family of human receptor domains," Nature Biotechnology, 2005, vol. 23, No. 12 (pp. 1556-1561).
Skerra et al., "Alternative binding proteins: Anticalins-harnessing the structural plasticity of the lipocalin ligand pocket to engineer novel binding activities," The FEBS Journal, 2008, vol. 275 (pp. 2677-2683).
Skerra et al., "Alternative non-antibody scaffolds for molecular recognition." Current Opinion in Biotechnology, 2007, vol. 18 (pp. 295-303).
Skerra, "Engineered protein scaffolds for molecular recognition," Journal of Molecular Recognition, 2000, vol. 13 (pp. 167-187).
Slaymaker et al., "Rationally engineered Cas9 nucleases with improved specificity," Science, Dec. 1, 2015, vol. 351, No. 6268 (pp. 84-88).
Smargon et al., "Casl3b Is a Type VI-B CRISPR-Associated RNA-Guided RNases Differentially Regulated by Accessory Proteins Csx27 and Csx28," Cell Press: Molecular Cell, Feb. 16, 2017, vol. 65, No. 4 (pp. 618-630).
Stegmaier et al., "Gene expression-based high-throughput screening (GE-HTS) and application to leukemia differentiation," Nature Genetics, 2004, vol. 36 (pp. 257-263).
Stumpp et al., "DARPins: a new generation of protein therapeutics," Drug Discovery Today, Aug. 2008, vol. 13, Nos. 15/16 (pp. 695-701).
Sturm et al., "Hotspot mutations in H3F3A and IDH1 define distinct epigenetic and biological subgroups of glioblastoma," Cancer Cell, Oct. 16, 2012, vol. 22 (pp. 425-437).
Swiech et al., "In vivo interrogation of gene function in the mammalian brain using CRISPR-Cas9," Nature Biotechnology, 2014, vol. 33 (pp. 102-106) [Including Supplemental information, 4 pages].
Tanay et al., "Scaling single-cell genomics from phenomenology to mechanism," Nature, Jan. 18, 2017, vol. 541, No. 7637 (pp. 331-338).
Tate et al., "Postnatal growth of the human pons: a morphometric and immunohistochemical analysis," The Journal of Comparative Neurology, Feb. 15, 2015, vol. 523, No. 3 (pp. 449-462).
Tirosh et al., "Dissecting the Multicellular Ecosystem of Metastatic Melanoma by Single-Cell RNA-Seq," Science, Apr. 8, 2016, vol. 352, No. 6282 (23 pages).
Tirosh et al., "Single-cell RNA-seq supports a developmental hierarchy in human oligodendroglioma," Nature, 2016, 539 (pp. 309-313).
Tran-Huu-Hue et al., "Practical Systems for the Generation of High Power Continuous Wave-Non Focused Ultrasound in the MHz Range," Acustica, acta acustica, 1997, vol. 83 (pp. 1103-1106).
Tsai et al., "Dimeric CRISPR RNA-guided FokI nucleases for highly specific genome editing," Nature Biotechnology, 2014, vol. 32, No. 6 (pp. 569-576).
Tuerk et al., "Systematic evolution of ligands by exponential enrichment: RNA ligands to bacteriophage T4 DNA polymerase," Science, Aug. 3, 1990, vol. 249, No. 4968 (pp. 505-510).
Twyman et al., "Glutamate Receptor Antibodies Activate a Subset of Receptors and Reveal an Agonist Binding Site," Neuron, Apr. 1995, vol. 14 (pp. 755-762).
Venneti et al., "Evaluation of Histone 3 Lysine 27 Trimethylation (H3K27me3) and Enhancer of Zest 2 (EZH2) in Pediatric Glial and Glioneuronal Tumors Shows Decreased H3K27me3 in H3F3A K27M Mutant Glioblastomas," Brain pathology, 2013, vol. 23 (pp. 558-564).
Venteicher et al., "Decoupling genetics, lineages, and microenvironment in IDH-mutant gliomas by single-cell RNA-seq", Science, Mar. 31, 2017, vol. 355 [with Supplementary Materials] (pp. 1-29).

Von Essen, "Constitutive and ligand-induced TCR degradation," Journal of Immunology, vol. 173, No. 1 (pp. 384-393).
Wakimoto et al., "Human glioblastoma-derived cancer stem cells: establishment of invasive glioma models and treatment with oncolytic herpes simplex virus vectors," Cancer Research, 2009, vol. 69 (pp. 3472-3481).
Wang et al., "CSPG4 protein as a new target for the antibody-based immunotherapy of triple-negative breast cancer," Journal of the National Cancer Institute, Oct. 6, 2010, vol. 102, No. 19 (pp. 1496-1512).
Wang et al., "Genetic Screens in Human Cells Using the CRISPR-Cas9 System", Science, 2014, vol. 343 (pp. 80-84).
Wang et al., "One-Step Generation of Mice Carrying Mutations In Multiple Genes By CRISPR/Cas-Mediated Genome Engineering," Cell, May 9, 2013, vol. 153 (pp. 910-918).
Watson et al., "SHP-1: the next checkpoint target for cancer immunotherapy?" Biochemical Society Transactions, Apr. 15, 2016, vol. 44, No. 2 (pp. 356-362).
Wu et al., "Remote control of therapeutic T cells through a small molecule-gated chimeric receptor," Science, Oct. 16, 2015, vol. 350, No. 6258 (pp. 1-21).
Wu et al., "Somatic histone H3 alterations in pediatric diffuse intrinsic pontine gliomas and non-brainstem glioblastomas," Nature Genetics, Mar. 2012, vol. 44, No. 3 (pp. 251-253).
Wu et al., "Genome-wide binding of the CRISPR endonuclease Cas9 in mammalian cells," Nature Biotechnology, 2014, Including Supplemental information, 2 pages (pp. 1-9).
Xu et al., "Sequence determinants of improved CRISPR sgRNA design," Genome Research, Aug. 2015, vol. 25 (pp. 1147-1157).
Yan et al., "Cas13d Is a Compact RNA-Targeting Type VI CRISPR Effector Positively Modulated by a WYL-Domain-Containing Accessory Protein," Molecular Cell, Apr. 19, 2018, vol. 70, No. 2 (pp. 327-339).
Yoon et al., "Antibodies to Domains II and III of the IL-1 Receptor Accessory Protein Inhibit IL-1-Beta Activity but Not Binding: Regulation of IL-1 Responses is Via Type I Receptor, Not the Accessory Protein," The Journal of Immunology, vol. 160, 1998 (pp. 3170-3179).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zetsche et al., "A split-Cas9 architecture for inducible genome editing and transcription modulation", Nature Biotechnology, Feb. 2015, vol. 33, No. 2 (pp. 139-142).
Zhang et al., "Efficient Construction of Sequence-Specific TAL Effectors for Modulating Mammalian Transcription," Nature Biotechnology, Feb. 2011, vol. 29, No. 2 (pp. 149-154).
Zhou et al., "Aptamer-targeted cell-specific RNA interference," Silence, Feb. 1, 2010, vol. 1, No. 4 (10 pages).
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry 2018, vol. 61 (pp. 462-481).
Zhou et al., "Long-term outcome after haploidentical stem cell transplant and infusion of T cells expressing the inducible caspase 9 safety transgene," Blood, Jun. 19, 2014, vol. 123, No. 25 (pp. 3895-3905).
Zhu et al., "Inhibition of Vascular Endothelial Growth Factor-induced Receptor Activation with Anti-Kinase Insert Domain-containing Receptor Single-Chain Antibodies from a Phage Display Library," Cancer Research, Aug. 1998, vol. 58 (pp. 3209-3214).
Zuker et al., "Optimal computer folding of large RNA sequences using thermodynamics and auxiliary information," Nucleic Acids Research, Jan. 10, 1981, vol. 9, No. 1 (pp. 133-148).

* cited by examiner

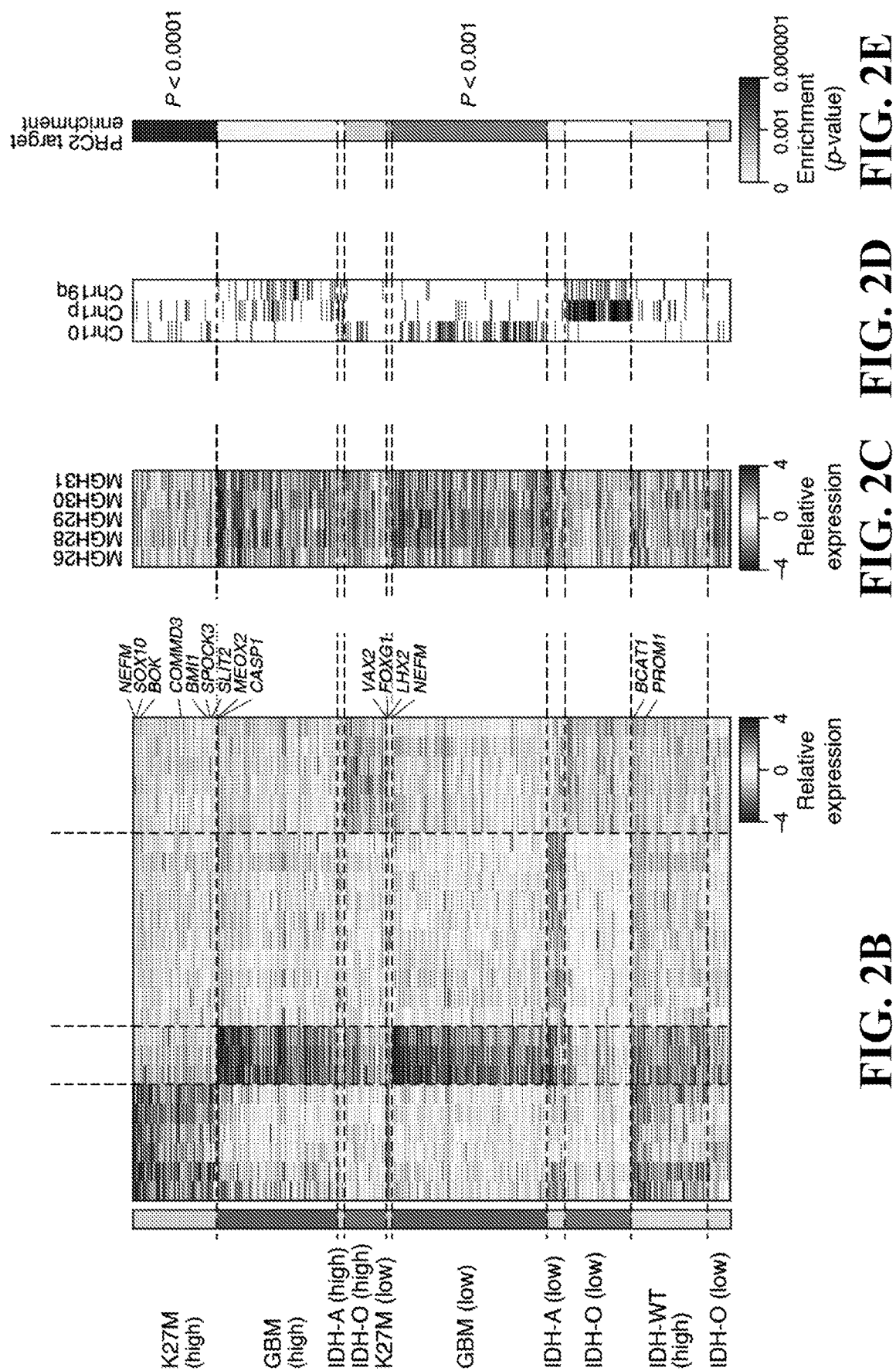

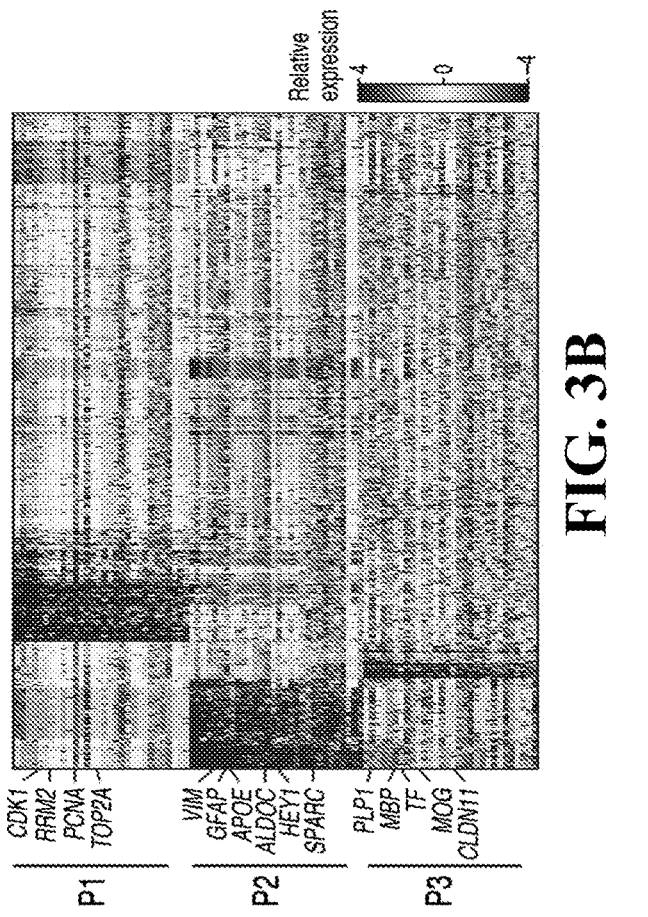
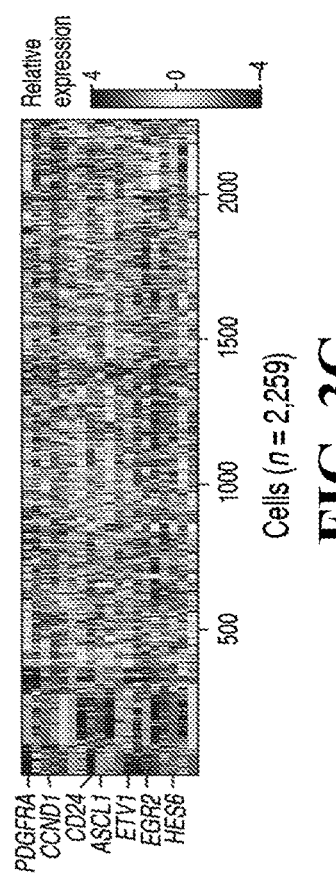
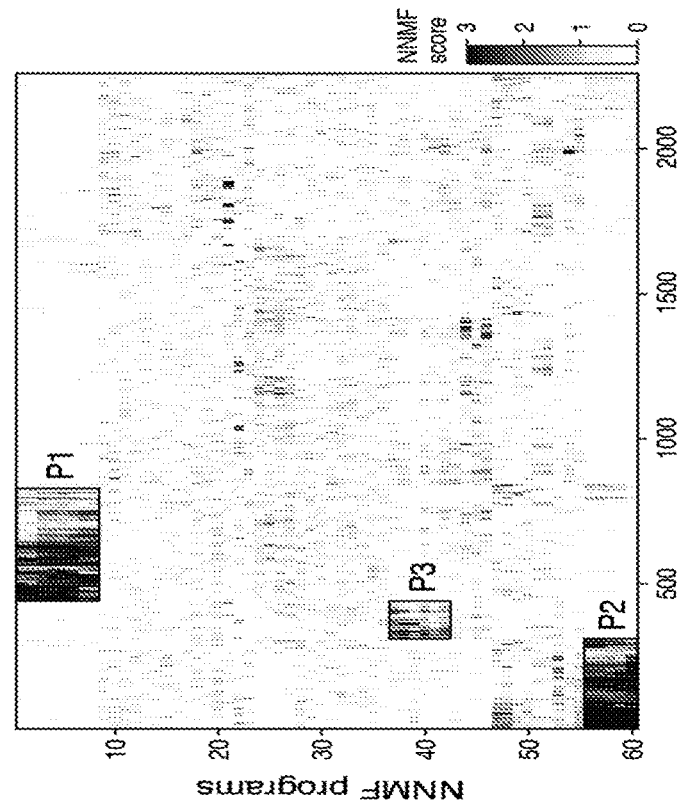
FIG. 3B
FIG. 3C
FIG. 3A

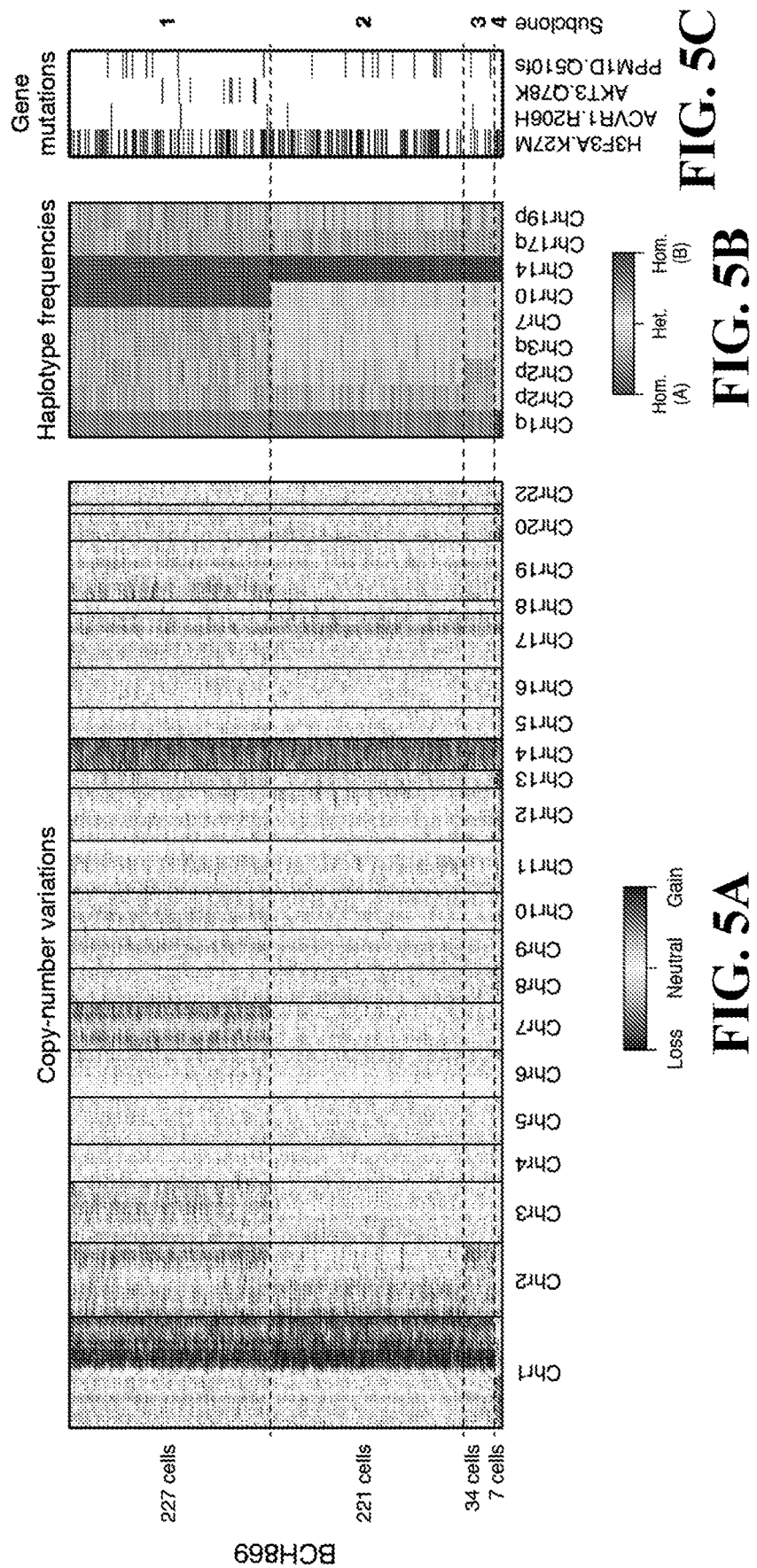

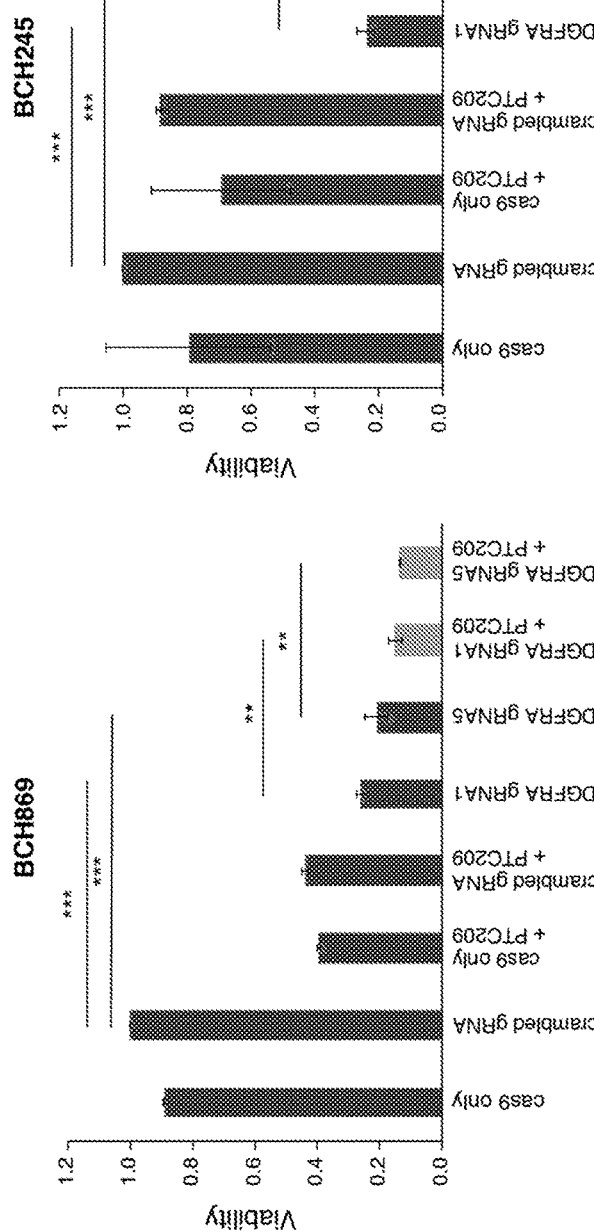
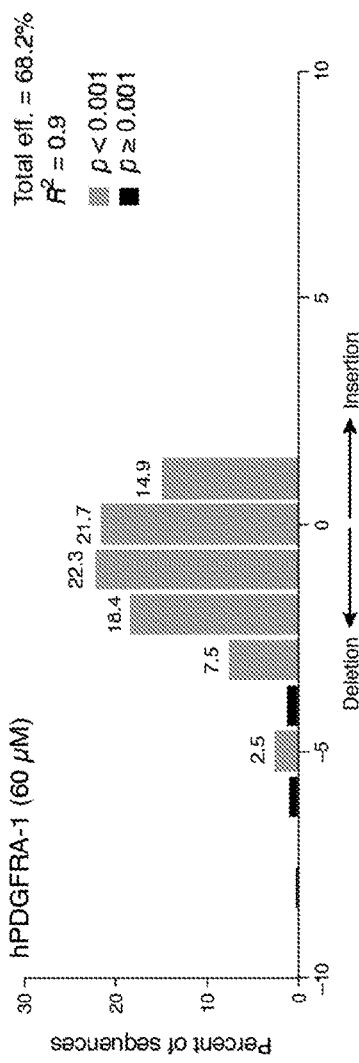
FIG. 13A
FIG. 13B
FIG. 13C

SEQUENCE LISTING

<160> NUMBER OF SEQ ID NOS: 22

<210> SEQ ID NO 1
<211> LENGTH: 288
<212> TYPE: PRT
<213> ORGANISM: Unknown
<220> FEATURE:
<223> OTHER INFORMATION: Proteobacteria

<400> SEQUENCE: 1

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270
```

```
Glu Ala Val His Ala Trp Arg Asn Ala Leu Thr Gly Ala Pro Leu Asn
        275                 280                 285

<210> SEQ ID NO 2
<211> LENGTH: 183
<212> TYPE: PRT
<213> ORGANISM: Unknown
<220> FEATURE:
<223> OTHER INFORMATION: Proteobacteria

<400> SEQUENCE: 2

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 107
<212> TYPE: PRT
<213> ORGANISM: Homo sapiens

<400> SEQUENCE: 3

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105
```

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
accactactg aatataaggt                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
caaagcacac acatcaggtg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tgtgactttc gccaaagtgg                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gtaaccttac acaacagtga                                                    20

<210> SEQ ID NO 8
<211> LENGTH: 192
<212> TYPE: DNA
<213> ORGANISM: Artificial Sequence
<220> FEATURE:
<223> OTHER INFORMATION: Synthetic

<400> SEQUENCE: 8
tagtctgtaa aacgtgtatt gttcgttacc tggagaccag caagtattgt cctatttgtg        60
atgtccaagt tcacaagacc agaccactac tagttagcta acaggaaact gttgaaattc       120
cttgtttgta attattattg gagttgtata atttactgaa ggcaaccctc tttatttctt       180
cacagaaaat tt                                                           192

<210> SEQ ID NO 9
<211> LENGTH: 192
<212> TYPE: DNA
<213> ORGANISM: Artificial Sequence
<220> FEATURE:
<223> OTHER INFORMATION: Synthetic

<400> SEQUENCE: 9
attatggcca ttatttctgt gtcttgcagg attttttatc aagcagaaat gcatcgaaca        60
acgagaatca agatcactga gctaaatccc taaaccggtt aagtgctttg tggagggtac       120

```
ttcattgatg ccacaaccat aatagaatgt ctacattcct gtaagtaccg agctttagct    180
ctcttttgta tc                                                        192
```

<210> SEQ ID NO 10
<211> LENGTH: 192
<212> TYPE: DNA
<213> ORGANISM: Artificial Sequence
<220> FEATURE:
<223> OTHER INFORMATION: Synthetic

<400> SEQUENCE: 10

```
cttcctggac tattttggcc aacaatgtct caaacatcat cacggagatc cactcccgag    60
acaggagtac cgtggagggc cgtgtgactt tagatagcta acaggagacc atcgccgtgc    120
gatgcctggc taagaatctc cttggagctg agaaccgaga gctgaagctg gtggctccca    180
gtgagttcct ca                                                        192
```

<210> SEQ ID NO 11
<211> LENGTH: 192
<212> TYPE: DNA
<213> ORGANISM: Artificial Sequence
<220> FEATURE:
<223> OTHER INFORMATION: Synthetic

<400> SEQUENCE: 11

```
aggaatgacg gattatttag tcatcgtgga ggatgatgat tctgccatta taccttgtcg    60
cacaactgat cccgagactc ctgtaacctt tagttagcta acgggggtgg tacctgcctc    120
ctacgacagc agacagggct ttaatgggac cttcactgta gggccctata tctgtgaggc    180
caccgtcaaa gg                                                        192
```

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12

```
ggggattgtg tggcgtctg                                                 19
```

<210> SEQ ID NO 13
<211> LENGTH: 25
<212> TYPE: DNA
<213> ORGANISM: Artificial Sequece
<220> FEATURE:
<223> OTHER INFORMATION: Synthetic Oligonucleotide

<400> SEQUENCE: 13

```
tagggaataa agaggaatgg aagcc                                          25
```

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 14

```
tgttggtaca aagtggtgaa g                                              21
```

```
<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
agtttggtag aactgattcc g                                           21

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
ctgaggatca tcgcaaccct                                             20

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
gggcagacac ctctacttca t                                           21

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
agacaaggtc ccaactcctt gccat                                       25

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tccatcagga gacaggcaat                                             20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tagggccgcc atagtcagga                                             20

<210> SEQ ID NO 21
<211> LENGTH: 21
<212> TYPE: DNA
<213> ORGANISM: Artificial Sequence
<220> FEATURE:
```

```
<223> OTHER INFORMATION: Synthetic oligonucleotide

<400> SEQUENCE: 21
tcaataatgc cagtgggata g                                        21

<210> SEQ ID NO 22
<211> LENGTH: 9
<212> TYPE: PRT
<213> ORGANISM: Homo sapiens

<400> SEQUENCE: 22

Ile Glu Val Met Tyr Pro Pro Pro Tyr
1               5
```

METHODS AND COMPOSITIONS FOR TARGETING DEVELOPMENTAL AND ONCOGENIC PROGRAMS IN H3K27M GLIOMAS

CROSS-REFERENCE TO RELATED APPLICATIONS

This application claims the benefit of U.S. Provisional Application Nos. 62/585,468, filed Nov. 13, 2017 and 62/586,093, filed Nov. 14, 2017. The entire contents of the above-identified applications are hereby fully incorporated herein by reference.

STATEMENT REGARDING FEDERALLY SPONSORED RESEARCH

This invention was made with government support under Grant Nos. CA180922, CA202820, CA014051, CA216873, CA165962, CA090354, and CA142536 awarded by the National Institutes of Health. The government has certain rights in the invention.

TECHNICAL FIELD

The subject matter disclosed herein is generally directed to compositions and methods for treating diffuse gliomas with histone H3 lysine27-to-methionine mutations (H3K27M-gliomas).

REFERENCE TO AN ELECTRONIC SEQUENCE LISTING

The contents of the electronic sequence listing (BROD_2296WP_ST25.txt"; Size is 10 Kilobytes and it was created on Nov. 2, 2018) is herein incorporated by reference in its entirety.

BACKGROUND

Pediatric malignancies arise at specific time points and locations during development and only harbor a limited set of genomic aberrations compared to their adult counterparts (1). This pattern is thought to result from the precise interplay between transforming genetic events and susceptible cellular contexts that expand at specific times during development. Deciphering both lineage-defined and somatically altered cellular states and gene regulatory programs in patient tumors thus has broad implications for pediatric oncology.

Diffuse midline gliomas with histone H3 lysine27-to-methionine mutations (H3K27M-gliomas), including diffuse intrinsic pontine glioma (DIPG), thalamic glioma and spinal cord glioma, are aggressive pediatric cancers that are uniformly fatal despite multimodal treatment strategies. These tumors are defined by a somatic mutation in H3F3A or HISTH3B/C, leading to K27M mutation in histone H3.3 or H3.1, respectively (2-5). H3K27M-gliomas are both spatially and temporally restricted: spatially, they are exclusive to midline structures of the brain (thalamus, pons, spinal cord); temporally, they occur primarily in young children. The occurrence of these tumors in precise anatomic locations and age groups suggests that a particular cell type, potentially undergoing rapid expansion at that time, is susceptible to transformation by H3K27M.

Consistently, experimental models have suggested that neural precursor cells (NPC) derived from iPS cells—but not more differentiated cell types—can be transformed in vitro by H3K27M in combination with TP53 mutation and PDGFRA overexpression, alterations frequently observed in midline gliomas (6). The transforming effect of H3K27M is thought to result from the ability of the mutant histone to suppress EZH2, the catalytic subunit of Polycomb Repressive Complex 2 (PRC2), and thereby compromise epigenetic repression (7-10). Transformation of neural precursors by H3K27M has been proposed to reset them into a more primitive stem cell state and to result in a differentiation block (6). While this model is experimentally supported in vitro, very little is known about its relevance in vivo, and more generally about the cellular composition of H3K27M-gliomas in patients, i.e. the stem and differentiated cells they harbor, and how specific cell types, developmental cell states and genetic events cooperate.

Single-cell RNA-sequencing (scRNA-seq) of human tumors can help address these questions through characterization of cancer cell states, their proliferative signatures and their similarity to normal or other malignant cell types. Furthermore, it is also possible to identify genetic aberrations in these same cells, either by computationally inferring chromosomal aberrations (11-15), or, when using full-length scRNA-seq (16), by detecting mutations in expressed transcripts, albeit with limited sensitivity (14). This strategy makes it possible to relate the genetic and epigenetic architecture of human malignancies at cellular resolution. In particular, Applicants recent studies indicate that adult IDH-mutant gliomas are driven by specific subpopulations of proliferative tumor cells with neural precursor cell-like (NPC-like) programs and capacity for differentiation (14, 15). However, it is currently unknown if these observations generalize to other classes of human gliomas, especially pediatric glioma, or if genetically-defined glioma subtypes display different cellular architectures and putative stem cell programs, as would be suggested by their distinct genotypes, age groups and anatomic locations. Notably, scRNA-seq in H3K27M-gliomas poses particular logistical hurdles compared to earlier studies in other tumor types (12-15), due to the rarity of this tumor, and the fact that only needle biopsies with minute pieces of tissue are sampled from the patients. Thus, there is a need to understand pathways and drivers involved in pediatric gliomas.

SUMMARY

In certain example embodiments, the present invention provides therapeutic targets and strategies for treating pediatric gliomas. Diffuse gliomas with histone H3 lysine27-to-methionine mutations (H3K27M-gliomas) arise nearly exclusively in the midline of the central nervous system, with peak incidence in young children, suggesting that tumorigenesis involves a cooperation between genetic factors and specific cellular contexts that arise during development. While the genetics of H3K27M-gliomas have been well-characterized, their cellular architecture remains uncharted. Here, Applicants performed single-cell RNA-sequencing (scRNA-seq) in 3,321 cells from six primary H3K27M-gliomas and matched cellular and xenograft models. Applicants found that H3K27M-gliomas exhibit unique oncogenic and developmental signatures, distinct from IDH-wildtype glioblastoma and IDH-mutant gliomas. H3K27M-gliomas are primarily composed of cells resembling oligodendrocyte precursor cells (OPC-like), while more differentiated malignant cells are a minority. In support for a developmental hierarchy of malignant cells, Applicants show that OPC-like cells exhibit greater proliferation signatures in patients and tumor-propagating potential in models than their differentiated malignant counterparts, and identify consistent cellular states across genetic subclones within individual tumors. Provided herein are characterizations of oncogenic and developmental programs in H3K27M-gliomas, identification of therapeutic targets in this disease, and a comprehensive map of the similarities and differences between the major classes of human gliomas at single-cell resolution.

In one aspect, the present invention provides for a method of treating histone H3 lysine 27-to-methionine mutant glioma (H3K27M-glioma) comprising administering to a subject in need thereof an agent capable of inhibiting expression or activity one or more genes or polypeptides selected from the group consisting of HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAP1B, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19 and SLC13A5. The one or more genes or polypeptides may be selected from the group consisting of BMI1 (PCGF4), NEFM, SOX10, BOK, COMMD3, SPOCK3, SLIT2, MEOX2 and CASP1.

In another aspect, the present invention provides for a method of treating H3K27M-glioma comprising administering to a subject in need thereof an agent capable of inhibiting expression or activity of one or more subunits of the PRC1 complex.

In certain embodiments, the agent may comprise a BMI1 inhibitor. The BMI1 inhibitor may comprise PTC209.

The method according to any embodiment herein may further comprise treating the subject with a kinase inhibitor. The kinase may be PDGFRA.

In another aspect, the present invention provides for a method of treating H3K27M-glioma by targeting oligodendrocyte precursor-like cells (OPC-like) comprising administering to a subject in need thereof an agent capable of inhibiting expression or activity of one or more genes or polypeptides selected from the group consisting of: PDGFRA, MEST, CCND1, KLRC2, ARC, SEZ6L, EGR1, CD24, ASCL1, FOS, LINC00643, ETV1, NNAT, EGR2, PCP4, BTG2, HES6, IER2 and MFNG; or PDGFRA, CSPG4, SERPINE2, PTPRZ1, CNTN1, COL9A1, GPM6A, NLGN3, GPM6B, SYT11 and SPRY4. The agent may comprise a PDGFRA inhibitor.

In certain embodiments, the agent capable of inhibiting expression or activity of one or more genes or polypeptides according to any embodiment herein may comprise a small molecule, small molecule degrader, genetic modifying agent, antibody, bi-specific antibody, antibody fragment, antibody-like protein scaffold, protein, or aptamer. The genetic modifying agent may comprise a CRISPR system, a zinc finger nuclease system, a TALE system, RNAi or a meganuclease. The CRISPR system may comprise Cas9, Cas12, or Cas14. The CRISPR system may comprise a dCas fused or otherwise linked to a nucleotide deaminase. The nucleotide deaminase may be a cytidine deaminase or an adenosine deaminase. The dCas may be a dCas9, dCas12, dCas13, or dCas14. The CRISPR system may comprise Cas9 or Cpf1. The CRISPR system may comprise a Cas13 system and targets mRNA. The Cas13 system may comprises Cas13-ADAR.

In another aspect, the present invention provides for a method of treating H3K27M-glioma by targeting oligodendrocyte precursor-like cells (OPC-like) comprising treating a subject in need thereof with an agent capable of targeting one or more surface genes or polypeptides selected from the group consisting of: PDGFRA, MEST, KLRC2, SEZ6L, CD24 and MFNG; or PDGFRA, CSPG4, SERPINE2, PTPRZ1, CNTN1, GPM6A, NLGN3, GPM6B and SYT11. The agent may comprise an antibody, an antibody-drug conjugate (ADC) or a bispecific antibody specific for a gene or polypeptide. The agent may comprise a CAR T cell specific for a gene or polypeptide.

In certain embodiments, the agent targets PDGFRA. In certain embodiments, the agent targets CSPG4.

In another aspect, the present invention provides for a method of treating H3K27M-glioma comprising administering to a subject in need thereof an agent capable of modulating expression or activity of a gene signature comprising one or more genes selected from the group consisting of HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAP1B, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19, SLC13A5, VAX2, SRI, LHX2, FOXG1, SQSTM1, SMOX, B4GALT7, AGMO, C21orf2, MKLN1, SWI5 and C7orf49.

In another aspect, the present invention provides for a method of treatment comprising a combination of treatments according to any embodiment herein.

In certain embodiments, the method according to any embodiment herein further comprises administering a histone demethylase.

In certain embodiments, the treatment according to any embodiment herein is administered as an adjuvant or neo-adjuvant therapy.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 13—PDGFRA knockout in H3K27M cell lines. (A) Viability of H3K27M patient-derived cell line BCH869 after 7 days of PDGFRA knockout with two different gRNAs (1 and 5), normalized to scrambled gRNA, alone or in combination with the BMI-1 inhibitor PTC-209 at 500 nM. Three technical replicates were performed in each of two independent experiments for a total of n=6. Error bars represent the s.e.m. Significance was analyzed using a mixed effects linear regression model for the normalized viability data, with a random effect for experiment and fixed effects for drugs. P<0.01 (), P<0.001 (*) (B) Viability of H3K27M patient-derived cell line BCH245 after 7 days of PDGFRA knockout with two different gRNAs, normalized to scrambled gRNA, alone or in combination with the BMI-1 inhibitor PTC-209 at 500 nM. Three technical replicates were performed in each of two independent experiments for a total of n=6. Error bars represent the s.e.m. Significance was analyzed using a mixed effects linear regression model for the normalized viability data, with a random effect for experiment and fixed effects for drugs. p<0.001 (***) (C) Representative cutting efficiency of PDGFRA gene. Frequencies of insertions and deletions for gRNA1 are shown. Total cutting efficiency equals 68.2%.

Figures 1A, 1B:
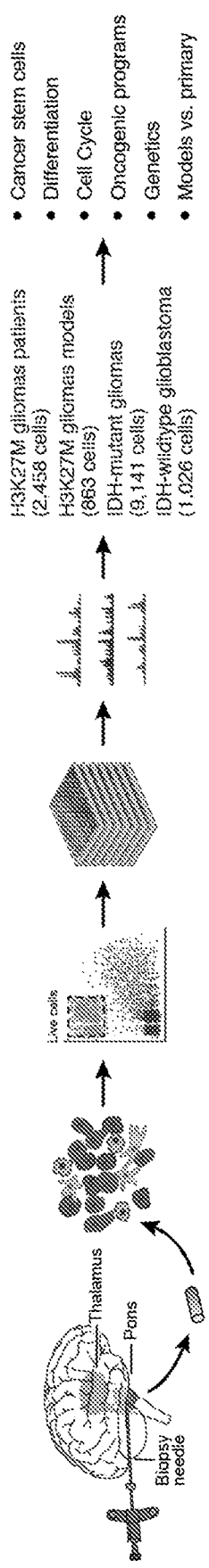
FIG. 1—Characterization of H3K27M-gliomas by single cell RNA-seq. (A) Clinical and molecular characteristics of six H3K27M-glioma samples profiled by scRNA-seq. (B) Workflow of scRNA-seq analysis of H3K27M-gliomas. Needle biopsies from patients are dissociated, and then FACS sorted to isolate individual live cells in 96 well plates; plates are profiled by the Smart-Seq2 protocol; the resulting single cell profiles are filtered by quality controls, and classified into malignant and non-malignant based on gene expression and inference of chromosomal aberrations. Malignant cells of H3K27M-gliomas are analyzed for patterns of intra-tumor heterogeneity and are compared to other classes of human gliomas profiled with the same protocol. (C) Heatmap depicts pairwise correlations between the expression profiles of 2,458 single cell from six H3K27M-glioma samples. Two clusters at the top left consist of immune cells and oligodendrocytes (non-malignant cells or 'NM'). The remaining clusters consist of malignant cells, and are ordered by tumor-of-origin, as indicated on the left. The right panel indicates the expression level of microglia and oligodendrocyte signatures. (D) Detection of gene mutations for H3K27M (left), and for all other mutations as identified per sample by WGS/WES (right; black line indicates that at least one mutated gene was identified in that cell). Cells are ordered as in (C). (E) Inferred CNV profiles defined by a moving average of the expression of 100 genes ordered by their chromosomal location (Methods). Cells are ordered as in (C). (F) CNV profiles as defined by WGS/WES for five of the six H3K27M-glioma samples are consistent with CNVs inferred from scRNA-seq data (E).

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide new therapeutic targets and therapeutic strategies for treating gliomas. In certain embodiments, the glioma is a pediatric glioma. In certain embodiments, the glioma is a H3 lysine 27-to-methionine mutant glioma (H3K27M-glioma). In certain embodiments, gliomas are treated differently based on the type of glioma, such as glioblastoma (GBM), IDH mutant gliomas (e.g., oligodendroglioma, astrocytoma), or H3 lysine 27-to-methionine mutant gliomas (H3K27M-glioma). In certain embodiments, the present invention provides for gene expression signatures that are highly expressed in one type of glioma and repressed in another type of glioma.

Here, Applicants combined expertise in single-cell genomics, a high-sensitivity approach for processing scarce needle biopsies, and a multi-center collaboration, to perform full-length single cell RNA sequencing (scRNA-seq) in 2,458 single-cells derived from six pontine or thalamic H3K27M-gliomas at diagnosis (FIG. 1A-B). Applicants found that H3K27M-glioma cells exhibit unique expression signatures, distinct from IDH-wildtype glioblastoma and IDH-mutant gliomas, including upregulation of PRC2 targets genes, as well as the PRC1 subunit BMI1. Analysis of intra-tumoral expression heterogeneity showed that, in contrast to IDH-mutant gliomas, H3K27M-gliomas are driven by glioma cells with oligodendrocyte precursor cell-like (OPC-like) programs. These OPC-like glioma cells, which comprise the majority of malignant cells in each tumor, are enriched for proliferation signatures and are at least in part maintained by PDGFRA signaling. In contrast, differentiated H3K27M cells represent a minority of tumor cells in patients and are depleted for proliferation signatures. Applicants leverage inferred copy number variations (CNVs) and single-nucleotide polymorphisms (SNPs) detected in the scRNA-seq data to demonstrate that different genetic clones evolving within the tumors share consistent developmental programs. Finally, analysis of 863 single cells from patient derived xenografts (PDX) and in vitro cellular models of H3K27M-gliomas, enabled Applicant to relate the transcriptional phenotypes of disease models to primary tumors, and show that the OPC-like cells, but not the differentiated-like cells, have tumor-propagating potential in vivo. In summary, this single-cell study provides newly detailed insights into H3K27M-glioma stem cell and oncogenic programs, and identifies specific regulators and pathways as therapeutic targets in this aggressive malignancy.

Use of Signature Genes

In certain embodiments, H3K27M-gliomas exhibit expression signatures. In certain embodiments, the signatures include upregulated and down regulated genes. While not being bound by a particular theory, in some embodiments H3K27M-gliomas repress PRC2 activity and PRC2 target genes are upregulated. In certain embodiments, the H3K27M-gliomas expression signature may include one or more genes selected from HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAPIB, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19, SLC13A5, VAX2, SRI, LHX2, FOXG1, SQSTM1, SMOX, B4GALT7, AGMO, C21orf2, MKLN1, SWI5 and C7orf49. In certain other embodiments, treating H3K27M-gliomas with an agent that modulates the expression of one or more of the PRC2 target genes or the entire signature may be used to provide a therapeutic effect in a subject in need thereof.

In certain other embodiments, the gene signature may include genes that are up or down regulated in response to the mutations present in H3K27M-gliomas. The up or down regulated genes may be necessary for tumor cell viability in the background of the mutations. In one embodiment, certain signature genes may be compensatory to the driver mutations in H3K27M-gliomas. In certain embodiments, the compensatory gene expression may be up regulation of a PRC1 subunit. In certain embodiments, BMI1 is upregulated. In certain embodiments, tumor cells are targeted by inhibiting BMI1. PRC1 activity may compensate for the derepression of PRC2 targets required for tumor viability. In certain embodiments, H3K27M glioma may be treated by inhibiting PRC1 activity.

In certain embodiments, gene signatures are identified for specific tumor cells. In certain embodiments, specific tumor cell subtypes are responsible for proliferation. In certain embodiments, oligodendrocyte precursor cell-like (OPC-like) are the proliferative cells in H3K27M-gliomas. In certain embodiments, cells having an OPC-like signature are targeted to treat a subject in need thereof. In certain embodiments, an OPC-like signature includes PDGFRA, MEST, CCND1, KLRC2, ARC, SEZ6L, EGR1, CD24, ASCL1, FOS, LINC00643, ETV1, NNAT, EGR2, PCP4, BTG2, HES6, IER2 and MFNG; or PDGFRA, CSPG4, SERPINE2, PTPRZ1, CNTN1, COL9A1, GPM6A, NLGN3, GPM6B, SYT11 and SPRY4. In certain embodiments, the top genes that distinguish the OPC-like signature are PDGFRA and CSPG4.

As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., tumor cells). In certain embodiments, the signature is dependent on epigenetic modification of the genes or regulatory elements associated with the genes (e.g., methylation, ubiquitination). Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. The signatures of the present invention may be microenvironment specific, such as their expression in a particular spatio-temporal context. In certain embodiments, signatures as discussed herein are specific to a particular pathological context. In certain embodiments, a combination of cell subtypes having a particular signature may indicate an outcome. The signatures may be used to deconvolute the network of cells present in a particular pathological condition. The presence of specific cells and cell subtypes may also be indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition, or linked to a particular outcome or progression of the disease, or linked to a particular response to treatment of the disease (e.g. resistance to therapy).

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different immune cells or immune cell (sub)populations (e.g., T cells), as well as comparing immune cells or immune cell (sub)populations with other immune cells or immune cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., proliferating) which can be distinguished or are uniquely identifiable and set apart from other cells of this cell type. The cell subpopulation may be phenotypically characterized, and is preferably characterized by the signature as discussed herein. A cell (sub) population as referred to herein may constitute of a (sub) population of cells of a particular cell type characterized by a specific cell state.

When referring to induction, or alternatively reducing or suppression of a particular signature, preferable is meant induction or alternatively reduction or suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

The invention further relates to various uses of the gene signatures, protein signature, and/or other genetic or epigenetic signature as defined herein. Particular advantageous uses include methods for identifying agents capable of inducing or suppressing particular tumor cell (sub)populations based on the gene signatures, protein signature, and/or other genetic or epigenetic signature as defined herein. The invention further relates to agents capable of inducing or suppressing particular tumor cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modify overall tumor composition, such as immune cell composition, such as immune cell subpopulation composition or distribution, or functionality.

The signature genes of the present invention were discovered by analysis of expression profiles of single-cells within a population of tumor cells, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient. Not being bound by a theory, many cells that make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. The signature genes may indicate the presence of one particular cell type. In one embodiment, the expression may indicate the presence of proliferating cell types. Not being bound by a theory, a combination of cell subtypes in a subject may indicate an outcome.

Modulating Agents

In certain embodiments, an H3 lysine 27-to-methionine mutant glioma (H3K27M-glioma) is treated with a modulating agent to alter expression or activity of one or more genes. As used herein the term "altered expression" may particularly denote altered production of the recited gene products by a cell. As used herein, the term "gene product(s)" includes RNA transcribed from a gene (e.g., mRNA), or a polypeptide encoded by a gene or translated from RNA.

Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve affecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

In certain embodiments, the present invention provides for gene signature screening to identify a modulating agent. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures of the present invention may be used to screen for drugs that reduce the signatures in cancer cells or cell lines as described herein (e.g., OPC-like signature). The signature may be used for GE-HTS. In certain embodiments, pharmacological screens may be used to identify drugs that promote differentiation of OPC-like cells. In certain embodiments, drugs selectively toxic to cancer cells having an OPC-like signature or capable of differentiating OPC-like tumor cells are used for treatment of a cancer patient. Targeting only the OPC-like signature may decrease adverse side effects.

In certain embodiments, cmap is used to screen for agents capable of modulating a signature in silico (e.g., an OPC-like signature). The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60).

In certain embodiments, the present invention provides for one or more therapeutic agents against one or more of the targets identified. In certain embodiments, combinations of agents may provide for enhanced or otherwise previously unknown activity in the treatment of disease. In certain embodiments, an agent against one of the targets in a combination may already be known or used clinically. In certain embodiments, targeting a combination may require less of the agent as compared to the current standard of care and provide for less toxicity and improved treatment. For example, in methods for treating cancer in a subject, an effective amount of a combination of inhibitors is any amount that provides an anti-cancer effect, such as reduces or prevents proliferation of a cancer cell or is cytotoxic towards a cancer cell. In certain embodiments, the effective amount of an inhibitor is reduced when an inhibitor is administered concomitantly or in combination with one or more additional inhibitors as compared to the effective amount of the inhibitor when administered in the absence of one or more additional inhibitors. In certain embodiments, the inhibitor does not reduce or prevent proliferation of a cancer cell when administered in the absence of one or more additional inhibitors.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

Polycomb Complexes—PRC1 and PRC2

PRC1 components were first described in Drosophila, four proteins were identified: polycomb (Pc), polyhomeotic (PH), dRING, and posterior sex combs (PSC) (Shao et al., 1999 Stabilization of chromatin structure by PRC1, a Polycomb complex. Cell 98, 37-46). The human homologs of these proteins are CBXs (Pc homolog), PHC1, 2, and 3 (PH homologs), Ring1a and Ring1b (dRING homologs), BMI1 and six minor others (PSC homologs) (Levine et al., 2002 The core of the polycomb repressive complex is compositionally and functionally conserved in flies and humans. Mol. Cell. Biol. 22, 6070-6078).

PRC2 contains three components: enhancer of zeste (EZ), suppressor of zeste 12 (Suz12), extra sex combs (Esc). Polycomblike (Pcl) also often associates with the other PRC2 proteins. The human homologs of these are EZH1/2, SUZ12, embryonic ectoderm development (EED) and RbBP4 respectively. There are additional homologs and variants of these proteins (see, e.g., Di Croce, L., and Helin, K. (2013). Transcriptional regulation by Polycomb group proteins. Nat. Struct. Mol. Biol. 20, 1147-1155).

PRC1 and PRC2 function to silence chromatin. PRC2 first binds to chromatin and its catalytic subunit, EZH2, trimethylates H3K27. H3K27me3 is then recognized by the CBX component of PRC1. The E3 ligases RING1/2 then monoubiquitinates H2A on K119 which leads to chromatin compaction and pausing of RNAPII (Francis et al., 2004, Chromatin compaction by a polycomb group protein complex. Science 306, 1574-1577). As shown herein, inhibition of BMI-1 in H3K27M gliomas leads to decreased tumor cell viability. In certain embodiments, inhibition of histone methylation at PRC2 targets may be partially compensated for by increased PRC1 activity.

In certain embodiments, the agent capable of inhibiting expression or activity one or more genes or polypeptides selected from the group consisting of HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAPIB, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19 and SLC13A5 or capable of modulating expression or activity of a gene signature comprising one or more genes selected from the group consisting of HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAPIB, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19, SLC13A5, VAX2, SRI, LHX2, FOXG1, SQSTM1, SMOX, B4GALT7, AGMO, C21orf2, MKLN1, SWI5 and C7orf49 may be a PRC2 activating agent.

In certain embodiments, tumor cell viability of H3K27M gliomas is dependent upon PRC1 complex activity. In certain embodiments, an inhibitor of PRC1 may be used to treat H3K27M gliomas. In certain embodiments, the agent capable of inhibiting expression or activity one or more genes or polypeptides selected from the group consisting of HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAPIB, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19 and SLC13A5 or capable of modulating expression or activity of a gene signature comprising one or more genes selected from the group consisting of HENMT1, FAM162B, CRYGD, ATF7IP2, NEFM, PLEKHG4, B3GNT7, SOX10, STPG1, SEMA3E, FRMD4B, C2orf40, NIPSNAP3B, ROR2, CPNE7, BOK, SLC6A15, MEGF10, UCP2, FAM26F, EDARADD, SEL1L3, FZD6, PPAP2C, AOX1, SGCD, TENM3, SULT1A1, CTHRC1, ACADL, CHRFAM7A, SNAI1, NMU, ST6GALNAC3, C10orf11, VRK2, RGS22, SLC30A10, RBP4, SLC30A3, PENK, SLC27A2, ENPP1, ACAN, GPR133, CTSC, GUCY1A3, C1orf114, ATP6VOA4, CAV2, FBLN2, FAM89A, COCH, OSR1, ENPP2, ABCA5, RBM11, CHAD, PDE3B, PRKCD, COL11A1, BMP8B, MPZ, GRAMD2, PCOLCE2, GBGT1, NRIP3, PDZRN3, KCNH5, NPY5R, THBS4, IRF8, DUSP23, S100A1, SIGIRR, GRHL1, LUZP2, BAMBI, TUBB6, SAMD12, IRX2, MMP17, DNAH14, STEAPIB, DNAJC1, LRAT, SGCA, TENM2, KLRG1, PERP, FHL2, CDH8, CYYR1, RAB6C, PDLIM1, MFAP2, PACSIN3, USP25, RPL39L, KMO, NNAT, ATP1B1, TEX14, PTGES, COMMD3, IGSF9, NGEF, ITGA9, PTMA, ZNF518B, SPEF2, MSRB3, ETNK2, NPY1R, LRRC7, SEMA3A, EXTL1, CNTN2, EPHA7, C11orf70, MEF2C, EPHX4, CACNG5, SCUBE3, PAQR3, RNF175, SIMC1, EPB41L4B, OR2A7, ME1, QPCT, NR4A2, NAALAD2, CHODL, CD55, LRRIQ1, RNF144A, LRFN2, FAM19A4, TMEM206, RAB11FIP1, ABCB4, CPPED1, DPP10, GABRA5, PCP4L1, MAL2, CHML, SORCS1, SCN9A, LACC1, ZNF618, BCL11A, HIST4H4, TFB2M, CCNA1, TES, HSPG2, CTAGE4, KY, BMI1, ZNF215, SCUBE2, PLXDC2, CLEC2B, SLC22A3, ELOVL7, AKR1E2, SPOCK3, EFNA5, CDH19, CYP26B1, SLIT2, GABRA2, POPDC3, RPP25, TEAD4, FAM160A1, RASSF3, RNF2, TSPAN19, SLC13A5, VAX2, SRI, LHX2, FOXG1, SQSTM1, SMOX, B4GALT7, AGMO, C21orf2, MKLN1, SWI5 and C7orf49 may be a PRC1 inhibitor. The PRC1 inhibitor may decrease expression of any of the subunits of the PRC1 complex (e.g., CRISPR, RNAi). The PRC1 inhibitor may be a BMI-1 inhibitor. The PRC1 inhibitor may inhibit E3 ubiquitin ligase activity.

In certain embodiments, the PRC1 inhibitor is an inhibitor of E3 ubiquitin ligase activity. In certain embodiments, the PRC1 inhibitor is an inhibitor of BMI-1. E3 ubiquitin ligase activity inhibitors include, but are not limited to 2-pyridine-3-yl-methylene-indan-1,3-dione (PRT4165) or derivatives thereof (see e.g., Ismail et al., A Small Molecule Inhibitor of Polycomb Repressive Complex 1 Inhibits Ubiquitin Signaling at DNA Double-strand Breaks. J Biol Chem. 2013 Sep. 13; 288(37): 26944-26954). PRT4165 is an inhibitor of Bmil/Ring1A. BMI inhibitors include, but are not limited to N-(2,6-Dibromo-4-methoxyphenyl)-4-(2-methylimidazo[1,2-a]pyrimidin-3-yl)-2-thiazolamine (PTC-209) or derivatives thereof.

PDGFRA Inhibitors

In certain embodiments, the present invention provides for treating H3K27M gliomas with a receptor tyrosine kinase (RTK) inhibitor. In certain embodiments, the inhibitor is administrated as part of a combination therapy (e.g., a PRC1 inhibitor, ACT). Exemplary RTK inhibitors and doses applicable for treating H3K27M gliomas according to the present invention are described herein.

Imatinib was the first receptor tyrosine kinase (RTK) inhibitor to be introduced into clinical oncology, and was then followed by the drugs sorafenib, dasatinib, sunitinib, nilotinib, pazopanib, and regorafenib. Dosages may be based on the dosages described herein.

Crenolanib besylate (CP-868,596-26; 4-piperidinamine, 1-[2-[5-[(3-Methyl-3-oxetanyl) methoxy]-1H-benzimidazol-1-yl]-8-quinolinyl]-, monobenzenesulfonate) is an investigational inhibitor being developed by AROG Pharmaceuticals, LLC. Crenolanib is an orally bioavailable benzimidazole that selectively and potently inhibits signaling of wild-type and mutant isoforms of class III receptor tyrosine kinases (RTK) FLT3 (FMS-like Tyrosine Kinase 3), PDGFR a (Platelet-Derived Growth Factor Receptor), and PDGFR 3. In clinical trial NCT01522469, subjects take crenolanib in doses of 200 mg/m$^2$/day divided in three doses daily (preferably every eight hours), taken orally at least 30 minutes pre or post meal until disease progression, death, or the patient discontinues treatment for adverse events, investigator's judgment, or other reasons.

In a phase 1 dose-escalation study, 119 patients with imatinib-resistant CML or acute lymphoblastic leukemia (ALL) received nilotinib orally at doses of 50 mg, 100 mg, 200 mg, 400 mg, 600 mg, 800 mg, and 1200 mg once daily and at 400 mg and 600 mg twice daily (Kantarjian, et al. N Engl J Med. 2006 Jun. 15; 354(24):2542-51). Preclinical in vitro studies have shown that nilotinib (AMN107), a BCR-ABL tyrosine kinase inhibitor, is more potent than imatinib against CML cells by a factor of 20 to 50.

Sorafenib (co-developed and co-marketed by Bayer and Onyx Pharmaceuticals as Nexavar), is a kinase inhibitor drug approved for the treatment of primary kidney cancer (advanced renal cell carcinoma), advanced primary liver cancer (hepatocellular carcinoma), and radioactive iodine resistant advanced thyroid carcinoma. Sorafenib is a multikinase inhibitor (including VEGF and PDGF receptor kinases), reduces tumor cell proliferation in vitro, and may act at least partially by inhibiting tumor angiogenesis. Dosages may be 400 mg PO q12 hr, or a regimen including: First dose reduction: 600 mg/day (divided as 2 doses of 400 mg and 200 mg 12 hr apart), Second dose reduction: 200 mg g12 hr, Third dose reduction: 200 mg qDay.

Dasatinib is a multikinase inhibitor that inhibits BCR-ABL, SRC family (SRC, LCK, YES, FYN), c-Kit, EPHA2 and PDGFR-beta kinases. Tyrosine kinase inhibition possibly blocks angiogenesis and cellular proliferation. Dosages may be 140 mg PO qDay, but may be increased to 180 mg PO qDay if there is an inadequate response.

Sunitinib is a multikinase inhibitor, including VEGF and PDGF receptor kinases. For GI Stromal Tumor and Metastatic Renal Cell Carcinoma the recommended dose is 50 mg PO qDay for 4 weeks, followed by 2 weeks drug-free, and then repeating the cycle. Dose modification for GI stromal tumor (GIST) or metastatic renal cell carcinoma (MRCC) may be an increase or reduction of dose in 12.5-mg increments based on individual safety and tolerability. For Pancreatic Neuroendocrine Tumors the standard dose is 37.5 mg PO qDay continuously without a scheduled off-treatment period. Dose modification for Pancreatic Neuroendocrine Tumors (PNET) may be to increase or reduce the dose in 12.5-mg increments based on individual safety and tolerability.

Pazopanib is a multikinase inhibitor, including VEGF and PDGF receptor kinases. Dosages for advanced Renal Cell Carcinoma are 800 mg PO qDay on an empty stomach (at least 1 hr ac or 2 hr pc). Dosages for Soft Tissue Sarcomas are 800 mg PO qDay on an empty stomach (at least 1 hr ac or 2 hr pc). In RCC, the initial dose reduction should be 400 mg, and an additional dose decrease or increase should be in 200 mg steps based on individual tolerability.

Regorafenib is a tyrosine kinase inhibitor shown to inhibit the activity of membrane-bound and intracellular kinases involved in normal cellular functions and in pathological processes (e.g., oncogenesis, tumor angiogenesis) such as, RET, VEGFR1, VEGFR2, VEGFR3, KIT, PDGFR-alpha, PDGFR-beta, FGFR1, FGFR2, TIE2, DDR2, Trk2A, Eph2A, RAF-1, BRAF, BRAFV600E, SAPK2, PTK5, and Abl. Dosages are 160 mg PO qDay for the first 21 days of each 28-day cycle.

Imatinib mesylate (Gleevec) is a protein tyrosine kinase inhibitor that inhibits the Bcr-Abl tyrosine kinase created by the Philadelphia chromosome abnormality in CML. Imatinib mesylate achieves this inhibitory result through binding to the adenosine triphosphate-binding site of the Bcr-Abl tyrosine kinase, which prevents phosphorylation of substrates and related malignant transformation. Through inhibition of this kinase, it is believed that imatinib mesylate inhibits cell proliferation and induces apoptosis. T. Schindler et al (2000) Science 289:1938 1942.

According to any of the above methods, in one variation, imatinib mesylate is administered to the subject at a dose of 100-800 mg/day, optionally at a dose of 200-400 mg/day, and optionally at a dose of 500-800 mg/day. Such administrations may optionally last for a period of at least 2, 3, 4, 5, 6, 8, 10 or more days. Preferably, administration is daily. However, upon amelioration of symptoms, it may be useful to administer less frequently unless symptoms re-emerge.

Present dosages recommended for treatment with imatinib mesylate are 400 mg/day for patients with chronic phase CML and 600 mg/day for patients with accelerated phase or blast phase CML. In the event of disease progression, failure to achieve a satisfactory hematologic response after at least 3 months of treatment; or loss of a previously achiever hematologic response, the dose of imatinib mesylate may be increased. Treatment dosage may be increased in patients with chronic phase CML from 400 mg/day to 600 mg/day in the absence of severe adverse drug reaction and sever non-leukemia related neutropenia or thrombocytopenia. Similarly, treatment dosage may be increased in patients with chronic phase CML from 600 mg/day to 800 mg/day (Novartis, Gleevec package insert T-2001-1490012401).

In a further embodiment, the subject is administered between about 200 mg to about 600 mg of imatinib mesylate daily. In one embodiment, the subject is administered either about 600 mg, 400 mg, or 200 mg daily. The skilled artisan will appreciate that certain factors may influence the dosage required to effectively treat a subject, including but not limited to the severity of the symptoms, previous treatments, the general health and/or age of the subject, and other diseases present. Moreover, treatment of a subject with a therapeutically effective amount of the active compound can include a single treatment or a series of treatments. In one example, a subject is treated with an active compound in the range of between about 200-400 mg daily, for between about 1 to 10 weeks, alternatively between 2 to 8 weeks, between about 3 to 7 weeks, or for about 4, 5, or 6 weeks. In some cases, prolonged, indefinite treatment (e.g. for months at a time, 1, 2, 3, 4, etc. 6 months or longer) will be optimal. In some circumstances, the subject should undergo treatment until amelioration of symptoms, with cessation of treatment, and re-initiation of treatment if and when symptoms again manifest. It will also be appreciated that the effective dosage of an active compound used for treatment may increase or decrease over the course of a particular treatment. It may be necessary to adjust dosage when the subject is exposed to drugs that alter imatinib mesylate plasma concentrations, such as inhibitors of cytochrome P450 isoenzyme (CYP3A4) which are expected to increase imatinib mesylate concentrations. Because warfarin is metabolized by CYP2C9 and CYP3A4, patients who require anticoagulation should receive standard heparin or monitor closely PT/INR on warfarin while on imatinib mesylate.

The skilled practitioner will recognize that the dose amounts and frequency of administration can be changed over the course of the regimen, especially as symptoms become alleviated or increase. The regimen can be for weeks or months, continual, intermittent, temporary or permanent, with determination on an individual basis by the skilled practitioner.

Imatinib mesylate is sold under brand name Gleevec®. Gleevec® film-coated tablets contain imatinib mesylate equivalent to 100 mg or 400 mg of imatinib free base. Gleevec® also includes the following inactive ingredients: colloidal silicon dioxide (NF), crospovidone (NF), magnesium stearate (NF) and microcrystalline cellulose (NF). The tablets are coated with ferric oxide, red (NF); ferric oxide, yellow (NF); hydroxypropyl methylcellulose (USP); polyethylene glycol (NF) and talc (USP).

Gleevec® is generally prescribed in dosages of 400 mg/day for adult patients in chronic phase CML and 600 mg/day for adult patients in accelerated phase or blast crisis. Additionally, Gleevec® is recommended at dosages of 400 mg/day or 600 mg/day for adult patients with unresectable and/or metastatic, malignant GIST. Gleevec® is generally prescribed to be administered orally, with a meal and a large glass of water, with doses of 400 mg or 600 mg administered once daily, and dosages of 800 mg administered as 400 mg twice a day.

Imatinib has excellent efficacy at low doses (100-400 mg daily) in FIP1L1-PDGFRA-positive neoplasms. Imatinib has a 250-fold lower IC50 as compared to BCR-ABL. Reports suggest that even once weekly doses of imatinib are adequate in the setting of FIP1L1-PDGFRA (Helbig, et al., British Journal of Haematology, 141, 200-204; and Shah et al., Journal of Hematology & Oncology 2014, 7:26). Any of these tyrosine kinase inhibitors may be used in treating H3K27M gliomas in combination with another agent described herein (e.g., BMI1 inhibitor, CSPG4 antibody, CAR T cell specific to OPC-like surface markers).

Histone Lysine Demethylase Inhibitors

In certain embodiments, an inhibitor of histone demethylation is administered in combination with a therapy described herein. Inhibition of a histone demethylase may result in increased methylation at the PRC2 target genes described herein and inhibition of PRC2 target expression (i.e., repression of the target genes). In certain embodiments, a combination therapy targeting PRC2 target genes, PRC1, and/or OPC-like cells in combination with a histone demethylase inhibitor may provide an improved therapeutic effect. Prior studies have described pharmacologic inhibition of histone demethylation as a therapy for pediatric brainstem glioma (see e.g., Hashizume et al. 2014 *Nature Medicine* 20, 1394-1396; Williams et al., Front. Oncol., 28 Mar. 2017). Hashizume showed that H3.3 K27M glioma cell lines had 50% growth reduction, more apoptosis, and complete inhibition of clonal growth with GSKJ4 treatment, while JMJD3 depleted glioma cell lines showed no significant reduction in proliferation. In certain embodiments, GSKJ4 is used as an inhibitor of histone demethylases. In certain embodiments, the histone lysine demethylation inhibitor is selected from the group consisting of pargyline, clorgyline, bizine, GSK2879552, GSK-J4, KDM5-C70, JIB-04, and tranylcypromine.

CSPG4 Inhibitors

Chondroitin-sulfate proteoglycan 4 (CSPG4), alternatively known as melanoma-associated chondroitin-sulphate proteoglycan (MCSP) or high molecular weight melanoma-associated antigen (HMW MAA), is a transmembrane glycoprotein overexpressed on malignant cells in several cancer types with only limited expression on normal cells. CSPG4 is implicated in several signaling pathways believed to drive cancer progression, particularly proliferation, motility and metastatic spread (see e.g., Jordaan et al., CSPG4: A Target for Selective Delivery of Human Cytolytic Fusion Proteins and TRAIL Biomedicines. 2017 September; 5(3): 37). In certain embodiments, CSPG4 is targeted on OPC-like cells in H3K27M gliomas. In certain embodiments, CSPG4 is targeted as part of a combination therapy targeting more than one OPC-like gene signature protein selected from the group consisting of: PDGFRA, MEST, CCND1, KLRC2, ARC, SEZ6L, EGR1, CD24, ASCL1, FOS, LINC00643, ETV1, NNAT, EGR2, PCP4, BTG2, HES6, IER2 and MFNG; or PDGFRA, CSPG4, SERPINE2, PTPRZ1, CNTN1, COL9A1, GPM6A, NLGN3, GPM6B, SYT11 and SPRY4.

Several monoclonal antibodies (mAb) targeting CSPG4 have been described which inhibit growth and progression of CSPG4-positive tumors, including mAb 9.2.27 (against melanoma) (Harper J R, Reisfeld R A, J Natl Cancer Inst. 1983 August; 71(2):259-63), mAb 225.28 (against breast cancer) (Wang et al., J Natl Cancer Inst. 2010 Oct. 6; 102(19):1496-512) and mAb TP41.2 (against mesothelioma) (Rivera et al., Clin Cancer Res. 2012 Oct. 1; 18(19): 5352-63). Additionally, CSPG4-targeted antibody-based agents with significantly enhanced anticancer activity have also been developed using antibody engineering (see e.g., Jordaan et al., 2017). These include, antibody drug conjugates, fusion proteins and bispecific antibodies.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., activating or blocking an enzyme active site or activating or blocking a receptor by binding to a ligand binding site or ligand).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Bondeson and Crews, Targeted Protein Degradation by Small Molecules, Annu Rev Pharmacol Toxicol. 2017 Jan. 6; 57: 107-123; Lai et al., Modular PROTAC Design for the Degradation of Oncogenic BCR-ABL Angew Chem Int Ed Engl. 2016 Jan. 11; 55(2): 807-810; and Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481).

In certain embodiments, small molecules target epigenetic proteins. Small molecules targeting epigenetic proteins are currently being developed and/or used in the clinic to treat disease (see, e.g., Qi et al., HEDD: the human epigenetic drug database. Database, 2016, 1-10; and Ackloo et al., Chemical probes targeting epigenetic proteins: Applications beyond oncology. Epigenetics 2017, VOL. 12, NO. 5, 378-400).

Binding Agents

In certain embodiments, binding agents are used for treatment of H3K27M gliomas. Binding agents may include, but are not limited to antibodies, aptamers, antibody fragments or antibody-like protein scaffolds.

The term "antigen" as used throughout this specification refers to a molecule or a portion of a molecule capable of being bound by an antibody, or by a T cell receptor (TCR) when presented by MHC molecules. At the molecular level, an antigen is characterized by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognized by the immune system. In some instances, an antigen is capable of eliciting a humoral immune response in a subject. In some instances, an antigen is capable of eliciting a cellular immune response in a subject, leading to the activation of B- and/or T-lymphocytes. In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognized by the immune system, specifically by antibodies, B cells, or T cells.

An antigen as contemplated throughout this specification may be obtained by any means available to a skilled person, e.g., may be isolated from a naturally-occurring material comprising the antigen, or may be produced recombinantly by a suitable host or host cell expression system and optionally isolated therefrom (e.g., a suitable bacterial, yeast, fungal, plant or animal host or host cell expression system), or may be produced recombinantly by cell-free transcription or translation, or non-biological nucleic acid or peptide synthesis.

The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc.

In certain embodiments, the aforementioned methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_A$ in the order $1\times10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilized, free in solution, or immobilized on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about 104-fold, or at least about 105-fold, or at least about 106-fold or more greater, than its affinity for a non-target molecule, such as for a suitable control molecule (e.g., bovine serum albumin, casein).

Preferably, the specific binding agent may bind to its intended target(s) with affinity constant ($K_A$) of such binding $K_A \geq 1 \times 10^6$ $M^{-1}$, more preferably $K_A \geq 1 \times 10^7$ $M^{-1}$, yet more preferably $K_A \geq 1 \times 10^8$ $M^{-1}$, even more preferably $K_A \geq 1 \times 10^9$ $M^{-1}$, and still more preferably $K_A \geq 1 \times 10^{10}$ $M^{-1}$ or $K_A \geq 1 \times 10^{11}$ $M^{-1}$ or $K_A \geq 1 \times 10^{12}$ $M^{-1}$, wherein $K_A = [SBA\_T]/[SBA][T]$, SBA denotes the specific-binding agent, T denotes the intended target. Determination of $K_A$ can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptidomimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridize to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridisation probes or amplification or sequencing primers and primer pairs) may typically be capable of annealing with (hybridizing to) the respective target nucleic acid sequences at high stringency conditions, and capable of hybridizing specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., Ni2+), maltose:maltose binding protein, etc.

The marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

By means of an example, an agent, such as a bi-specific antibody, capable of specifically binding to a gene product expressed on the cell surface of tumor cells (e.g., OPC-like cells) and an immune cell (e.g., TILs) may be used for targeting immune cells to a tumor.

Antibody Drug Conjugates

In certain embodiments, the agent capable of specifically binding to a gene product expressed on the cell surface of the tumor cell (e.g., OPC-like cell) is an antibody.

By means of an example, an agent, such as an antibody, capable of specifically binding to a gene product expressed on the cell surface of the immune cells may be conjugated with a therapeutic or effector agent for targeted delivery of the therapeutic or effector agent to the immune cells.

Examples of such therapeutic or effector agents include immunomodulatory classes as discussed herein, such as without limitation a toxin, drug, radionuclide, cytokine, lymphokine, chemokine, growth factor, tumor necrosis factor, hormone, hormone antagonist, enzyme, oligonucleotide, siRNA, RNAi, photoactive therapeutic agent, anti-angiogenic agent and pro-apoptotic agent.

Example toxins include ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, or *Pseudomonas* endotoxin.

Example radionuclides include $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In $^{119}$Sb, $^{11}$C, $^{121m}$Te, $^{122m}$Te $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Y, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo or $^{99m}$Tc. Preferably, the radionuclide may be an alpha-particle-emitting radionuclide.

Example enzymes include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase or acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

Genetic Modifying Agents

In certain embodiments, a therapy or therapeutic agent as described herein may be or may result in a genetic modification (e.g., mutation, editing, transgenesis, or combinations thereof) of a tumor cell, for example, a genetic perturbation, such as a knock-out (i.e., resulting in a complete absence of expression and/or activity) of one or more endogenous genes/gene products, or a knock-down (i.e., resulting in a partial absence of expression and/or activity) of one or more endogenous genes/gene products, or another type of genetic modification modulating the expression and/or activity of one or more endogenous genes/gene products, or for example, introduction of one or more transgenes, such as one or more transgenes encoding one or more gene products. Such transgene may be suitably operably linked to suitable regulatory sequences, e.g., may be comprised in an expression cassette or an expression vector comprising suitable regulatory sequences, or may be configured to become operably linked to suitable regulatory sequences once inserted into the genetic material (e.g., genome) of the cell.

Any types of mutations achieving the intended effects are contemplated herein. For example, suitable mutations may include deletions, insertions, and/or substitutions. The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the open reading frame (ORF) encoding a gene product. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon are apparent to a skilled person. For example but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF encoding a gene product. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift are apparent to a skilled person. For example but without limitation, a suitable insertion or deletion of one or more (not multiple of 3) nucleotides in the ORF may lead to a frame shift.

In further embodiments, a mutation may delete at least a portion of the ORF encoding a gene product. Such deletion may lead to production of an N-terminally truncated form, a C-terminally truncated form and/or an internally deleted form of said polypeptide (this may preferably affect, such as diminish or abolish, some or all biological function(s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In further embodiments, a mutation may delete at least a portion of a gene promoter, leading to impaired transcription of the gene product.

In certain other embodiments, a mutation may be a substitution of one or more nucleotides in the ORF encoding a gene product resulting in substitution of one or more amino acids of the polypeptide. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding a gene product. In the absence of native splicing, the pre-mRNA may be degraded, or the pre-mRNA may be alternatively spliced, or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing. The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions +2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2.

In certain embodiments, the genetic modifying agent may comprise a CRISPR system, a zinc finger nuclease system, a TALEN, a meganuclease or RNAi system.

CRISPR Systems

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein HisA, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, I-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'-phosphorothioate (MS), S-constrained ethyl(cEt), or 2'-O-methyl 3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS, E*7110-E7111; Allerson et al., *J. Med. Chem.* 2005, 48:901-904; Bramsen et al., *Front. Genet.,* 2012, 3:154; Deng et al., *PNAS,* 2015, 112:11870-11875; Sharma et al., *MedChemComm.,* 2014, 5:1454-1471; Hendel et al., *Nat. Biotechnol.* (2015) 33(9): 985-989; Li et al., *Nature Biomedical Engineering,* 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3'-phosphorothioate (MS), S-constrained ethyl(cEt), or 2'-O-methyl 3'-thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS, E*7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methylguanosine, 2'-O-methyl 3'-phosphorothioate (MS), S-constrained ethyl (cEt), phosphorothioate (PS), or 2'-O-methyl 3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrazone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the omplementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www-.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100·mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In certain other example embodiments, the CRISPR system effector protein is a C2c2 nuclease (also referred to as Cas13a). The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016 bearing Broad Institute No. 10035.PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: Leptotrichia, *Listeria, Corynebacterium, Sutterella, Legionella, Treponema, Filifactor, Eubacterium, Streptococcus, Lactobacillus, Mycoplasma, Bacteroides, Fluviicola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of: Leptotrichia shahii, Leptotrichia *wadei, Listeria seeligeri, Clostridium aminophilum, Carnobacterium gallinarum, Paludibacter propionicigenes, Listeria weihenstephanensis*, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and Ruminococcus. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYLL. WYL1 is a single WYL-domain protein associated primarily with Ruminococcus.

In other example embodiments, the Type VI RNA-targeting Cas enzyme is Cas13d. In certain embodiments, Cas13d is *Eubacterium siraeum* DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or Drosophila adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of. Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or Drosophila adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present invention may also use a Cas12 CRISPR enzyme. Cas12 enzymes include Cas12a (Cpf1), Cas12b (C2c1), and Cas12c (C2c3), described further herein.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, PD., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, NE., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, FA., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp PA. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp PA. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp PA, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct. 25.

Gaudelli et al. "Programmable base editing of A-T to G-C in genomic DNA without DNA cleavage" Nature 464(551); 464-471 (2017).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of Streptococcuspneumoniae and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcuspyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Also, Harrington et al. "Programmed DNA destruction by miniature CRISPR-Cas14 enzymes" Science 2018 doi:10/1126/science.aav4293, relates to Cas14.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 June 15, PROTECTED GUIDE RNAS (PGRNAS); U.S. application 62/091,455, filed, 12 December 14, PROTECTED GUIDE RNAS (PGRNAS); U.S. application 62/096,708, 24 December 14, PROTECTED GUIDE RNAS (PGRNAS); U.S. applications 62/091,462, 12 December 14, 62/096,324, 23 December 14, 62/180,681, 17 Jun. 2015, and 62/237,496, 5 Oct. 2015, DEAD GUIDES FOR CRISPR TRANSCRIPTION FACTORS; U.S. application 62/091, 456, 12 December 14 and 62/180,692, 17 Jun. 2015, ESCORTED AND FUNCTIONALIZED GUIDES FOR CRISPR-CAS SYSTEMS; U.S. application 62/091,461, 12 December 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 December 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 December 14, ENGINEERING OF SYSTEMS, METHODS AND OPTIMIZED ENZYME AND GUIDE SCAFFOLDS FOR SEQUENCE MANIPULATION; U.S. application 62/098,059, 30 December 14, 62/181,641, 18 Jun. 2015, and 62/181,667, 18 Jun. 2015, RNA-TARGETING SYSTEM; U.S. application 62/096,656, 24 December 14 and 62/181,151, 17 Jun. 2015, CRISPR HAVING OR ASSOCIATED WITH DESTABILIZATION DOMAINS; U.S. application 62/096,697, 24 December 14, CRISPR HAVING OR ASSOCIATED WITH AAV; U.S. application 62/098,158, 30 December 14, ENGINEERED CRISPR COMPLEX INSERTIONAL TARGETING SYSTEMS; U.S. application 62/151,052, 22 April 15, CELLULAR TARGETING FOR EXTRACELLULAR EXOSOMAL REPORTING; U.S. application 62/054,490, 24 September 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 February 14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 September 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 December 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 September 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 October 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 September 14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 September 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 September 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 September 14, MULTIFUNCTIONAL-CRISPR COMPLEXES AND/OR OPTIMIZED ENZYME LINKED FUNCTIONAL-CRISPR COMPLEXES; U.S. application 62/087,475, 4 December 14 and 62/181,690, 18 Jun. 2015, FUNCTIONAL SCREENING WITH OPTIMIZED FUNCTIONAL CRISPR-CAS SYSTEMS; U.S. application 62/055,487, 25 September 14, FUNCTIONAL SCREENING WITH OPTIMIZED FUNCTIONAL CRISPR-CAS SYSTEMS; U.S. application 62/087,546, 4 December 14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 December 14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle EL. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church GM. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ. I.D. No. 1)
M D P I R S R T P S P A R E L L S G P Q P D G V Q
P T A D R G V S P P A G G P L D G L P A R R T M S
R T R L P S P P A P S P A F S A D S F S D L L R Q
F D P S L F N T S L F D S L P P F G A H H T E A A
T G E W D E V Q S G L R A A D A P P P T M R V A V
T A A R P P R A K P A P R R R A A Q P S D A S P A
A Q V D L R T L G Y S Q Q Q Q E K I K P K V R S T
V A Q H H E A L V G H G F T H A H I V A L S Q H P
A A L G T V A V K Y Q D M I A A L P E A T H E A I
V G V G K Q W S G A R A L E A L L T V A G E L R G
P P L Q L D T G Q L L K I A K R G G V T A V E A V
H A W R N A L T G A P L N

An exemplary amino acid sequence of a C-terminal capping region is:

(SEQ. I.D. No. 2)
R P A L E S I V A Q L S R P D P A L A A L T N D H
L V A L A C L G G R P A L D A V K K G L P H A P A
L I K R T N R R I P E R T S H R V A D H A Q V V R
V L G F F Q C H S H P A Q A F D D A M T Q F G M S
R H G L L Q L F R R V G V T E L E A R S G T L P P
A S Q R W D R I L Q A S G M K R A K P S P T S T Q
T P D Q A S L H A F A D S L E R D L D A P S P M H
E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008

(2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Delivery

The programmable nucleic acid modifying agents and other modulating agents, or components thereof, or nucleic acid molecules thereof (including, for instance HDR template), or nucleic acid molecules encoding or providing components thereof, may be delivered by a delivery system herein described.

Vector delivery, e.g., plasmid, viral delivery: the modulating agents, can be delivered using any suitable vector, e.g., plasmid or viral vectors, such as adeno associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Adoptive Cell Therapy

In certain embodiments, H3K27M-glioma is treated by targeting the tumor cells with immune cells transferred to a subject in need thereof. In certain embodiments, the transferred cells express chimeric antigen receptors (CAR) or exogenous T cell receptors (TCR). In certain embodiments, CAR T cells are transferred to a subject. In certain embodiments, oligodendrocyte precursor-like cells (OPC-like) are targeted. In certain embodiments, the CAR T cells express a CAR specific for an OPC-like surface marker. In certain embodiments, the surface marker may be selected from PDGFRA, MEST, KLRC2, SEZ6L, CD24 and MFNG; or PDGFRA, CSPG4, SERPINE2, PTPRZ1, CNTN1, GPM6A, NLGN3, GPM6B and SYT11.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); x-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyltransferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAPI (carcinoembryonic antigen peptide 1); CASP-8 (caspase-8); CDC27m (cell-division cycle 27 mutated); CDK4/m (cyclin-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triosephosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD134, CD137, CD154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHT), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3):

(SEQ. ID. No. 3)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS)).

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native aPTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 22) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY and continuing all the way to the carboxy-terminus of the protein. The sequence is reproduced herein: IEVMYPPPYLDNEKSNGTIIHVKGKHLCPSPLFPGPSKPFWVLVVVGGVLACYSLLVTVA FIIFWVRSKRSRLLHSDYMNMTPRRPGPTRKHYQPYAPPRDFAAYRS. Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3(4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am.J.Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+ CTLs to induce a synergistic antitumour response (see, e.g., Li et al., Adoptive cell therapy with CD4+T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHIC constituent proteins in a cell; to activate a T cell; to modulate cells such that the cells are resistant to exhaustion or dysfunction; and/or increase the differentiation and/or proliferation of functionally exhausted or dysfunctional CD8+

T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRa or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRO, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3x28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

Pharmaceutical Compositions

In certain embodiments, the agents or cells of the present invention are administered in a pharmaceutical composition. A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilizers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatizers, thickeners, agents for achieving a depot effect, coatings, antifungal agents, preservatives, stabilizers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infusion. The skilled person will understand that compositions which are to be administered orally or topically will usually not comprise cells, although it may be envisioned for oral compositions to also comprise cells, for example when gastro-intestinal tract indications are treated. Each of the cells or active components as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

Any compositions or methods provided herein can be combined with one or more of any of the other compositions and methods provided herein.

The invention is further described in the following examples, which do not limit the scope of the invention described in the claims.

EXAMPLES

Example 1—Single Cell RNA-Seq in H3K27M-Gliomas

Figure 7:
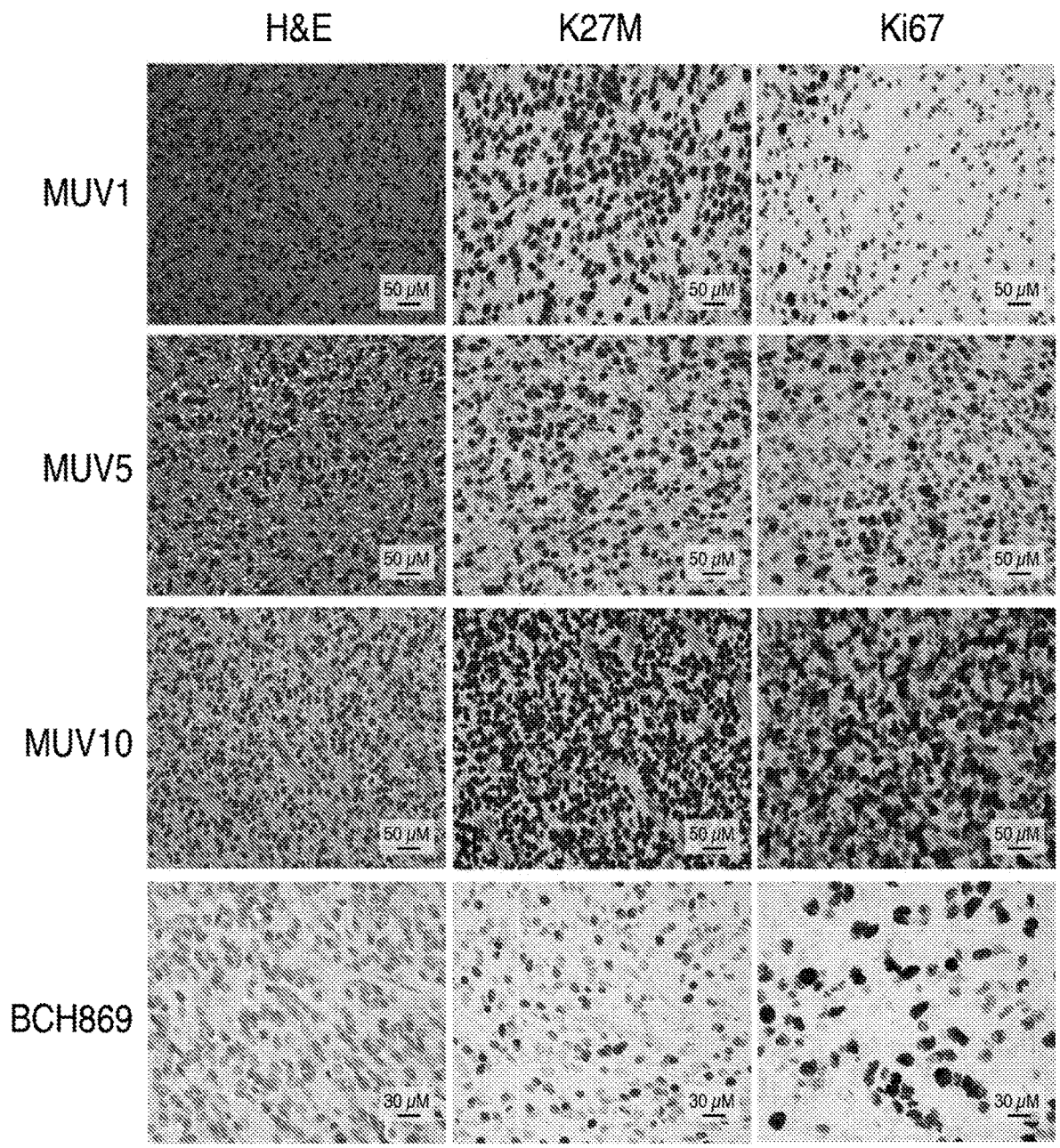
FIG. 7—Representative histology of four H3K27M gliomas in the cohort. Hematoxyline and eosin (H&E) stains of tumors shows densely cellular tumors with important cytonuclear pleomorphism. H3K27M immunohistochemistry shows strong nuclear immunoreactivity of malignant cells. Ki-67 immunohistochemistry is used for proliferation and shows estimated rates of 10%, 20%, 60% and 25% of cycling cells for tumors MUV1, MUV5, MUV10, and BCH869 respectively.

Applicants obtained fresh tumor tissue from diagnostic biopsies of six pediatric midline gliomas with confirmed H3K27M mutation (FIG. 1A, FIG. 7). Each sample was mechanically and enzymatically dissociated (12, 14, 15), and then flow sorted and profiled by scRNA-seq using Smart-Seq2 (16) (FIG. 7, materials and methods). Applicants profiled between 384 and 960 cells from each sample, with an average sequencing depth of 1.24M reads per cell. A total of 2,458 cells that passed quality controls (materials and methods), with an average of ~5,300 detected genes per cell, were used for all downstream analyses (Table S1).

Comparing the expression profiles of all cells by hierarchical clustering (FIG. 8A, B), or by t-SNE analysis (FIG. 8C, D) indicated that cells group primarily by their tumor-of-origin. However, two clusters contain cells from multiple tumors, with high cell-to-cell correlations between patients. Cells in these two clusters express markers of microglia (e.g., CD14, CX3CR1 and AIF1) or oligodendrocytes (e.g., MBP and PLP1) (FIG. 1C), suggesting that they correspond to non-malignant cells, while the remaining cells are malignant and display more differences between patients.

Figure 9A:
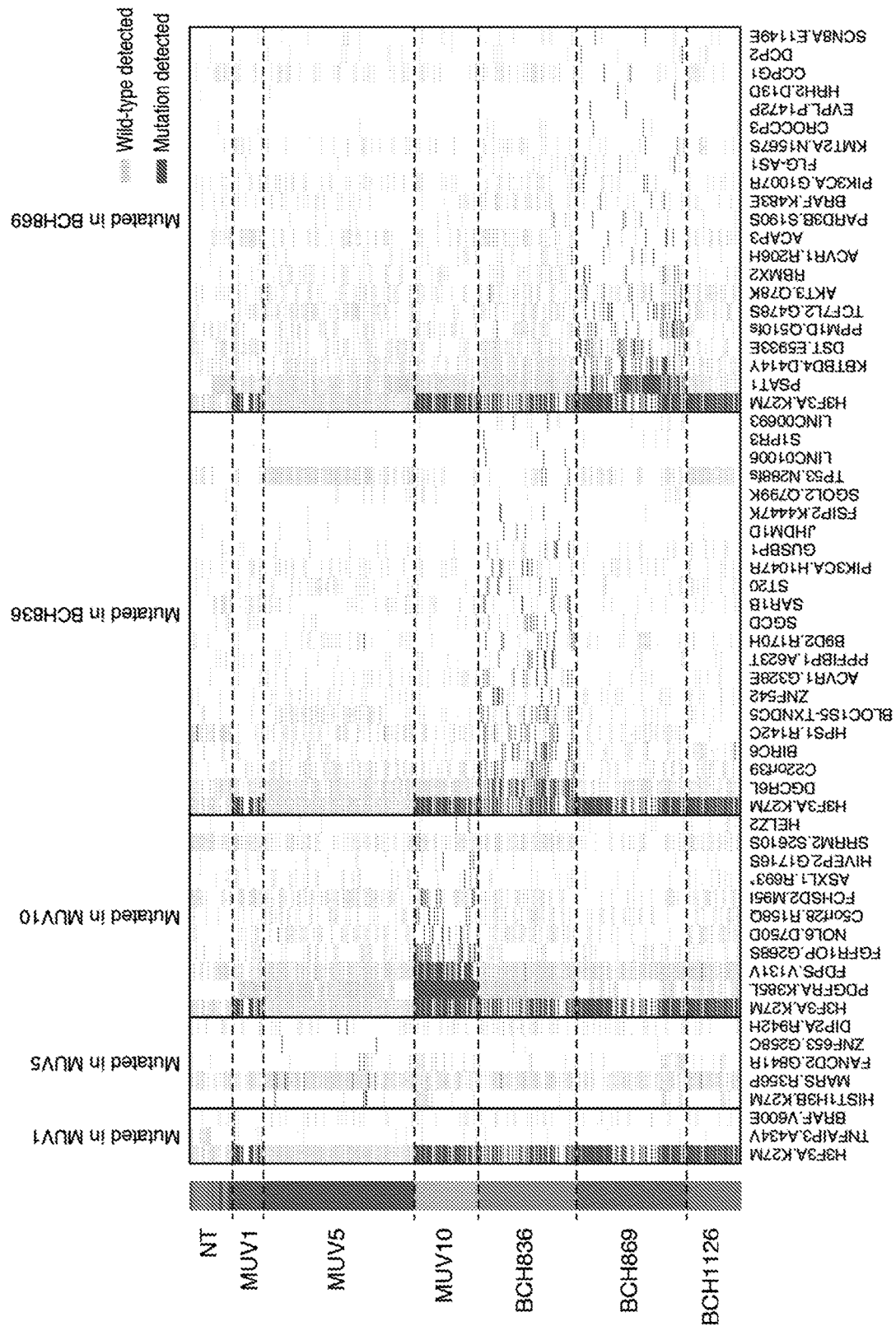
FIG. 9—Detection of genetic alterations in single-cell data. (A) Evidence for mutations in genes identified as mutated by WGS/WES in scRNA-seq data. Genes that showed evidence for a mutation in one (MUV5) or at least two (all other tumors) cells are included. (B) tSNE map as presented in FIG. 8, color-coded by gene mutations identified in H3F3A or HIST1H3B (red, left), or all other mutations (red, right). (C) Scatter plots showing CNV signal strength and CNV pattern correlation (see Methods) for each of the four samples in the cohort with copy-number alterations. Cells are colored in black (malignant) or grey (non-malignant) based on gene expression clustering (see FIG. 8). In total, Applicants identified 6 cells (arrows) with a discordance between the two approaches. 5 cells without inferred CNVs did not cluster with the non-malignant cell populations defined in FIG. 8. Conversely, 1 cell showed CNV patterns of malignant cells but expression profile of non-malignant cells. To avoid any uncertainty, all cells with discordant classification were excluded from further analysis.

Example 2—Point Mutations and Inferred CNVs Allow Genetic Characterization of Individual Cells from scRNA-Seq Profiles Applicants further distinguished malignant from non-malignant cells by evidence for genetic alterations, both point mutations and CNVs in single cells. First, Applicants detected H3K27M mutations from scRNA-seq reads mapping to H3F3A or HISTH3B/C in 34% (833/2,458) of the cells, but not in any cells in microglia and oligodendrocytes clusters, consistent with their non-malignant classification (FIG. 1D, FIG. 9A). The partial sensitivity to detect H3K27M among presumed malignant cells reflects two distinct limitations: first, in one of the six tumors (MUV5), the H3K27M mutation is in histone H3.1 (HISTH3B C) rather than the more common H3.3 (H3F3A). Since H3.1 transcripts (like those of most histone genes) are not polyadenylated, they are not effectively captured by the SMART-Seq2 protocol and consequently the mutation was only detected in six cells in that tumor; second, although H3.3

(which is polyadenylated) is mutated and highly expressed in the remaining five tumors, scRNA-seq protocols have inherent limitations in transcriptome coverage (14), thus resulting in sensitivity of 41-67% across the malignant cells of the other five tumors.

Second, Applicants called additional point mutations in the individual cells. Here, Applicants relied on bulk whole-genome or -exome sequencing (WGS/WES) of 5 of the 6 tumors to identify a set of gene mutations for each tumor, including potential driver events in TP53, PIK3CA, ACVR1 and PDGFRA (FIG. 1A, Table S1) (2). Applicants then scanned the scRNA-seq reads to call mutations in individual cells. As with H3K27M, Applicants detected those mutations only in presumed malignant cells but not in the non-malignant clusters (FIG. 1D, right panel, FIG. 9A). These mutations were detected in variable numbers of malignant cells in each tumor, but were less frequent than H3K27M mutations, reflecting both the lower expression of those genes and the subclonality of some mutations.

Figure 1E:
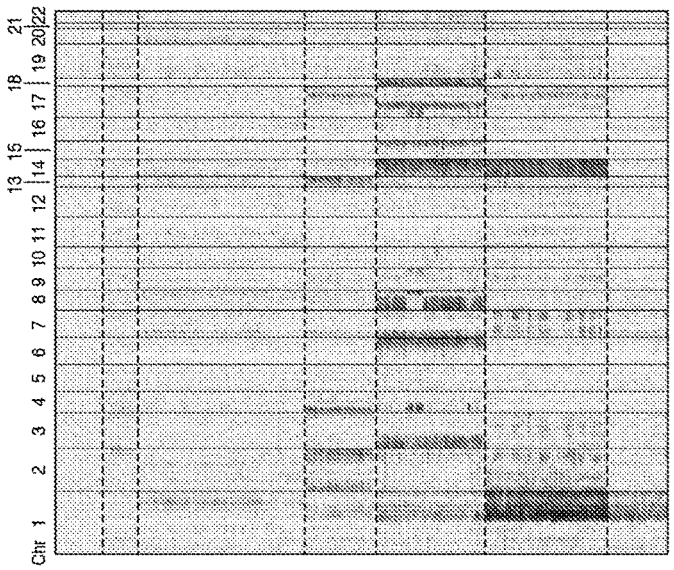
Figure 1F:
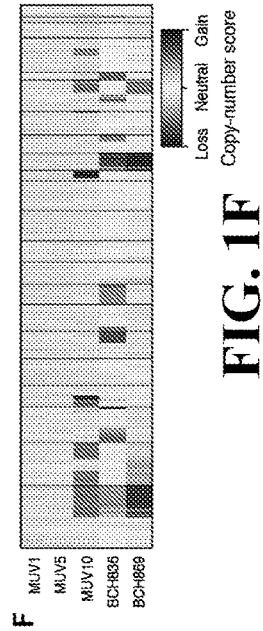
Figure 1D:

Third, Applicants inferred the landscape of large chromosomal CNVs for each cell, based on the average expression of many genes in each chromosomal region in its scRNA-seq profile (11-14) (FIG. 1E). The resulting CNV profiles were highly consistent with those defined by WGS/WES of the respective tumors (FIG. 1F). Four of the six tumors had abnormal karyotypes, with patterns that were largely unique to each tumor but included recurrent amplifications of chromosome 1q and deletions of chromosome 14, both of which are well-characterized genetic alterations in H3K27M-gliomas (17). Some CNVs were only detected in subsets of malignant cells in the same tumor, suggesting the existence of genetic subclones (see below). Non-malignant cells from all tumors were predicted to have a normal karyotype, as were the malignant cells from two tumors (MUV1 and MUV5), consistent with their bulk WES/WGS profiles (FIG. 1E-F) and with previous reports that pediatric H3K27M-gliomas frequently lack CNVs (18).

Taken together, Applicants found evidence for cancer-specific aberrations—point mutations and/or CNVs—in 68% of the presumed malignant cells and none of the presumed non-malignant cells. The minority of presumed malignant cells for which Applicants could not find any such evidence were primarily from MUV5, the tumor with an H3.1 mutation and a normal karyotype. Nonetheless, these cells clustered together with the few cells from the same tumor in which Applicants did detect mutations (FIG. 8C), and their profiles were similar to malignant cells from other tumors and distinct from those of non-malignant glial cells (FIG. 10), which strongly supports their classification as malignant.

Example 3—Malignant Cell Expression Programs Uncover a PRC2-Related Signature and a PRC1 Vulnerability in H3K27M-Gliomas Applicants leveraged the single-cell transcriptomes acquired directly from patient samples to compare malignant cells across different glioma types with minimal confounding effects from the tumor microenvironment (TME) (15). Applicants specifically integrated the six H3K27M-gliomas profiled here with six IDH-mutant oligodendrogliomas (IDH-O), ten IDH-mutant astrocytomas (IDH-A), and three IDH-wildtype glioblastomas (GBM) (Table S2), all of which were profiled using the same protocol (14, 15, 19). Applicants first defined a malignant-cell specific program for each tumor, by averaging the expression of all malignant cells in that tumor, and then compared these programs across tumors.

Figure 2A:
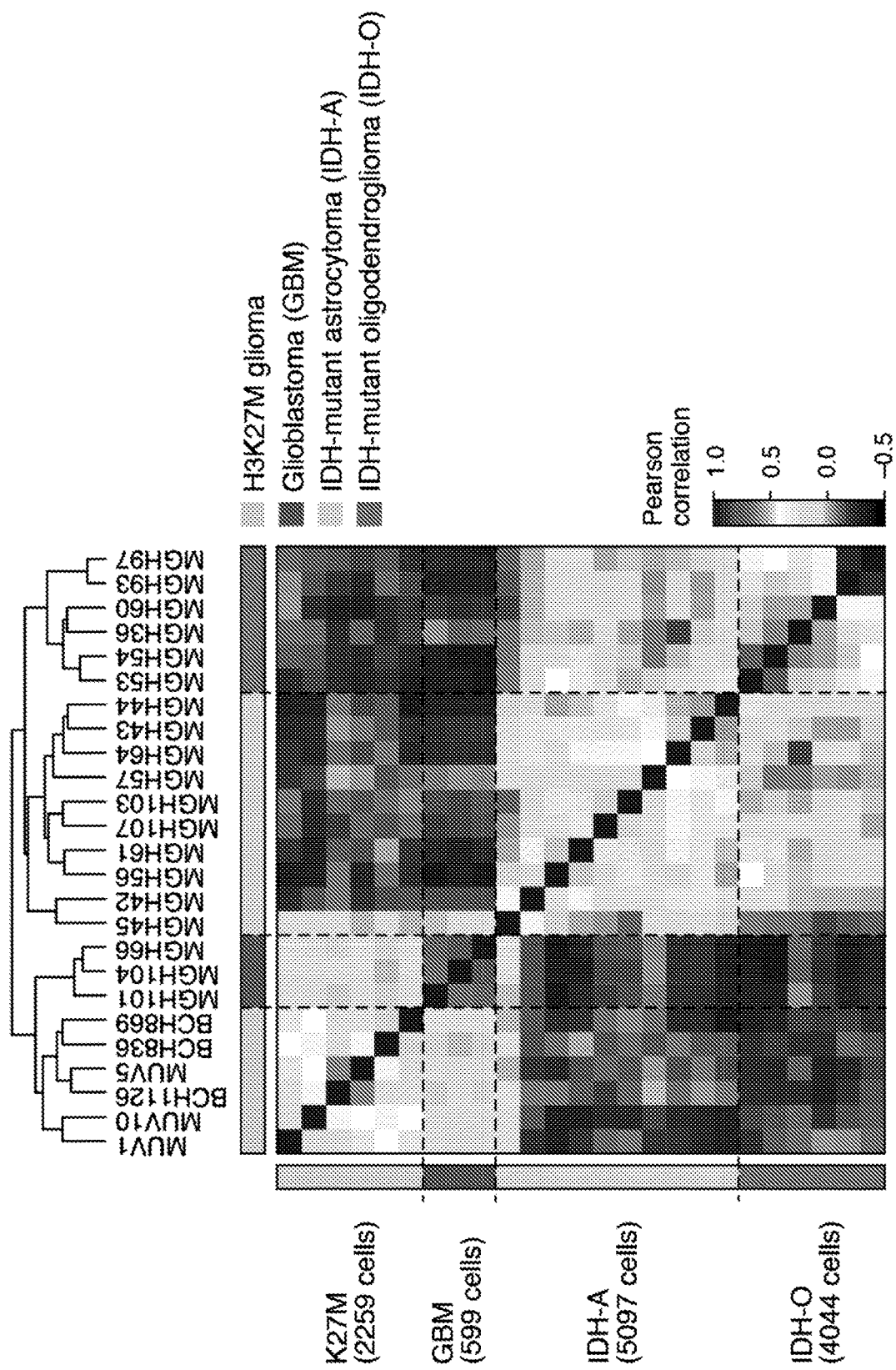
FIG. 2—Comparison of malignant cell expression profiles across gliomas types. (A) Pairwise correlation between the average expression profiles of malignant cells from 25 gliomas, ordered by hierarchical clustering as indicated by the dendrogram (top). Tumors clusters according to their clinical classification to glioma subtype as indicated by the top and left panels and labels. (B) Heatmap shows average relative expression of all differentially-expressed genes (rows) across the 25 gliomas samples (columns), ordered as in (A). Selected genes are highlighted by name. (C) Heatmap shows average relative expression of these genes, ordered as in (B), in 5 additional IDH-wildtype GBM samples profiled using the original Smart-Seq protocol (12). (D) Black lines indicate genes located on chromosome 10, which is frequently deleted in GBM, or chromosome arms 1p and 19q, which are frequently deleted in IDH-O. Genes are ordered as in (B). Deleted chromosomal regions are enriched for genes that are down-regulated in the corresponding class of glioma. (E) Heatmap depicts enrichment of PRC2 targets (20) in each set of differentially expressed genes (Fisher's exact test). (F) Plot shows relative viability of H3K27M (BCH869, DIPG012) and H3 wildtype (MGG8) patient-derived cell lines 7 days after BMI1 knockout with two different guide RNAs (gRNA), normalized to scrambled gRNA as a control; N=4 repeats with two technical replicates in each of two independent experiments. *=$p<0.05$ by paired, two-tailed t-test. Error bars: ±S.E.M. (G) Graph depicts relative viability of H3K27M (BCH869, DIPG012) and H3 wildtype (MGG4, MGG6) patient-derived cell lines upon treatment with indicated concentration of the BMI1 inhibitor PTC209. Error bars represent the s.e.m.
Figure 2G:
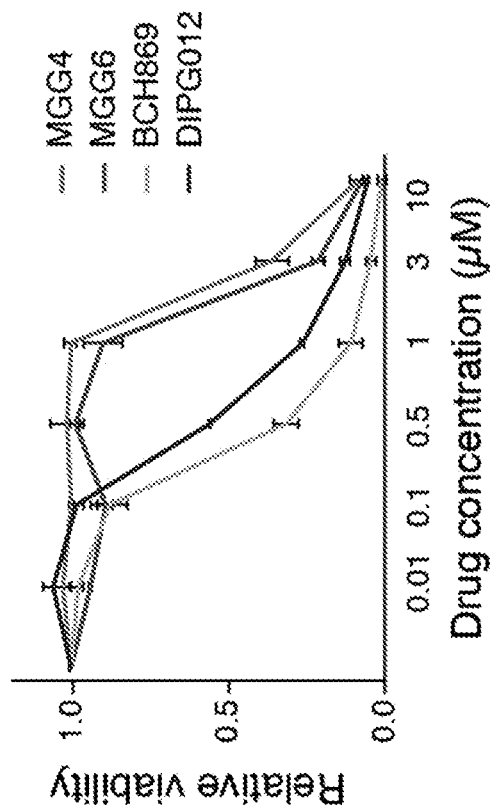

The malignant-specific programs partition into four clusters that corresponded precisely to their clinical classification (FIG. 2A), and were distinguished by 1081 differentially regulated genes (FIG. 2B, 2C, Table S3; P<0.001, ANOVA). Although some expression differences could be attributed to signature genetic events (e.g. downregulation of genes on chromosome 1p and 19q co-deletion in IDH-O and chromosome 10 deletion in GBM; FIG. 2D), most lacked any obvious genetic explanation. A case in point was the downregulation of 262 genes in GBM (FIG. 2B), which Applicants also validated in a second cohort of GBMs profiled with an earlier scRNA-seq protocol (12) (FIG. 2C). Interestingly, many of these genes are direct targets of PRC2 (20) (FIG. 2E; P<0.001, Fisher's exact test), consistent with its over-expression in GBM (21, 22).

A large number of genes were upregulated in H3K27M-gliomas relative to the other tumor types (n=182), but only a few genes were down-regulated (n=12). This may indicate that genetic events specific to H3K27M-gliomas are primarily associated with transcriptional upregulation, and is consistent with the model where H3K27M suppresses repression by PRC2 (8, 9). Indeed, PRC2 target genes (20) are significantly enriched among these H3K27M glioma-upregulated genes (FIG. 2E; P<0.0001, hypergeometric test).

Figure 2F:
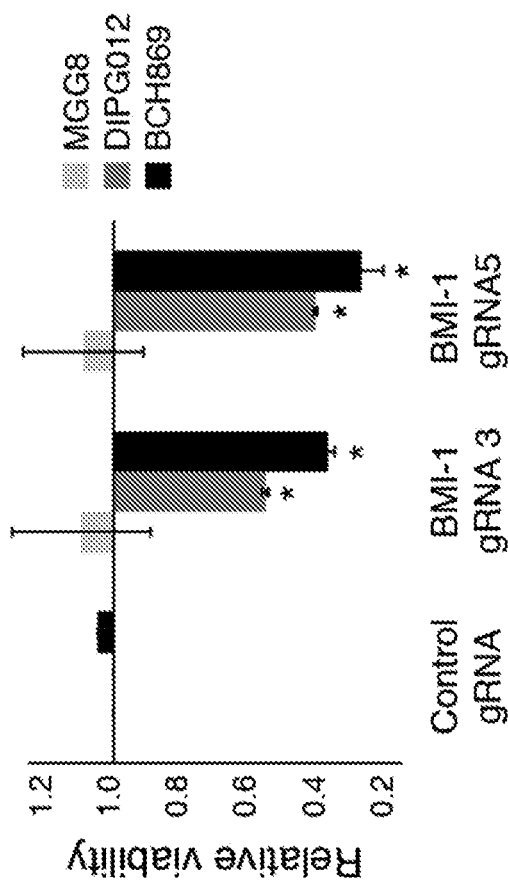
Figure 11:
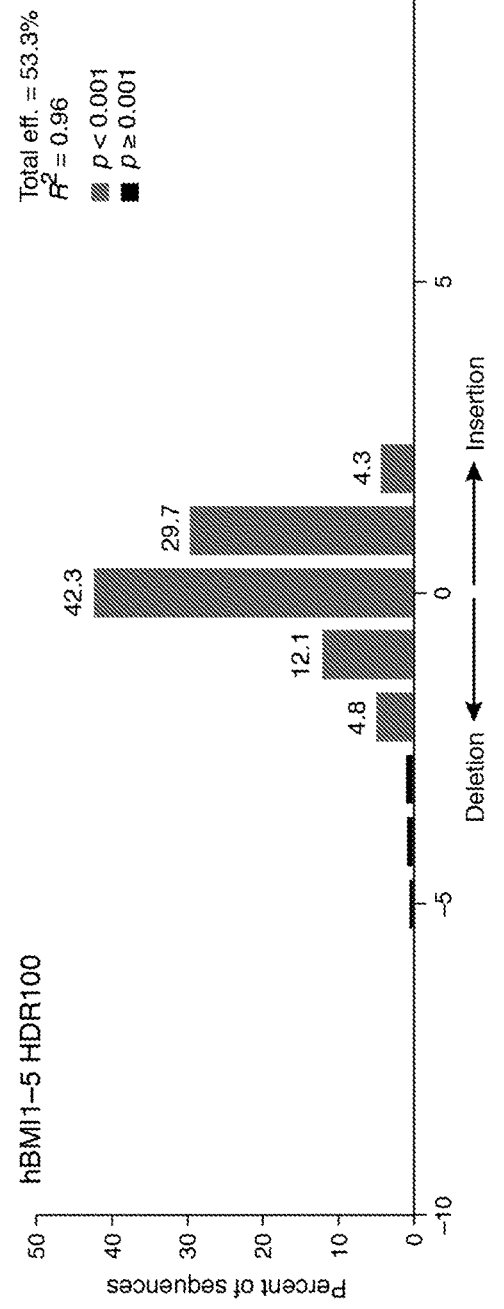
FIG. 11—BMI-1 CRISPR cutting efficiency. Representative cutting efficiency of BMI-1 gene. Frequencies of insertions and deletions for gRNA5 in BCH869 are shown. Total cutting efficiency equals 53.3%.

Notably, the PRC1 subunit BMI1 was significantly upregulated in H3K27M-gliomas, relative to other gliomas, raising the possibility of a compensatory mechanism for PRC2 suppression. Accordingly, suppression of BMI1 by CRISPR knock-out or pharmacologic treatment with the compound PTC209 reduced viability of H3K27M glioma cells, relative to both treatment controls and other non-H3K27M glioma models (23) (FIG. 2F, G, FIG. 11). Thus, the direct comparison of the expression programs of malignant cells from the major classes of human gliomas highlights expression signatures specific to each glioma type, including a PRC2-related program, and suggests a potential vulnerability in H3K27M-gliomas that could be exploited for therapy.

Figure 3E:
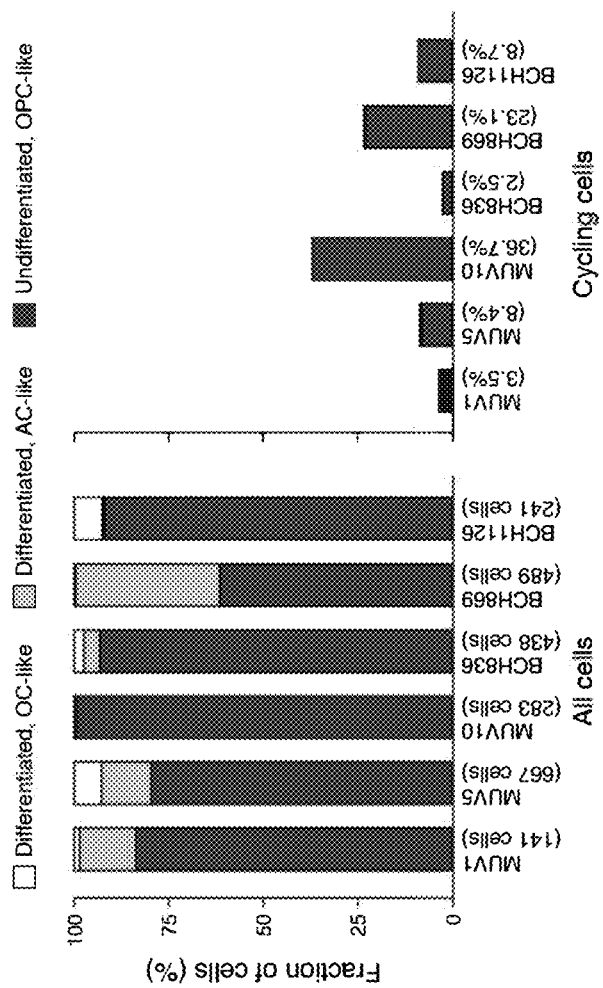
FIG. 3—NNMF analysis of intra-tumor heterogeneity in H3K27M-gliomas. (A) Heatmap shows expression scores of 2,259 malignant cells (from 6 H3K27M-glioma samples) for 60 programs derived from NNMF analysis of individual H3K27M-glioma samples. Cells and NNMF programs are ordered by hierarchical clustering, and three sets of correlated programs (P1, P2 and P3) are highlighted. (B) Heatmap shows relative expression across 2,259 malignant cells, ordered as in (A). Included are the top 30 genes for each of the combined expression programs P1, P2 and P3; selected genes are labeled. (C) Heatmap shows relative expression across 2,259 malignant cells, ordered as in (A). Included are 19 genes (OPC-shared program) that are preferentially expressed in cells with low expression of P1, P2 and P3; selected genes are labeled. (D) Hierarchy plot depicting lineage score and stemness score for 2,259 malignant cells from the combined H3K27M-glioma samples. Cells are colored by their expression score for the cell cycle program. Proliferative expression signatures are largely exclusive to undifferentiated OPC-like cells. (E) Barplot indicates the relative number of cells classified into OPC-, AC-, or OC-like expression state for all cells in each tumor (left), or restricted to cells classified as cycling (right). (F) In situ RNA hybridization (RNA-ISH) images for H3K27M glioma specimen sections show mutually exclusive expression of astrocytic (APOE, blue) and stem-like cell (PDGFRA, red) lineage markers; co-expression of stem-like (PDGFRA, red) and proliferation (Ki-67, blue, arrowheads) markers; and mutually exclusive expression of proliferation (Ki-67, red) and astrocytic (APOE, blue) markers. (G) Viability of H3K27M patient-derived cell lines BCH245 and BCH869 7 days after PDGFRA knockout with two different guide RNAs (gRNA), normalized to scrambled gRNA as a control; on N=4 repeats with two technical replicates in each of two independent experiments. *=$p<0.05$ by paired, two-tailed t-test. Error bars: ±S.E.M.

Example 4—Intra-Tumoral Transcriptional Heterogeneity and Putative Cellular Hierarchies of H3K27M-Gliomas Applicants next sought to distinguish subpopulations of malignant cells within each H3K27M-glioma tumor by defining variable expression programs using non-negative matrix factorization (NNMF). Applicants focused on variable programs that were observed across multiple tumors, reasoning that these might be functionally important. Applicants scored malignant cells from all six tumors for all variable expression programs and clustered both the cells and the expression programs based on these scores (FIG. 3A). This revealed three meta-programs, each relating to at least five programs from at least four different tumors, and corresponding to subsets of high-scoring cells within each tumor.

Figure 12B:
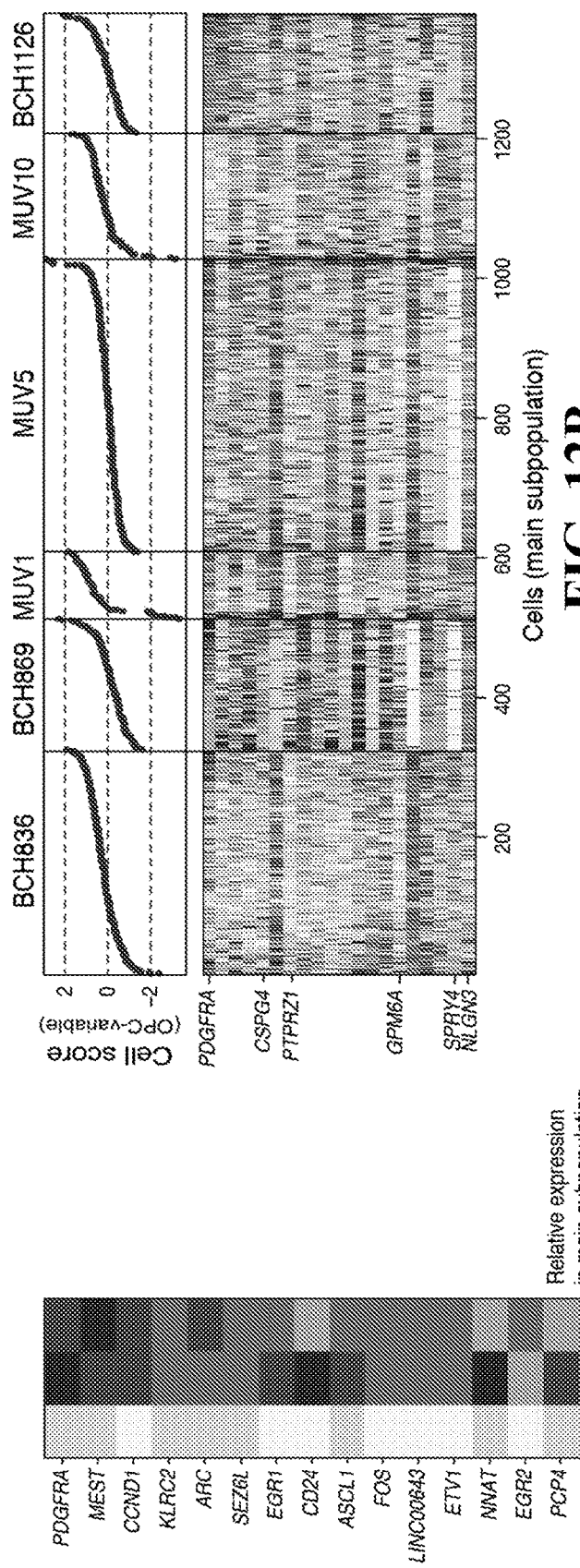
FIG. 12—Intra-tumor expression programs H3K27M-gliomas and comparison to normal development. (A) Upregulation of genes in the main subpopulation compared to the three other subpopulations (OC-like, AC-like and cycling cells). Zero cells were upregulated compared to all three subpopulations but twenty genes were identified as upregulated compared to two of the three subpopulations (Methods); the average expression log-ratio of these 20 genes (in main subpopulation compared to each of the three subpopulations) is presented in the heatmap, and genes were ranked from top to bottom by their average upregulation compared to the three subpopulations; of the twenty genes, 19 are upregulated compared to both AC-like and OC-like cells, but not cycling cells. These genes form the OPC-shared program. (B) OPC-variable gene signature, defined by PCA (Methods). Bottom panel displays the relative expression of the 20 top-scoring genes for the OPC-variable program across the six tumors; in each tumor, cells were ranked by their OPC-variable program scores, which are shown in the top panel. (C) Average expression in normal brain cell types (rows) of the five programs (columns) identified form analysis of intra-tumor heterogeneity: AC-like (P2), OC-like (P3), OPC-shared and OPC-variable. (D) Heatmap showing expression levels of the OPC-variable and OPC-shared gene signatures in 1,357 single-cells from the developing human ventral midbrain (embryonal week 6 to 11, as published in (25)). Cells are grouped by cell type as described in the original publication. Select genes are highlighted. (E) Heatmap showing expression levels of the OPC-variable, OPC-shared, and OC-like gene signatures in 4,993 single-cells from normal oligodendrocyte linage differentiation in mouse (postnatal day 21 to 60, as published in (26)). Cells are grouped by cell type as described in the original publication. Select genes are highlighted.
Figure 12B:
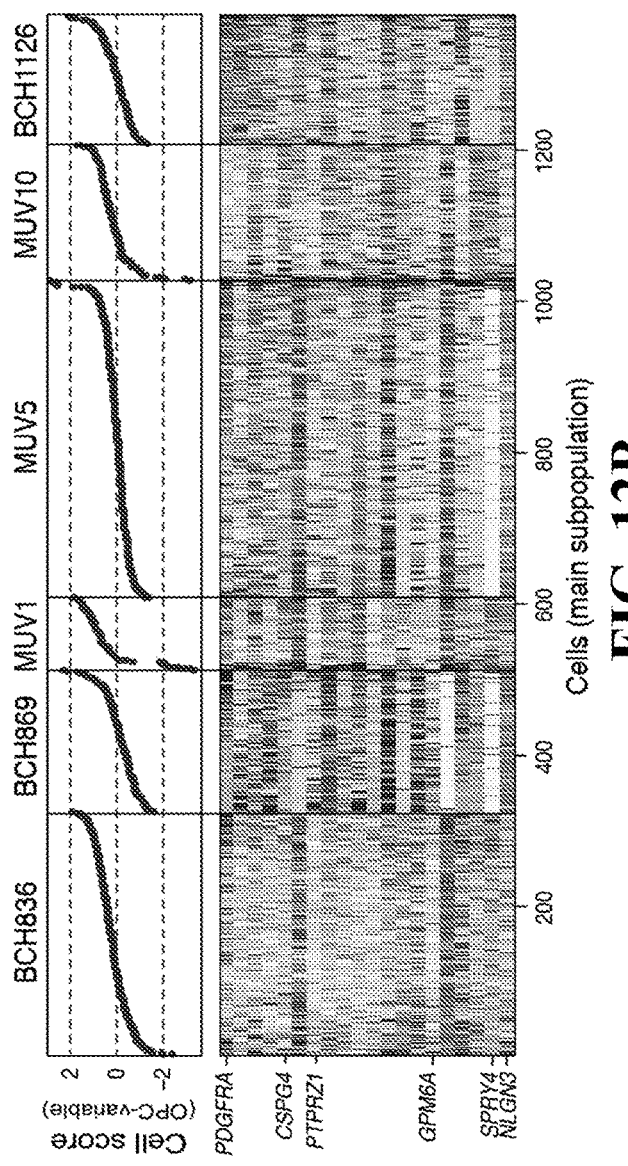
Figure 12C:
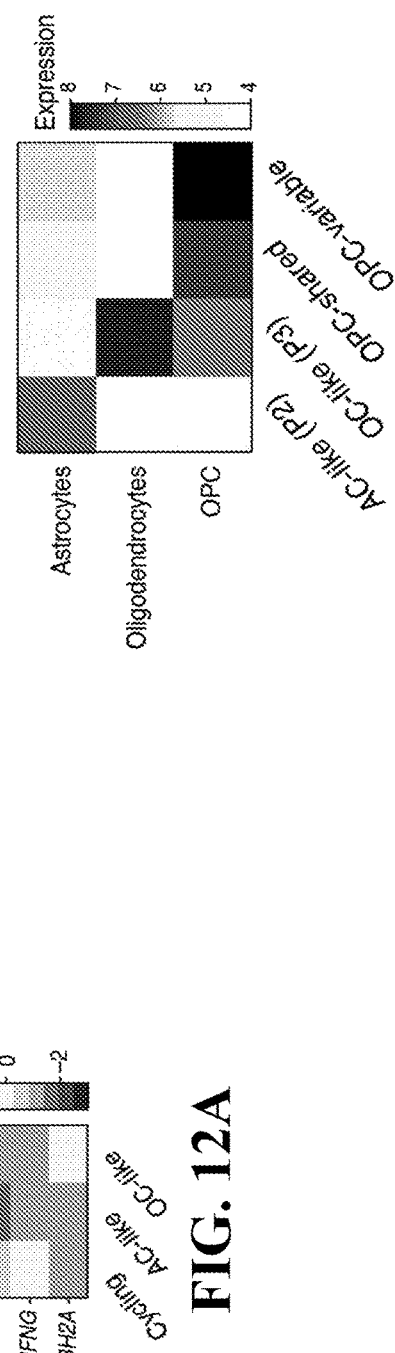
Figure 12C:
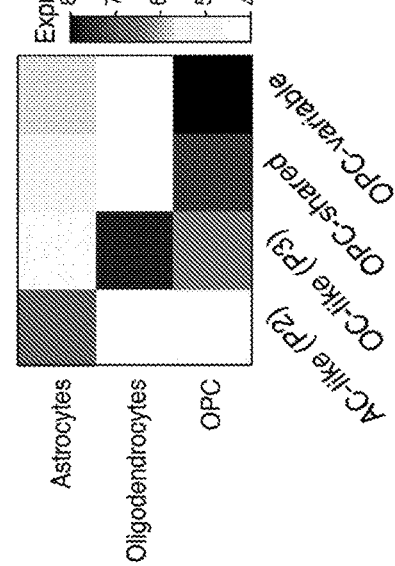

The three programs were associated with cell cycle (e.g., PCNA, CDK1), astrocytic differentiation (e.g., GFAP, APOE) and oligodendrocytic differentiation (e.g., MBP, PLP1) (FIG. 3B, Table S4). Genes in the first program were consistent with previously defined cell cycle signatures (14), while genes in the second (AC-like) and third programs (OC-like) were significantly upregulated in normal astrocytes and oligodendrocytes, respectively, compared to other brain cell types (FIG. 12C). However, while each of these three programs highlighted a subset of high-scoring cells, most cells (64%) did not score highly for any of these programs (FIG. 3A).

Figure 12A:
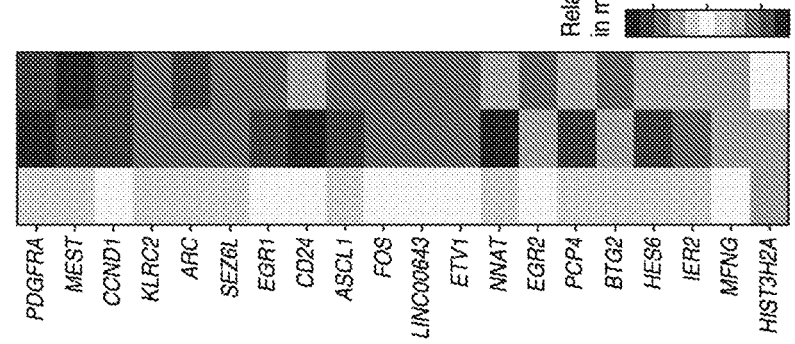
Figures 12D, 12E:
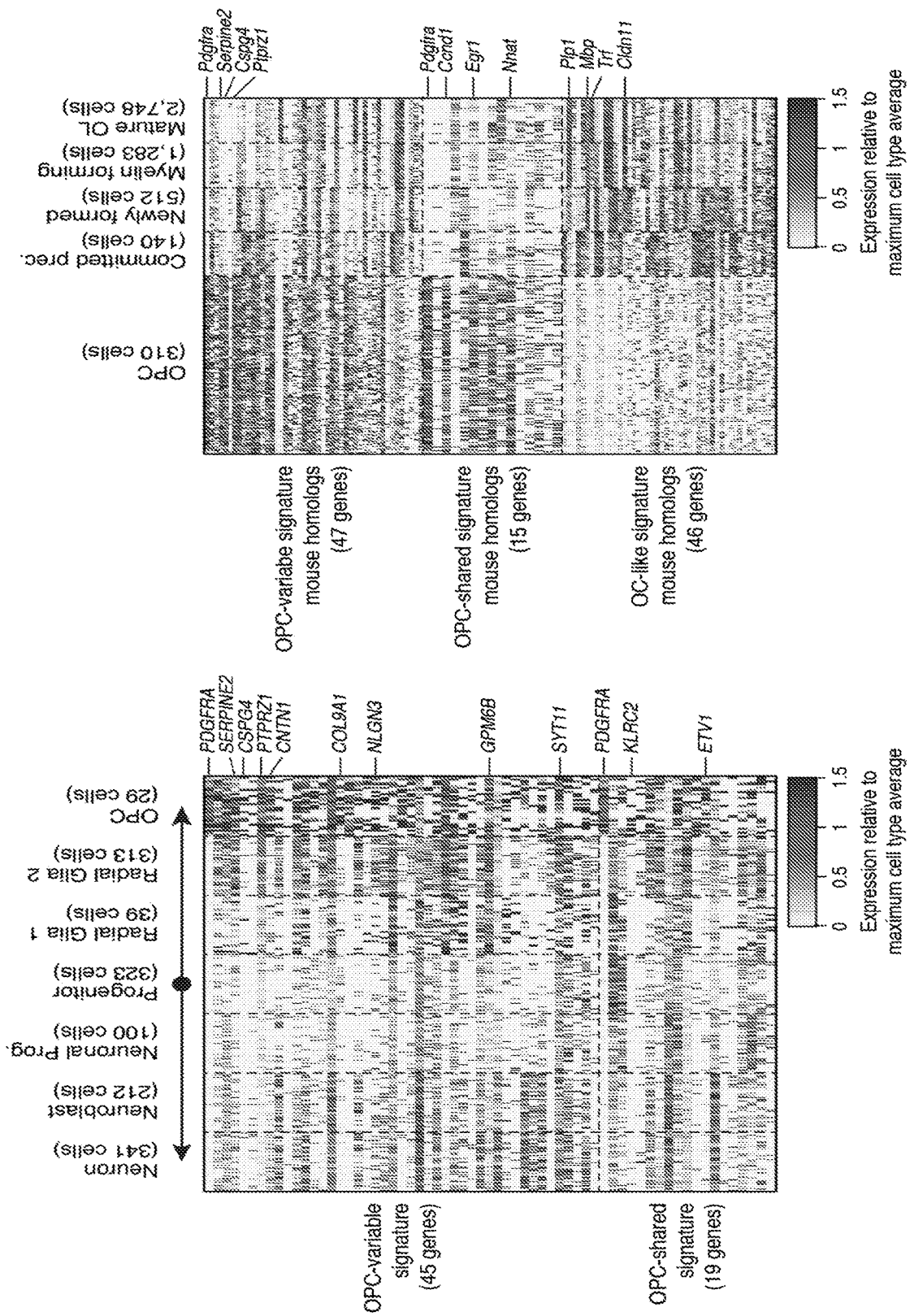

Applicants therefore considered whether this main group of remaining cells reflects a coherent subpopulation with preferential expression of particular genes. Applicants detected a signature of 19 genes that were significantly higher in the main subpopulation than in either the AC-like or the OC-like subpopulations, but which were comparably expressed in the cycling population (FIG. 3C, FIG. 12A, Table S4). Top genes in this set were PDGFRA and CSPG4 (NG2), two established markers of OPCs, and all 19 genes were preferentially expressed by OPCs, compared to other types of cells in the brain (FIG. 12C) (24, 25). Principal Component Analysis (PCA) of the main subpopulation (materials and methods) revealed an additional expression program that varied among those cells and was also highly expressed by OPCs (FIG. 12B-E, Table S4). PDGFRA was the top gene also in this signature, highlighting its notable expression in OPC-like cells. However, all other genes in this signature where distinct from those in the program described above. Applicants thus identified two OPC-related programs, one that is expressed across all cells in the main subpopulation as well as in the cycling cells (OPC-shared) and another that varies between the cells within these subpopulations (OPC-variable). Taken together, this strongly suggests that the majority of H3K27M-glioma cells reflect an OPC-like state.

Figure 3D:
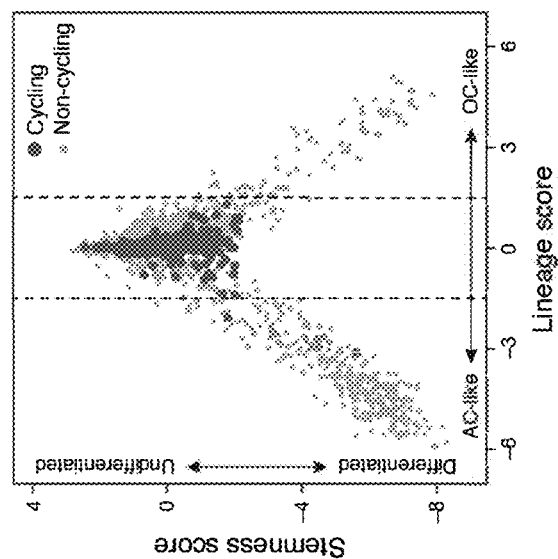

Scoring each cell for these expression programs (materials and methods) highlighted a putative developmental hierarchy in which cycling cells are enriched among OPC-like cells, but depleted among differentiated cells of either lineage (FIG. 3D). The relative fraction of cells in each compartment (OPC-like, AC-like, OC-like) varied substantially between tumors, but OPC-like cells are consistently the most prevalent cell types. Moreover, some tumors (MUV10 and BCH1126) had little if any evidence of lineage differentiation (FIG. 3E), potentially indicative of a differentiation block in some H3K27M tumors.

Figure 3G:
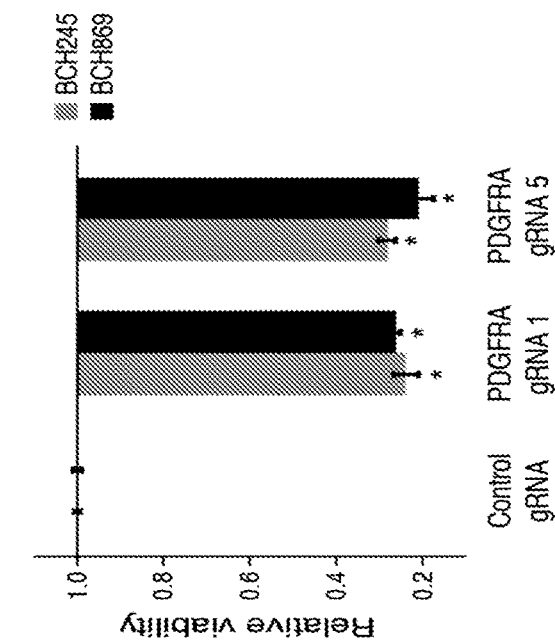
Figure 3F:
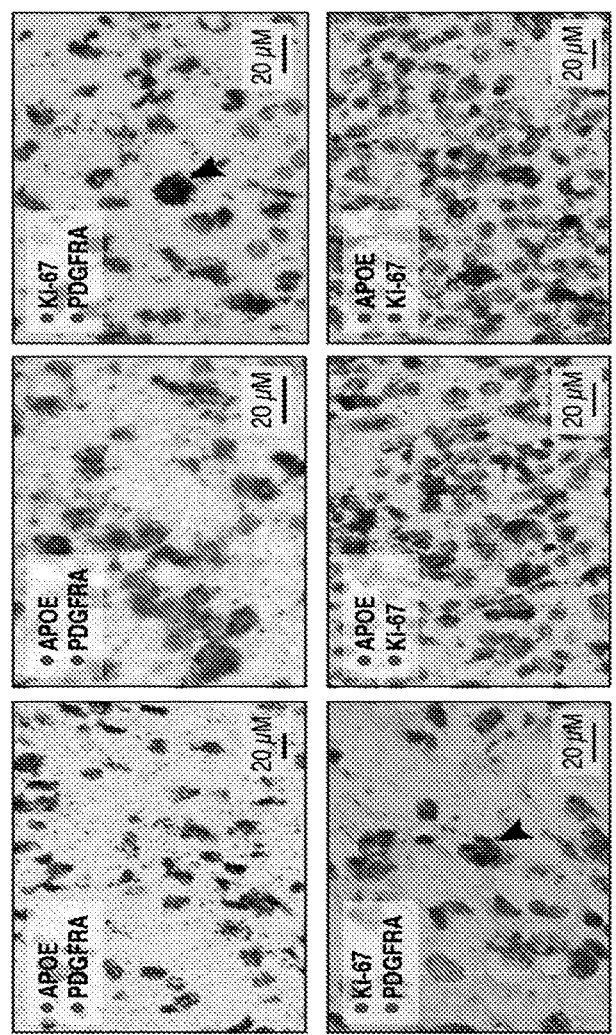

To validate this cellular composition, Applicants performed RNA in situ hybridization (ISH) on two tumor specimens (MUV1 and MUV10) for which Applicants could obtain sufficient tissue for evaluation and for an independent cohort of five additional patient samples (Table S2). ISH analysis of these tumors demonstrated (i) mutually exclusive expression of the OPC marker PDGFRA and the astrocytic lineage marker APOE; (ii) mutually exclusive expression of APOE and the proliferation marker Ki-67; and (iii) co-expression of Ki-67 and PDGFRA (FIG. 3F). Functionally, knock out of PDGFRA using CRISPR/Cas9 or its pharmacologic blockade with crenolanib, significantly reduced cell viability in two in vitro models of H3K27M-gliomas (FIG. 3G, FIG. 13). Combined targeting of PDGFRA and BMI1 further reduced cellular viability in these models (FIG. 13). Thus, OPC-like cells are the predominant subpopulation of H3K27M tumors, propagate the disease in patients, and may be susceptible to therapeutic strategies that concurrently target lineage-defined and somatically-altered cellular programs.

Example 5—H3K27M and IDH-Mutant Gliomas Harbor Distinct Developmental Hierarchies The proposed H3K27M-glioma hierarchy is reminiscent of IDH-mutant gliomas, which also contain a cycling stem-like subpopulation and two differentiated subpopulations (14, 15). To directly compare H3K27M and IDH-mutant glioma, Applicants scored malignant cells from both cohorts by the signatures described here and by those Applicants described previously for IDH-mutant gliomas (14, 15).

Figure 4A:
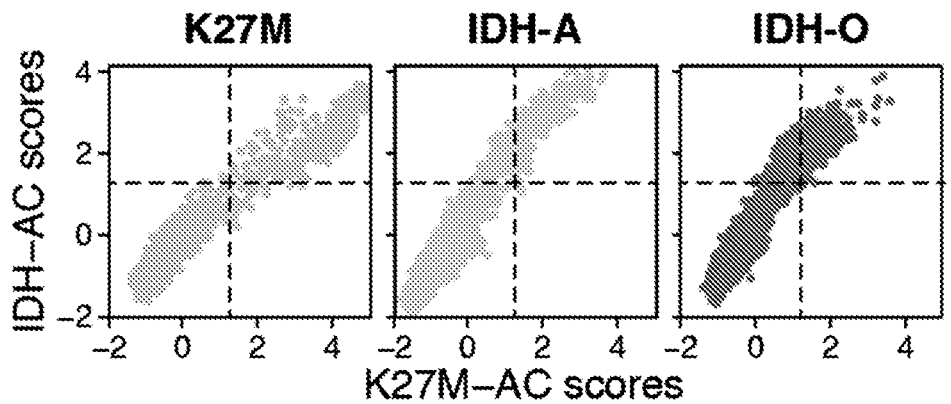
FIG. 4—Cellular hierarchies of H3K27M-gliomas and IDH-mutant gliomas. (A) Dotplot shows malignant cells from H3K27M (green), IDH-A (yellow) and IDH-O (purple) scored for the OC-like signatures of H3K27M-gliomas (X axis) and of IDH-mutant gliomas (Y axis). (B) Heatmap shows relative expression in OC-like cells in each glioma class (rows). Included are genes with preferential expression in OC-like cells, classified into those in common between H3K27M and IDH-mutant gliomas (left), and those specific to either H3K27M or IDH-mutant gliomas (right). Selected genes are labeled. (C, D) Same as (A,B) for AC-like signatures. (E, F) Same as (A,B) for stem-like signatures. (G) Heatmap depicts average expression of OC-like genes and stem-like genes specific to H3K27M-gliomas and IDH-mutant gliomas in oligodendrocytes, astrocytes, OPCs and NPCs (14); see also FIG. 12. (H) Plot depicts percentage of cycling cells (X axis) and undifferentiated cells (Y axis) in each glioma sample, denoted according to the glioma type and grade.
Figure 4B:
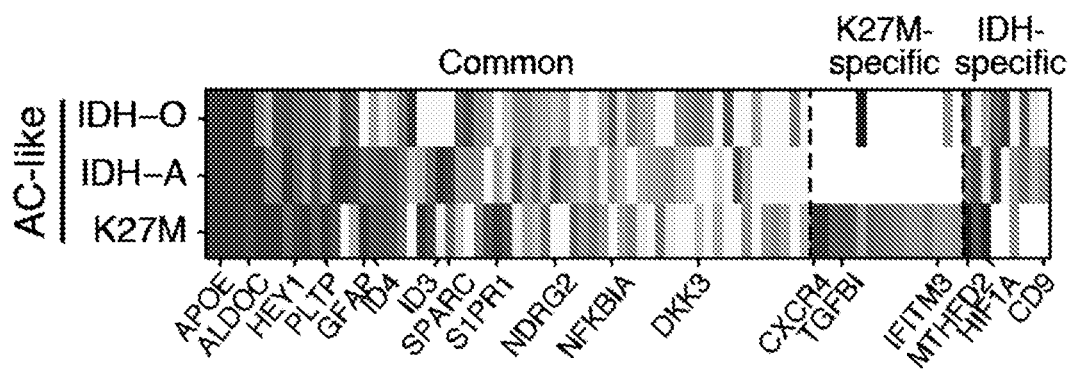
Figure 4C:
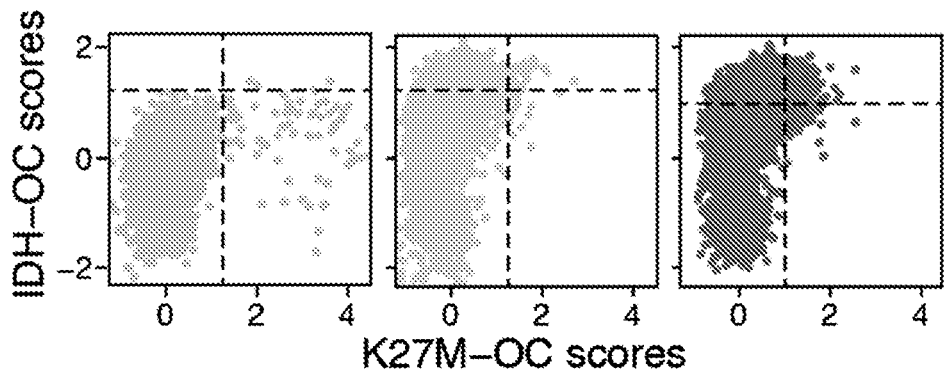
Figure 4D:
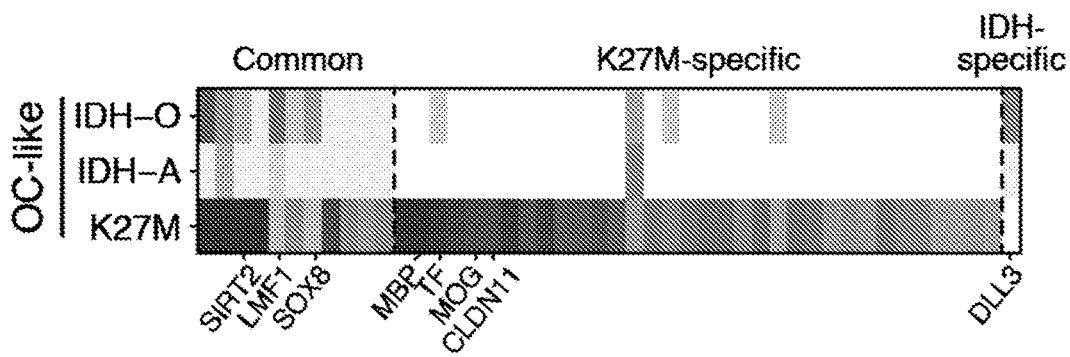
Figure 4E:
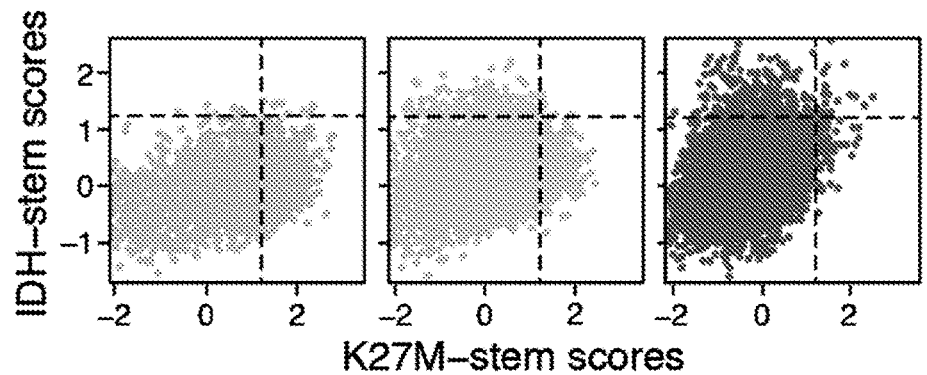
Figure 4F:
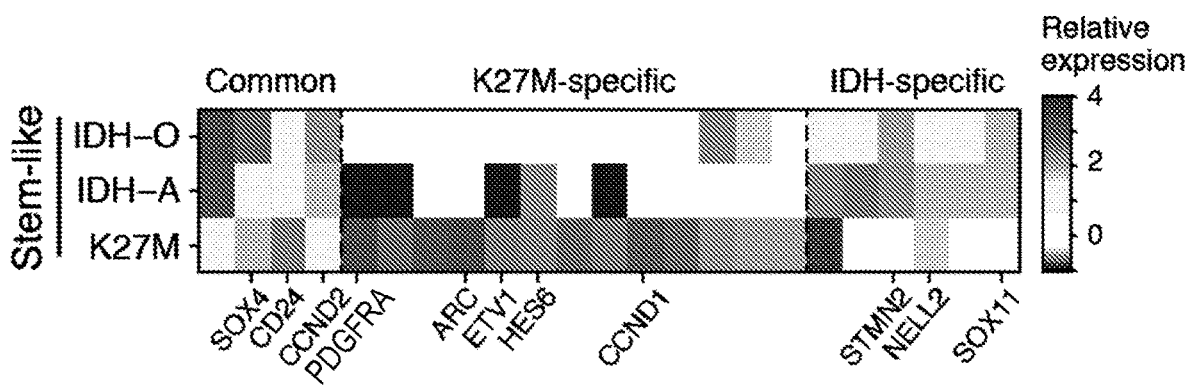
Figure 4G:
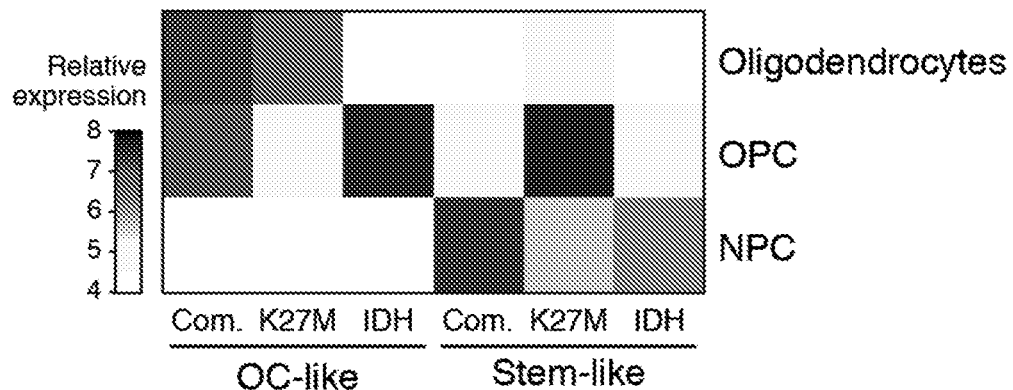
Figure 4H:
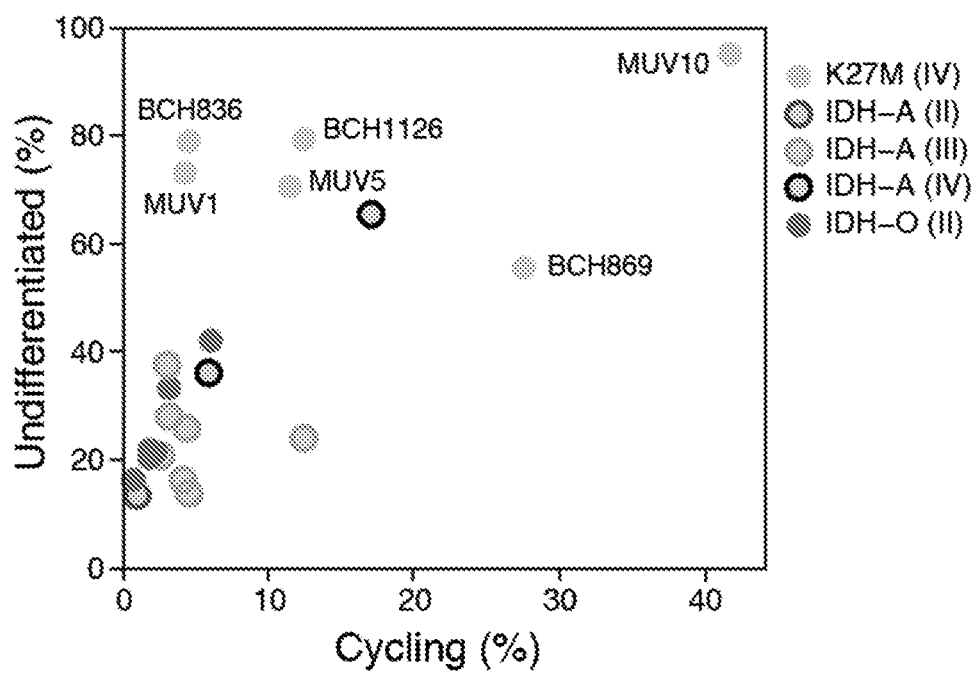

Whereas H3K27M and IDH-mutant gliomas harbor similar astrocytic programs, their oligodendrocytic and stem-like programs are largely distinct (FIG. 4A-B). Astrocytic signatures derived for either tumor type contained similar genes (e.g., APOE, ALDOC and vimentin), and yielded similar scores and AC-like subpopulations when applied to single cells in the respective datasets (FIG. 4A-B). This is indicative of similar AC-like differentiation programs in both tumor types. Conversely, the oligodendrocytic differentiation programs were distinct, with only a small subset of shared genes (FIG. 4D). Moreover, cells in each cohort scored highly only for the OC-like expression signature derived for the corresponding tumor type (FIG. 4C), suggesting considerable differences in OC-like differentiation programs. Interestingly, markers of mature oligodendrocytes (e.g., MBP, PLP1 and TF) were associated with the OC-like program in H3K27M-gliomas but not with IDH-mutant gliomas (FIG. 4G). Stem-like programs were also distinct between cohorts: the respective gene signatures were largely distinct, and cells in each tumor type scored primarily for the stem-like program derived for the corresponding cohort (FIG. 4E-F). H3K27M-specific stem cell genes included PDGFRA and other genes expressed highly by OPCs (FIG. 4G), while IDH-specific genes included SOX4, SOX11 (FIG. 4F) and were most consistent with NPCs (14, 15) (FIG. 4G). Notably, the sizes of the stem cell compartments also varied considerably between disease types. H3K27M-gliomas harbored significantly more cycling and undifferentiated cells than IDH-mutant gliomas (FIG. 4H). This may account for the more aggressive nature of H3K27M-gliomas, compared to IDH-mutant gliomas.

Figures 5D, 5E, 5F:
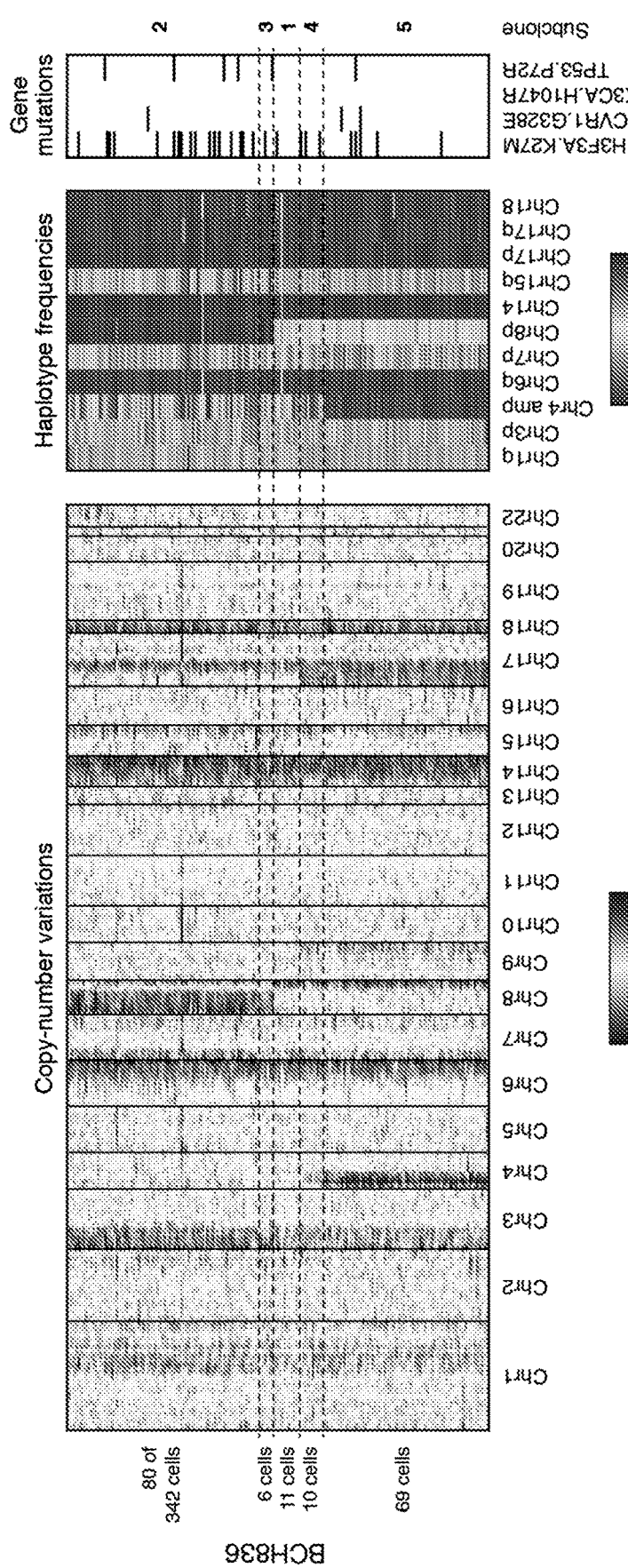
FIG. 5—Genetic subclones in H3K27M-gliomas. (A) Plot depicts CNVs inferred for individual malignant cells (rows) from BCH869, and (B) haplotype frequencies inferred for selected chromosome arms, ordered as in (A). Cells from this tumor are classified into 4 subclones (dashed lines) based on their CNV and haplotype profiles. (C) Mutations in selected genes identified by WGS, as detected in the BCH869 scRNA-seq data. AKT3.Q78K appears to be specific to subclone 1, but the other mutations are shared between subclones. (D-F) Same as (A-C) for BCH836. Cells from this tumor are classified into 5 subclones based on their CNV and haplotype profiles. (G) Diagram depicts the most parsimonious phylogenetic tree explaining the evolutionary relationships between individual subclones detected for BCH869. Circle sizes indicate the relative number of cells in the respective subclone. Molecular events (copy-number variations and gene mutations) are indicated at the point of their first detection. (H) Barplot indicates the relative number of cells classified into OPC-, AC-, or OC-like expression state for BCH869 subclone 1 or the combination of subclones 2 and 3. (I, J) Same as (G, H) for BCH836. Developmental hierarchies are largely recapitulated in the different subclones.
Figure 5J:
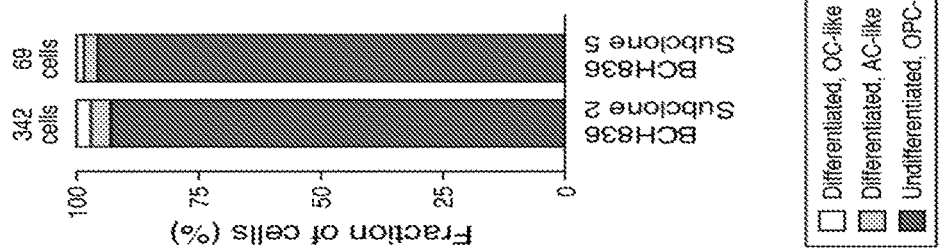

Example 6—Distinct Genetic Sub-Clones Share the Same Developmental Hierarchy in H3K27M-Gliomas Applicants next considered how this putative cellular hierarchy within H3K27M-gliomas relates to the genetic heterogeneity that co-exists in any given tumor. Applicants focused initially on the inferred large-scale CNVs, which are more robustly detectable in single cells than any individual point mutation. Two of the six H3K27M-gliomas (BCH836 and BCH869) had multiple subclonal CNVs (FIG. 5A, D). Applicants next improved the definition of genetic subclones in these two tumors by complementing the CNV analysis with inference of haplotypes. Briefly, CNVs generate an imbalance in the allelic fraction of heterozygous SNPs, which can be used to infer haplotypes and haplotype frequencies in single cells (FIG. 14; materials and methods). Germline SNPs that fall within CNV regions provide a means to distinguish which parental chromosome is affected by a given CNV in a given subclone. When Applicants examined the allelic fractions of SNPs contained within the predicted CNVs in the single-cell data, Applicants found differences between subclones in the haplotype frequencies of amplified and deleted chromosomes (FIG. 5B, E). Interestingly, some of the differences in haplotype frequencies distinguished convergent CNV events that could not be appreciated by CNV patterns alone. For example, while all cells in BCH869 have lost one copy of chromosome 14, distinct subclones had different haplotypes (subclones 2-4 had haplotype B while subclone 1 had the alternate haplotype A), indicating that two distinct events led to loss of alternate chromosome 14 alleles in distinct subclones (FIG. 5B). Thus, the haplotype analysis both supported the inferred CNV subclones and further dissected the evolutionary events that generated these subclones and their chronological ordering. Applicants also found that certain somatic gene mutations could be assigned to individual subclones (FIG. 5C, F). For example, Applicants identified a mutation in AKT3 specific to BCH869 subclone 1 (P<0.001, Fisher's exact test).

Figure 5I:
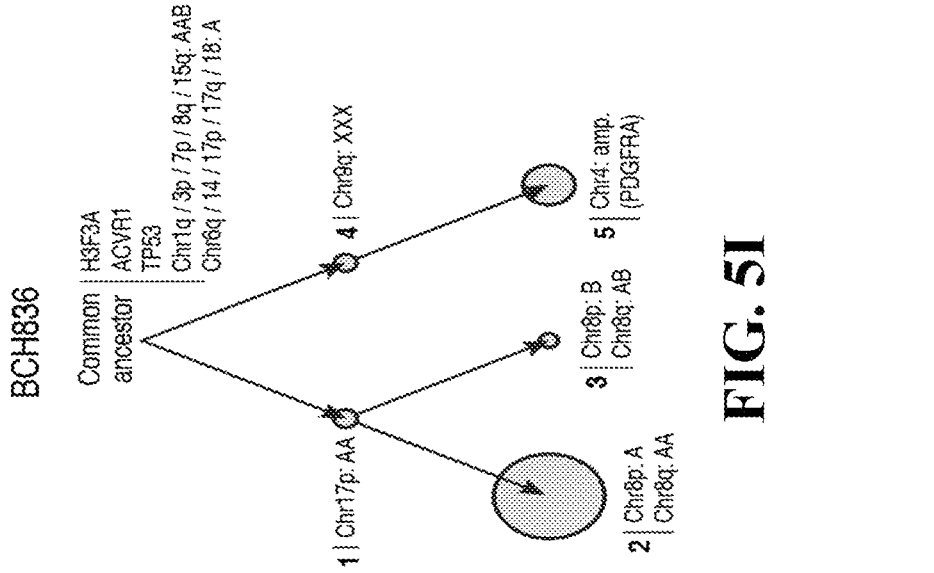
Figure 5H:
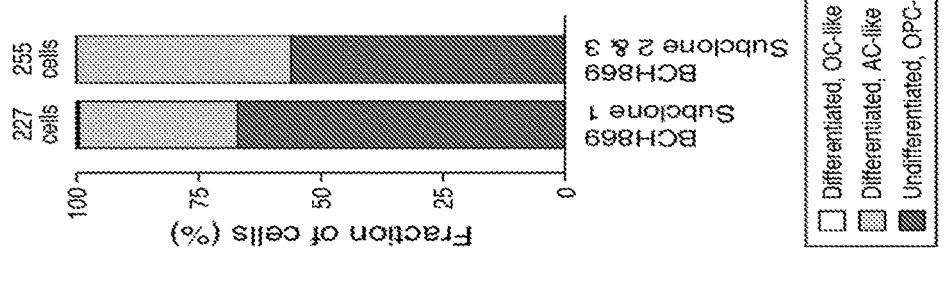
Figure 5G:
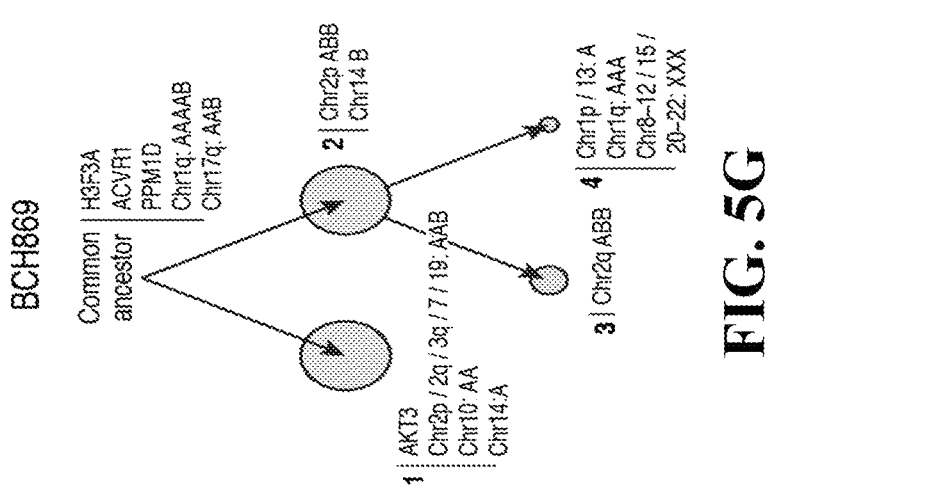

Using the patterns of CNVs and haplotype frequencies, Applicants inferred the most parsimonious phylogenetic trees of BCH869 (FIG. 5G) and BCH836 (FIG. 5I). These trees are based on the assumptions that haplotypes cannot be regained after they have been lost and that CNVs are unlikely to be reversed. Hence, if subclones 1 and 2 share most CNVs but an additional CNV is specific to 2, then Applicants would conclude that 1 likely preceded 2. When Applicants projected these subclones onto the cellular hierarchies, Applicants found that each genetic subclone contained a similar diversity of cellular states, although with some variation in their relative proportions (FIG. 5H, J). This approach thus provides a novel strategy to parse the genetic phylogeny of a tumor at cellular resolution, and indicates that distinct genetic subclones recapitulate consistent developmental hierarchies in H3K27M gliomas.

Figure 15:
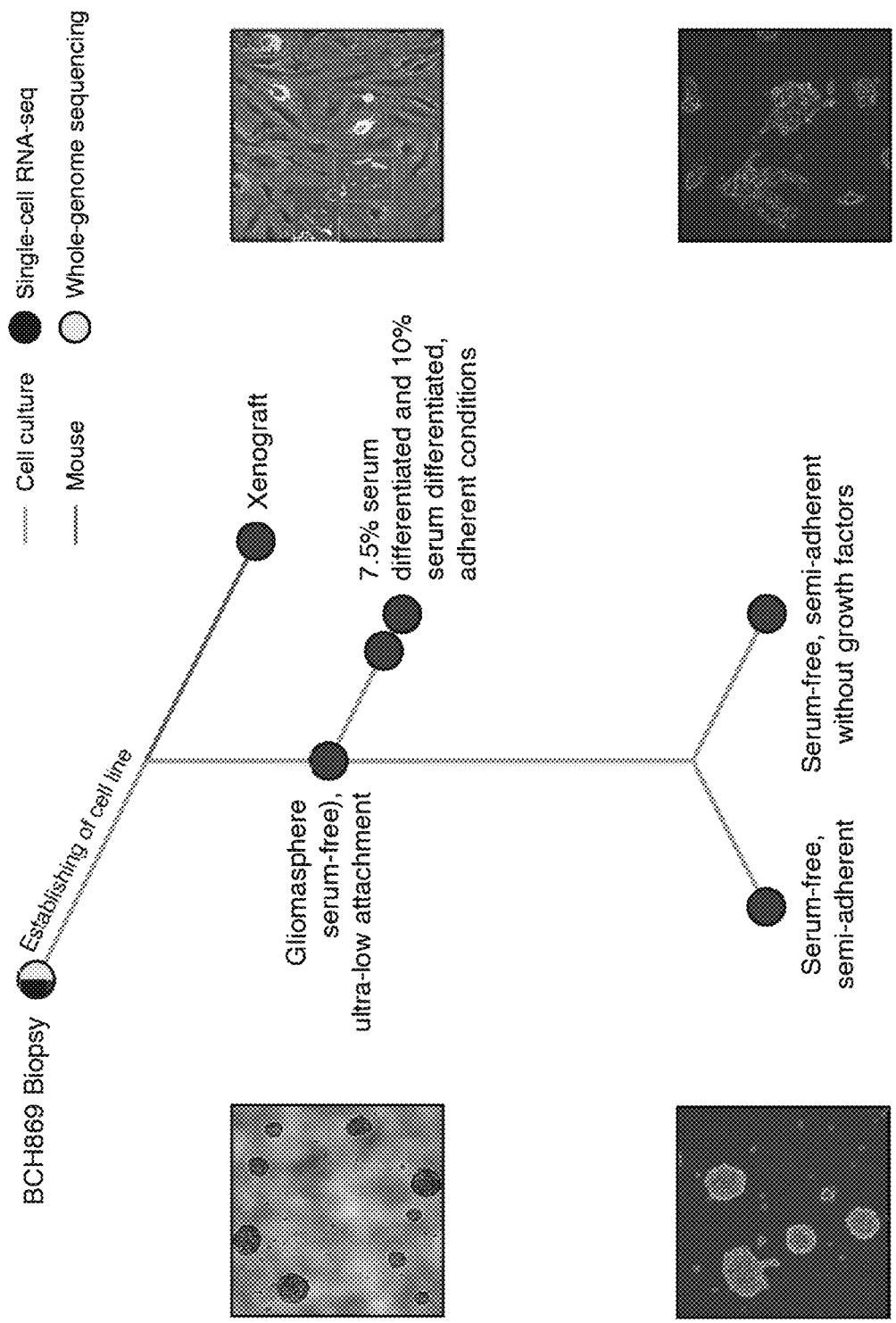
FIG. 15—BCH869 Patient sample. In vitro and in vivo models. Schematic showing generation and conditions of in vitro and in vivo models from patient sample BCH869. Representative phase-contrast images are shown for all in vitro models.

Example 7—Single-Cell Analysis of Patient-Derived Cell Line and Xenograft Models of H3K27M-Gliomas Animal and cellular models of gliomas are widely used to dissect tumor biology and uncover new therapeutic vulnerabilities. Yet, it remains unclear if models of gliomas are faithful to their parent tumor, whether they comprehensively represent malignant cell states, or whether alternate in vitro or in vivo growth conditions favor specific tumor compartments. Single cell RNA-seq provides an opportunity to assess the ability to faithfully model H3K27M-gliomas, as it can allow us to compare these models to alternate malignant sub-populations in the tumor from which they were derived. To this end, Applicants generated animal and cell culture models from one of the H3K27M glioma samples (BCH869). BCH869 was modeled as PDX in mice as well as in different in vitro conditions (FIG. 15), which have been associated with varied functional phenotypes (26). Applicants expanded BCH869 (i) as gliomaspheres (GS) in serum-free conditions that represent putative tumor-propagating cells (27, 28); (ii) in serum-free (SF) conditions on semi-adherent plastic with or without growth factors (SF_Adh and GF-, respectively); and (iii) in adherent conditions with the addition of serum (7.5% or 10%) as putative differentiated glioma cells (DGC) (FIG. 15). Applicants then profiled a total of 863 single-cells from these in vitro models and from the BCH869 PDX by scRNA-seq.

Figure 6A:
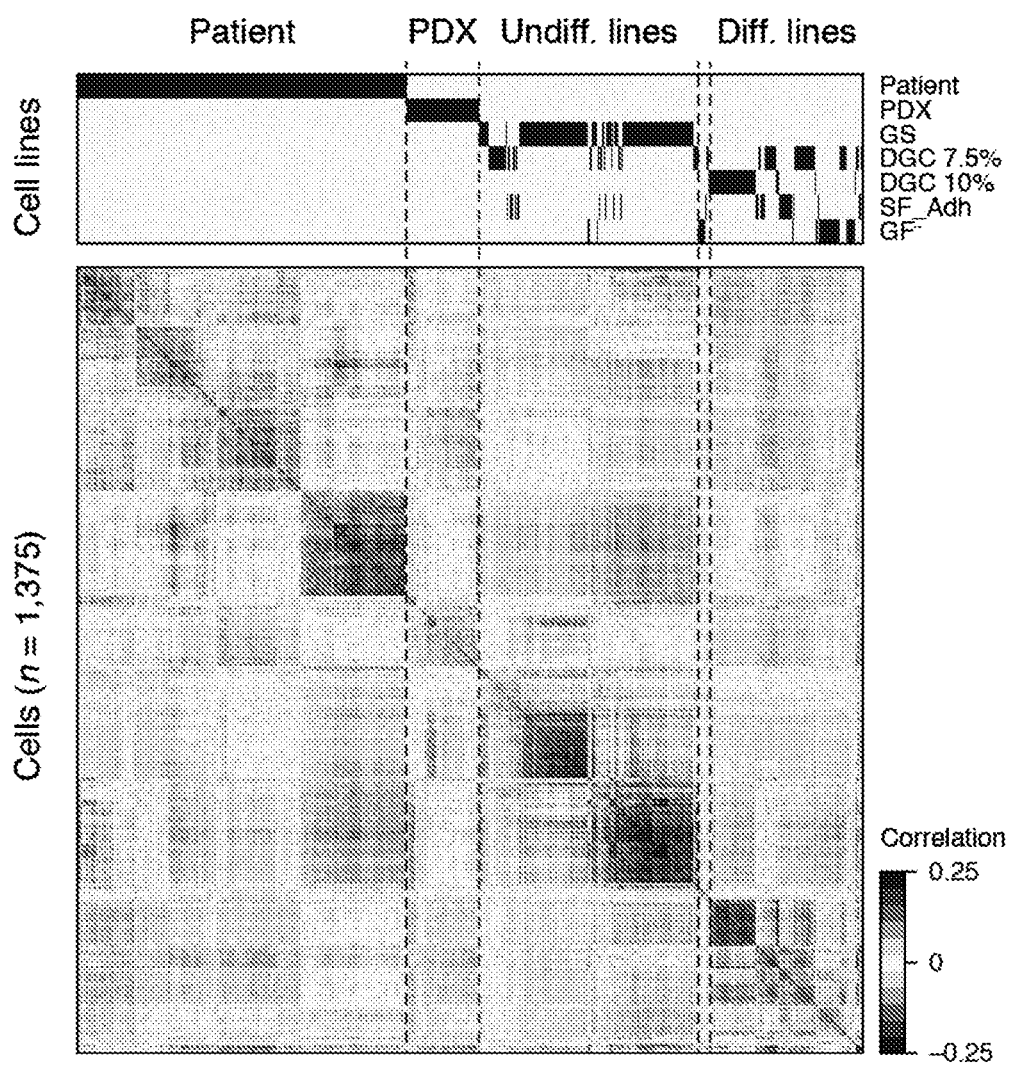
FIG. 6—Comparisons of matched H3K27M-gliomas patient samples, PDX and culture models. (A) Heatmap depicts pairwise correlations between the expression profiles of cells from tumor, PDX and culture models. Cells were ordered by sample type (patient, PDX and culture) and within each sample type by hierarchical clustering; assignment of cells to samples is shown in the top panel and cell-to-cell correlations are shown in the bottom panel. The clustering partitioned two groups of cultured cells (differentiated and undifferentiated). (B) Heatmap shows expression of the top 30 genes of the cell cycle and lineage programs described in FIG. 3, for cells ordered as in (A). (C) Kaplan-Meier analysis shows different survival of mice injected with 100,000 or 200,000 BCH869 cells grown as gliomaspheres ("OPC-like") or under differentiating conditions ("differentiated"); p=0.0091 Log-rank (Mantel-Cox) for OPC-like vs differentiated at each cell dose. (D) Left: example of mouse MRIs (left column) with 3D reconstruction (right column) at 22 weeks after injecting either BCH869 cells grown under differentiating conditions (top panel) or BCH869 cells grown as gliomaspheres (bottom panel). Right: tumor volume reconstruction by MRI at 22 and 30 weeks after injection **=p<0.01 by paired, two-tailed t-test. Error bars: +S.E.M. (E) Representative histology of BCH869-derived xenograft (PDX), orthotopically implanted into mouse brains. Hematoxyline & Eosin (H&E) stain showing high cellularity and cytonuclear pleomorphism, H3K27M immunohistochemistry shows nuclear staining of malignant cells. Ki-67 staining highlights proliferative cells. (F) Heatmap shows expression of differentially expressed genes between sample types, for each pairwise comparison (with cultured cells separated to the two clusters); cells ordered as in (A). Right panel shows the average expression in each sample type (and cluster for cultured cells).
Figure 6B:
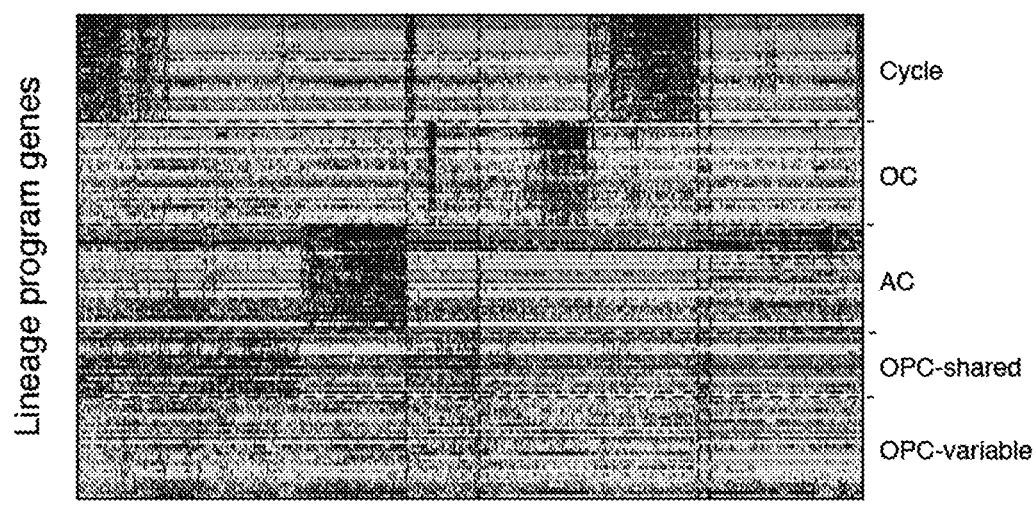

Applicants found that the PDX model most closely approximated malignant cell states and heterogeneity in the primary tumors, whereas each in vitro model recapitulated some, but not all aspects of the key cellular programs in vivo (FIG. 6A). The PDX partially recapitulated all four of the expression programs that Applicants defined in H3K27M-gliomas: OPC-like, OC-like, AC-like, and the cell cycle (FIG. 6B). However, the in vitro models presented a more nuanced story. Clustering of all cells from the culture models distinguished two main subsets (FIG. 6A). The first subset (cluster 1) contained almost all (>99%) of the cells from the GS conditions, a small fraction (9-40%) of the cells from three other serum-free or low-serum conditions, but none of the cells from the 10% serum condition. This cluster contained a high fraction of cycling cells, partially recapitulated the OPC-like and the OC-like programs, but lacked the AC-like program (FIG. 6B). The second subset (cluster 2) primarily contained cells from differentiation conditions. This cluster contained far fewer cycling cells and recapitulated AC-like but not OPC-like or OC-like programs (FIG. 6B). Thus, cells grown in vitro as GS recapitulate partially the OPC and OC-like states, while cells grown as DGC recapitulated partially the AC-like program.

Figure 6C:
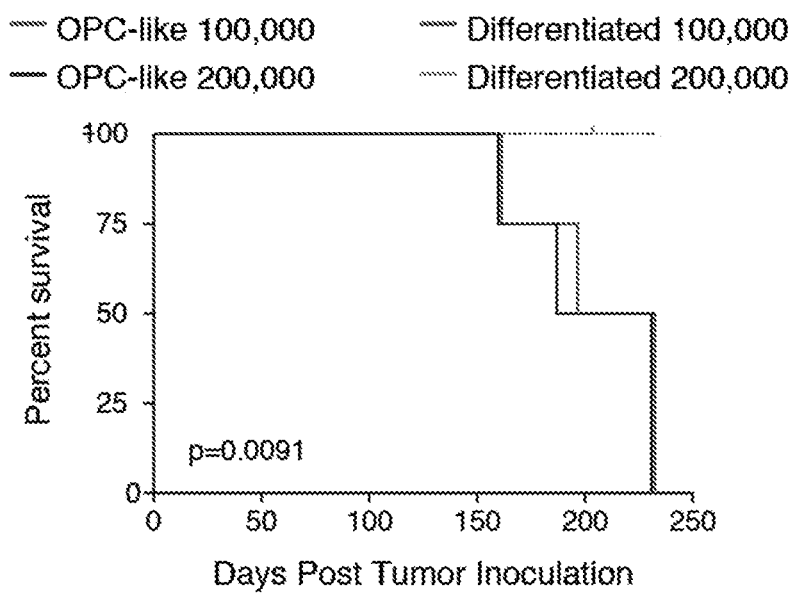
Figure 6D:
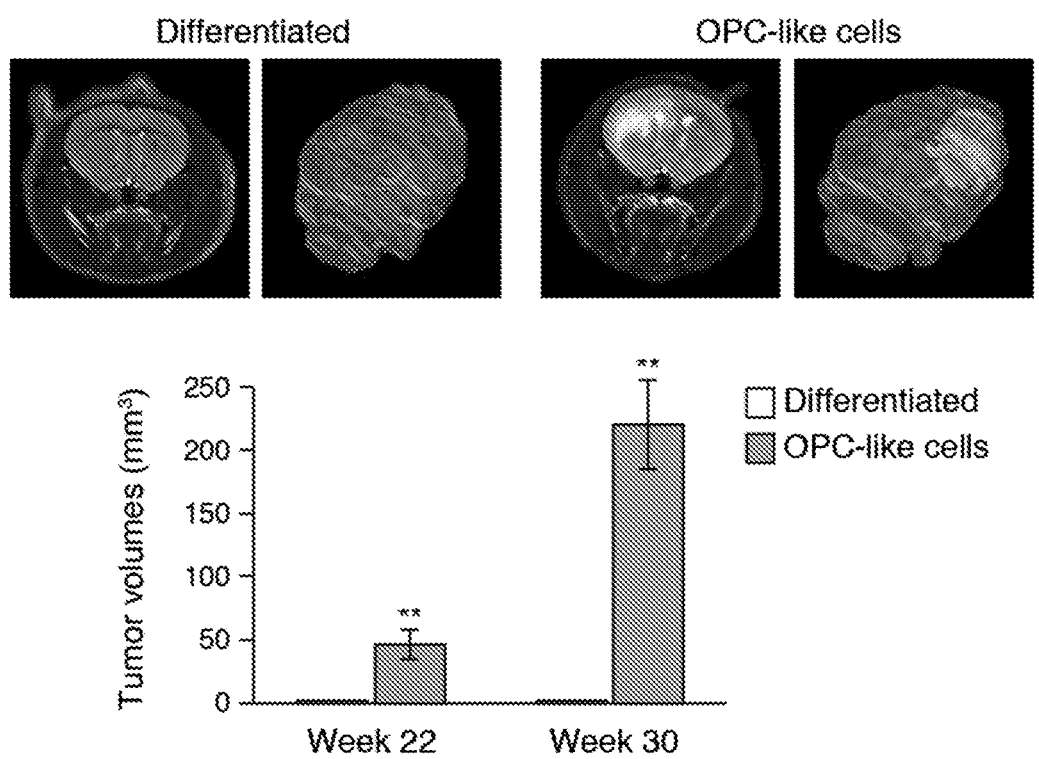
Figure 6E:
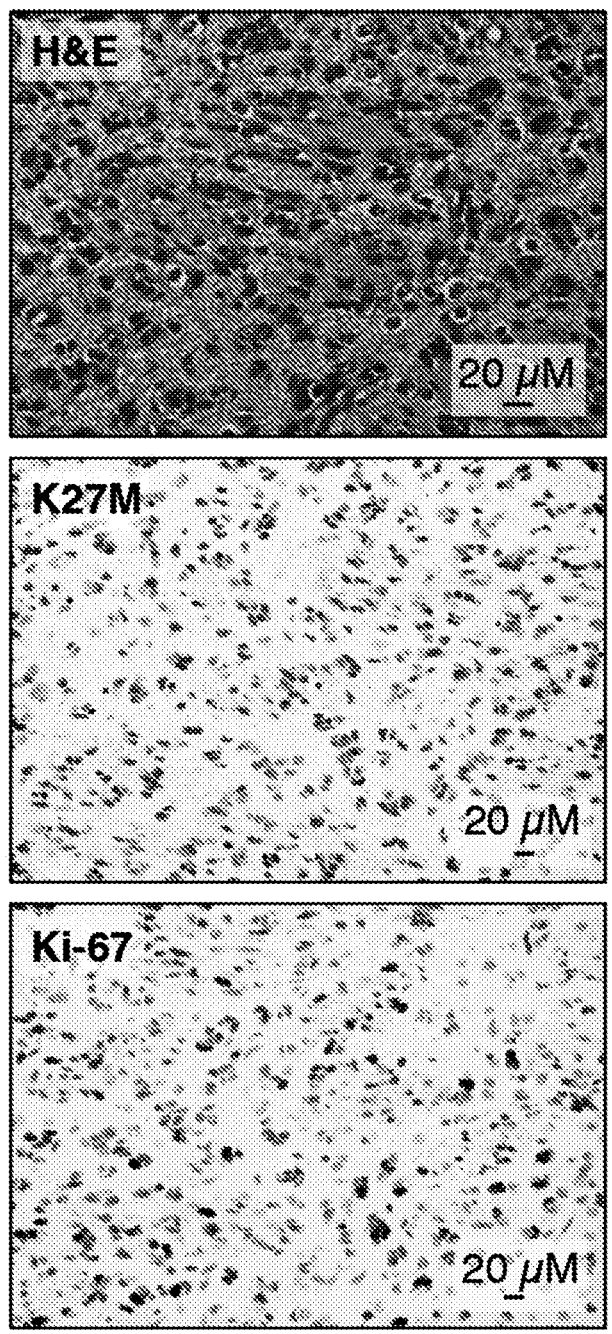

To test the functional relevance of these models and signatures, Applicants orthotopically transplanted 100,000 or 200,000 H3K27M cells grown as either GS or DGC in mice. Consistent with previous studies (26), BCH869 cells grown in GS conditions initiated tumors upon xenotransplantation to immunodeficient mice (n=8/8), while identical number of cells grown as DGC failed to form tumors (n=0/8) (FIG. 6C, D, E). Thus, in vitro models that partially recapitulate distinct compartments of patient tumors have different tumor-propagating potential, supporting the functional relevance of the inferred cellular hierarchies.

Figure 6F:
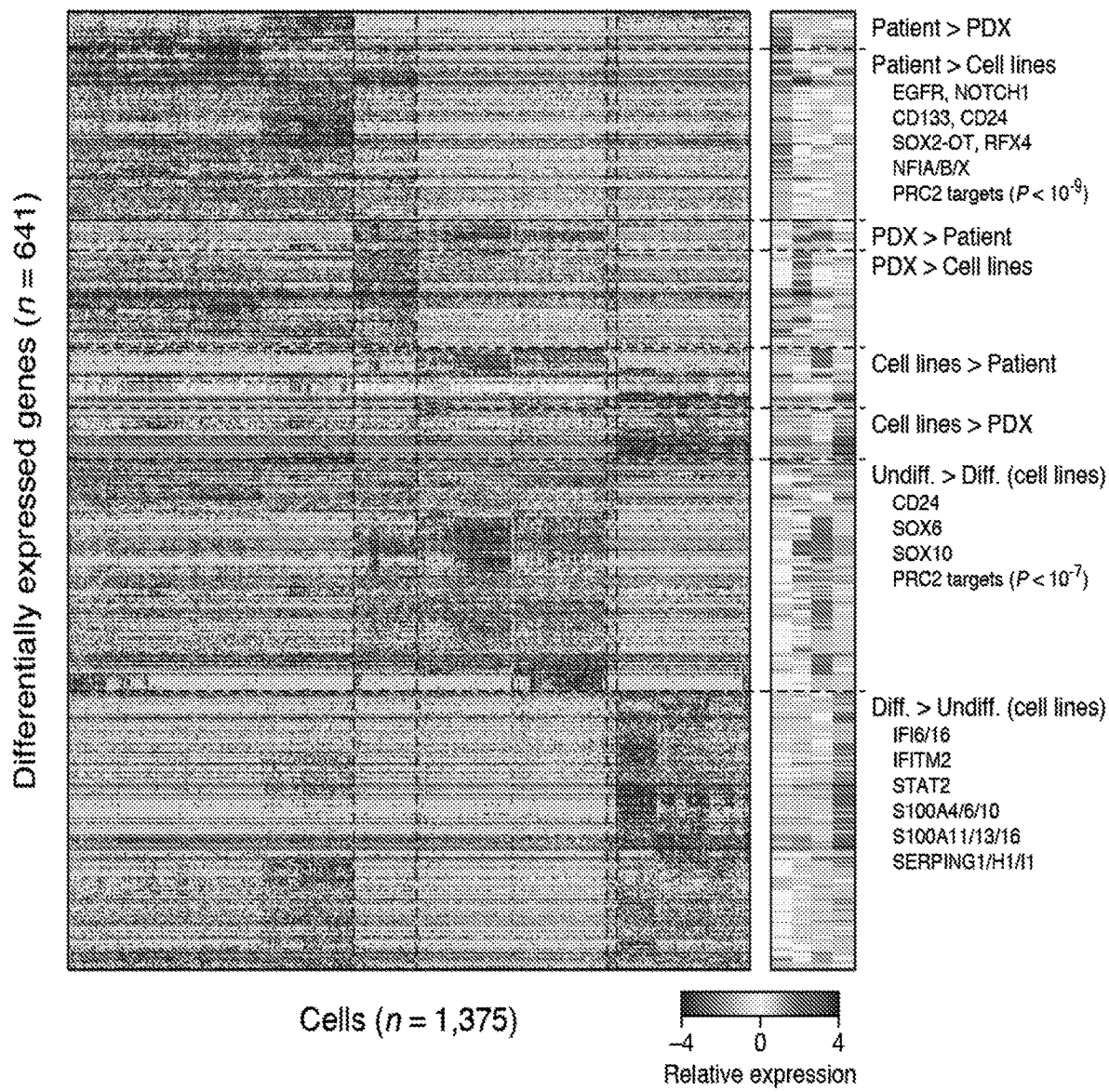

Finally, Applicants identified differentially expressed genes between each pairwise comparison of patient, PDX and culture models (FIG. 6F and Table S5). In particular, a large number of genes was downregulated in culture models compared to cells from the patient tumor. These included important glioma-related genes, such as oncogenes (e.g. EGFR) and putative stemness transcription factors and markers (e.g. SOX2, RFX4, CD133). Furthermore, the top functional enrichment of these in vitro downregulated genes are PRC2-targets (20) ($P<10^{-9}$) which relate to the oncogenic mechanism of H3K27M-glioma. Notably, PRC2 targets were further depleted in DGC, along with neurodevelopmental regulators such as SOX6 and SOX10 (FIG. 6F). Taken together, the results highlight the specificities and limitations of each glioma model, support the relevance of cellular state in H3K27M-gliomas for tumor propagation in vivo, and underscore the changes of PRC2 target genes in vitro, thus warranting caution when these models are evaluated for therapeutics (29).

Example 8—Discussion

Hierarchies of cellular differentiation that minor normal development are appreciated to play a central role in cancer (30). Seminal studies in leukemia identified stem-like cells with tumor-propagating potential that give rise to more differentiated progeny, laying the foundation for the development of differentiation therapies (31). Recent studies have established analogous hierarchies in some solid malignancies, including gliomas, and highlight the importance of understanding the regulatory circuits of their most aggressive subpopulations (26, 27, 31). While functional assays such as mouse xenotransplantation and in vitro colony forming assays have traditionally been used to identify such subpopulations (27, 31), scRNA-seq has emerged as a powerful means to identify cell types in normal development and cancer as it offers a comprehensive view of the programs of each profiled cell in an analyzed tissue and can be applied directly to patient samples (32).

Here Applicants define a putative developmental hierarchy in H3K27M-gliomas by scRNA-seq, and contrast the underlying stem cell and differentiation programs with other classes of glioma. First, Applicants find that the most primitive and undifferentiated cells in this pediatric cancer are reminiscent of OPC-like cells, and distinct from those identified in IDH-mutant gliomas, which are more like NPCs (14, 15). This distinction is critical as both OPCs and NPCs have been suggested as cell-of-origin and putative cancer stem cell in gliomas (6, 28, 33). OPCs have been previously suggested as the cell-of-origin for H3K27M-gliomas of the pons given the pattern of Olig2+ precursor cells in the human postnatal brainstem (28, 34), and the observation that the spatiotemporal incidence of H3K27M-gliomagenesis maps well onto discrete developmental waves of myelination during childhood (35). The finding that stem-like cells in this disease retain corresponding neuro-developmental transcription factors and circuits provides strong support for the hypothesis that OPCs are the cell-of-origin for H3K27M-gliomas.

Second, Applicants find that the relative size of the stem-like compartment is much larger in H3K27M tumors than in IDH mutant-gliomas. This observation that OPC-like cells represent a majority of cells in H3K27M-gliomas is consistent with a recent study that identified many OPC-like super-enhancers in chromatin maps for bulk tumor specimens (36). Yet despite the enrichment of primitive stem-like cells, the single cell data also reveal significant numbers of differentiated cells that are largely non-proliferative and lack tumor-initiating potential. This putative H3K27M-glioma hierarchy is thus distinct both from IDH mutant-gliomas, for which scRNA-seq primarily identified differentiated cells, and from GBM, for which scRNA-seq revealed limited evidence of clear differentiation programs (11, 12, 19).

Thus, one might consider an emerging cancer stem cell model for gliomas wherein: (i) genetically-defined glioma classes, such as IDH-mutant gliomas and H3K27M-gliomas contain different types of stem cells (14, 15, 27); (ii) the fraction of stem-like cells can vary substantially between glioma types: this extends the traditional cancer stem cell model which posits as requirement that stem cells represent a minority of malignant cells (31); (iii) differentiation hierarchies play a critical role in the functional properties of glioma cells, with the most primitive cells in a tumor being endowed with self-renewing and tumor-propagating potential, and the more differentiated cells lacking such properties (27); and (iv) coincident genetic evolution modulates the phenotypes and relative proportions of stem-like and differentiated states, but is not the primary driver of the cellular hierarchies in H3K27M-gliomas or in IDH-mutant tumors.

The central role of OPC-like cells in driving H3K27M-gliomas is also supported by the fact that a third of patients harbor a genetic amplification of the PDGFRA locus and the observation that PDGFRA over-expression facilitates H3K27M-mediated transformation in experimental models of NPCs (6, 37). OPC-like cells with intrinsically high PDGFRA expression would thus represent a favorable cellular environment for transformation by H3K27M. Thus, PDGFRA could be a lineage-defined therapeutic target in H3K27M-gliomas, relevant even in the absence of genetic amplification or mutation, as it has been shown in IDH-mutant gliomas where PDGFRA expression is epigenetically driven by insulator dysfunction (38). Renewed attempts could be made not only to block PDGFRA signaling, but also to exploit PDGFRA expression to target the OPC-like lineage in H3K27M tumors, for example with chimeric antigen receptors (CAR) T cells (39).

An additional distinguishing feature highlighted by this study relates to the expression of Polycomb targets, which have uniquely higher expression in H3K27M-gliomas relative to other classes of gliomas that Applicants have examined by scRNA-seq (IDH-mutant gliomas and GBM). This is consistent with H3K27M mutation leading to a dysfunction of PRC2, as supported by previous studies (9, 29, 36). Interestingly, Applicants find that malignant cells with H3K27M overexpress BMIJ, a core subunit of the PRC1 complex (40), potentially hinting at a compensatory mechanism for the dysfunction of PRC2; accordingly, the functional data supports a sensitivity of H3K27M-gliomas to BMI1 inhibition, potentially in combination with the targeting of PDGFRA. Thus, lineage-defined and somatically altered cellular programs may offer complementary opportunities for therapeutic intervention.

Finally, Applicants interrogated commonly used in vitro and in vivo models of H3K27M-gliomas at single-cell resolution, and compared them to the original tumors. Applicants find that orthotopic in vivo PDX in mice most closely recapitulate the programs and states present in patients, while in vitro models only partially reproduce subsets of states. Notably, models varied substantially in their expression of PRC2 target genes, suggesting that alternate growth conditions might influence PRC2 activity (or at a minimum, the expression of its target genes). This may present a challenge for the evaluation of epigenetic drugs in tumor models (29) and for successfully translating promising therapies from the bench to the bedside.

In summary, this study represents the first scRNA-seq analysis of H3K27M-glioma patient tumors, defines and contrasts their cellular architecture with experimental models and with other classes of gliomas, and suggests candidate tumor dependencies.

Example 9—Materials and Methods

Tumor Acquisition and Preparation

Patients and their parents at Boston Children's hospital and the Medical University of Vienna were consented preoperatively in all cases according to Institutional Review Boards. Fresh tumors were collected at the time of surgery and presence of malignant cells was confirmed by frozen section. Tumor tissues were mechanically and enzymatically dissociated using a papain-based brain tumor dissociation kit (Miltenyi Biotec) as previously reported (14, 15).

Fluorescence-Activated Cell Sorting (FACS)

Tumor cells were blocked in 1% bovine serum albumin in Phosphate Buffered Saline (BSA/PBS). Cells were washed with cold PBS, and then resuspended in 1.5 mL of BSA/PBS containing 1uM calcein AM (Life Technologies) and 0.33 uM TO-PRO-3 iodide (Life Technologies) to co-stain for 15 min before sorting. Sorting was performed with FACSAria Fusion Special Order System (Becton Dickinson) using 488 nm (calcein AM, 530/30 filter) and 640 nm (TO-PRO-3, 670/14 filter) lasers. Non-stained controls were included with all tumors. Standard, strict forward scatter height versus area criteria were used to discriminate doublets and gate only singleton cells. Viable cells were identified by staining positive with calcein AM but negative for TO-PRO-3. Single cells were sorted into 96-well plates containing cold TCL buffer (Qiagen) containing 1% beta-mercaptoethanol, snap frozen on dry ice, and then stored at −80° C. prior to whole transcriptome amplification, library preparation and sequencing.

Single Cell RNA-Seq Data Generation and Processing

Whole transcriptome amplification, library construction and sequencing of single cell transcriptomes was performed as previously published (13-15). Expression levels were quantified as $E_{i,j}=\log_2(TPM_{i,j}/10+1)$, where $TPM_{i,j}$ refers to transcript-per-million for gene i in sample j, as calculated by RSEM (41). TPM values are divided by 10 since Applicants estimate the complexity of single cell libraries in the order of 100,000 transcripts and would like to avoid counting each transcript ~10 times, as would be the case with TPM, which may inflate the difference between the expression level of a gene in cells in which the gene is detected and those in which it is not detected.

For each cell, Applicants calculated two quality measures: the number of genes for which at least one read was mapped, and the average expression level of a curated list of housekeeping genes. Applicants then conservatively excluded all cells with either fewer than 2,500 detected genes or an average housekeeping expression level (E, as defined above) below 2.5. For the remaining cells, Applicants calculated the aggregate expression of each gene as $E_a(i)=\log_2(\text{average}(TPM_{i,1...n})+1)$, and excluded genes with $E_a<4$. For the remaining cells and genes, Applicants defined relative expression by centering the expression levels, $Er_{i,j}=E_{i,j}-\text{average}[E_{i,1...n}]$.

Correlation Analysis of Single-Cell Expression Profiles

Figure 1C:
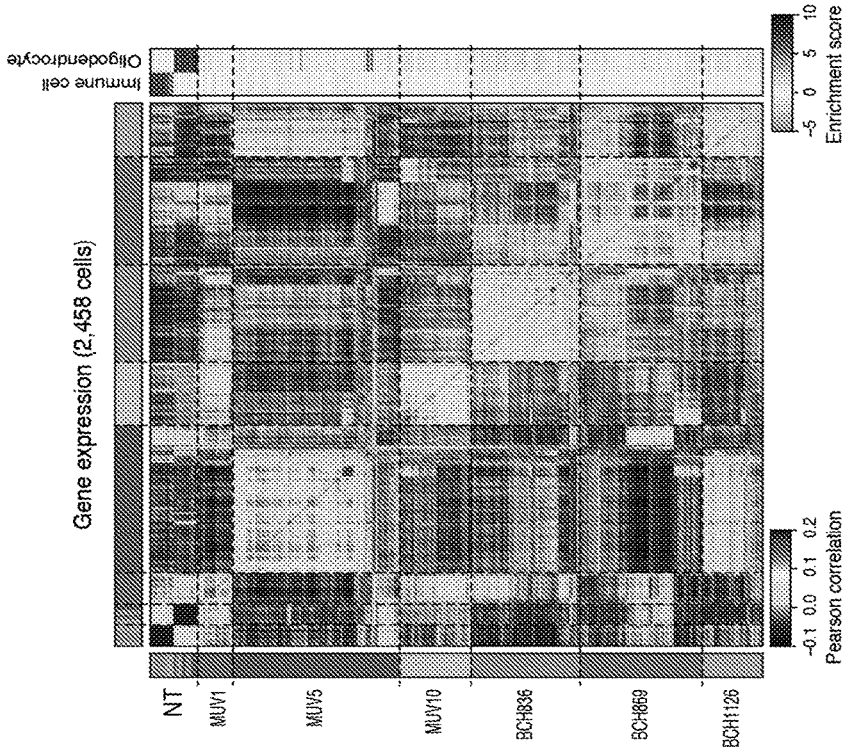
Figure 8A:
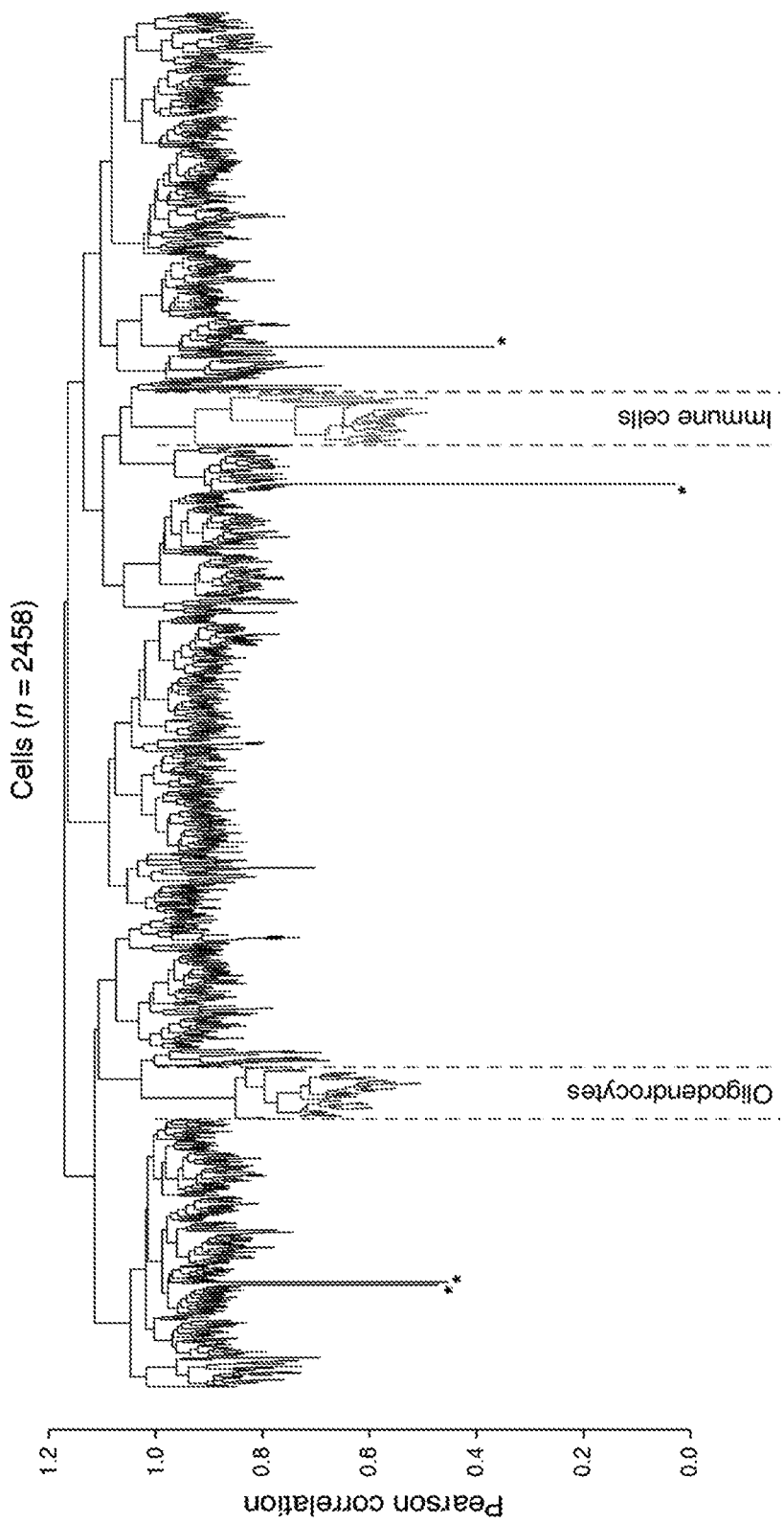
FIG. 8—Unsupervised clustering of H3K27M-glioma single-cell expression data. (A) Hierarchical clustering using 1-Pearson correlation as distance measure and complete linkage of 2,458 cells that pass quality filtering. Two clusters of cells show particularly high cell-to-cell correlations and express markers of non-malignant cell populations (see B for expression, and FIG. 9, 10). Four pairs of cells showed very high correlation (indicated by*), and might reflect a technical artefact, as most of them were located on neighboring wells after flow sorting. These cells were removed from subsequent analysis. (B) Heatmap of relative gene expression levels for genes previously described as markers for microglia and oligodendrocytes. (C) 2D representation of sample correlations by tSNE dimensionality reduction, color-coded by tumor sample as in (B). (D) Identical 2D representation, color-coded for non-malignant cell populations as defined in (A, B). (see also FIG. 1 and FIG. 9, 10 for a more detailed analysis).
Figure 8B:
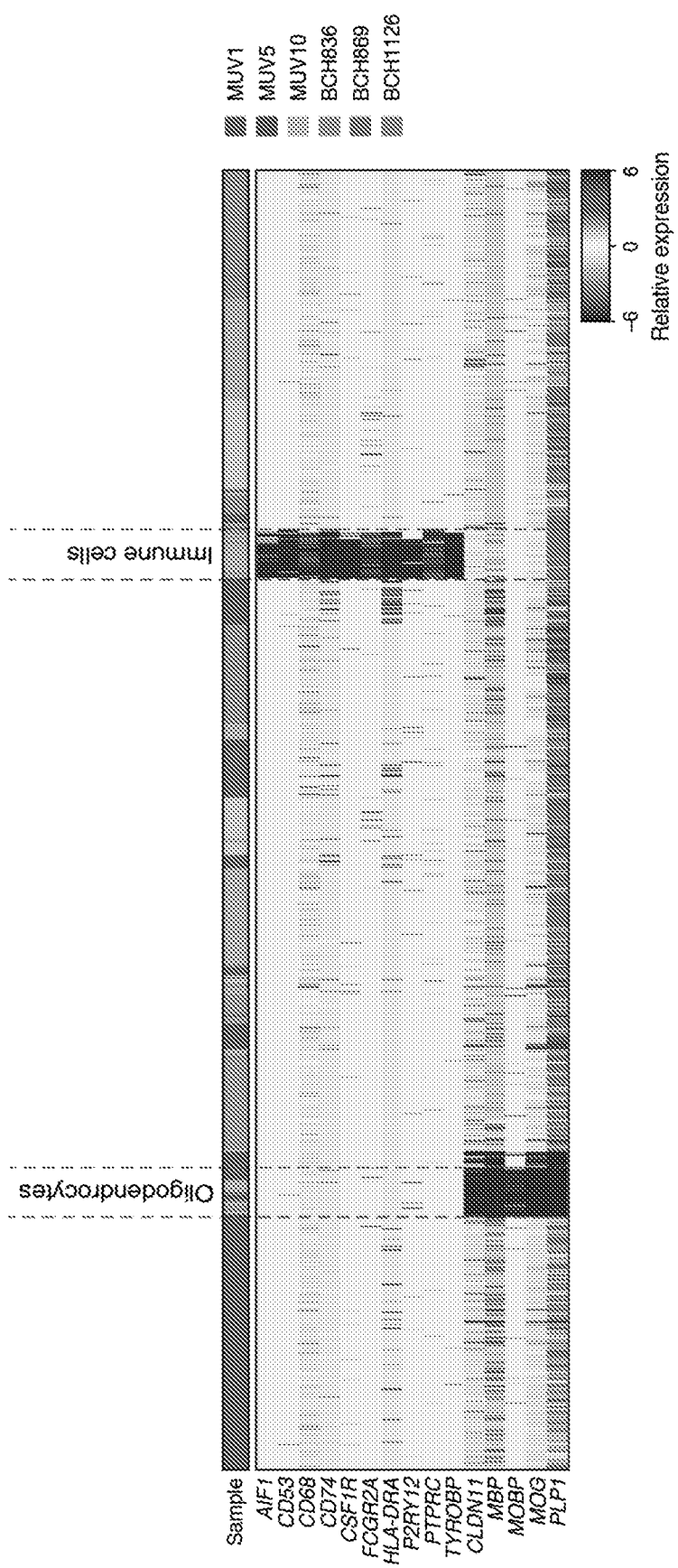
Figure 8D:
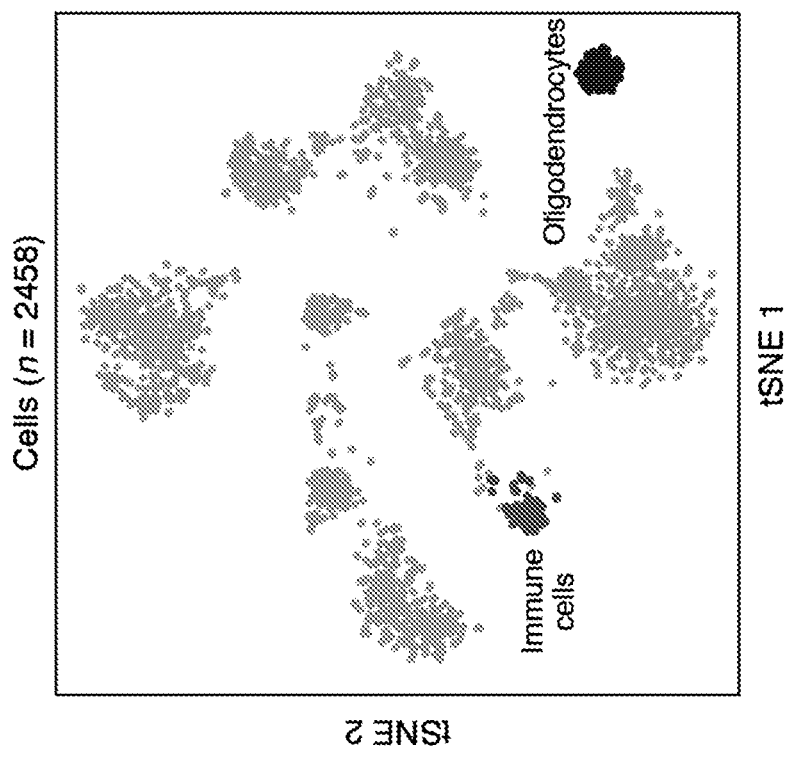
Figure 8C:
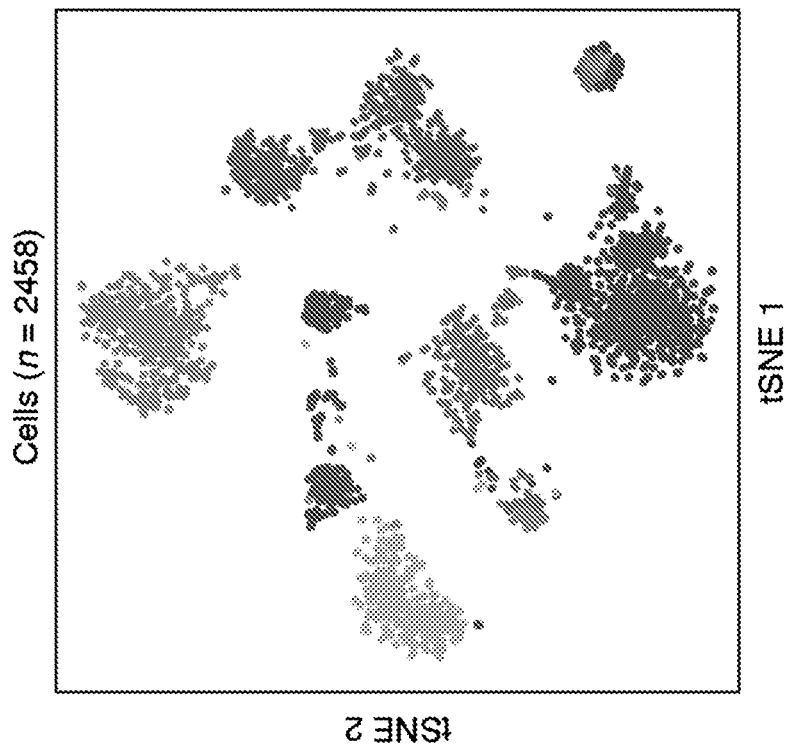
Figure 9B:
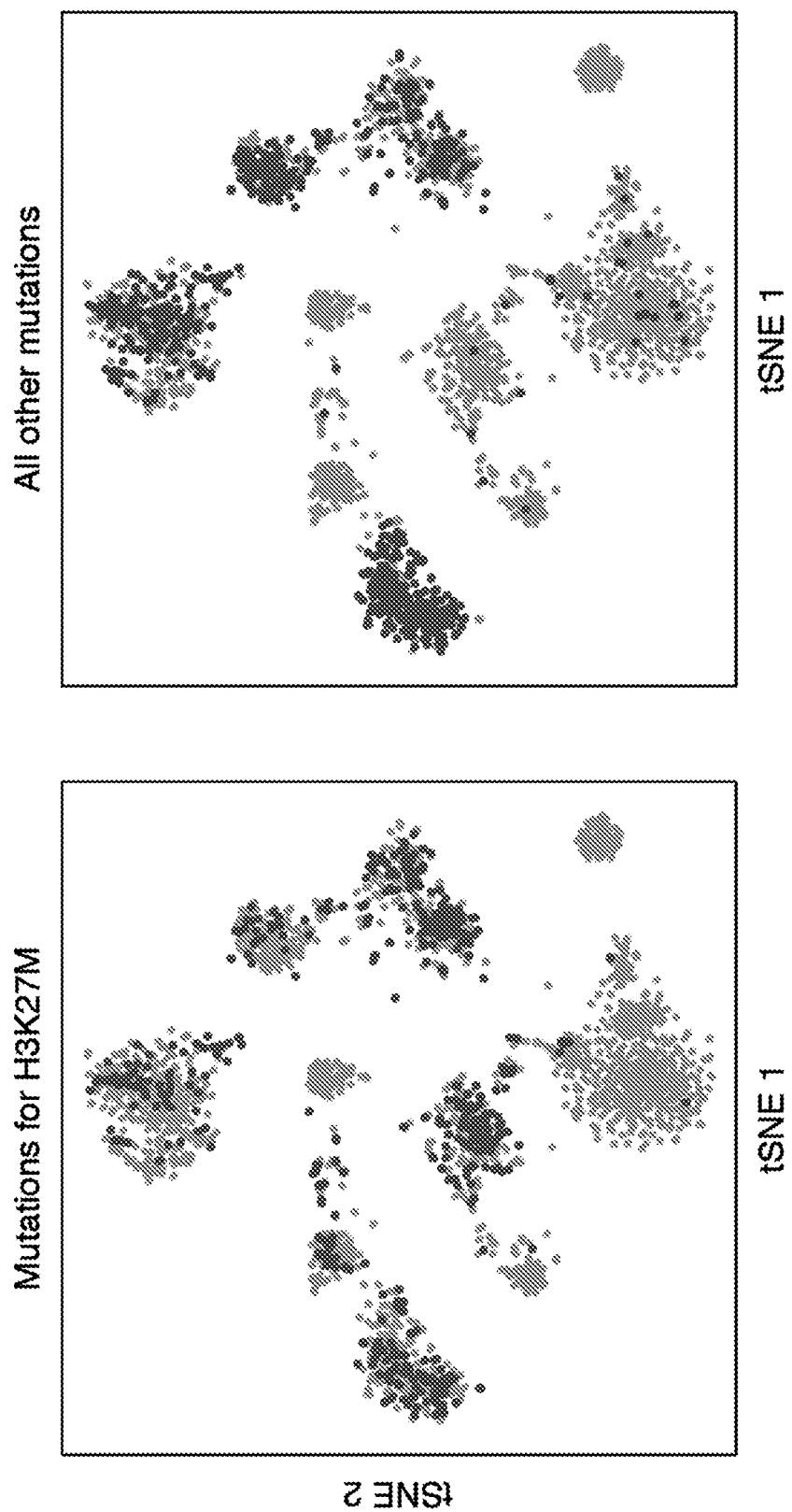

Pearson correlation coefficients between expression profiles of all cells that passed quality filtering was calculated using centered gene expression levels. Cells were ordered by hierarchical clusterin using 1-correlation coefficient as the distance measure and complete linkage across all cells (FIG. 8A), or within each sample and the presumed normal cell types (FIG. 1C). The same distance measure was used for tSNE dimensionality reduction (FIGS. 8C-D, 9B). Applicants used the Rtsne implementation in R (version 3.3.0) with the following non-default parameters: pca=F, is_distance=T.

Definition of Single-Cell Gene Signature Scores

Given a set of genes ($G_j$) reflecting a specific cell type or biological function, Applicants calculate for each cell i, a score, $SC_j(i)$, quantifying the relative expression of $G_j$ in cell i, as the average relative expression (Er) of the genes in $G_j$, compared to the average relative expression of a control gene-set ($G_j^{cont}$): $SC_j(i)=\text{average}[Er(G_j,i)]-\text{average}[Er(G_j^{cont},i)]$. The control gene-set is defined by first binning all analyzed genes into 25 bins of aggregate expression levels and then, for each gene in the considered gene-set, randomly selecting 100 genes from the same expression bin. In this way, the control gene-set has a comparable distribution of expression levels to that of the considered gene-set, and the control gene set is 100-fold larger, such that its average expression is analogous to averaging over 100 randomly-selected gene-sets of the same size as the considered gene-set.

Whole Exome and Whole Genome Sequencing

DNA and RNA was extracted from single core DIPG biopsies using the AllPrep DNA/RNA extraction kit (Qiagen). Whole genome sequencing: DNA was randomly fragmented, and libraries (Kapa Biosciences) prepared for paired-end sequencing (2×150 bp reads) on an Illumina HiSeq 2500. DNA from germline control was sequenced to ×30 coverage and DNA from tumors to ×60 coverage. Whole exome sequencing: fragmented DNA was subjected to library preparation for whole-exome sequencing using the Illumina exome as previously described (42, 43). Flowcell cluster amplification and sequencing were performed according to the manufacturer's protocols using either the HiSeq 2000 v3 or HiSeq 2500. Each run was a 76 bp paired-end with a dual eight-base index barcode read. Tumor DNA was sequenced to ×150 coverage. Output from Illumina software was processed by the Picard processing pipeline to yield BAM files containing aligned reads to the NCBI Human Reference Genome Build hg19 with well-calibrated quality scores (44, 45). Sample contamination by DNA originating from a different individual was assessed using ContEst (46). Somatic single nucleotide variations (sSNVs) were then detected using MuTect (47). Following this standard procedure, Applicants filter sSNVs by (1) removing potential DNA oxidation artifacts (48); (2) removing events seen in sequencing data of a large panel of ~8,000 TCGA normal samples; (3) realigning identified sSNVs with NovoAlign (www.novocraft.com) for WES and with Blat for WGS (49), and performing an additional iteration of MuTect with the newly aligned BAM files. sSNVs were finally annotated using Oncotator (50). Copy-ratio profiles were inferred using ReCAPSEG (gatkforums.broadinstitute.org/gatk/categories/recapseg-documentation). Read depth at capture probes in tumor samples was normalized using a panel of normal samples to model noise and other biases.

Analysis of Point Mutations in Single-Cell Data

To detect gene mutations in the single-cell expression data (FIG. 1D, FIG. 9A-B), sequencing reads were first aligned to the human genome NCBI Human Reference Genome Build hg38 using STAR version 2.5.1b. Gene annotations were supplied to guide alignment. Mutations were then quantified in each cell at the genomic position in which they were detected in the WGS/WES data using the htslib pileup engine as implemented in pysam. To quantify mutant and wild-type alleles Applicants required at least two concordant reads per cell for H3F3A and PDGFRA. For all other genes that are less highly expressed Applicants only required a single read. Applicants then filtered mutations that were not detected in any cell, or that were likely to be erroneously called because they were detected in samples in which they were not detected in the genome sequencing data.

Analysis of CNVs in Single-Cell Data

Figure 9C:
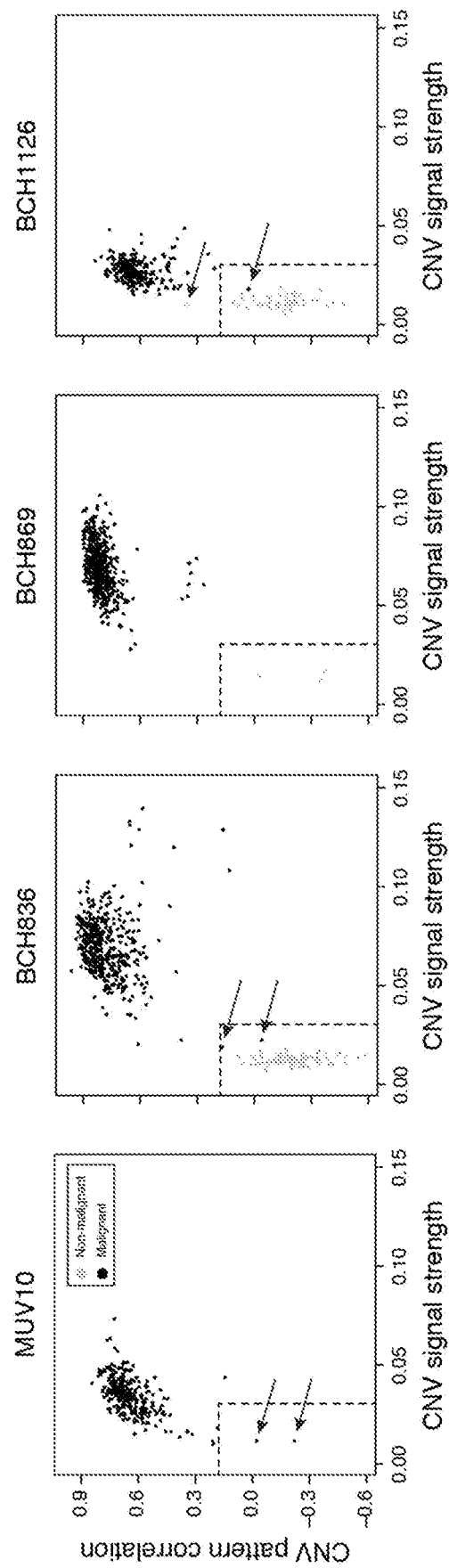

CNVs were estimated by sorting the analyzed genes by their chromosomal location and applying a moving average to the relative expression values, with a sliding window of 100 genes within each chromosome (FIG. 1E). The approach has been previously described (12, 14). To check for agreement in the definition of malignant and non-malignant cells based on gene expression and copy-number alterations, Applicants scored each cell for the extent of CNV signal, defined as the sum of squares of CNV values across the genome, and for the correlation between the CNV profile of each cell with the average CNV profile of all cells from the corresponding tumor that are classified by expression as malignant (FIG. 9C). Applicants defined non-malignant cells as those with CNV signal below 0.03 and CNV pattern correlation below 0.2. Six cells for which expression- and CNV-based definitions did not agree were excluded from subsequent analyses and likely represent less frequent normal cell types.

Definition of Malignant and Non-Malignant Gene Signatures

Figure 10A:
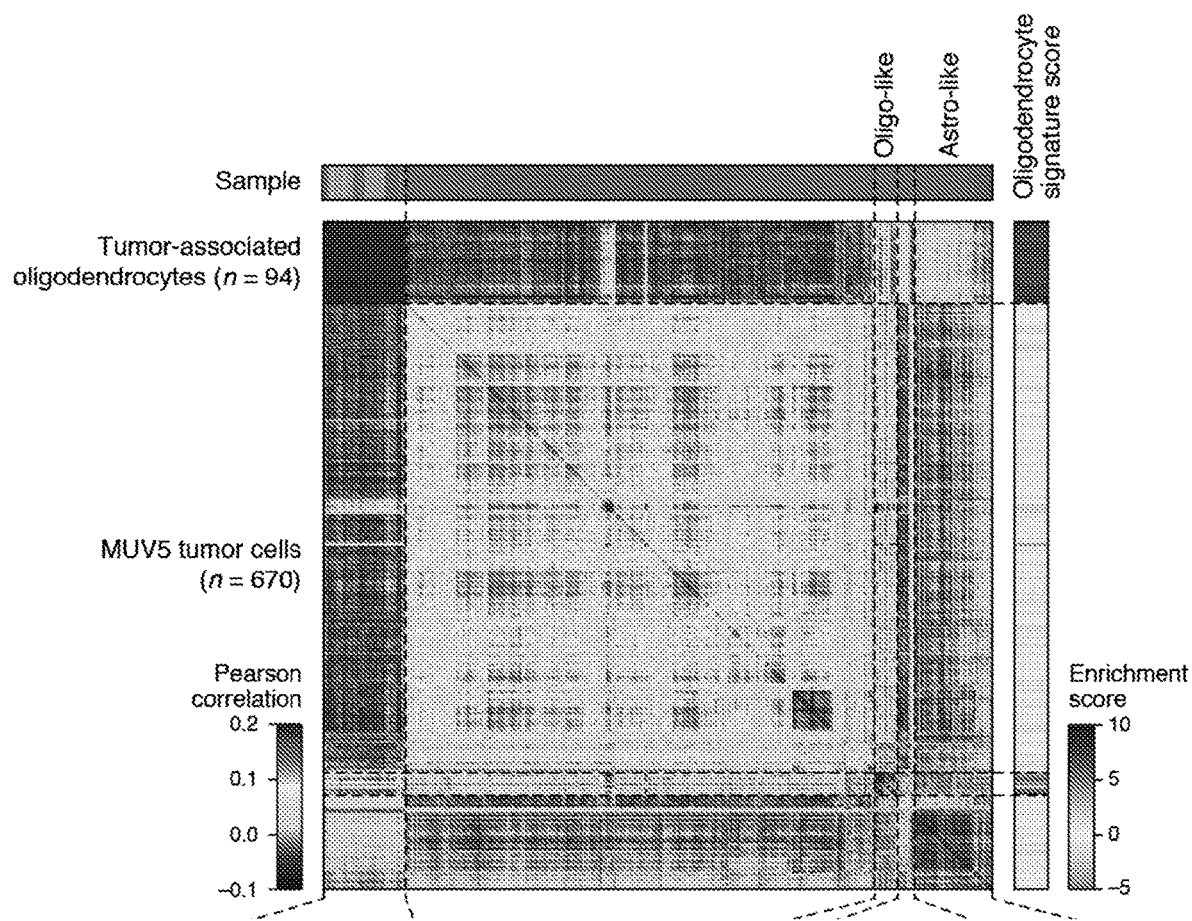
FIG. 10—Detailed analysis of MUV5 cells and non-malignant cells in the cohort. (A) Heatmap representation of cell-to-cell correlations as presented in FIG. 1C, restricted to cells from sample MUV5 and non-malignant oligodendrocytes. MUV5 tumor cells (n=670) form a cluster of 28 cells enriched for oligodendrocytic genes (OC-like cells), and another cluster of 88 cells enriched for astrocytic genes (AC-like cells). (B) Heatmap representation of relative gene expression levels for genes defined as either specific to OC-like cancer cells (from definitive malignant cells with detected genetic alterations), or specific to non-malignant oligodendrocytes, showing that MUV5 OC-like cells are more similar to malignant cells from other tumors than to non-malignant oligodendrocytes (left). Similar heatmap representation for genes specific to AC-like cancer cells (from definitive malignant cells with detected genetic alterations), or non-malignant astrocytes (unpublished), supporting MUV5 AC-like cells are more similar to malignant cells from other tumors than to non-malignant astrocytes (right). (C) Signature scores for gene sets as defined in (B).
Figure 10B:
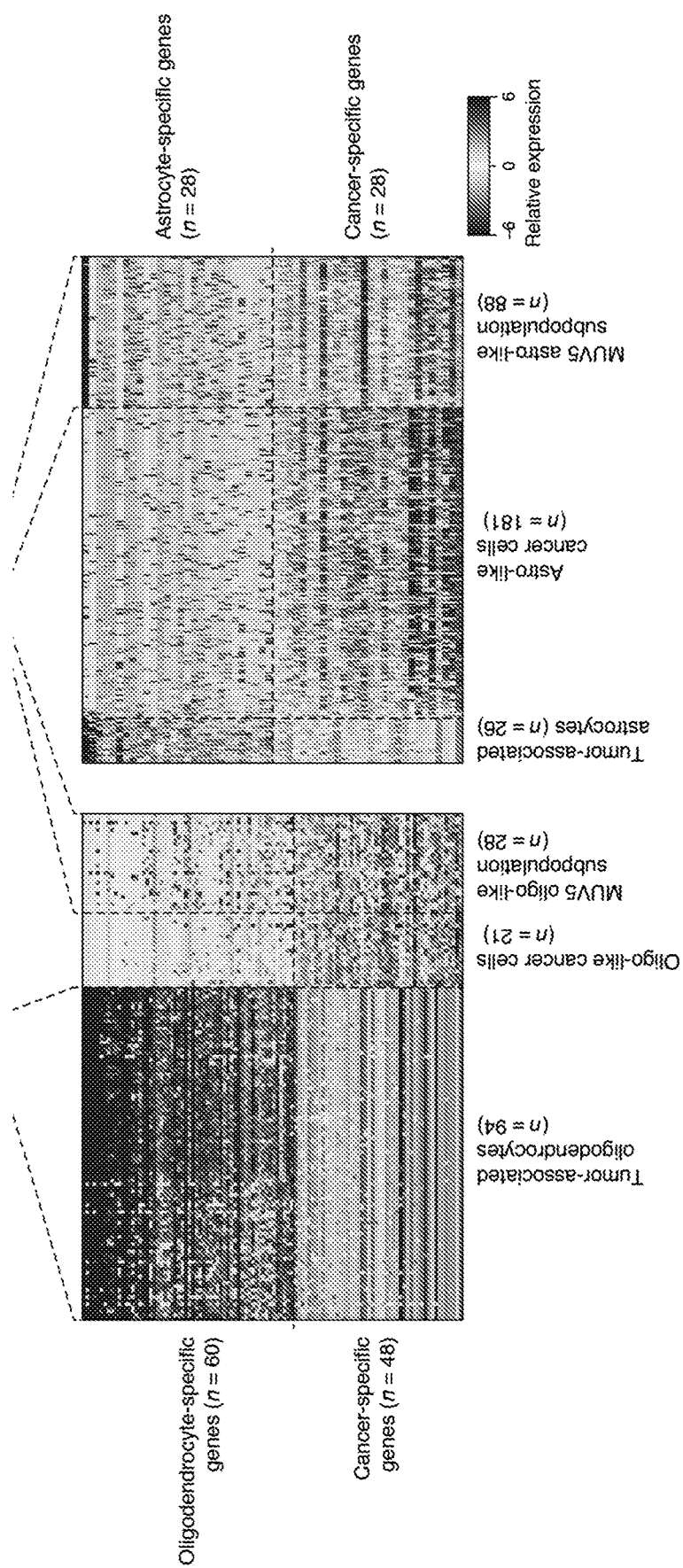
Figure 10C:
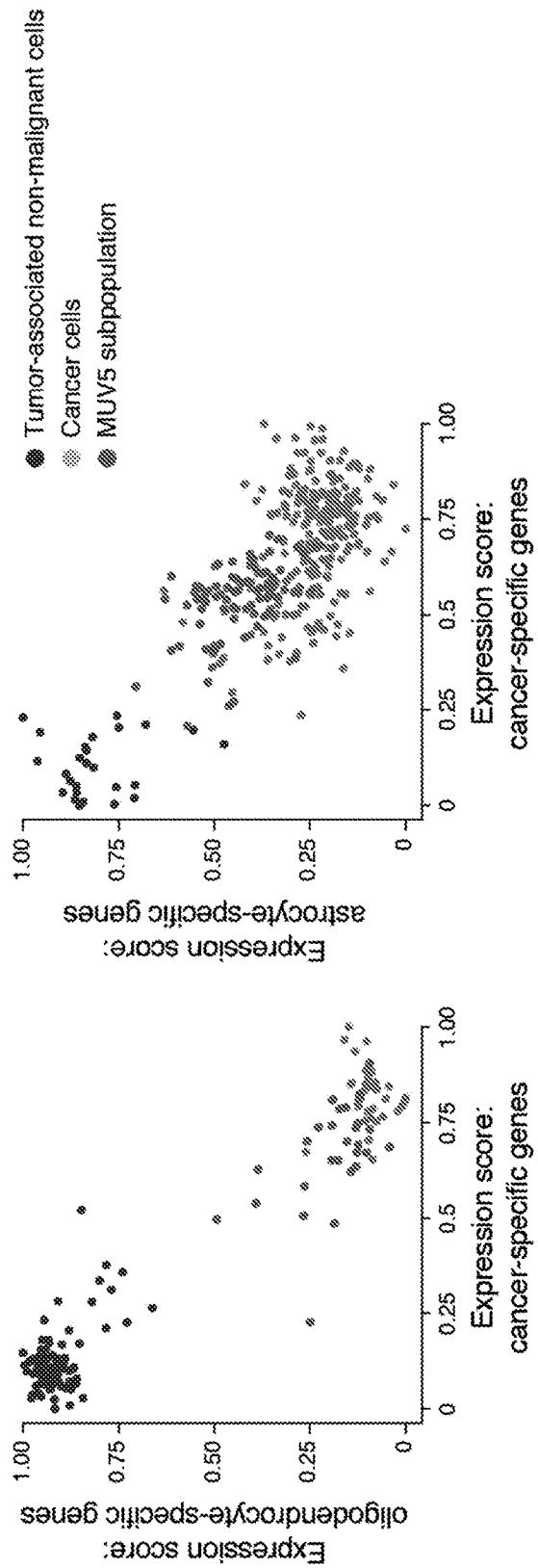

Two subpopulations of cells from the MUV5 tumor that are enriched for oligodendrocytic (n=28 cells) and astrocytic genes (n=88 cells) were analyzed in more detail. To verify their definition as malignant cells, Applicants used definite non-malignant and malignant cells of the respective differentiation lineage from other tumors (as defined in FIG. 3) to generate four separate gene signatures that were then applied to the MUV5 subpopulations (FIG. 10). Gene signatures were generated by applying a permutation test as implemented in the coin package (independence_test function, R version 3.3.0). A P-value threshold of <0.001 was used. To refine signatures, Applicants filtered for genes that were detected in more than 80% of non-malignant oligodendrocytes and less than 20% of OC-like cancer cells, and vice versa. For non-malignant astrocytes and AC-like cancer cells, Applicants used detection thresholds of 70% and 20%.

Identification of Differentially Expressed Genes

When comparing average expression values across tumors (FIG. 2B) Applicants used Analysis of Variance (ANOVA) with an FDR of <0.001, and Tukey's post-hoc test (P-value <0.05) to compare between tumor types as indicated. A complete list of differentially expressed genes is given in Table S3.

When comparing the values of individual cells across tumors and models (FIG. 6), Applicants used (1) a two-fold threshold for the average expression; (2) $P<10^{-4}$ based on a permutation test: Applicants shuffled the assignments of cells to populations 100,000 times and counted the fraction of times where an equal or larger difference was obtained between the two populations; (3) since the different samples vary in the proportions of cells of the same kind of subpopulations (e.g., cycling or differentiated subpopulations), many genes will appear as differentially expressed between samples, although there are no changes in their expression within the same subpopulation in the two samples; Applicants wanted to focus on differentially expressed genes which are not driven by the proportions of small subpopulations but instead are expressed by a large proportion of cells in one sample more highly than the highest-expressing cells in the other sample; Applicants thus added a third criterion that at least 30% of the cells in one sample express the gene more highly than the 5% highest expressing cells of the other sample; the rationale for not further increasing this threshold beyond 30% is that genes are often "dropped-out" (i.e., not detected despite being expressed) by a subset of cells in each sample and hence a higher threshold would exclude many genes. This analysis was repeated for each pairwise comparison of sample types, and genes are included in FIG. 6F and Table S5 in each of the comparisons for which they were significant such that the same gene may appear twice; the total number of differentially expressed genes (across the four comparisons) was 641, corresponding to 519 unique genes.

Identification of Intra-Tumor Variability Programs Using NNMF

For each of the six tumors, Non-Negative Matrix Factorization (as implemented by the Matlab nnmf function, with number of factors set to 10) was applied to the centered expression data of malignant cells from that tumor, after converting all negative values to zero. For each of the resulting 10 factors, Applicants considered the 30 genes with highest NNMF scores as a signature for scoring of a variable expression program in that tumor (see "Definition of single-cell gene signature scores"). Applicants then aggregated the 60 signatures across the 6 tumors. All malignant cells (across tumors) were then scored for each of the 60 programs. The NNMF programs and the malignant cells were then each ordered by hierarchical clustering (FIG. 3A), revealing three correlated sets of programs (P1, P2 and P3) corresponding to cell cycle and two differentiation programs. For each of those sets, Applicants ranked genes by their correlation with the average cell scores of the programs in the set, and used the top 30 genes to redefine the scores for the three meta-programs.

Applicants then searched for genes preferentially expressed in the remaining cells that do not score highly for any of these three meta-programs. For each of the three meta-programs, Applicants calculated average fold-change and permutation p-value between all cells that score for that program (score>1) and the fourth subpopulation of cells that do not score for any of the programs (score<0.5) and defined differentially expressed genes with a fold-change>2 and FDR<0.05. No genes were significantly higher in the fourth subpopulation than in all three subpopulations; 20 genes were significantly higher in the fourth subpopulation than in two of the three subpopulations, and, of these, 19 were significantly higher in the fourth subpopulation than in the AC-like and OC-like cells, but not the cycling cells; these 19 genes were defined as the OPC-shared program.

To identify expression programs that vary within the fourth subpopulation, Applicants performed principal component analysis (PCA) for cells of the fourth subpopulation from each of the six tumors. Applicants focused on the first two principal components (PCs) in each tumor, and excluded PCs that appear to be dominated by technical quality based on a high correlation (R>0.4) with the number of detected genes per cell. Of the remaining 7 PCs, 3 PCs from distinct tumors were correlated in their gene loadings (R>0.25) and were all associated with high PDGFRA expression, which was the highest scoring gene for two of these three PCs. Notably, apart from PDGFRA, the other top scoring genes for these three PCs were also preferentially expressed by OPCs (FIG. 12, Table 10). Applicants thus defined an OPC-variable expression program, as the top 30 genes based on average loadings over these three PCs (FIG. 12, Table S4).

Lineage and Stemness Score of Individual Malignant Cells

Cells are first ordered by their stemness, defined as expression of the OPC-shared program minus the maximal expression of the two differentiation programs, and the differentiated cells are further classified by a lineage score distinguishing the oligodendrocytic from astrocytic lineages (FIG. 3D).

Comparison Between Lineage and Stemness Programs of H3K27M-Gliomas and IDH-Mutant Gliomas To enable a direct comparison between H3K27M, IDH-A and IDH-O gliomas Applicants combined the malignant cells from all tumors which were processed by the same protocols, and centered the expression of each gene across all cells in the combined dataset. Applicants then scored all cells for the lineage and stemness programs defined here and in previous studies of IDH-A and IDH-O glioma (the gene-sets of IDH-A and IDH-O (14, 15) were combined to define IDH glioma gene-sets). This approach—scoring all cells for gene-sets of both H3K27M- and IDH-mutant gliomas—enabled us to test the specificity of gene-sets to glioma types; Applicants found that the AC-like gene-sets are comparable and highlight the same cells in each of the glioma types, while OC-like and stem-like gene-sets showed specificity, with H3K27M-gliomas scoring primarily for H3K27M gene-sets and vice versa (FIG. 4A). To further compare the expression programs between tumor types Applicants identified, for each program (AC-like, OC-like and stem-like) and in each tumor type, Applicants used the cells that score highly for that program (score>1) and the cells that score lowly for that program (score<0), to define the average expression differences between those subsets and to focus on differentially expressed genes with fold-change above 4 in at least one of the tumor types. Applicants then defined differentially expressed genes which are common (i.e. with fold-change above 2 in the three tumor types), H3K27M-specific (with fold-change above 4 in H3K27M, and less than 1.5 in both IDH-mutant tumors) and IDH-mutant specific (with fold-change above 3 in both IDH-mutant tumors but less than 1.5 in H3K27M). Finally, Applicants defined the fraction of undifferentiated cells in each tumor as those with score <1 for both the AC-like and OC-like programs of the respective tumor type.

Genetic Intra-Tumor Heterogeneity by Haplotype Analysis

Figure 14A:
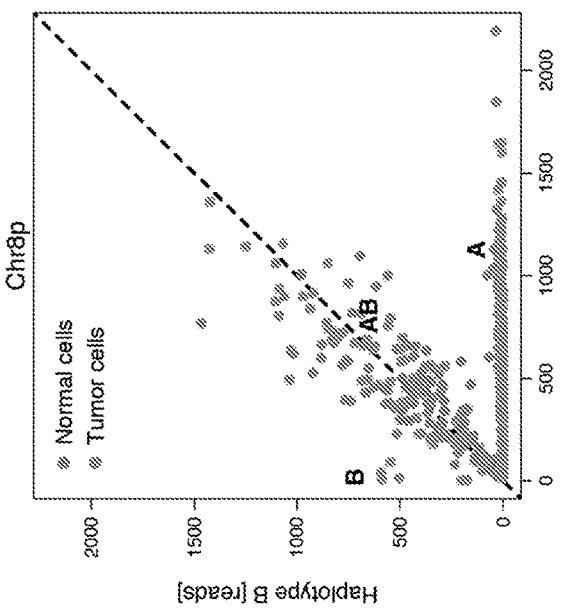
FIG. 14—Combined CNV and haplotype analysis from scRNA-seq data. (A) Flowchart illustrating the computational approach: Patient-specific heterozygous SNPs are defined from germline control WGS data (displaying a normal karyotype). (B, C) The allele frequencies of the heterozygous SNPs in the tumor WGS data are then used to phase haplotypes of chromosomes or sub-chromosomal regions that show copy-number variations (e.g. gains and losses, as colored). Rare events, such as copy-number neutral loss-of-heterozygosity of chr17q (harboring TP53, which is mutated in this patient), are also detected. (D) The allele frequency of the combined SNPs of each haplotype are then calculated from the scRNA-seq data. Chromosome 8p is shown as an example, in which most tumor cells score for haplotype A, few tumor cells score for haplotype B, and a number of cells tumor score for both haplotypes, as do the normal cells in this tumor. The combined analysis of single-cell derived CNV profiles and haplotypes frequencies improves the ability to define genetic subclones and helps the inference of their evolutionary relationships.
Figure 14B:
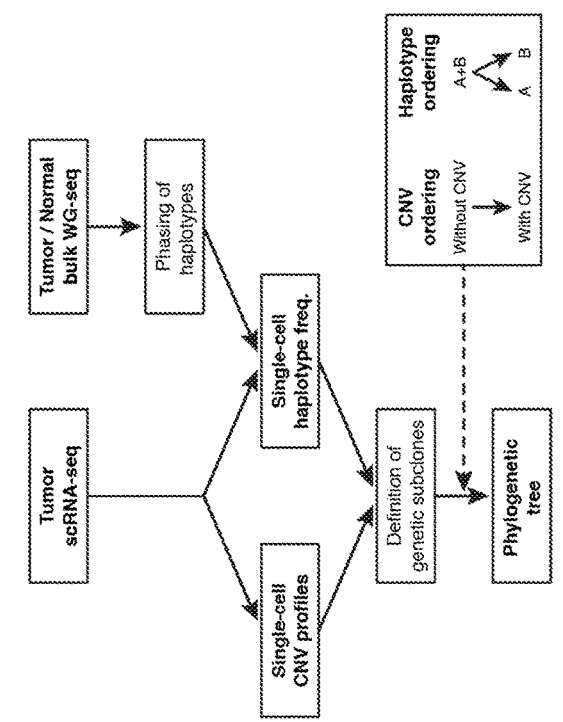

For the inference of haplotypes from single-cell data Applicants used high-coverage whole-genome sequencing data from both germline (i.e. blood) and tumor samples from two patients that showed multiple subclonal CNVs (BCH836 and BCH869). For each patient, Applicants first called variants from germline DNA using samtools mpileup (version 1.3, arguments -ug) and bcftools call (version 1.1, arguments -vm). Applicants then excluded sites with quality less the 30 using bcftools filter, and retained only heterozygous SNPs using bcftools view (arguments -v snps -m2 -M2 -g het). Remaining positions were called from both germline and tumor samples (single biopsy for BCH836, biopsy and six different tumor regions from autopsy tissue for BCH869) using samtools mpileup (arguments -v -t DP,AD -max-depth 1000000). The resulting vcf files were processed in R (version 3.3.0) with the VariantAnnotation Bioconductor package (version 1.18.7). For each patient, positions with less than 0.5 or more than 1.5-fold coverage in the germline sample compared to the genome average were excluded. Next, positions with an allele frequency less than ¼ or more than ¾ in the germline sample were excluded. Remaining positions (≥2 million) were considered high-confidence heterozygous SNPs and used for subsequent analysis. For phasing of haplotypes, Applicants considered SNP allele frequencies in the tumor samples in chromosomal or sub-chromosomal regions that showed broad copy-number variations (FIG. 14B, C). SNPs were phased into haplotypes based on the frequency of reference and alternate alleles. For patient BCH869, for which Applicants profiled a biopsy and six different tumor regions from autopsy tissue, Applicants chose the sample that provided the best separation of alleles for a given genomic region. Applicants excluded SNPs that showed an allele frequency between 0.45 and 0.55, as these could not be confidently resolved. Using this approach, typically ≥10,000 SNPs were combined in a haplotype.

Figure 14D:
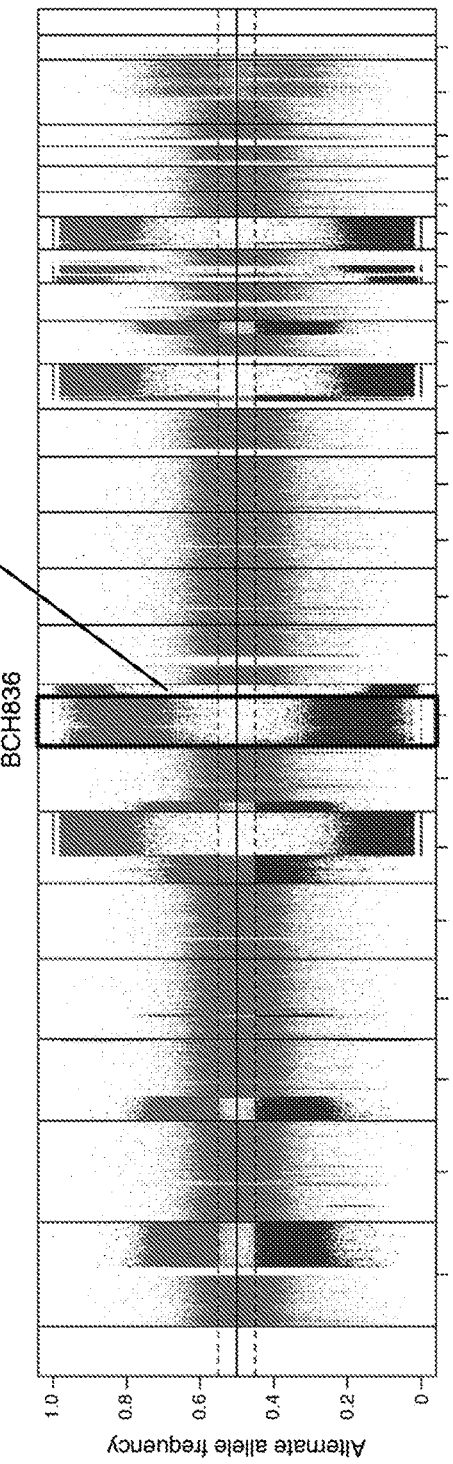
Figure 14C:
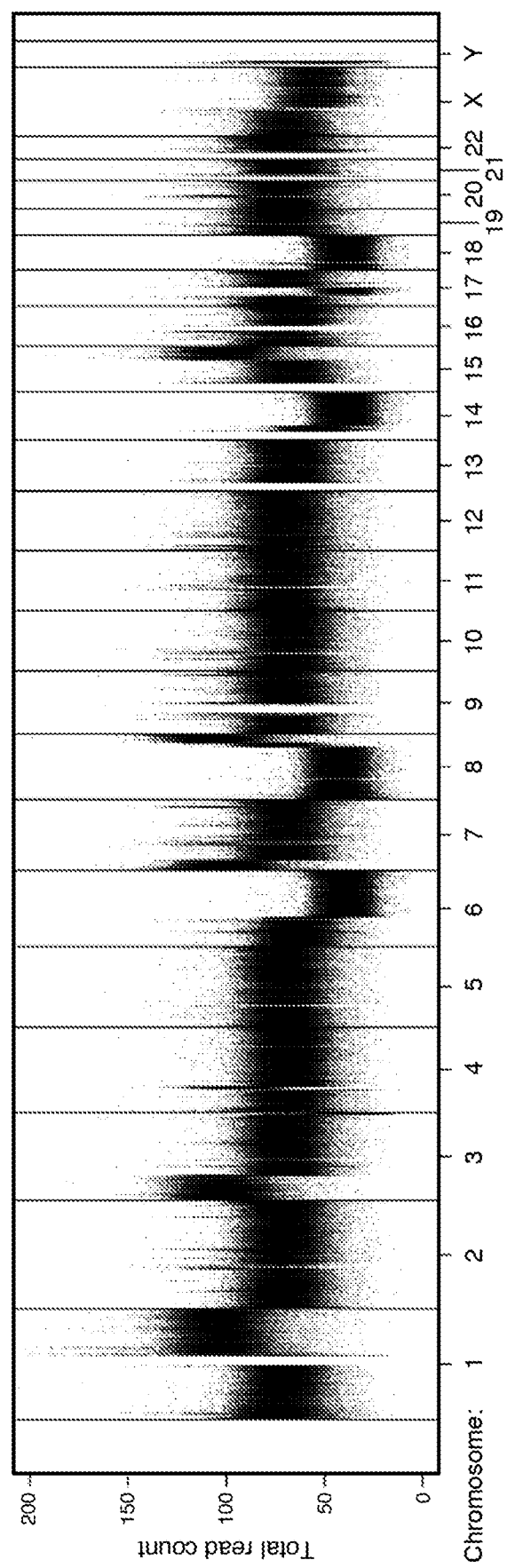

To account for the much sparser and more uneven coverage of SNPs in the single-cell RNA-seq data, Applicants jointly quantified all SNPs in each haplotype: First, the single-cell reads were aligned to the hg19 reference genome using STAR (version 2.5.2b), guided by gene annotations. Second, allele read counts for all SNPs as defined above were generated using samtools mpileup (arguments -v -t DP,AD -max-depth 1000000). Third, read counts supporting each haplotype were summed up for each genomic region and each single cell (FIG. 14D). In this way, depending on the size of the region and the prevalence of expressed heterozygous SNPs in the respective sample, up to thousands of supporting reads were combined, providing accurate estimates of haplotype frequencies at the single-cell level.

Single-cell haplotype frequencies were jointly analyzed with CNV profiles to define tumor subclones (FIG. 5). Subclones were first defined by hierarchical clustering of a distance matrix derived from genome-wide haplotype frequencies and CNV profiles, and then further refined by considering only select chromosomal regions that differ between subclones. In many instances, haplotype frequencies provided additional information that enabled inference of a more parsimonious phylogenetic tree. For example, haplotypes cannot be regained after they have been lost, indicating the existing of an unobserved common ancestor to all observed subclones in both analyzed tumors.

RNA In Situ Hybridization

Paraffin-embedded tissue sections from human tumors from Boston Children's Hospital, the Medical University of Vienna, Austria, the Medical University of Ljubljana, Slovenia, and Hospital Sant Joan de Deu Barcelona, Spain, were obtained according to Institutional Review Board-approved protocols. Sections were mounted on glass slides and stored at −80° C. Slides were stained using the RNAscope 2.5 HD Duplex Detection Kit (Advanced Cell Technologies, Cat. No. 322430). Slides were baked for 1 hour at 60° C., deparaffinized and dehydrated with xylene and ethanol. The tissue was pretreated with RNAscope Hydrogen Peroxide (Cat. No. 322335) for 10 minutes at room temperature and RNAscope Target Retrieval Reagent (Cat. No. 322000) for 15 minutes at 98° C. RNAscope Protease Plus (Cat. No. 322331) was then applied to the tissue for 30 minutes at 40° C. Hybridization probes were prepared by diluting the C2 probe (red) 1:50 into the C1 probe (green). Advanced Cell Technologies RNAscope Target Probes used included Hs-MKI67 (Cat. No. 591771-C2; 591771), Hs-PDGFRA (Cat. No. 604481-Cs) and Hs-ApoE (Cat.No 433091). Probes were added to the tissue and hybridized for 2 hours at 40° C. A series of 10 amplification steps were performed using instructions and reagents provided in the RNAscope 2.5 HD Duplex Detection Kit. Tissue was counterstained with Gill's hematoxylin for 25 seconds at room temperature followed by mounting with VectaMount mounting media (Vector Laboratories).

Cell Culture

Human H3K27M glioma cell lines (BCH869, BCH245, DIPG012) were derived from patients treated at Boston Children's Hospital, Massachusetts General Hospital and Hospital Sant Joan de Deu Barcelona, Spain according to Institutional Review Board-approved protocols. Human IDH-wildtype glioblastoma lines MGG4 and MGG6 were previously characterized (26, 51). For all functional experiments, H3K27M cell cultures were grown as gliomaspheres in Tumor Stem Medium (TSM) base supplemented with B27 Minus Vitamin A, EGF, FGF, PDGFA, PDGFB and heparin (28). All GBM cell cultures were grown as gliomaspheres in Neurobasal Medium, supplemented with N2 supplement, B27 supplement, Glutamax, Pen/Strep (all Life Technologies), EGF and FGF (Shenandoah Biotechnology INC). For adherent conditions, cells were either (i) cultured in TSM base supplemented with 7.5% or 10% Fetal Bovine Serum (Atlas Biologicals) in TC-treated flasks or (ii) cultured in gliomasphere TSM base supplemented with B-27 Minus Vitamin A+/−EGF, FGF, PDGFA, PDGFB and heparin in non-TC treated flasks. Viability was determined by CellTiter-Glo Luminescent Cell Viability Assay (Promega) at the end of treatment (day 7 or day 10). For drug treatment experiments, PTC-209 (SML1142, Sigma-Aldrich) and Crenolanib (CP-868596, Selleckchem) were suspended in DMSO and used at the concentrations indicated.

Intracranial Xenotransplantation

The primary H3K27M-glioma cell line BCH869, grown as gliomasphere or under adherent conditions in 10% serum were injected stereotactically into the right striatum of 5 weeks-old female NSG mice (NOD.Cg-Prkdcscid Il2rgtm1Wjl/SzJ, The Jackson Laboratory, Bar Harbor, ME). Briefly, mice were anesthetized with 2% isoflurane mixed with medical air, and placed on a stereotactic frame. The skull of the mouse was exposed through a small skin incision, and a small burr hole was made using a 25-gauge needle at the selected stereotactic coordinates. The BCH869 cells (100,000 or 200,000 cells in 2 µL PBS) were loaded on a 33-gauge Hamilton syringe, and injected slowly using the following coordinates: 2.0 mm lateral of the bregma, and 2 mm deep to the cortical surface of the brain. Upon completing injection, the needle was left in place for another minute, then withdrawn slowly to help reduce cell reflux. After closing the scalp with suture and staple, mice were returned to their cages placed on a warming pad and visually monitored until full recovery. Mice were then checked daily for signs of distress, including seizures, ataxia, weight loss, and tremors, and euthanized as they developed neurological symptoms, including head tilt, seizures, sudden weight loss, loss of balance, and ataxia. All animal studies were performed according to Dana-Farber Cancer Institute Institutional Animal Care and Use Committee (IACUC)-approved protocols.

Small Animal MRI

MRI experiments were performed on a Bruker BioSpec 7T/30 cm USR horizontal bore Superconducting Magnet System (Bruker Corp., Billerica, MA) equipped with the B-GA12S2 gradient and integrated with up to $2^{nd}$ order room temperature shim system, which provides a maximum gradient amplitude of 440 mT/m and slew rate of 3440 T/m/s. The Bruker-made 23 mm ID birdcage volume radiofrequency (RF) coil was used for both RF excitation and receiving. The Bruker AutoPac with laser positioning was used for accurate definition of the region of interest. Animals were anesthetized with 1.5% isoflurane mixed in medical air at a flow rate of 2 L/min. Body temperature was maintained at 37° using a warm air fan. A pressure-transducer for respiratory gating was placed on the abdomen. Animal respiration and temperature were monitored and regulated by the SAII (Sa Instruments Inc., Stony Brook, NY) monitoring and gating system model 1025T. Bruker Paravision 6.0.1 was used for MRI data acquisition. T2-weighted images were obtained by a fast spin echo (RARE) sequence with fat suppression using the following parameters: TR=6000 ms, TE=36 ms, FOV=19.2×19.2 mm$^2$, matrix size=256×192, spatial resolution=75×100 µm$^2$, slice thickness=0.5 mm, number of slices=29, rare factor=15, number of averages=8, acquisition time 7 min. Images were analyzed and tumor volumes extracted using the semi-automatic segmentation analysis software ClinicalVolumes (ClinicalVolumes, London, UK). Osirix imaging software was used to generate 3D reconstructed images.

Cas9-Mediated Gene Knockout

CrisprRNA and tracerRNA were synthesized by Integrated DNA Technologies (Coralville, IA) and co-incubated to form guide RNA (gRNA) complexes (95° C. for 5 minutes) based on the manufacturer's instructions). gRNA complexes were incubated with Cas9 protein (provided by QB3 Macrolab, University of California Berkeley, Berkeley, CA) at 37° C. for 15 minutes to assemble ribonucleoprotein (RNP) complexes. Next, RNP complexes (3 µL) were electroporated together with corresponding single-stranded homology-directed repair (HDR) oligonucleotides (200 pmol) into the indicated cells lines using a 4D-Nucleofector 96-well shuttle system (Lonza Group LTD, Basel, Switzerland) with program DS-150. Genomic DNA was extracted from electroporated cells at the indicated time points and the relevant DNA segments were amplified by polymerase chain reaction (PCR) to assess the efficiency of editing. The PCR products were purified from 1% agarose gels using MinElute Gel Extraction columns (Qiagen, Hilden, Germany). Purified DNA was analyzed by Sanger sequencing (Quintarabio, South San Francisco, CA). The efficiency of Cas9-mediated gene editing was determined by comparing DNA sequences from cells electroporated with control RNPs (Cas9 and scrambled gRNA) or target RNPs (Cas9+ gene-specific gRNA) using Tracking of Indels by Decomposition (TIDE) analysis (52).

CrisprRNA Sequences and Ultramer Repair Templates

CrisprRNA (crRNA) were 20 nucleotides in length and were obtained from Integrated DNA Technologies with the following sequences: BMI1-3: ACCACTACT-GAATATAAGGT (SEQ. I.D. No. 4); BMI1-5: CAAAGCACACACATCAGGTG (SEQ. I.D. No. 5); PDG-FRA-1: TGTGACTTTCGCCAAAGTGG (SEQ. I.D. No. 6); PDGFRA-5: GTAACCTTACACAACAGTGA (SEQ. I.D. No. 7). Homology directed repair (HDR) templates were obtained from Integrated DNA Technologies as single stranded ultramers that were 192 nucleotides in length with the following sequences specific for the following crRNA cut sites:

BMI1-3 HDR:

(SEQ. I.D. No. 8)
TAGTCTGTAAAACGTGTATTGTTCGTTACCTGGAGACCAGCAAGTATTGT

CCTATTTGTGATGTCCAAGTTCACAAGACCAGACCACTACTAGTTAGCTA

ACAGGAAACTGTTGAAATTCCTTGTTTGTAATTATTATTGGAGTTGTATA

ATTTACTGAAGGCAACCCTCTTTATTTCTTCACAGAAAATTT;

BMI1-5 HDR:

-continued (SEQ. I.D. No. 9)
ATTATGGCCATTATTTCTGTGTCTTGCAGGATTTTTTATCAAGCAGAAAT

GCATCGAACAACGAGAATCAAGATCACTGAGCTAAATCCCTAAACCGGTT

AAGTGCTTTGTGGAGGGTACTTCATTGATGCCACAACCATAATAGAATGT

CTACATTCCTGTAAGTACCGAGCTTTAGCTCTCTTTTGTATC;

PDGFRA-1 HDR:
(SEQ. I.D. No. 10)
CTTCCTGGACTATTTTGGCCAACAATGTCTCAAACATCATCACGGAGATC

CACTCCCGAGACAGGAGTACCGTGGAGGGCCGTGTGACTTTAGATAGCTA

ACAGGAGACCATCGCCGTGCGATGCCTGGCTAAGAATCTCCTTGGAGCTG

AGAACCGAGAGCTGAAGCTGGTGGCTCCCAGTGAGTTCCTCA;

PDGFRA-5 HDR:
(SEQ. I.D. No. 11)
AGGAATGACGGATTATTTAGTCATCGTGGAGGATGATGATTCTGCCATTA

TACCTTGTCGCACAACTGATCCCGAGACTCCTGTAACCTTTAGTTAGCTA

ACGGGGGTGGTACCTGCCTCCTACGACAGCAGACAGGGCTTTAATGGGAC

CTTCACTGTAGGGCCCTATATCTGTGAGGCCACCGTCAAAGG.

The following oligonucleotides were used to amplify the edited DNA segment for Sanger sequencing and TIDE analysis. BMI1 FWD: GGGGATTGTGTGGCGTCTG (SEQ. I.D. No. 12); BMI1 REV: TAGGGAATAAAGAG-GAATGGAAGCC (SEQ. I.D. No. 13); BMI1-3 Sequencing: TGTTGGTACAAAGTGGTGAAG (SEQ. I.D. No. 14); BMI1-5 Sequencing: AGTTTGGTAGAACTGAT-TCCG (SEQ. I.D. No. 15). PDGFRA-1 FWD: CTGAG-GATCATCGCAACCCT (SEQ. I.D. No. 16); PDGFRA-1 REV: GGGCAGACACCTCTACTTCAT (SEQ. I.D. No. 17); PDGFRA-1 Sequencing: AGACAAGGTCC-CAACTCCTTGCCAT (SEQ. I.D. No. 18). PDGFRA-5 FWD: TCCATCAGGAGACAGGCAAT (SEQ. I.D. No. 19); PDGFRA-5 REV: TAGGGCCGCCATAGTCAGGA (SEQ. I.D. No. 20); PDGFRA-5 Sequencing: TCAATAATGCCAGTGGGATAG (SEQ. I.D. No. 21).

Tables

TABLE S1

Clinical and molecular characteristics of six H3K27M-glioma samples profiled by scRNA-seq.

| Patient ID | Age [years] | Gender | Survival [months] | Location | K27M mutation | Additional oncogene mutations |
|---|---|---|---|---|---|---|
| MUV1 | 4 | F | >22 | Thalamus | H3F3A | BRAF (V600E) |
| MUV5 | 2.5 | M | >19 | Pons | HIST1H3B | none detected |
| MUV10 | 9 | F | 8 | Thalamus | H3F3A | ASXL1, PDGFRA |
| MUV17 | 12 | F | 6 | Pons | H3F3A | NA |
| BCH836 | 5 | F | 3.5 | Pons | H3F3A | ACVR1, PIK3CA, TP53 |
| BCH869 | 7 | F | 10.5 | Pons | H3F3A | ACVR1, PIK3CA, PPM1D |
| BCH1126 | 10 | F | >8 | Pons | H3F3A | NA |

TABLE S2

Single-cell cohort characteristics
The number of detected mutations is provided for all genes as described in FIG. 9A.

| Sample | High-quality cells | Immune cells | Oligodendrocytes | Filtered cells | Tumor cells | Genome sequencing | Cancer gene mutations | Detetcted mutations in tumor cells |
|---|---|---|---|---|---|---|---|---|
| MUV1 | 146 | 1 | 4 | 0 | 141 | WES | H3F3A.K27M, BRAF.V600E | 41 |
| MUV5 | 708 | 2 | 36 | 3 | 667 | WES | HIST1H3B.K27M | 21 |
| MUV10 | 286 | 0 | 0 | 3 | 283 | WES | H3F3A.K27M, ASXL1.R693*, PDGFRA.K385L | 250 |
| BCH836 | 527 | 53 | 34 | 2 | 438 | WGS | H3F3A.K27M, ACVR1.G328E, PIK3CA.H1047R, TP53.N288fs | 218 |
| BCH869 | 492 | 1 | 2 | 0 | 489 | WGS | H3F3A.K27M, ACVR1.R206H, PIK3CA.E39K, PIK3CA.G1007R, PPM1D.Q510fs | 290 |
| BCH1126 | 299 | 38 | 18 | 2 | 241 | NA | H3F3A.K27M | 103 |
| Total | 2,458 | 95 | 94 | 10 | 2,259 | | | |

TABLE S3

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| HENMT1 | 5.73 | 0.01 | 0.32 | 0.04 | 2.7E−18 | K27M high |
| MEOX2 | 0.10 | 6.77 | 0.17 | 0.10 | 4.7E−17 | GBM high |
| FAM162B | 4.51 | 0.00 | 0.18 | 0.08 | 2.8E−12 | K27M high |
| VAX2 | 0.01 | 2.01 | 4.23 | 4.65 | 3.2E−12 | K27M low |
| TSTD1 | 0.53 | 7.19 | 0.69 | 0.64 | 5.1E−12 | GBM high |
| OCIAD2 | 6.81 | 8.59 | 0.86 | 0.24 | 2.4E−11 | GBM high |
| EMP3 | 3.11 | 7.60 | 0.18 | 0.14 | 4.2E−11 | GBM high |
| CPQ | 3.57 | 4.98 | 0.10 | 0.34 | 4.2E−11 | GBM high |
| CRYGD | 5.17 | 0.00 | 0.03 | 0.00 | 1.3E−10 | K27M high |
| ATF7IP2 | 2.84 | 0.03 | 0.13 | 0.13 | 2.0E−10 | K27M high |
| SNAP91 | 4.54 | 0.06 | 5.02 | 5.81 | 2.3E−10 | IDH-O high & GBM low |
| MYL12A | 6.53 | 7.36 | 0.90 | 1.05 | 3.6E−10 | IDH-WT high |
| SWAP70 | 4.33 | 5.39 | 1.37 | 1.56 | 1.0E−09 | GBM high |
| DRG2 | 5.51 | 5.40 | 1.91 | 6.25 | 1.2E−09 | IDH-A low |
| NEFM | 4.22 | 0.04 | 1.52 | 1.01 | 1.3E−09 | K27M high & GBM low |
| FBXO17 | 4.28 | 4.97 | 1.51 | 1.39 | 2.6E−09 | IDH-WT high |
| GALNT13 | 4.45 | 0.56 | 6.27 | 6.17 | 3.2E−09 | GBM low |
| PLEKHG4 | 4.35 | 0.23 | 0.46 | 0.22 | 3.2E−09 | K27M high |
| CHRNA9 | 0.05 | 2.74 | 0.03 | 0.05 | 3.9E−09 | GBM high |
| B3GNT7 | 5.81 | 2.81 | 1.24 | 1.07 | 4.3E−09 | K27M high |
| ECHDC2 | 5.37 | 4.65 | 1.22 | 0.87 | 4.3E−09 | IDH-WT high |
| SOX10 | 6.63 | 0.47 | 1.45 | 1.18 | 4.3E−09 | K27M high |
| STPG1 | 2.89 | 0.32 | 0.06 | 0.08 | 4.3E−09 | K27M high |
| THBS2 | 4.64 | 5.08 | 1.81 | 5.81 | 4.3E−09 | IDH-A low |
| TOM1L1 | 4.41 | 3.66 | 0.15 | 0.26 | 4.3E−09 | IDH-WT high |
| SEMA3E | 5.62 | 0.99 | 0.60 | 0.71 | 4.5E−09 | K27M high |
| RAB3C | 5.14 | 0.10 | 4.05 | 5.90 | 4.6E−09 | GBM low |
| NUDT7 | 3.95 | 0.31 | 3.43 | 5.16 | 5.1E−09 | IDH-O high & GBM low |
| CASP1 | 0.68 | 4.38 | 0.24 | 0.02 | 5.3E−09 | GBM high |
| FRMD4B | 3.93 | 1.91 | 0.53 | 1.76 | 6.4E−09 | K27M high & IDH-A low |
| C2orf40 | 5.28 | 0.04 | 0.22 | 0.05 | 7.1E−09 | K27M high |
| NIPSNAP3B | 2.94 | 0.72 | 0.14 | 0.17 | 7.5E−09 | K27M high |
| C6orf15 | 0.01 | 6.12 | 0.02 | 0.07 | 1.2E−08 | GBM high |
| ACSS3 | 2.81 | 5.28 | 0.20 | 0.22 | 1.5E−08 | GBM high |
| TMBIM1 | 5.37 | 6.06 | 1.68 | 2.09 | 1.5E−08 | IDH-WT high |
| TMEM246 | 5.74 | 0.39 | 5.73 | 6.38 | 2.2E−08 | GBM low |
| TRAM1L1 | 5.67 | 0.00 | 4.25 | 4.86 | 2.5E−08 | GBM low |
| CHI3L1 | 3.71 | 10.66 | 0.28 | 0.81 | 2.5E−08 | GBM high |
| HVCN1 | 3.42 | 3.33 | 0.95 | 0.48 | 2.5E−08 | IDH-WT high |
| SMOC1 | 7.37 | 0.43 | 8.25 | 8.40 | 2.6E−08 | GBM low |
| ROR2 | 2.61 | 0.03 | 0.18 | 0.01 | 4.4E−08 | K27M high |
| BCAT1 | 5.46 | 6.33 | 1.55 | 0.99 | 5.1E−08 | IDH-WT high |
| CPNE7 | 1.78 | 0.00 | 0.18 | 0.30 | 5.1E−08 | K27M high |
| BOK | 3.95 | 0.08 | 0.45 | 0.37 | 5.4E−08 | K27M high |
| SLC6A15 | 5.37 | 0.03 | 1.06 | 0.39 | 5.8E−08 | K27M high |
| STXBP1 | 6.03 | 3.87 | 6.77 | 7.25 | 6.7E−08 | GBM low |
| FKBP5 | 4.35 | 6.83 | 1.61 | 1.61 | 7.4E−08 | GBM high |
| MEGF10 | 4.67 | 0.26 | 0.59 | 0.75 | 7.4E−08 | K27M high |
| UCP2 | 5.43 | 3.41 | 0.36 | 0.36 | 8.5E−08 | K27M high |
| ARHGAP25 | 3.03 | 3.39 | 0.09 | 0.02 | 8.9E−08 | IDH-WT high |
| ARL9 | 3.04 | 2.58 | 0.32 | 0.09 | 1.1E−07 | IDH-WT high |
| PHACTR3 | 6.94 | 0.92 | 7.00 | 6.91 | 1.1E−07 | GBM low |
| CARD16 | 0.12 | 4.35 | 0.05 | 0.06 | 1.2E−07 | GBM high |
| TMEFF2 | 5.70 | 0.80 | 8.00 | 7.36 | 1.3E−07 | GBM low |
| FAM26F | 3.14 | 0.25 | 0.16 | 0.23 | 1.4E−07 | K27M high |
| LOC100127983 | 4.80 | 4.29 | 1.05 | 0.65 | 1.4E−07 | IDH-WT high |
| PDPN | 3.98 | 7.89 | 0.48 | 0.41 | 1.4E−07 | GBM high |
| PPP1R1C | 2.78 | 4.93 | 0.46 | 1.35 | 1.4E−07 | GBM high & IDH-A low |
| ANXA5 | 8.77 | 10.68 | 7.32 | 7.53 | 1.4E−07 | GBM high |
| SDC4 | 4.24 | 6.03 | 0.42 | 0.84 | 1.4E−07 | GBM high |
| TAGLN2 | 7.48 | 8.71 | 3.57 | 3.53 | 1.6E−07 | IDH-WT high |
| EDARADD | 3.05 | 0.22 | 0.13 | 0.57 | 1.6E−07 | K27M high |
| DPP4 | 0.81 | 3.75 | 0.18 | 0.12 | 1.7E−07 | GBM high |
| LRRC4C | 6.46 | 2.79 | 5.99 | 7.50 | 1.7E−07 | IDH-O high & GBM low |
| PTPN14 | 4.01 | 3.84 | 1.49 | 1.17 | 1.9E−07 | IDH-WT high |
| SEL1L3 | 5.33 | 0.96 | 1.08 | 0.50 | 1.9E−07 | K27M high |
| PTRF | 2.19 | 5.35 | 1.40 | 0.42 | 2.0E−07 | GBM high & IDH-O low |
| DSCAML1 | 4.00 | 0.84 | 5.30 | 5.47 | 2.1E−07 | GBM low |
| FZD6 | 4.90 | 2.21 | 0.33 | 0.50 | 2.1E−07 | K27M high |
| PPAP2C | 5.69 | 0.92 | 0.63 | 2.27 | 2.1E−07 | K27M high |
| TRIP4 | 4.45 | 4.97 | 0.73 | 4.43 | 2.1E−07 | IDH-A low |
| SLC2A10 | 3.34 | 4.67 | 0.71 | 0.46 | 2.2E−07 | GBM high |
| MDGA2 | 4.36 | 0.44 | 4.90 | 4.92 | 2.2E−07 | GBM low |
| AOX1 | 2.97 | 0.30 | 0.33 | 0.23 | 2.2E−07 | K27M high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| EVA1C | 2.52 | 4.23 | 1.09 | 0.44 | 2.6E−07 | GBM high |
| RANBP17 | 3.77 | 0.02 | 4.01 | 4.15 | 2.9E−07 | GBM low |
| MTAP | 4.70 | 1.05 | 4.61 | 4.43 | 2.9E−07 | GBM low |
| RTN1 | 8.71 | 1.34 | 8.85 | 9.86 | 2.9E−07 | GBM low |
| NETO1 | 4.42 | 0.01 | 4.15 | 3.38 | 4.0E−07 | GBM low |
| RIN1 | 2.05 | 4.62 | 0.59 | 1.20 | 4.3E−07 | GBM high |
| PCDH15 | 6.81 | 1.22 | 7.84 | 6.64 | 4.3E−07 | GBM low |
| SGCD | 4.31 | 0.05 | 2.69 | 2.56 | 4.3E−07 | K27M high & GBM low |
| TENM3 | 3.90 | 1.12 | 0.23 | 0.11 | 4.3E−07 | K27M high |
| RGS7 | 3.12 | 0.18 | 2.24 | 3.69 | 4.5E−07 | GBM low |
| SULT1A1 | 5.04 | 3.43 | 0.78 | 1.24 | 4.5E−07 | K27M high |
| CTHRC1 | 6.66 | 0.77 | 0.87 | 1.32 | 4.5E−07 | K27M high |
| MTPAP | 5.99 | 4.50 | 6.58 | 6.31 | 4.5E−07 | GBM low |
| SHISA7 | 5.17 | 0.36 | 4.56 | 4.89 | 4.5E−07 | GBM low |
| ACADL | 3.92 | 1.14 | 0.64 | 0.05 | 4.6E−07 | K27M high |
| CHRFAM7A | 2.91 | 0.78 | 0.37 | 0.84 | 4.6E−07 | K27M high |
| PINLYP | 4.66 | 5.59 | 0.90 | 0.82 | 4.7E−07 | IDH-WT high |
| C6orf141 | 0.60 | 3.81 | 0.12 | 0.04 | 5.1E−07 | GBM high |
| ITGA7 | 4.04 | 7.09 | 1.69 | 2.98 | 5.1E−07 | GBM high & IDH-A low |
| CDHR1 | 3.20 | 1.06 | 4.78 | 6.31 | 5.7E−07 | IDH-O high & GBM low |
| LGALS3 | 5.36 | 9.92 | 2.03 | 2.30 | 5.7E−07 | GBM high |
| MARCH1 | 4.82 | 1.26 | 5.23 | 5.02 | 5.9E−07 | GBM low |
| SNAI1 | 2.77 | 0.88 | 0.52 | 0.19 | 6.1E−07 | K27M high |
| NMU | 4.68 | 0.00 | 0.75 | 0.39 | 6.4E−07 | K27M high |
| BASP1 | 5.14 | 0.29 | 4.78 | 5.09 | 6.7E−07 | GBM low |
| GABRB3 | 5.38 | 0.34 | 4.65 | 5.60 | 6.7E−07 | GBM low |
| JPH4 | 3.70 | 0.78 | 3.99 | 4.54 | 6.7E−07 | GBM low |
| TUSC3 | 5.20 | 0.01 | 4.47 | 5.12 | 6.7E−07 | GBM low |
| GYPC | 4.59 | 3.50 | 0.26 | 0.11 | 6.8E−07 | IDH-WT high |
| ST6GALNAC3 | 3.87 | 0.05 | 1.91 | 1.87 | 6.8E−07 | K27M high & GBM low |
| SLC35G2 | 5.17 | 6.59 | 1.53 | 1.67 | 7.0E−07 | IDH-WT high |
| C10orf11 | 3.78 | 1.71 | 0.06 | 0.12 | 7.2E−07 | K27M high |
| GPR85 | 3.98 | 0.10 | 3.65 | 4.15 | 7.2E−07 | GBM low |
| OSMR | 3.51 | 5.61 | 1.62 | 1.46 | 7.8E−07 | GBM high |
| KCNC2 | 0.26 | 0.00 | 0.20 | 3.03 | 8.1E−07 | IDH-O high |
| RIPPLY2 | 3.19 | 0.34 | 3.47 | 4.17 | 8.1E−07 | GBM low |
| PPP5C | 5.87 | 6.71 | 6.13 | 5.01 | 9.2E−07 | GBM high & IDH-O low |
| VRK2 | 4.36 | 1.29 | 0.28 | 0.48 | 9.2E−07 | K27M high |
| MT1M | 5.31 | 6.22 | 0.28 | 0.93 | 9.3E−07 | IDH-WT high |
| RGS22 | 2.88 | 1.11 | 0.03 | 0.01 | 9.3E−07 | K27M high |
| NECAB1 | 3.99 | 3.43 | 1.03 | 0.96 | 9.6E−07 | IDH-WT high |
| SLC30A10 | 3.49 | 0.02 | 0.17 | 0.40 | 9.6E−07 | K27M high |
| UNC93B1 | 0.81 | 2.65 | 0.53 | 0.35 | 1.0E−06 | GBM high |
| GDAP1L1 | 5.26 | 2.09 | 5.76 | 6.61 | 1.1E−06 | GBM low |
| RBP4 | 4.84 | 0.00 | 0.21 | 0.72 | 1.1E−06 | K27M high |
| DNM3 | 6.28 | 1.72 | 6.30 | 5.64 | 1.1E−06 | GBM low |
| CD58 | 5.00 | 6.83 | 1.72 | 0.37 | 1.1E−06 | IDH-WT high |
| TNNT1 | 3.24 | 0.08 | 0.91 | 4.64 | 1.1E−06 | IDH-O high |
| TNFRSF1A | 4.46 | 6.61 | 0.76 | 0.93 | 1.2E−06 | GBM high |
| DCTD | 6.12 | 6.45 | 4.13 | 0.20 | 1.2E−06 | IDH-O low |
| NOS2 | 1.13 | 4.81 | 0.89 | 0.71 | 1.2E−06 | GBM high |
| FZD5 | 2.22 | 4.81 | 1.45 | 0.98 | 1.2E−06 | GBM high |
| FKBP9 | 5.58 | 7.79 | 3.06 | 2.19 | 1.3E−06 | GBM high |
| OR4N2 | 0.23 | 0.02 | 5.56 | 0.97 | 1.3E−06 | IDH-A high |
| CLIC1 | 2.37 | 8.39 | 0.67 | 0.39 | 1.3E−06 | GBM high |
| VAMP5 | 3.88 | 6.25 | 1.42 | 2.77 | 1.3E−06 | GBM high & IDH-A low |
| SLC30A3 | 3.85 | 0.59 | 0.43 | 0.14 | 1.4E−06 | K27M high |
| CLGN | 5.20 | 0.06 | 4.66 | 4.40 | 1.4E−06 | GBM low |
| MMP14 | 1.77 | 3.59 | 0.37 | 0.07 | 1.4E−06 | GBM high |
| SCP2 | 8.28 | 8.34 | 8.43 | 6.80 | 1.4E−06 | IDH-O low |
| KIAA0040 | 2.67 | 4.01 | 0.58 | 0.13 | 1.5E−06 | GBM high |
| ATCAY | 6.67 | 3.56 | 6.71 | 7.92 | 1.6E−06 | IDH-O high & GBM low |
| PION | 2.53 | 4.90 | 0.40 | 0.51 | 1.7E−06 | GBM high |
| WIPF3 | 2.90 | 4.05 | 0.74 | 0.98 | 1.7E−06 | IDH-WT high |
| PENK | 5.41 | 0.35 | 0.70 | 0.26 | 1.7E−06 | K27M high |
| DGKI | 4.12 | 1.04 | 3.89 | 3.84 | 1.8E−06 | GBM low |
| LGALS8 | 4.80 | 4.27 | 1.93 | 1.69 | 1.8E−06 | IDH-WT high |
| SSH3 | 2.98 | 3.04 | 0.27 | 0.33 | 1.8E−06 | IDH-WT high |
| CPVL | 4.47 | 7.33 | 0.81 | 5.58 | 2.2E−06 | IDH-A low |
| GPX8 | 0.78 | 3.29 | 0.73 | 0.71 | 2.3E−06 | GBM high |
| ASB13 | 5.13 | 3.36 | 5.38 | 5.82 | 2.4E−06 | GBM low |
| SERBP1 | 7.04 | 6.51 | 6.46 | 5.49 | 2.4E−06 | IDH-O low |
| SLC27A2 | 3.19 | 0.00 | 0.01 | 0.25 | 2.4E−06 | K27M high |
| HDHD3 | 2.33 | 3.56 | 0.24 | 0.13 | 2.5E−06 | IDH-WT high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| ENPP1 | 2.57 | 1.19 | 1.21 | 1.22 | 2.5E−06 | K27M high |
| ACAN | 3.51 | 0.08 | 0.14 | 0.81 | 2.9E−06 | K27M high |
| SERPINH1 | 4.47 | 6.38 | 1.81 | 0.56 | 2.9E−06 | GBM high |
| NFKBIZ | 4.52 | 6.52 | 1.93 | 1.54 | 3.1E−06 | GBM high |
| SHD | 3.81 | 1.67 | 6.78 | 6.78 | 3.1E−06 | GBM low |
| EFEMP2 | 4.93 | 6.57 | 1.55 | 1.41 | 3.1E−06 | IDH-WT high |
| GPR133 | 1.65 | 0.01 | 0.13 | 0.29 | 3.3E−06 | K27M high |
| POP4 | 4.51 | 5.78 | 4.53 | 3.86 | 3.5E−06 | GBM high & IDH-O low |
| DUSP26 | 5.59 | 1.05 | 6.24 | 7.00 | 3.6E−06 | GBM low |
| PLA2G5 | 0.97 | 5.38 | 0.18 | 0.00 | 3.7E−06 | GBM high |
| TPPP3 | 5.72 | 6.05 | 2.11 | 2.21 | 3.7E−06 | IDH-WT high |
| XKR8 | 3.48 | 3.16 | 0.60 | 0.67 | 3.7E−06 | IDH-WT high |
| KHNYN | 3.17 | 4.03 | 2.33 | 2.05 | 3.7E−06 | GBM high |
| CTSC | 5.94 | 4.83 | 3.76 | 3.58 | 3.9E−06 | K27M high |
| SLC7A14 | 2.14 | 1.07 | 2.23 | 4.22 | 3.9E−06 | IDH-O high & GBM low |
| CCNY | 3.60 | 1.88 | 3.82 | 3.74 | 4.1E−06 | GBM low |
| ANKS1B | 6.30 | 0.46 | 5.09 | 5.84 | 4.2E−06 | GBM low |
| GUCY1A3 | 3.86 | 0.43 | 0.59 | 2.64 | 4.2E−06 | K27M high |
| VIM | 8.21 | 11.82 | 7.91 | 1.76 | 4.2E−06 | GBM high & IDH-O low |
| CASP4 | 2.25 | 4.79 | 0.08 | 0.21 | 4.3E−06 | GBM high |
| NMI | 3.90 | 5.63 | 2.32 | 2.54 | 4.3E−06 | GBM high |
| CHRNA1 | 0.91 | 6.18 | 0.13 | 0.99 | 4.4E−06 | GBM high |
| EMP1 | 3.75 | 7.16 | 1.62 | 0.20 | 4.4E−06 | GBM high |
| CYR61 | 5.53 | 7.18 | 3.72 | 0.82 | 4.4E−06 | IDH-O low |
| LRRC20 | 3.51 | 1.73 | 3.58 | 4.13 | 4.4E−06 | IDH-O high & GBM low |
| FNDC3B | 4.04 | 4.77 | 2.71 | 2.18 | 4.5E−06 | IDH-WT high |
| METTL7B | 2.50 | 9.34 | 1.36 | 0.46 | 4.5E−06 | GBM high |
| SERP2 | 4.64 | 2.22 | 4.83 | 5.66 | 4.6E−06 | IDH-O high & GBM low |
| SLITRK1 | 4.87 | 0.64 | 5.55 | 5.69 | 4.6E−06 | GBM low |
| TMEM97 | 6.19 | 5.50 | 5.75 | 7.60 | 4.6E−06 | IDH-O high |
| TTF2 | 3.25 | 4.14 | 2.26 | 1.62 | 4.6E−06 | GBM high & IDH-O low |
| DOK6 | 2.17 | 0.14 | 2.83 | 2.82 | 4.6E−06 | GBM low |
| KCTD14 | 0.81 | 5.00 | 1.45 | 2.03 | 4.6E−06 | GBM high |
| TRPM3 | 1.60 | 5.31 | 0.34 | 0.71 | 4.7E−06 | GBM high |
| PPA1 | 9.17 | 7.47 | 8.88 | 9.02 | 4.7E−06 | GBM low |
| RCAN1 | 4.68 | 8.45 | 3.77 | 3.73 | 4.8E−06 | GBM high |
| ELMO1 | 6.29 | 1.68 | 7.12 | 7.40 | 4.9E−06 | GBM low |
| MCF2L2 | 2.29 | 1.20 | 3.81 | 3.53 | 4.9E−06 | GBM low |
| ATP5F1 | 8.04 | 8.04 | 7.94 | 7.16 | 4.9E−06 | IDH-O low |
| THRA | 5.01 | 3.46 | 6.88 | 6.65 | 4.9E−06 | GBM low |
| C1orf114 | 5.56 | 3.88 | 3.16 | 2.51 | 4.9E−06 | K27M high |
| ATP6V0A4 | 2.37 | 0.00 | 0.12 | 0.17 | 5.0E−06 | K27M high |
| CAV2 | 4.62 | 1.46 | 1.76 | 1.58 | 5.0E−06 | K27M high |
| FBLN2 | 4.34 | 0.01 | 0.80 | 0.55 | 5.0E−06 | K27M high |
| TUBB4A | 6.48 | 1.96 | 6.54 | 6.57 | 5.0E−06 | GBM low |
| SMAD7 | 2.32 | 0.21 | 2.85 | 3.12 | 5.1E−06 | GBM low |
| CAPG | 2.78 | 5.30 | 0.51 | 0.47 | 5.3E−06 | GBM high |
| CMKLR1 | 0.26 | 0.01 | 0.70 | 2.89 | 5.3E−06 | IDH-O high |
| GNG5 | 7.69 | 9.08 | 6.76 | 4.79 | 5.3E−06 | GBM high & IDH-O low |
| STEAP1 | 3.45 | 3.22 | 0.36 | 1.54 | 5.3E−06 | IDH-A low |
| MGST2 | 2.86 | 4.48 | 0.17 | 0.45 | 5.6E−06 | IDH-WT high |
| SLC8A3 | 3.16 | 0.18 | 3.27 | 4.09 | 5.6E−06 | GBM low |
| G0S2 | 4.54 | 5.10 | 0.69 | 0.53 | 5.6E−06 | IDH-WT high |
| ABCC3 | 0.35 | 3.55 | 0.33 | 0.09 | 5.9E−06 | GBM high |
| CEP112 | 3.30 | 4.67 | 1.10 | 0.11 | 6.1E−06 | IDH-WT high |
| TGFB2 | 4.02 | 4.72 | 0.88 | 0.78 | 6.2E−06 | IDH-WT high |
| FAM89A | 4.68 | 0.00 | 2.09 | 0.50 | 6.4E−06 | K27M high |
| CD63 | 8.89 | 11.10 | 8.35 | 8.57 | 6.4E−06 | GBM high |
| COCH | 5.39 | 0.49 | 1.55 | 0.55 | 6.4E−06 | K27M high |
| GNAI1 | 6.92 | 3.07 | 7.06 | 6.91 | 6.5E−06 | GBM low |
| OSR1 | 4.94 | 1.07 | 1.13 | 0.34 | 6.5E−06 | K27M high |
| POLR2F | 6.03 | 5.49 | 7.60 | 7.97 | 6.5E−06 | IDH-mut high |
| PPAPDC1A | 5.72 | 0.38 | 4.18 | 5.43 | 6.5E−06 | GBM low |
| SLC44A5 | 4.32 | 0.44 | 4.36 | 2.36 | 6.5E−06 | GBM low |
| AJUBA | 1.14 | 3.96 | 1.30 | 0.23 | 6.7E−06 | GBM high |
| ALCAM | 7.32 | 4.00 | 8.16 | 7.92 | 6.7E−06 | GBM low |
| FAM155A | 4.18 | 0.82 | 4.04 | 5.55 | 6.7E−06 | IDH-O high & GBM low |
| IDI1 | 8.05 | 6.17 | 7.93 | 9.02 | 6.7E−06 | IDH-O high & GBM low |
| IQGAP1 | 3.06 | 5.61 | 1.89 | 0.64 | 6.7E−06 | GBM high & IDH-O low |
| PLD1 | 1.30 | 1.84 | 0.11 | 0.15 | 6.7E−06 | IDH-WT high |
| RBP1 | 7.69 | 6.64 | 1.96 | 3.18 | 6.7E−06 | IDH-WT high |
| TOX3 | 3.85 | 1.46 | 4.97 | 4.36 | 6.7E−06 | GBM low |
| CCDC102B | 1.77 | 5.09 | 2.42 | 2.50 | 6.9E−06 | GBM high |
| VIPR2 | 5.71 | 1.48 | 6.69 | 6.90 | 6.9E−06 | GBM low |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| C2orf27A | 5.01 | 1.85 | 5.57 | 5.86 | 7.0E−06 | GBM low |
| CASP9 | 3.62 | 4.62 | 6.70 | 5.27 | 7.0E−06 | IDH-A high |
| MRPS15 | 5.49 | 6.31 | 5.57 | 4.42 | 7.4E−06 | GBM high & IDH-O low |
| VWC2L | 0.29 | 0.65 | 0.61 | 4.21 | 7.6E−06 | IDH-O high |
| RAB13 | 5.43 | 7.18 | 5.31 | 3.88 | 7.7E−06 | GBM high & IDH-O low |
| SEC61G | 7.16 | 11.39 | 6.56 | 6.76 | 8.0E−06 | GBM high |
| ENPP2 | 3.58 | 0.18 | 0.64 | 1.06 | 8.1E−06 | K27M high |
| ABCA5 | 3.86 | 1.68 | 0.62 | 0.56 | 8.1E−06 | K27M high |
| ACTL6B | 4.67 | 0.07 | 4.82 | 6.66 | 8.1E−06 | IDH-O high & GBM low |
| RBM11 | 3.67 | 0.01 | 0.47 | 0.03 | 8.2E−06 | K27M high |
| CKMT1B | 4.64 | 0.35 | 4.11 | 5.07 | 8.4E−06 | GBM low |
| CSMD3 | 4.12 | 0.19 | 5.22 | 5.59 | 8.4E−06 | GBM low |
| NDN | 5.37 | 0.01 | 5.14 | 4.82 | 8.4E−06 | GBM low |
| TUB | 5.21 | 2.55 | 4.80 | 5.74 | 8.4E−06 | GBM low |
| CHAD | 5.68 | 0.07 | 0.27 | 0.27 | 8.5E−06 | K27M high |
| TICAM2 | 2.08 | 3.18 | 0.43 | 0.55 | 8.5E−06 | GBM high |
| MAGEL2 | 2.03 | 0.27 | 2.20 | 3.08 | 8.6E−06 | IDH-O high & GBM low |
| SERTAD3 | 4.53 | 5.42 | 3.37 | 1.40 | 8.8E−06 | IDH-O low |
| ZNF423 | 3.42 | 0.53 | 4.02 | 4.17 | 8.9E−06 | GBM low |
| PDE3B | 3.10 | 0.16 | 1.82 | 1.94 | 9.2E−06 | K27M high & GBM low |
| S100A11 | 3.70 | 7.10 | 1.10 | 0.40 | 9.3E−06 | GBM high |
| LPPR1 | 7.39 | 1.71 | 7.84 | 9.04 | 9.5E−06 | GBM low |
| PRKCD | 2.22 | 0.41 | 0.19 | 0.13 | 9.8E−06 | K27M high |
| RUNDC3A | 4.38 | 2.47 | 5.34 | 5.52 | 9.9E−06 | GBM low |
| CHGB | 6.85 | 1.53 | 6.40 | 8.54 | 1.0E−05 | GBM low |
| CD200 | 6.33 | 1.73 | 5.94 | 6.19 | 1.0E−05 | GBM low |
| COL11A1 | 6.19 | 0.38 | 4.07 | 0.70 | 1.0E−05 | K27M high |
| DHCR7 | 6.91 | 6.28 | 5.38 | 7.94 | 1.0E−05 | IDH-O high |
| MYO1E | 2.71 | 4.22 | 0.88 | 1.17 | 1.0E−05 | GBM high |
| TAGLN3 | 7.20 | 4.49 | 7.29 | 7.43 | 1.1E−05 | GBM low |
| HMGN2 | 9.73 | 10.15 | 9.17 | 8.37 | 1.1E−05 | IDH-O low |
| C19orf55 | 2.54 | 3.70 | 2.39 | 1.39 | 1.1E−05 | GBM high & IDH-O low |
| BMP8B | 3.14 | 1.00 | 2.31 | 0.72 | 1.1E−05 | K27M high |
| FABP5 | 5.00 | 10.01 | 2.76 | 2.06 | 1.1E−05 | GBM high |
| TXLNA | 6.20 | 6.84 | 6.11 | 4.86 | 1.2E−05 | IDH-O low |
| CSDE1 | 7.85 | 7.55 | 8.07 | 6.81 | 1.2E−05 | IDH-O low |
| MPZ | 2.20 | 0.08 | 0.45 | 0.57 | 1.2E−05 | K27M high |
| ACADM | 6.39 | 6.63 | 6.31 | 5.16 | 1.2E−05 | IDH-O low |
| ATP1A3 | 5.20 | 2.48 | 5.91 | 5.50 | 1.2E−05 | GBM low |
| LATS2 | 1.58 | 1.55 | 0.22 | 0.14 | 1.2E−05 | IDH-WT high |
| GRAMD2 | 3.01 | 0.31 | 0.42 | 0.60 | 1.3E−05 | K27M high |
| DDB2 | 3.55 | 5.13 | 2.05 | 1.83 | 1.3E−05 | GBM high |
| COL4A1 | 2.65 | 4.72 | 0.84 | 0.31 | 1.3E−05 | GBM high |
| FZD7 | 0.23 | 2.78 | 0.65 | 0.04 | 1.4E−05 | GBM high |
| PROM1 | 6.34 | 4.42 | 1.65 | 0.35 | 1.4E−05 | IDH-WT high |
| ZDHHC22 | 5.90 | 2.44 | 6.62 | 8.17 | 1.4E−05 | IDH-O high & GBM low |
| WWTR1 | 1.75 | 6.14 | 1.27 | 0.71 | 1.4E−05 | GBM high |
| EID3 | 3.55 | 2.85 | 1.39 | 1.37 | 1.4E−05 | IDH-WT high |
| NAMPT | 5.42 | 7.58 | 4.79 | 4.98 | 1.4E−05 | GBM high |
| WAC | 5.55 | 4.25 | 6.15 | 5.96 | 1.4E−05 | GBM low |
| ABCG1 | 4.10 | 1.31 | 5.49 | 6.47 | 1.5E−05 | GBM low |
| SHROOM3 | 1.15 | 2.82 | 0.13 | 0.10 | 1.5E−05 | GBM high |
| VSTM2B | 4.15 | 0.13 | 3.67 | 3.23 | 1.5E−05 | GBM low |
| DNAJA4 | 4.86 | 4.24 | 1.01 | 0.28 | 1.5E−05 | IDH-WT high |
| ADAM12 | 2.22 | 3.70 | 0.40 | 0.71 | 1.5E−05 | GBM high |
| FAM129A | 1.77 | 4.13 | 0.59 | 0.45 | 1.5E−05 | GBM high |
| MAPT | 5.39 | 4.10 | 6.72 | 6.46 | 1.5E−05 | GBM low |
| ENPP4 | 4.28 | 0.02 | 3.59 | 4.31 | 1.6E−05 | GBM low |
| FAM192A | 6.45 | 6.30 | 6.98 | 7.27 | 1.6E−05 | IDH-O high |
| NEXN | 1.51 | 2.84 | 1.16 | 0.63 | 1.6E−05 | GBM high & IDH-O low |
| TFAM | 4.56 | 3.04 | 4.52 | 4.41 | 1.6E−05 | GBM low |
| PCOLCE2 | 4.94 | 0.39 | 1.87 | 3.34 | 1.6E−05 | K27M high |
| ZMPSTE24 | 6.10 | 6.57 | 5.43 | 4.92 | 1.6E−05 | IDH-O low |
| CA2 | 3.22 | 7.02 | 1.38 | 1.13 | 1.7E−05 | GBM high |
| PSRC1 | 5.03 | 7.75 | 4.05 | 2.84 | 1.7E−05 | GBM high & IDH-O low |
| CD302 | 4.81 | 5.13 | 2.89 | 1.75 | 1.7E−05 | IDH-O low |
| GNAI3 | 6.54 | 6.84 | 6.32 | 5.36 | 1.7E−05 | IDH-O low |
| CYB5R2 | 3.66 | 2.46 | 0.20 | 0.21 | 1.7E−05 | IDH-WT high |
| ARSJ | 1.35 | 5.10 | 0.46 | 0.27 | 1.7E−05 | GBM high |
| PSENEN | 6.35 | 7.21 | 6.03 | 5.44 | 1.8E−05 | GBM high & IDH-O low |
| RGS11 | 4.84 | 0.42 | 4.84 | 5.51 | 1.8E−05 | GBM low |
| APOBEC3G | 1.16 | 3.46 | 0.04 | 0.05 | 1.9E−05 | GBM high |
| RDH10 | 2.71 | 5.33 | 2.38 | 2.80 | 2.0E−05 | GBM high |
| ABCC8 | 2.51 | 0.66 | 2.85 | 5.20 | 2.0E−05 | IDH-O high & GBM low |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
| --- | --- | --- | --- | --- | --- | --- |
| EIF3L | 9.52 | 7.56 | 9.53 | 9.76 | 2.0E−05 | GBM low |
| ELOVL1 | 5.15 | 7.01 | 4.78 | 4.22 | 2.0E−05 | GBM high |
| SLC2A1 | 5.00 | 5.06 | 4.82 | 3.68 | 2.0E−05 | IDH-O low |
| MRPL17 | 4.78 | 5.32 | 3.74 | 4.69 | 2.0E−05 | IDH-A low |
| GBGT1 | 3.21 | 0.13 | 1.06 | 0.94 | 2.1E−05 | K27M high |
| SAMD9L | 1.40 | 4.47 | 0.60 | 0.46 | 2.1E−05 | GBM high |
| MINOS1 | 4.66 | 5.37 | 4.41 | 3.54 | 2.1E−05 | GBM high & IDH-O low |
| CNRIP1 | 7.57 | 4.47 | 7.30 | 7.72 | 2.2E−05 | GBM low |
| PHYH | 5.87 | 4.98 | 4.20 | 0.88 | 2.2E−05 | IDH-O low |
| BCL7A | 4.22 | 2.52 | 5.17 | 4.80 | 2.2E−05 | GBM low |
| PDGFA | 3.96 | 6.88 | 3.03 | 3.61 | 2.2E−05 | GBM high |
| AKAP1 | 4.56 | 2.58 | 4.59 | 4.49 | 2.3E−05 | GBM low |
| C9orf64 | 5.13 | 3.61 | 1.16 | 1.34 | 2.3E−05 | IDH-WT high |
| KIAA1755 | 3.04 | 0.94 | 3.91 | 5.46 | 2.3E−05 | IDH-O high & GBM low |
| NRIP3 | 5.39 | 2.13 | 2.82 | 2.50 | 2.3E−05 | K27M high |
| EFS | 4.09 | 2.56 | 5.21 | 5.36 | 2.5E−05 | GBM low |
| PDZRN3 | 4.35 | 1.36 | 2.53 | 0.46 | 2.5E−05 | K27M high |
| ARPP21 | 5.12 | 2.84 | 6.12 | 6.73 | 2.6E−05 | GBM low |
| TBC1D1 | 3.10 | 3.48 | 0.95 | 0.79 | 2.6E−05 | IDH-WT high |
| SCARA5 | 0.11 | 0.00 | 0.21 | 2.86 | 2.7E−05 | IDH-O high |
| CRY2 | 4.29 | 3.02 | 4.94 | 5.85 | 2.7E−05 | IDH-O high & GBM low |
| KCNIP3 | 4.27 | 1.18 | 5.44 | 6.64 | 2.7E−05 | GBM low |
| HERC5 | 4.13 | 3.76 | 0.77 | 0.56 | 2.7E−05 | IDH-WT high |
| CD274 | 0.73 | 3.16 | 0.42 | 0.37 | 2.8E−05 | GBM high |
| KCNH5 | 3.10 | 0.00 | 0.47 | 0.55 | 2.8E−05 | K27M high |
| PPIC | 3.78 | 5.88 | 1.69 | 0.99 | 2.8E−05 | GBM high |
| NPY5R | 3.64 | 0.12 | 0.26 | 0.26 | 2.9E−05 | K27M high |
| PRPF38B | 6.34 | 5.89 | 6.31 | 5.23 | 2.9E−05 | IDH-O low |
| CCDC109B | 3.62 | 6.83 | 1.18 | 0.77 | 3.0E−05 | GBM high |
| ATRNL1 | 4.03 | 0.50 | 4.40 | 4.27 | 3.0E−05 | GBM low |
| KLRC3 | 6.45 | 1.45 | 7.62 | 6.70 | 3.0E−05 | GBM low |
| ERI1 | 4.53 | 6.62 | 4.03 | 4.11 | 3.0E−05 | GBM high |
| GNAL | 3.67 | 1.36 | 3.19 | 4.20 | 3.0E−05 | GBM low |
| ATP2B1 | 5.83 | 5.51 | 3.76 | 4.26 | 3.1E−05 | IDH-WT high |
| C7orf41 | 3.66 | 0.90 | 3.82 | 3.78 | 3.1E−05 | GBM low |
| HOXD11 | 0.01 | 2.25 | 0.04 | 0.00 | 3.1E−05 | GBM high |
| SLC29A3 | 4.01 | 1.14 | 3.86 | 4.15 | 3.1E−05 | GBM low |
| EMILIN3 | 3.42 | 4.25 | 0.94 | 0.23 | 3.1E−05 | IDH-WT high |
| KIAA1244 | 4.04 | 1.42 | 4.29 | 5.27 | 3.1E−05 | IDH-O high & GBM low |
| AFAP1L1 | 2.14 | 4.11 | 1.40 | 1.03 | 3.1E−05 | GBM high |
| CELF2 | 6.07 | 4.33 | 6.83 | 5.66 | 3.2E−05 | IDH-A high & GBM low |
| CUEDC2 | 8.44 | 6.79 | 8.58 | 8.64 | 3.2E−05 | GBM low |
| OR2L13 | 0.50 | 0.00 | 0.70 | 3.80 | 3.2E−05 | IDH-O high |
| HOPX | 5.79 | 10.25 | 2.95 | 3.46 | 3.2E−05 | GBM high |
| ELK3 | 2.91 | 3.71 | 1.18 | 0.57 | 3.2E−05 | IDH-WT high |
| AATK | 2.21 | 0.48 | 2.74 | 2.80 | 3.2E−05 | GBM low |
| FAM83D | 3.80 | 4.33 | 1.89 | 1.02 | 3.2E−05 | IDH-WT high |
| ADPRH | 1.73 | 2.83 | 0.23 | 0.11 | 3.2E−05 | IDH-WT high |
| PRDX6 | 7.85 | 8.29 | 6.91 | 6.61 | 3.2E−05 | IDH-WT high |
| DNTTIP2 | 6.38 | 6.26 | 6.34 | 5.46 | 3.3E−05 | IDH-O low |
| THBS4 | 6.38 | 3.72 | 3.31 | 3.80 | 3.3E−05 | K27M high |
| TXNDC17 | 5.67 | 6.47 | 4.96 | 4.91 | 3.4E−05 | GBM high |
| RHOJ | 1.91 | 6.20 | 1.88 | 2.12 | 3.4E−05 | GBM high |
| FAM21C | 4.53 | 2.93 | 4.93 | 5.18 | 3.4E−05 | GBM low |
| KLHL26 | 2.94 | 1.94 | 0.19 | 0.09 | 3.4E−05 | IDH-WT high |
| AGAP4 | 4.01 | 1.41 | 3.80 | 3.95 | 3.6E−05 | GBM low |
| MMD2 | 4.81 | 3.05 | 3.57 | 7.04 | 3.6E−05 | IDH-O high |
| PSMD8 | 7.61 | 8.36 | 7.46 | 6.62 | 3.6E−05 | GBM high & IDH-O low |
| RNF165 | 3.98 | 0.86 | 4.69 | 4.39 | 3.6E−05 | GBM low |
| IRF8 | 2.02 | 0.00 | 0.32 | 0.12 | 3.7E−05 | K27M high |
| HJURP | 3.62 | 4.74 | 2.02 | 1.62 | 3.7E−05 | IDH-WT high |
| DUSP23 | 5.21 | 2.40 | 2.44 | 1.51 | 3.7E−05 | K27M high |
| GAL3ST1 | 3.69 | 0.25 | 2.43 | 4.21 | 3.7E−05 | GBM low |
| HSF2BP | 2.07 | 2.82 | 4.49 | 4.86 | 3.7E−05 | IDH-mut high |
| NTN4 | 3.63 | 0.04 | 5.02 | 4.03 | 3.7E−05 | GBM low |
| PHYHIPL | 8.19 | 6.14 | 8.98 | 9.31 | 3.7E−05 | GBM low |
| PPP1R15A | 7.31 | 8.76 | 5.95 | 4.72 | 3.7E−05 | IDH-O low |
| RBMS1 | 3.91 | 3.78 | 2.32 | 1.93 | 3.7E−05 | IDH-WT high |
| SNRNP40 | 6.80 | 6.92 | 6.59 | 5.77 | 3.7E−05 | IDH-O low |
| SOCS2 | 1.05 | 6.27 | 0.73 | 0.18 | 3.7E−05 | GBM high |
| SSX2IP | 3.45 | 4.44 | 2.30 | 1.67 | 3.7E−05 | IDH-WT high |
| TMOD3 | 3.69 | 4.91 | 3.09 | 2.76 | 3.7E−05 | GBM high |
| CRTAC1 | 3.09 | 0.00 | 3.56 | 5.57 | 3.7E−05 | IDH-O high & GBM low |
| S100A1 | 1.74 | 0.24 | 0.20 | 0.32 | 3.8E−05 | K27M high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
| --- | --- | --- | --- | --- | --- | --- |
| SH3BGRL2 | 4.57 | 1.57 | 4.24 | 4.71 | 3.8E-05 | GBM low |
| ISG20 | 1.12 | 4.26 | 0.77 | 0.78 | 3.8E-05 | GBM high |
| PSMB2 | 6.06 | 6.33 | 6.25 | 5.28 | 3.8E-05 | IDH-O low |
| PVRL1 | 2.68 | 1.03 | 3.58 | 3.58 | 3.8E-05 | GBM low |
| ELAVL2 | 3.27 | 0.34 | 3.65 | 3.95 | 3.9E-05 | GBM low |
| ACOX2 | 1.37 | 4.34 | 0.38 | 0.43 | 3.9E-05 | GBM high |
| BMP2 | 3.49 | 2.66 | 5.87 | 6.74 | 3.9E-05 | IDH-mut high |
| GBP1 | 1.54 | 5.61 | 0.51 | 0.20 | 3.9E-05 | GBM high |
| C12orf68 | 4.08 | 3.70 | 1.37 | 1.90 | 4.0E-05 | IDH-WT high |
| OPLAH | 2.23 | 2.70 | 0.10 | 0.11 | 4.0E-05 | IDH-WT high |
| CAP1 | 6.93 | 7.11 | 6.61 | 5.77 | 4.1E-05 | IDH-O low |
| TNFAIP6 | 2.19 | 5.76 | 1.05 | 0.10 | 4.1E-05 | GBM high |
| PSMA5 | 5.80 | 6.30 | 5.83 | 5.05 | 4.1E-05 | GBM high & IDH-O low |
| TEAD3 | 2.54 | 2.81 | 0.55 | 0.82 | 4.1E-05 | IDH-WT high |
| EYA2 | 4.19 | 5.03 | 1.01 | 1.75 | 4.1E-05 | IDH-WT high |
| SIGIRR | 3.20 | 0.54 | 0.52 | 0.18 | 4.2E-05 | K27M high |
| INA | 4.96 | 0.01 | 5.59 | 7.84 | 4.2E-05 | IDH-O high & GBM low |
| TF | 5.48 | 1.50 | 4.11 | 6.86 | 4.2E-05 | GBM low |
| GRHL1 | 3.76 | 0.33 | 1.59 | 2.54 | 4.2E-05 | K27M high & GBM low |
| CEBPG | 5.25 | 5.68 | 4.93 | 3.79 | 4.2E-05 | IDH-O low |
| ABCA3 | 4.47 | 3.47 | 5.08 | 5.37 | 4.2E-05 | GBM low |
| CSNK1E | 5.87 | 5.01 | 7.47 | 6.85 | 4.2E-05 | IDH-mut high |
| TMCC1 | 5.10 | 3.97 | 6.04 | 5.69 | 4.2E-05 | GBM low |
| SCD5 | 8.57 | 8.43 | 9.97 | 10.46 | 4.2E-05 | IDH-mut high |
| GFRA1 | 4.05 | 0.26 | 4.12 | 5.88 | 4.2E-05 | IDH-O high & GBM low |
| GLIS2 | 2.61 | 1.76 | 3.01 | 3.49 | 4.2E-05 | IDH-O high & GBM low |
| EIF3I | 8.26 | 8.20 | 7.89 | 7.04 | 4.3E-05 | IDH-O low |
| LUZP2 | 7.31 | 0.72 | 5.59 | 5.10 | 4.3E-05 | K27M high & GBM low |
| IGSF10 | 2.26 | 4.12 | 1.37 | 2.22 | 4.3E-05 | GBM high & IDH-A low |
| USP53 | 1.73 | 3.34 | 0.38 | 0.51 | 4.4E-05 | GBM high |
| TMEM154 | 2.21 | 4.99 | 0.55 | 0.88 | 4.5E-05 | GBM high |
| WDR37 | 3.55 | 1.94 | 4.04 | 4.07 | 4.5E-05 | GBM low |
| CFI | 1.57 | 5.35 | 0.25 | 0.04 | 4.5E-05 | GBM high |
| PPFIA2 | 5.22 | 0.92 | 4.34 | 5.28 | 4.5E-05 | GBM low |
| FES | 1.47 | 2.29 | 0.12 | 0.10 | 4.6E-05 | IDH-WT high |
| BAMBI | 5.61 | 1.08 | 4.23 | 3.31 | 4.7E-05 | K27M high & GBM low |
| CADM3 | 4.28 | 0.19 | 4.24 | 4.25 | 4.7E-05 | GBM low |
| FAP | 0.92 | 3.35 | 0.37 | 0.36 | 4.7E-05 | GBM high |
| HS3ST2 | 0.05 | 0.09 | 0.22 | 3.07 | 4.7E-05 | IDH-O high |
| MAPK8 | 4.01 | 1.68 | 4.92 | 4.69 | 4.7E-05 | GBM low |
| TUBB6 | 5.21 | 0.43 | 2.57 | 0.68 | 4.7E-05 | K27M high |
| REST | 3.83 | 3.96 | 3.20 | 0.50 | 4.7E-05 | IDH-O low |
| C19orf66 | 4.15 | 5.14 | 1.76 | 4.65 | 4.8E-05 | IDH-A low |
| CAPZB | 6.75 | 6.78 | 6.72 | 5.82 | 4.8E-05 | IDH-O low |
| PODXL2 | 5.79 | 2.82 | 6.01 | 6.43 | 4.8E-05 | GBM low |
| SAMD12 | 2.98 | 0.09 | 0.82 | 1.74 | 4.8E-05 | K27M high |
| UNC79 | 3.39 | 0.51 | 4.17 | 5.66 | 4.8E-05 | IDH-O high & GBM low |
| SLC18A2 | 3.43 | 0.56 | 2.83 | 2.98 | 4.9E-05 | GBM low |
| LSM14A | 6.23 | 6.98 | 6.17 | 5.20 | 5.0E-05 | GBM high & IDH-O low |
| LY96 | 0.12 | 3.85 | 0.50 | 0.30 | 5.0E-05 | GBM high |
| CTTNBP2 | 5.85 | 3.97 | 6.73 | 6.39 | 5.1E-05 | GBM low |
| GPI | 7.45 | 8.72 | 6.85 | 6.45 | 5.1E-05 | GBM high |
| IRX2 | 3.80 | 0.00 | 2.64 | 1.23 | 5.1E-05 | K27M high |
| VMP1 | 7.10 | 8.73 | 6.59 | 6.86 | 5.1E-05 | GBM high |
| GABARAP | 9.20 | 9.04 | 9.76 | 9.85 | 5.2E-05 | IDH-mut high |
| RPRM | 3.88 | 0.34 | 5.21 | 4.09 | 5.2E-05 | GBM low |
| SGMS1 | 4.82 | 2.82 | 5.27 | 5.41 | 5.2E-05 | GBM low |
| SLC1A1 | 6.99 | 2.16 | 5.87 | 6.26 | 5.2E-05 | GBM low |
| PPIH | 5.76 | 5.91 | 5.58 | 4.71 | 5.2E-05 | IDH-O low |
| MMP17 | 3.71 | 0.57 | 1.38 | 2.18 | 5.3E-05 | K27M high |
| HNRNPR | 8.25 | 8.16 | 8.18 | 7.25 | 5.3E-05 | IDH-O low |
| AGTRAP | 5.00 | 6.92 | 4.03 | 3.03 | 5.3E-05 | GBM high |
| CYB561 | 3.70 | 4.05 | 1.54 | 1.68 | 5.3E-05 | IDH-WT high |
| CAMLG | 7.16 | 6.34 | 7.18 | 7.61 | 5.4E-05 | IDH-O high & GBM low |
| DNAH14 | 4.88 | 0.09 | 0.36 | 1.19 | 5.4E-05 | K27M high |
| GNG12 | 6.41 | 6.48 | 1.73 | 0.96 | 5.4E-05 | IDH-WT high |
| HDAC1 | 5.95 | 6.17 | 5.21 | 3.88 | 5.4E-05 | IDH-O low |
| MRTO4 | 5.16 | 4.79 | 5.21 | 4.11 | 5.4E-05 | IDH-O low |
| TMEM147 | 7.87 | 8.63 | 7.74 | 6.98 | 5.4E-05 | GBM high & IDH-O low |
| IL12A | 2.27 | 3.49 | 0.76 | 0.79 | 5.4E-05 | IDH-WT high |
| PAK7 | 3.26 | 0.00 | 3.46 | 3.51 | 5.4E-05 | GBM low |
| FRA10AC1 | 4.85 | 3.30 | 4.94 | 5.19 | 5.5E-05 | GBM low |
| CHRM1 | 3.23 | 0.02 | 2.16 | 3.70 | 5.5E-05 | GBM low |
| IFITM3 | 4.06 | 9.45 | 2.22 | 1.38 | 5.5E-05 | GBM high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| CALU | 6.62 | 8.15 | 6.25 | 6.30 | 5.5E−05 | GBM high |
| RPL22 | 8.36 | 6.31 | 8.65 | 7.65 | 5.6E−05 | GBM low |
| RUVBL2 | 7.35 | 7.99 | 6.95 | 6.30 | 5.6E−05 | IDH-O low |
| STEAP1B | 3.54 | 0.12 | 0.14 | 0.10 | 5.6E−05 | K27M high |
| DNAJC1 | 5.60 | 4.01 | 3.35 | 3.39 | 5.6E−05 | K27M high |
| DR1 | 6.01 | 6.01 | 5.72 | 4.66 | 5.6E−05 | IDH-O low |
| TRIM59 | 3.86 | 3.28 | 1.91 | 1.83 | 5.6E−05 | IDH-WT high |
| OSTC | 7.78 | 7.99 | 6.84 | 6.72 | 5.6E−05 | IDH-WT high |
| SRI | 8.72 | 9.83 | 10.25 | 10.52 | 5.6E−05 | K27M low |
| TRIM22 | 1.35 | 6.41 | 0.78 | 2.36 | 5.7E−05 | GBM high |
| SLC25A24 | 3.81 | 3.01 | 0.84 | 0.53 | 5.8E−05 | IDH-WT high |
| SMPD3 | 1.85 | 0.62 | 3.20 | 3.76 | 5.8E−05 | IDH-mut high |
| PFN2 | 9.16 | 6.62 | 9.76 | 9.42 | 5.8E−05 | GBM low |
| NPY2R | 0.64 | 3.88 | 0.02 | 0.27 | 5.8E−05 | GBM high |
| STIL | 2.35 | 3.34 | 1.78 | 1.15 | 5.8E−05 | GBM high & IDH-O low |
| DDOST | 8.26 | 8.19 | 7.90 | 7.09 | 5.8E−05 | IDH-O low |
| GPR17 | 7.03 | 1.84 | 6.15 | 7.96 | 5.8E−05 | GBM low |
| LRAT | 4.14 | 1.33 | 0.93 | 0.66 | 5.9E−05 | K27M high |
| POLL | 4.39 | 3.20 | 4.69 | 5.20 | 5.9E−05 | GBM low |
| ATG13 | 4.93 | 5.14 | 5.87 | 6.07 | 5.9E−05 | IDH-mut high |
| PLCB4 | 3.32 | 0.24 | 2.98 | 2.21 | 5.9E−05 | GBM low |
| PTGR1 | 5.51 | 5.73 | 2.88 | 1.99 | 5.9E−05 | IDH-WT high |
| SAE1 | 6.79 | 7.69 | 6.06 | 5.90 | 5.9E−05 | GBM high |
| SCD | 7.47 | 6.86 | 6.89 | 9.43 | 5.9E−05 | IDH-O high |
| ZNF644 | 6.04 | 5.89 | 6.20 | 5.12 | 6.0E−05 | IDH-O low |
| ADCY5 | 3.04 | 0.44 | 2.61 | 3.37 | 6.1E−05 | GBM low |
| FXYD6 | 9.61 | 8.68 | 11.19 | 11.33 | 6.1E−05 | IDH-mut high |
| NKAIN1 | 3.16 | 0.18 | 3.22 | 2.49 | 6.3E−05 | GBM low |
| CAPZA1 | 7.07 | 7.91 | 7.27 | 6.40 | 6.4E−05 | GBM high & IDH-O low |
| CXXC4 | 4.76 | 2.00 | 5.24 | 4.90 | 6.4E−05 | GBM low |
| GSTA4 | 8.12 | 6.27 | 8.05 | 8.27 | 6.4E−05 | GBM low |
| SGCA | 1.30 | 0.09 | 0.18 | 0.05 | 6.4E−05 | K27M high |
| TMEM48 | 4.95 | 4.55 | 4.10 | 3.13 | 6.4E−05 | IDH-O low |
| KCND2 | 6.42 | 1.79 | 5.84 | 5.08 | 6.6E−05 | GBM low |
| SRSF4 | 6.29 | 6.44 | 6.71 | 5.36 | 6.6E−05 | IDH-O low |
| NUCB1 | 6.19 | 7.28 | 5.71 | 5.37 | 6.6E−05 | GBM high |
| TENM2 | 3.91 | 0.61 | 1.02 | 0.77 | 6.7E−05 | K27M high |
| SPOCD1 | 0.62 | 3.72 | 0.29 | 0.15 | 6.7E−05 | GBM high |
| TRIT1 | 4.55 | 4.35 | 5.47 | 3.96 | 6.7E−05 | IDH-A high |
| SEPT3 | 5.58 | 3.18 | 5.58 | 6.00 | 6.8E−05 | GBM low |
| C1QL1 | 3.71 | 0.38 | 3.79 | 3.71 | 6.8E−05 | GBM low |
| FABP7 | 8.74 | 10.56 | 4.15 | 7.96 | 6.8E−05 | IDH-A low |
| KLRG1 | 4.94 | 2.62 | 3.60 | 3.41 | 6.8E−05 | K27M high |
| TMEM151B | 2.11 | 0.41 | 1.94 | 4.10 | 6.9E−05 | IDH-O high & GBM low |
| GPBP1L1 | 4.05 | 4.46 | 4.65 | 3.27 | 6.9E−05 | IDH-O low |
| TM7SF2 | 6.25 | 5.56 | 7.01 | 7.97 | 6.9E−05 | IDH-O high |
| PRKCZ | 5.61 | 1.96 | 5.49 | 4.70 | 6.9E−05 | GBM low |
| VAV3 | 1.53 | 3.57 | 0.50 | 0.23 | 7.0E−05 | GBM high |
| PERP | 4.58 | 0.73 | 1.53 | 2.44 | 7.0E−05 | K27M high |
| MYOF | 0.48 | 2.52 | 0.08 | 0.37 | 7.0E−05 | GBM high |
| CCDC178 | 0.99 | 0.26 | 3.52 | 1.40 | 7.1E−05 | IDH-A high |
| DDX25 | 5.14 | 0.03 | 4.57 | 4.87 | 7.1E−05 | GBM low |
| HS2ST1 | 4.60 | 5.69 | 3.40 | 2.93 | 7.1E−05 | IDH-WT high |
| MRC2 | 2.67 | 5.18 | 1.19 | 1.33 | 7.1E−05 | GBM high |
| MRPS12 | 5.51 | 6.63 | 5.49 | 4.88 | 7.1E−05 | GBM high & IDH-O low |
| RBBP4 | 7.05 | 6.87 | 7.04 | 6.09 | 7.1E−05 | IDH-O low |
| TNFRSF14 | 1.19 | 3.46 | 0.33 | 0.15 | 7.1E−05 | GBM high |
| FHL2 | 4.09 | 1.13 | 0.68 | 0.23 | 7.1E−05 | K27M high |
| LIPA | 5.81 | 5.17 | 5.33 | 7.08 | 7.1E−05 | IDH-O high |
| NAT16 | 1.87 | 0.07 | 2.56 | 3.10 | 7.1E−05 | GBM low |
| SLC16A7 | 2.86 | 0.58 | 2.44 | 3.12 | 7.1E−05 | GBM low |
| CDH8 | 3.74 | 0.43 | 0.99 | 1.25 | 7.2E−05 | K27M high |
| SLC22A15 | 1.96 | 1.14 | 0.10 | 0.04 | 7.2E−05 | IDH-WT high |
| PHF13 | 3.47 | 3.78 | 3.61 | 2.11 | 7.2E−05 | IDH-O low |
| AMZ1 | 3.52 | 2.45 | 4.07 | 6.06 | 7.4E−05 | IDH-O high |
| SP140L | 2.06 | 3.80 | 0.98 | 0.93 | 7.8E−05 | GBM high |
| CYYR1 | 2.71 | 0.07 | 0.19 | 0.06 | 7.9E−05 | K27M high |
| TRIM8 | 4.06 | 2.61 | 4.56 | 4.82 | 7.9E−05 | GBM low |
| GRAMD1C | 3.91 | 3.61 | 1.34 | 1.35 | 8.0E−05 | IDH-WT high |
| MT1E | 4.77 | 6.52 | 1.26 | 0.74 | 8.0E−05 | IDH-WT high |
| PDCD5 | 7.81 | 8.36 | 7.46 | 6.64 | 8.0E−05 | IDH-O low |
| TFCP2L1 | 0.50 | 2.89 | 0.21 | 0.19 | 8.1E−05 | GBM high |
| ELOVL2 | 1.41 | 6.73 | 1.04 | 1.23 | 8.1E−05 | GBM high |
| CA10 | 7.77 | 0.82 | 5.33 | 7.34 | 8.1E−05 | GBM low |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| NSUN7 | 3.45 | 3.30 | 1.79 | 1.48 | 8.1E−05 | IDH-WT high |
| TUBGCP2 | 5.40 | 4.24 | 5.75 | 6.10 | 8.2E−05 | GBM low |
| MAGOH | 4.97 | 5.75 | 5.12 | 4.09 | 8.2E−05 | GBM high & IDH-O low |
| RNF150 | 3.66 | 0.79 | 4.32 | 3.83 | 8.4E−05 | GBM low |
| SPATA6 | 5.43 | 6.59 | 4.26 | 1.30 | 8.4E−05 | IDH-O low |
| HFM1 | 3.27 | 0.76 | 3.68 | 2.60 | 8.4E−05 | GBM low |
| HIST1H1D | 2.83 | 4.84 | 0.96 | 0.06 | 8.4E−05 | GBM high |
| RAB6C | 1.95 | 0.07 | 0.45 | 1.03 | 8.4E−05 | K27M high |
| MELK | 4.09 | 5.61 | 2.41 | 1.73 | 8.6E−05 | IDH-WT high |
| ENHO | 4.14 | 1.55 | 5.57 | 6.19 | 8.6E−05 | GBM low |
| PDLIM1 | 5.41 | 2.00 | 0.93 | 0.33 | 8.6E−05 | K27M high |
| SDHB | 7.70 | 7.88 | 7.75 | 6.81 | 8.7E−05 | IDH-O low |
| SLC2A6 | 4.26 | 2.12 | 4.63 | 5.19 | 8.7E−05 | GBM low |
| C1orf122 | 4.21 | 5.98 | 4.90 | 4.10 | 8.8E−05 | GBM high |
| YPEL2 | 2.11 | 0.35 | 2.74 | 2.20 | 8.8E−05 | GBM low |
| KLHL9 | 6.24 | 1.64 | 5.65 | 6.46 | 8.8E−05 | GBM low |
| CCNA2 | 4.50 | 5.03 | 2.43 | 1.76 | 8.9E−05 | IDH-WT high |
| PAK1 | 4.27 | 3.88 | 1.42 | 2.69 | 8.9E−05 | IDH-A low |
| PTHLH | 0.15 | 4.58 | 1.81 | 0.69 | 8.9E−05 | GBM high |
| FGF12 | 6.60 | 1.48 | 6.88 | 5.92 | 9.0E−05 | GBM low |
| SOD2 | 4.80 | 7.76 | 5.05 | 5.48 | 9.0E−05 | GBM high |
| MFAP2 | 5.34 | 0.32 | 1.79 | 0.14 | 9.1E−05 | K27M high |
| LRRC37B | 3.23 | 2.84 | 4.52 | 4.81 | 9.1E−05 | IDH-mut high |
| PACSIN3 | 3.04 | 1.51 | 0.59 | 1.21 | 9.1E−05 | K27M high |
| GALNT9 | 1.26 | 0.04 | 3.62 | 2.33 | 9.3E−05 | IDH-A high |
| MT1F | 5.67 | 4.69 | 1.59 | 0.85 | 9.3E−05 | IDH-WT high |
| PIK3IP1 | 5.25 | 2.17 | 6.01 | 6.73 | 9.3E−05 | GBM low |
| RAB34 | 1.77 | 6.81 | 0.46 | 0.42 | 9.3E−05 | GBM high |
| FOXRED1 | 4.68 | 4.35 | 5.51 | 5.91 | 9.4E−05 | IDH-mut high |
| PANK1 | 2.60 | 1.19 | 2.20 | 3.32 | 9.4E−05 | IDH-O high & GBM low |
| S100A13 | 3.87 | 6.62 | 2.99 | 3.33 | 9.5E−05 | GBM high |
| MYADM | 4.72 | 6.15 | 3.29 | 2.79 | 9.7E−05 | IDH-WT high |
| SATB1 | 5.86 | 2.22 | 5.53 | 5.28 | 9.8E−05 | GBM low |
| BMP4 | 1.76 | 1.23 | 4.52 | 4.98 | 9.8E−05 | IDH-mut high |
| FAM19A5 | 4.52 | 2.05 | 4.47 | 5.02 | 9.8E−05 | GBM low |
| USP25 | 3.57 | 0.95 | 2.77 | 2.64 | 1.0E−04 | K27M high & GBM low |
| LHX2 | 0.15 | 2.86 | 2.71 | 2.88 | 1.0E−04 | K27M low |
| PRR24 | 2.73 | 5.66 | 2.93 | 1.95 | 1.0E−04 | GBM high |
| NRAS | 5.99 | 6.20 | 5.79 | 4.76 | 1.0E−04 | IDH-O low |
| HIST1H3G | 1.61 | 3.44 | 0.23 | 0.01 | 1.0E−04 | GBM high |
| IQGAP3 | 2.81 | 3.18 | 1.00 | 0.51 | 1.0E−04 | IDH-WT high |
| FAM110B | 5.76 | 5.52 | 7.93 | 7.84 | 1.0E−04 | IDH-mut high |
| PDGFD | 1.37 | 4.27 | 0.77 | 0.53 | 1.0E−04 | GBM high |
| DEDD2 | 4.88 | 5.74 | 3.55 | 2.91 | 1.0E−04 | IDH-WT high |
| SOX8 | 6.39 | 4.53 | 7.96 | 8.01 | 1.0E−04 | GBM low |
| OAT | 8.26 | 5.60 | 7.53 | 7.82 | 1.1E−04 | GBM low |
| TNFRSF12A | 3.52 | 7.80 | 2.09 | 1.69 | 1.1E−04 | GBM high |
| F3 | 5.46 | 8.94 | 2.66 | 3.60 | 1.1E−04 | GBM high |
| FOXG1 | 0.09 | 5.09 | 3.58 | 4.40 | 1.1E−04 | K27M low |
| TTF1 | 4.35 | 3.13 | 4.86 | 4.96 | 1.1E−04 | GBM low |
| KDELR1 | 6.20 | 7.18 | 5.74 | 5.22 | 1.1E−04 | GBM high |
| RNF112 | 2.29 | 1.71 | 3.46 | 4.12 | 1.1E−04 | IDH-mut high |
| RPL39L | 4.23 | 0.04 | 0.13 | 0.11 | 1.1E−04 | K27M high |
| ELFN2 | 2.80 | 0.22 | 2.91 | 3.23 | 1.1E−04 | GBM low |
| KMO | 1.73 | 0.19 | 0.23 | 0.35 | 1.1E−04 | K27M high |
| VSTM2A | 3.90 | 0.10 | 2.56 | 6.24 | 1.1E−04 | IDH-O high & GBM low |
| LRRC41 | 6.69 | 6.79 | 7.05 | 5.92 | 1.2E−04 | IDH-O low |
| AKNA | 2.45 | 1.22 | 3.35 | 3.52 | 1.2E−04 | GBM low |
| NNAT | 6.85 | 1.82 | 0.44 | 0.28 | 1.2E−04 | K27M high |
| FAM84A | 4.15 | 5.93 | 3.00 | 4.27 | 1.2E−04 | GBM high & IDH-A low |
| ATP1B1 | 7.42 | 4.11 | 3.89 | 4.69 | 1.2E−04 | K27M high |
| EXTL2 | 5.97 | 5.23 | 5.13 | 4.25 | 1.2E−04 | IDH-O low |
| SLC39A4 | 1.59 | 2.20 | 0.55 | 0.46 | 1.2E−04 | IDH-WT high |
| PLCE1 | 4.22 | 3.74 | 2.24 | 1.69 | 1.2E−04 | IDH-WT high |
| CLDN10 | 4.64 | 4.98 | 2.15 | 2.43 | 1.2E−04 | IDH-WT high |
| RUNX1 | 2.92 | 4.20 | 1.25 | 0.49 | 1.2E−04 | IDH-WT high |
| IGFBP2 | 3.80 | 6.49 | 1.36 | 0.33 | 1.2E−04 | GBM high |
| KIF18A | 3.02 | 3.94 | 1.09 | 0.96 | 1.2E−04 | IDH-WT high |
| UBE2E2 | 6.52 | 3.38 | 6.67 | 6.99 | 1.2E−04 | GBM low |
| SRSF11 | 7.32 | 6.98 | 7.47 | 6.09 | 1.2E−04 | IDH-O low |
| TEX14 | 2.63 | 0.99 | 0.46 | 0.67 | 1.2E−04 | K27M high |
| RIMS2 | 3.83 | 0.14 | 3.30 | 5.28 | 1.2E−04 | GBM low |
| CYFIP2 | 6.07 | 4.61 | 6.10 | 6.35 | 1.2E−04 | GBM low |
| CBR1 | 7.18 | 7.96 | 2.17 | 1.54 | 1.2E−04 | IDH-WT high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| SEPW1 | 8.80 | 9.20 | 8.24 | 7.58 | 1.2E-04 | IDH-O low |
| TMEM100 | 5.08 | 3.70 | 7.15 | 7.55 | 1.2E-04 | IDH-mut high |
| SLC1A5 | 4.74 | 3.61 | 2.49 | 1.02 | 1.3E-04 | IDH-O low |
| SLCO5A1 | 1.73 | 0.08 | 1.89 | 2.39 | 1.3E-04 | GBM low |
| ZFP36 | 6.56 | 9.90 | 3.53 | 3.22 | 1.3E-04 | GBM high |
| HIVEP3 | 2.07 | 5.34 | 2.20 | 2.04 | 1.3E-04 | GBM high |
| BCL2L12 | 1.20 | 3.24 | 1.04 | 0.42 | 1.3E-04 | GBM high |
| CYTH1 | 5.00 | 3.97 | 6.05 | 6.21 | 1.3E-04 | GBM low |
| CDCA3 | 3.52 | 5.03 | 2.50 | 1.81 | 1.3E-04 | GBM high |
| CTIF | 2.90 | 2.14 | 4.03 | 4.03 | 1.3E-04 | IDH-mut high |
| TBC1D2 | 4.21 | 2.26 | 4.49 | 4.50 | 1.3E-04 | GBM low |
| S100A10 | 6.02 | 8.51 | 2.79 | 2.39 | 1.3E-04 | IDH-WT high |
| KIAA1199 | 1.12 | 3.37 | 0.74 | 1.83 | 1.3E-04 | GBM high |
| APITD1 | 3.72 | 4.57 | 2.86 | 2.40 | 1.3E-04 | IDH-WT high |
| PC | 4.38 | 2.87 | 4.27 | 5.04 | 1.3E-04 | GBM low |
| ARPC1B | 2.30 | 5.43 | 2.70 | 1.66 | 1.3E-04 | GBM high |
| GRIK1 | 4.80 | 4.76 | 1.30 | 1.58 | 1.3E-04 | IDH-WT high |
| H2AFY2 | 6.24 | 3.08 | 5.66 | 6.01 | 1.3E-04 | GBM low |
| MARC2 | 3.83 | 3.02 | 0.31 | 2.04 | 1.3E-04 | IDH-A low |
| NECAB2 | 2.32 | 0.21 | 2.51 | 3.31 | 1.3E-04 | GBM low |
| PCDH7 | 5.15 | 0.91 | 3.87 | 4.14 | 1.3E-04 | GBM low |
| TMCC2 | 3.73 | 0.99 | 4.06 | 3.27 | 1.3E-04 | GBM low |
| ENPP6 | 3.11 | 2.62 | 0.58 | 0.86 | 1.3E-04 | IDH-WT high |
| PTGES | 3.31 | 1.36 | 0.83 | 1.58 | 1.3E-04 | K27M high |
| S100A6 | 6.48 | 9.40 | 5.43 | 5.86 | 1.3E-04 | GBM high |
| P2RX7 | 6.17 | 3.67 | 6.50 | 6.50 | 1.3E-04 | GBM low |
| TSHZ1 | 3.68 | 1.94 | 4.13 | 4.16 | 1.3E-04 | GBM low |
| YIPF1 | 5.19 | 5.64 | 3.28 | 4.12 | 1.3E-04 | IDH-WT high |
| LDHA | 8.73 | 10.48 | 7.43 | 5.99 | 1.3E-04 | IDH-O low |
| CYTL1 | 5.94 | 5.75 | 1.67 | 0.43 | 1.4E-04 | IDH-WT high |
| STAC | 2.27 | 3.97 | 0.14 | 0.07 | 1.4E-04 | IDH-WT high |
| TEF | 2.37 | 2.22 | 3.61 | 4.34 | 1.4E-04 | IDH-mut high |
| COMMD3 | 7.89 | 6.67 | 7.22 | 6.58 | 1.4E-04 | K27M high |
| MED12L | 2.99 | 4.78 | 2.40 | 3.44 | 1.4E-04 | GBM high |
| GPSM1 | 4.57 | 2.74 | 5.11 | 5.22 | 1.4E-04 | GBM low |
| TBC1D3F | 3.78 | 3.46 | 5.24 | 4.19 | 1.4E-04 | IDH-A high |
| USP43 | 3.66 | 0.17 | 3.51 | 2.94 | 1.4E-04 | GBM low |
| IGSF9 | 3.53 | 0.41 | 0.69 | 0.88 | 1.4E-04 | K27M high |
| GSDMD | 1.77 | 4.53 | 0.41 | 0.32 | 1.4E-04 | GBM high |
| KDELR2 | 7.73 | 8.52 | 7.13 | 7.22 | 1.4E-04 | GBM high |
| TPPP | 2.61 | 1.05 | 3.05 | 4.26 | 1.4E-04 | IDH-O high & GBM low |
| TRIM38 | 0.56 | 2.48 | 0.46 | 0.26 | 1.4E-04 | GBM high |
| ITGA3 | 1.66 | 3.61 | 0.66 | 1.52 | 1.4E-04 | GBM high |
| KIAA0226L | 2.36 | 4.22 | 0.13 | 0.23 | 1.4E-04 | IDH-WT high |
| NDUFS5 | 8.43 | 8.90 | 8.52 | 7.67 | 1.4E-04 | IDH-O low |
| NGEF | 1.80 | 0.58 | 0.15 | 0.38 | 1.4E-04 | K27M high |
| NIPSNAP3A | 5.41 | 4.84 | 2.19 | 2.18 | 1.4E-04 | IDH-WT high |
| RBPJ | 7.02 | 5.52 | 7.30 | 6.59 | 1.4E-04 | GBM low |
| TULP2 | 0.57 | 1.05 | 0.09 | 0.04 | 1.4E-04 | GBM high |
| ITGA9 | 2.54 | 0.19 | 0.65 | 0.46 | 1.4E-04 | K27M high |
| PTMA | 10.89 | 9.53 | 9.60 | 8.88 | 1.4E-04 | K27M high |
| PARPBP | 3.01 | 4.11 | 1.75 | 1.76 | 1.5E-04 | IDH-WT high |
| CKMT1A | 4.76 | 0.30 | 3.70 | 4.99 | 1.5E-04 | GBM low |
| CHGA | 3.62 | 0.18 | 3.92 | 6.47 | 1.5E-04 | IDH-O high & GBM low |
| SLC1A6 | 4.47 | 0.01 | 3.67 | 4.45 | 1.5E-04 | GBM low |
| ZNF518B | 4.58 | 1.64 | 2.50 | 0.09 | 1.5E-04 | K27M high |
| SERPINE1 | 1.29 | 5.15 | 0.78 | 0.21 | 1.5E-04 | GBM high |
| PDE6B | 2.63 | 2.90 | 1.53 | 1.54 | 1.5E-04 | IDH-WT high |
| PEG3 | 5.99 | 4.28 | 3.80 | 0.17 | 1.5E-04 | IDH-O low |
| RAB31 | 8.05 | 7.36 | 8.47 | 9.69 | 1.5E-04 | IDH-O high |
| BCAN | 11.10 | 10.16 | 12.03 | 11.82 | 1.5E-04 | GBM low |
| MYT1L | 0.82 | 0.01 | 1.48 | 5.19 | 1.5E-04 | IDH-O high |
| TNK2 | 4.78 | 3.67 | 6.10 | 6.84 | 1.6E-04 | IDH-mut high |
| SPEF2 | 2.57 | 1.11 | 0.20 | 0.49 | 1.6E-04 | K27M high |
| UCN | 2.09 | 2.41 | 4.83 | 4.69 | 1.6E-04 | IDH-mut high |
| LAP3 | 6.79 | 8.22 | 6.38 | 5.99 | 1.6E-04 | GBM high |
| KIF2C | 3.90 | 4.75 | 2.50 | 0.94 | 1.6E-04 | IDH-O low |
| LPAR1 | 2.96 | 4.16 | 0.85 | 0.56 | 1.6E-04 | IDH-WT high |
| SYNJ2 | 1.05 | 2.64 | 0.26 | 0.28 | 1.6E-04 | GBM high |
| FAM211B | 3.03 | 2.43 | 4.06 | 4.73 | 1.6E-04 | IDH-mut high |
| IFT57 | 5.40 | 5.94 | 4.34 | 4.11 | 1.6E-04 | IDH-WT high |
| RNF220 | 3.83 | 5.08 | 3.79 | 3.02 | 1.6E-04 | GBM high & IDH-O low |
| HSPB11 | 5.53 | 6.14 | 5.08 | 3.98 | 1.6E-04 | IDH-O low |
| CDK5R1 | 4.05 | 2.01 | 5.11 | 5.13 | 1.6E-04 | GBM low |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| FUCA2 | 5.71 | 6.38 | 2.31 | 2.43 | 1.6E−04 | IDH-WT high |
| MSRB3 | 4.02 | 1.51 | 2.95 | 2.18 | 1.6E−04 | K27M high |
| SYNGR2 | 3.91 | 4.50 | 3.45 | 1.75 | 1.6E−04 | IDH-O low |
| ACTB | 12.07 | 12.54 | 11.40 | 12.31 | 1.6E−04 | IDH-A low |
| ETNK2 | 4.20 | 2.80 | 2.36 | 2.22 | 1.6E−04 | K27M high |
| PLOD1 | 4.73 | 6.42 | 5.25 | 4.08 | 1.6E−04 | GBM high |
| RHBDF1 | 3.26 | 3.28 | 0.88 | 0.55 | 1.6E−04 | IDH-WT high |
| RHBDL1 | 1.77 | 1.34 | 2.60 | 4.18 | 1.6E−04 | IDH-O high |
| SDHAF1 | 5.32 | 6.11 | 5.50 | 4.58 | 1.6E−04 | GBM high & IDH-O low |
| DNAJC12 | 5.65 | 2.14 | 5.18 | 6.25 | 1.6E−04 | GBM low |
| FRMD4A | 4.00 | 1.34 | 3.84 | 3.81 | 1.7E−04 | GBM low |
| ST3GAL5 | 6.15 | 4.22 | 6.45 | 7.07 | 1.7E−04 | GBM low |
| TMEM8B | 4.11 | 1.83 | 4.41 | 4.73 | 1.7E−04 | GBM low |
| NPY1R | 2.84 | 0.00 | 0.49 | 0.10 | 1.7E−04 | K27M high |
| FAS | 3.66 | 3.59 | 0.37 | 2.56 | 1.7E−04 | IDH-A low |
| CDCA8 | 3.74 | 4.54 | 1.97 | 1.06 | 1.7E−04 | IDH-WT high |
| CREB3L1 | 1.96 | 3.01 | 0.65 | 3.47 | 1.7E−04 | IDH-A low |
| HEBP1 | 5.07 | 4.90 | 2.62 | 0.83 | 1.7E−04 | IDH-O low |
| ZBTB8OS | 5.58 | 6.10 | 5.22 | 4.50 | 1.7E−04 | IDH-O low |
| ZNF233 | 4.23 | 0.96 | 2.45 | 3.45 | 1.7E−04 | GBM low |
| ATAD1 | 7.12 | 5.81 | 6.86 | 7.26 | 1.7E−04 | GBM low |
| LRRC16A | 3.17 | 5.81 | 0.96 | 2.56 | 1.7E−04 | GBM high & IDH-A low |
| ADAMTS13 | 2.28 | 1.20 | 3.20 | 3.82 | 1.7E−04 | IDH-mut high |
| CDCA7L | 5.57 | 7.40 | 3.41 | 4.84 | 1.7E−04 | GBM high & IDH-A low |
| EHD2 | 3.16 | 6.25 | 2.41 | 2.45 | 1.7E−04 | GBM high |
| ZIM2 | 3.31 | 3.36 | 2.06 | 0.22 | 1.7E−04 | IDH-O low |
| C9orf89 | 4.74 | 4.84 | 2.39 | 0.28 | 1.7E−04 | IDH-O low |
| GDI2 | 8.06 | 6.97 | 8.16 | 8.03 | 1.7E−04 | GBM low |
| TNR | 8.38 | 4.33 | 7.77 | 8.95 | 1.7E−04 | GBM low |
| LRRC7 | 3.00 | 0.08 | 0.81 | 0.97 | 1.8E−04 | K27M high |
| CDC20 | 5.14 | 6.36 | 3.05 | 1.69 | 1.8E−04 | IDH-WT high |
| SLC30A7 | 4.61 | 5.07 | 4.48 | 3.28 | 1.8E−04 | IDH-O low |
| UNC13A | 2.70 | 1.41 | 3.35 | 4.24 | 1.8E−04 | IDH-O high & GBM low |
| ETV5 | 5.53 | 5.99 | 2.20 | 6.52 | 1.8E−04 | IDH-A low |
| ACAT2 | 7.16 | 6.99 | 6.41 | 8.87 | 1.8E−04 | IDH-O high |
| UBXN1 | 7.87 | 7.29 | 8.48 | 8.76 | 1.8E−04 | IDH-mut high |
| SIX5 | 0.65 | 1.91 | 0.53 | 0.21 | 1.8E−04 | GBM high |
| PUS3 | 6.00 | 3.68 | 5.46 | 5.60 | 1.8E−04 | GBM low |
| FGFBP3 | 3.79 | 2.17 | 3.77 | 5.99 | 1.8E−04 | IDH-O high |
| SEMA3A | 3.59 | 0.64 | 1.48 | 0.16 | 1.8E−04 | K27M high |
| SQSTM1 | 5.85 | 7.23 | 6.57 | 7.08 | 1.9E−04 | K27M low |
| C19orf53 | 6.64 | 7.54 | 6.28 | 6.55 | 1.9E−04 | GBM high |
| HSPB6 | 1.34 | 4.89 | 1.25 | 0.15 | 1.9E−04 | GBM high |
| FCHSD2 | 5.19 | 4.28 | 6.38 | 6.45 | 1.9E−04 | IDH-mut high |
| CPEB3 | 2.96 | 0.56 | 3.79 | 3.73 | 1.9E−04 | GBM low |
| MRPL37 | 6.69 | 7.10 | 6.81 | 5.93 | 1.9E−04 | IDH-O low |
| PPM1H | 2.29 | 0.33 | 2.51 | 3.09 | 1.9E−04 | GBM low |
| SLC50A1 | 4.81 | 4.04 | 4.52 | 5.18 | 1.9E−04 | GBM low |
| PDE2A | 3.04 | 1.67 | 4.97 | 6.06 | 1.9E−04 | IDH-mut high |
| ACACB | 1.60 | 2.40 | 0.85 | 0.41 | 1.9E−04 | IDH-WT high |
| GRAMD1A | 4.51 | 4.45 | 5.07 | 3.89 | 1.9E−04 | IDH-A high |
| VAT1L | 4.72 | 0.00 | 3.87 | 5.56 | 1.9E−04 | GBM low |
| ZNF600 | 1.06 | 3.30 | 0.64 | 0.56 | 1.9E−04 | GBM high |
| SMIM3 | 3.42 | 6.92 | 2.29 | 1.29 | 1.9E−04 | GBM high |
| TYSND1 | 3.15 | 1.86 | 4.11 | 4.72 | 1.9E−04 | GBM low |
| AIG1 | 6.28 | 6.57 | 4.91 | 7.10 | 1.9E−04 | IDH-A low |
| EXTL1 | 4.57 | 0.32 | 2.40 | 2.61 | 2.0E−04 | K27M high & GBM low |
| SLC25A16 | 3.76 | 1.45 | 3.83 | 4.15 | 2.0E−04 | GBM low |
| ADAMTS9 | 2.31 | 4.71 | 1.06 | 1.62 | 2.0E−04 | GBM high |
| EPC1 | 4.93 | 3.50 | 5.60 | 5.41 | 2.0E−04 | GBM low |
| PLEKHG1 | 2.18 | 3.87 | 0.74 | 0.54 | 2.0E−04 | GBM high |
| SSBP3 | 2.96 | 1.09 | 3.17 | 2.76 | 2.0E−04 | GBM low |
| CNTN2 | 3.71 | 0.95 | 0.55 | 2.09 | 2.0E−04 | K27M high |
| PDE8A | 3.64 | 3.90 | 2.73 | 0.83 | 2.0E−04 | IDH-O low |
| ENO1 | 9.53 | 10.12 | 9.11 | 8.12 | 2.0E−04 | IDH-O low |
| PRMT1 | 7.24 | 8.09 | 7.31 | 6.36 | 2.0E−04 | GBM high & IDH-O low |
| EPHA7 | 3.30 | 0.71 | 1.40 | 0.10 | 2.0E−04 | K27M high |
| BCAS2 | 6.97 | 7.15 | 6.91 | 6.07 | 2.1E−04 | IDH-O low |
| CLSTN2 | 2.56 | 0.62 | 4.40 | 3.20 | 2.1E−04 | GBM low |
| SOX6 | 6.48 | 4.11 | 6.35 | 5.98 | 2.1E−04 | GBM low |
| CD83 | 4.48 | 3.48 | 3.19 | 2.14 | 2.1E−04 | IDH-O low |
| MB21D2 | 4.03 | 1.62 | 4.70 | 4.30 | 2.1E−04 | GBM low |
| SLIT1 | 4.86 | 3.97 | 6.52 | 7.14 | 2.1E−04 | IDH-mut high |
| HS3ST3B1 | 1.37 | 3.67 | 0.18 | 0.07 | 2.2E−04 | GBM high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| ZNF568 | 5.54 | 5.65 | 5.41 | 4.59 | 2.2E−04 | IDH-O low |
| CPEB2 | 3.27 | 3.56 | 1.32 | 2.19 | 2.2E−04 | IDH-WT high |
| KIF20A | 3.17 | 3.80 | 1.43 | 0.67 | 2.2E−04 | IDH-WT high |
| GRIK4 | 3.81 | 2.00 | 4.23 | 4.68 | 2.2E−04 | GBM low |
| SLITRK5 | 2.88 | 0.21 | 2.24 | 3.11 | 2.2E−04 | GBM low |
| ANGPTL2 | 5.71 | 4.53 | 6.60 | 7.22 | 2.2E−04 | IDH-mut high |
| UQCRFS1 | 8.14 | 8.65 | 7.99 | 7.45 | 2.3E−04 | IDH-O low |
| ANXA1 | 3.03 | 8.46 | 1.27 | 0.48 | 2.3E−04 | GBM high |
| TGIF1 | 4.87 | 6.69 | 4.61 | 2.63 | 2.3E−04 | GBM high & IDH-O low |
| SEC31B | 3.79 | 2.73 | 4.90 | 4.70 | 2.3E−04 | GBM low |
| TEX30 | 5.62 | 4.60 | 6.54 | 5.07 | 2.3E−04 | IDH-A high |
| BDH2 | 3.85 | 5.11 | 2.76 | 0.97 | 2.3E−04 | IDH-O low |
| EHD3 | 6.28 | 3.28 | 5.59 | 6.21 | 2.4E−04 | GBM low |
| COL8A1 | 1.27 | 3.59 | 0.39 | 0.42 | 2.4E−04 | GBM high |
| LRRC4 | 3.85 | 1.27 | 3.96 | 4.24 | 2.4E−04 | GBM low |
| DEPDC1B | 3.86 | 4.39 | 1.79 | 1.60 | 2.4E−04 | IDH-WT high |
| TMX2 | 7.82 | 7.88 | 7.74 | 8.73 | 2.4E−04 | IDH-O high |
| UBA2 | 5.59 | 5.50 | 5.48 | 4.21 | 2.4E−04 | IDH-O low |
| ARHGEF1 | 5.12 | 5.52 | 4.67 | 3.70 | 2.5E−04 | IDH-O low |
| DLGAP5 | 3.02 | 4.49 | 1.63 | 0.66 | 2.5E−04 | IDH-WT high |
| MUS81 | 5.27 | 5.11 | 5.43 | 5.97 | 2.5E−04 | IDH-O high |
| C11orf70 | 3.85 | 1.70 | 1.77 | 1.88 | 2.5E−04 | K27M high |
| THTPA | 5.20 | 5.84 | 5.99 | 6.52 | 2.5E−04 | IDH-O high |
| PLEKHA5 | 4.81 | 1.98 | 4.62 | 3.85 | 2.5E−04 | GBM low |
| GAS7 | 2.31 | 4.65 | 1.80 | 1.42 | 2.5E−04 | GBM high |
| XAF1 | 3.18 | 5.50 | 2.67 | 2.61 | 2.5E−04 | GBM high |
| MB | 0.01 | 0.00 | 0.20 | 2.33 | 2.6E−04 | IDH-O high |
| NRSN1 | 4.02 | 2.41 | 5.35 | 7.27 | 2.6E−04 | IDH-O high |
| RAD54L | 2.57 | 3.82 | 1.92 | 1.02 | 2.6E−04 | GBM high & IDH-O low |
| RCN3 | 2.98 | 3.50 | 2.57 | 2.01 | 2.6E−04 | IDH-O low |
| EXD3 | 2.51 | 1.49 | 3.82 | 4.11 | 2.6E−04 | IDH-mut high |
| ZAK | 4.42 | 4.36 | 1.84 | 2.31 | 2.6E−04 | IDH-WT high |
| MEF2C | 4.94 | 2.18 | 1.98 | 2.24 | 2.6E−04 | K27M high |
| C11orf71 | 5.27 | 1.47 | 5.08 | 5.81 | 2.6E−04 | GBM low |
| PSME2 | 5.96 | 8.25 | 6.13 | 6.14 | 2.6E−04 | GBM high |
| TSPAN4 | 4.04 | 5.40 | 2.81 | 3.61 | 2.6E−04 | GBM high |
| WIPI1 | 2.75 | 4.66 | 1.39 | 2.45 | 2.6E−04 | GBM high |
| GRWD1 | 5.29 | 6.25 | 4.81 | 4.19 | 2.6E−04 | GBM high |
| PALM | 3.15 | 0.81 | 3.24 | 3.28 | 2.6E−04 | GBM low |
| BUB1B | 4.11 | 4.44 | 2.55 | 1.71 | 2.6E−04 | IDH-WT high |
| SVOP | 2.21 | 0.73 | 2.83 | 5.90 | 2.6E−04 | IDH-O high |
| GLCCI1 | 5.67 | 2.99 | 6.83 | 5.66 | 2.6E−04 | GBM low |
| NUSAP1 | 5.56 | 6.74 | 3.89 | 3.23 | 2.6E−04 | IDH-WT high |
| IER3 | 1.82 | 3.18 | 1.09 | 1.59 | 2.6E−04 | GBM high |
| GAS2L3 | 3.21 | 3.81 | 1.70 | 0.35 | 2.6E−04 | IDH-O low |
| FA2H | 2.42 | 0.15 | 1.72 | 4.02 | 2.6E−04 | IDH-O high |
| CDK11B | 3.62 | 3.82 | 4.18 | 3.12 | 2.6E−04 | IDH-O low |
| EPHX4 | 3.04 | 0.08 | 1.16 | 0.90 | 2.6E−04 | K27M high |
| EVL | 4.08 | 1.95 | 5.02 | 5.09 | 2.6E−04 | GBM low |
| TXNDC12 | 6.17 | 6.30 | 6.10 | 5.00 | 2.6E−04 | IDH-O low |
| CACNG5 | 4.00 | 1.13 | 0.24 | 0.05 | 2.7E−04 | K27M high |
| GLIS3 | 2.78 | 2.92 | 1.05 | 0.52 | 2.7E−04 | IDH-WT high |
| CHN2 | 3.29 | 3.01 | 1.13 | 3.15 | 2.7E−04 | IDH-A low |
| TRIP6 | 2.37 | 5.55 | 2.17 | 2.56 | 2.7E−04 | GBM high |
| THEM4 | 4.46 | 1.52 | 3.07 | 3.84 | 2.7E−04 | GBM low |
| SCUBE3 | 3.22 | 0.91 | 2.07 | 2.11 | 2.7E−04 | K27M high & GBM low |
| FNBP1L | 5.99 | 5.42 | 5.06 | 2.30 | 2.7E−04 | IDH-O low |
| CHAF1B | 3.31 | 4.51 | 1.65 | 1.02 | 2.7E−04 | IDH-WT high |
| FADS1 | 6.54 | 5.75 | 6.61 | 7.41 | 2.8E−04 | IDH-O high & GBM low |
| CACNA1A | 2.12 | 0.12 | 2.64 | 3.16 | 2.8E−04 | GBM low |
| RAB8A | 5.61 | 6.52 | 4.81 | 5.76 | 2.8E−04 | IDH-A low |
| SPP1 | 4.60 | 7.90 | 1.46 | 1.74 | 2.8E−04 | GBM high |
| CCNB1 | 5.34 | 6.69 | 3.43 | 3.40 | 2.8E−04 | IDH-WT high |
| KIF23 | 3.79 | 4.47 | 1.72 | 1.26 | 2.8E−04 | IDH-WT high |
| HPS1 | 3.87 | 3.15 | 0.33 | 0.15 | 2.8E−04 | IDH-WT high |
| HILPDA | 5.35 | 7.74 | 5.55 | 5.16 | 2.8E−04 | GBM high |
| CABYR | 3.62 | 0.24 | 2.11 | 3.96 | 2.8E−04 | GBM low |
| HECW2 | 1.92 | 0.08 | 2.56 | 2.23 | 2.8E−04 | GBM low |
| MOXD1 | 2.70 | 6.44 | 0.49 | 0.71 | 2.8E−04 | GBM high |
| PAQR3 | 4.42 | 2.49 | 3.23 | 3.21 | 2.8E−04 | K27M high |
| ASPM | 3.60 | 3.78 | 1.50 | 0.48 | 2.8E−04 | IDH-WT high |
| AURKB | 4.07 | 5.05 | 2.49 | 1.40 | 2.8E−04 | IDH-WT high |
| JAKMIP3 | 2.39 | 0.04 | 1.32 | 2.68 | 2.8E−04 | GBM low |
| WEE1 | 4.95 | 5.94 | 3.28 | 2.68 | 2.8E−04 | IDH-WT high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| NADK | 3.59 | 4.40 | 4.04 | 2.76 | 2.8E−04 | IDH-O low |
| ALG14 | 4.76 | 5.37 | 5.15 | 4.25 | 2.9E−04 | IDH-O low |
| RBM47 | 0.21 | 2.21 | 0.12 | 0.13 | 3.0E−04 | GBM high |
| RNF175 | 5.06 | 0.83 | 1.08 | 0.83 | 3.0E−04 | K27M high |
| SIMC1 | 3.90 | 1.08 | 1.34 | 0.15 | 3.0E−04 | K27M high |
| EPB41L4B | 3.20 | 0.19 | 2.04 | 1.61 | 3.0E−04 | K27M high & GBM low |
| FAM50B | 2.91 | 3.42 | 0.13 | 0.35 | 3.0E−04 | IDH-WT high |
| ZNF74 | 5.13 | 3.21 | 5.34 | 4.99 | 3.0E−04 | GBM low |
| RAB36 | 3.32 | 4.49 | 1.92 | 1.84 | 3.1E−04 | IDH-WT high |
| GALNT4 | 1.62 | 3.87 | 0.73 | 0.74 | 3.1E−04 | GBM high |
| LAMB1 | 3.44 | 3.50 | 2.35 | 1.05 | 3.1E−04 | IDH-O low |
| PPCS | 5.44 | 5.88 | 3.42 | 0.75 | 3.1E−04 | IDH-O low |
| ANXA2 | 4.72 | 9.66 | 4.66 | 4.34 | 3.1E−04 | GBM high |
| CD151 | 4.65 | 6.30 | 4.32 | 4.62 | 3.1E−04 | GBM high |
| RAP1A | 4.75 | 5.27 | 4.73 | 3.71 | 3.1E−04 | IDH-O low |
| TTC3 | 7.38 | 6.48 | 7.98 | 7.89 | 3.1E−04 | GBM low |
| MRPL43 | 7.17 | 6.08 | 7.17 | 7.43 | 3.2E−04 | GBM low |
| PDZD8 | 2.86 | 0.86 | 2.96 | 3.14 | 3.2E−04 | GBM low |
| ZNF691 | 4.68 | 4.77 | 4.68 | 3.93 | 3.2E−04 | IDH-O low |
| CHCHD10 | 1.59 | 1.92 | 0.30 | 1.21 | 3.2E−04 | IDH-A low |
| CMYA5 | 2.66 | 3.30 | 0.25 | 0.32 | 3.2E−04 | IDH-WT high |
| CSTF2T | 5.91 | 3.73 | 5.42 | 5.71 | 3.2E−04 | GBM low |
| OR2A7 | 2.22 | 0.13 | 0.37 | 0.09 | 3.3E−04 | K27M high |
| CTBS | 3.94 | 3.39 | 2.77 | 1.14 | 3.3E−04 | IDH-O low |
| SLC9B1 | 2.11 | 0.82 | 2.91 | 3.50 | 3.3E−04 | GBM low |
| FAM109B | 2.30 | 2.32 | 0.71 | 0.47 | 3.3E−04 | IDH-WT high |
| WDR62 | 2.13 | 3.68 | 1.50 | 0.72 | 3.3E−04 | GBM high |
| ME1 | 3.72 | 0.00 | 0.24 | 1.35 | 3.4E−04 | K27M high |
| TMEM87A | 6.31 | 6.55 | 6.73 | 7.38 | 3.4E−04 | IDH-O high |
| SMOX | 4.48 | 6.65 | 5.63 | 6.05 | 3.4E−04 | K27M low |
| RAPGEF5 | 1.97 | 0.50 | 1.28 | 3.18 | 3.4E−04 | IDH-O high |
| MYT1 | 5.71 | 2.12 | 5.30 | 5.81 | 3.4E−04 | GBM low |
| QPCT | 2.56 | 0.00 | 0.07 | 0.11 | 3.4E−04 | K27M high |
| ZNF326 | 5.66 | 5.54 | 5.62 | 4.60 | 3.4E−04 | IDH-O low |
| AK2 | 6.10 | 6.65 | 6.02 | 5.23 | 3.5E−04 | IDH-O low |
| SCN3B | 3.72 | 1.33 | 3.80 | 5.61 | 3.5E−04 | IDH-O high & GBM low |
| TSPO | 7.29 | 7.06 | 6.97 | 4.65 | 3.5E−04 | IDH-O low |
| PARD3 | 3.35 | 2.01 | 3.75 | 3.57 | 3.5E−04 | GBM low |
| WSB1 | 7.78 | 7.59 | 9.06 | 9.31 | 3.5E−04 | IDH-mut high |
| ERRFI1 | 5.28 | 5.46 | 4.98 | 3.96 | 3.5E−04 | IDH-O low |
| ANKRD26 | 3.36 | 2.07 | 3.93 | 3.91 | 3.5E−04 | GBM low |
| CDH13 | 5.22 | 1.75 | 5.92 | 6.27 | 3.5E−04 | GBM low |
| HMGCR | 6.49 | 5.29 | 5.98 | 7.31 | 3.5E−04 | IDH-O high |
| ISYNA1 | 5.12 | 4.92 | 2.95 | 1.74 | 3.5E−04 | IDH-WT high |
| NR4A2 | 4.04 | 0.99 | 2.07 | 1.88 | 3.5E−04 | K27M high |
| POLR2L | 5.71 | 6.86 | 5.06 | 5.49 | 3.5E−04 | GBM high |
| NCOA4 | 7.23 | 6.11 | 7.32 | 7.53 | 3.5E−04 | GBM low |
| NAALAD2 | 5.33 | 1.02 | 1.16 | 2.17 | 3.7E−04 | K27M high |
| DIRAS3 | 4.37 | 6.29 | 2.61 | 1.69 | 3.7E−04 | IDH-WT high |
| PRSS48 | 3.37 | 1.25 | 3.84 | 2.77 | 3.7E−04 | GBM low |
| C19orf12 | 4.41 | 4.20 | 4.30 | 3.48 | 3.7E−04 | IDH-O low |
| PSTK | 3.25 | 1.45 | 3.50 | 4.01 | 3.7E−04 | GBM low |
| CHODL | 2.85 | 0.65 | 0.53 | 0.14 | 3.8E−04 | K27M high |
| TMED9 | 6.58 | 8.04 | 6.33 | 6.83 | 3.8E−04 | GBM high |
| EXOSC10 | 6.82 | 6.96 | 6.86 | 5.70 | 3.8E−04 | IDH-O low |
| PPP1R3E | 1.67 | 1.48 | 2.95 | 3.60 | 3.8E−04 | IDH-mut high |
| FCGRT | 4.89 | 6.92 | 4.76 | 4.59 | 3.8E−04 | GBM high |
| CDC123 | 7.27 | 5.78 | 7.46 | 7.40 | 3.8E−04 | GBM low |
| B4GALT7 | 4.08 | 5.20 | 4.72 | 5.10 | 3.8E−04 | K27M low |
| MVD | 5.44 | 5.51 | 5.56 | 7.23 | 3.8E−04 | IDH-O high |
| CGREF1 | 4.20 | 1.62 | 3.63 | 3.97 | 3.8E−04 | GBM low |
| PNRC2 | 7.55 | 7.27 | 7.55 | 6.51 | 3.8E−04 | IDH-O low |
| SLAIN1 | 5.24 | 4.63 | 5.95 | 7.27 | 3.8E−04 | IDH-O high |
| ZNF45 | 4.34 | 4.86 | 3.57 | 2.88 | 3.8E−04 | IDH-WT high |
| CALCRL | 6.32 | 2.72 | 6.88 | 6.43 | 3.9E−04 | GBM low |
| SH3GLB1 | 5.54 | 6.38 | 5.60 | 4.46 | 3.9E−04 | IDH-O low |
| AKIRIN1 | 6.64 | 7.25 | 6.75 | 5.68 | 3.9E−04 | IDH-O low |
| TM4SF1 | 7.15 | 6.87 | 2.67 | 0.34 | 4.0E−04 | IDH-WT high |
| RGS6 | 0.82 | 4.60 | 0.46 | 0.17 | 4.0E−04 | GBM high |
| SLC25A29 | 4.22 | 3.42 | 5.10 | 5.03 | 4.0E−04 | IDH-mut high |
| FOXJ3 | 5.16 | 5.99 | 5.50 | 4.36 | 4.0E−04 | IDH-O low |
| CA12 | 4.83 | 6.00 | 1.87 | 5.21 | 4.1E−04 | IDH-A low |
| ACAA2 | 5.68 | 5.68 | 2.89 | 2.54 | 4.1E−04 | IDH-WT high |
| CSRP2 | 5.51 | 8.84 | 3.82 | 2.84 | 4.2E−04 | GBM high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| CD55 | 4.36 | 0.24 | 1.52 | 2.60 | 4.2E-04 | K27M high |
| IGSF21 | 4.32 | 0.64 | 4.64 | 4.77 | 4.2E-04 | GBM low |
| SH2D4A | 1.46 | 2.50 | 0.31 | 0.36 | 4.2E-04 | IDH-WT high |
| CLVS1 | 2.17 | 1.59 | 1.51 | 5.02 | 4.2E-04 | IDH-O high |
| LRRIQ1 | 1.71 | 0.08 | 0.03 | 0.06 | 4.2E-04 | K27M high |
| CARD8 | 4.93 | 4.70 | 4.33 | 3.87 | 4.2E-04 | IDH-O low |
| RNF144A | 5.92 | 2.95 | 4.36 | 4.03 | 4.3E-04 | K27M high |
| NR2C2AP | 4.84 | 5.95 | 4.57 | 4.62 | 4.3E-04 | GBM high |
| CDC42 | 7.36 | 7.86 | 7.60 | 6.32 | 4.3E-04 | IDH-O low |
| FAM13C | 4.14 | 2.17 | 5.57 | 5.58 | 4.3E-04 | GBM low |
| MAP1LC3A | 5.56 | 5.86 | 2.13 | 4.46 | 4.4E-04 | IDH-A low |
| LRFN2 | 2.33 | 0.00 | 0.55 | 1.25 | 4.4E-04 | K27M high |
| DNER | 7.26 | 3.34 | 7.29 | 7.76 | 4.4E-04 | GBM low |
| HINFP | 4.49 | 3.70 | 5.19 | 5.22 | 4.4E-04 | IDH-mut high |
| KLHL23 | 5.64 | 3.63 | 5.11 | 5.58 | 4.4E-04 | GBM low |
| TFRC | 5.31 | 7.31 | 5.05 | 4.51 | 4.4E-04 | GBM high |
| LMO2 | 1.99 | 5.17 | 0.74 | 1.16 | 4.4E-04 | GBM high |
| BRD3 | 6.34 | 4.56 | 6.87 | 6.77 | 4.5E-04 | GBM low |
| VRK3 | 4.64 | 5.84 | 4.95 | 4.43 | 4.5E-04 | GBM high |
| SP100 | 2.99 | 5.16 | 2.23 | 2.13 | 4.5E-04 | GBM high |
| LIMS2 | 2.87 | 0.43 | 3.15 | 4.50 | 4.5E-04 | IDH-O high & GBM low |
| AOAH | 0.82 | 0.19 | 2.01 | 2.07 | 4.5E-04 | IDH-mut high |
| MCC | 3.56 | 4.79 | 2.00 | 2.36 | 4.5E-04 | IDH-WT high |
| PELI2 | 3.97 | 2.21 | 4.68 | 4.65 | 4.5E-04 | GBM low |
| SH3GL2 | 4.53 | 0.49 | 4.73 | 5.51 | 4.5E-04 | GBM low |
| FLRT1 | 4.04 | 2.93 | 5.38 | 5.72 | 4.6E-04 | IDH-mut high |
| CPLX2 | 1.53 | 0.63 | 2.39 | 4.10 | 4.6E-04 | IDH-O high |
| PTTG1 | 6.13 | 6.92 | 4.60 | 3.45 | 4.6E-04 | IDH-WT high |
| CCDC152 | 3.01 | 3.93 | 0.31 | 0.14 | 4.6E-04 | IDH-WT high |
| WSCD2 | 0.64 | 0.00 | 0.87 | 2.58 | 4.6E-04 | IDH-O high |
| CACNG2 | 1.34 | 0.04 | 2.55 | 4.44 | 4.6E-04 | IDH-O high |
| MEGF11 | 6.26 | 3.92 | 6.16 | 6.92 | 4.6E-04 | GBM low |
| SNAPC2 | 4.47 | 4.88 | 4.57 | 2.92 | 4.6E-04 | IDH-O low |
| TMEM106C | 6.55 | 7.08 | 5.60 | 5.61 | 4.7E-04 | IDH-WT high |
| SNURF | 7.57 | 7.00 | 8.06 | 8.14 | 4.7E-04 | IDH-mut high |
| ZFYVE27 | 5.18 | 4.12 | 5.61 | 5.88 | 4.7E-04 | GBM low |
| MSRB2 | 2.75 | 1.79 | 3.79 | 3.78 | 4.7E-04 | IDH-mut high |
| FCGR2A | 0.98 | 3.57 | 0.63 | 0.63 | 4.7E-04 | GBM high |
| ITPR2 | 4.43 | 4.70 | 2.07 | 2.91 | 4.7E-04 | IDH-WT high |
| CCDC34 | 3.19 | 4.27 | 2.19 | 2.39 | 4.7E-04 | GBM high |
| YIF1A | 7.27 | 7.35 | 7.38 | 8.09 | 4.7E-04 | IDH-O high |
| CEP135 | 3.52 | 3.64 | 2.46 | 1.77 | 4.8E-04 | IDH-WT high |
| KAT6B | 4.73 | 2.87 | 5.14 | 5.16 | 4.8E-04 | GBM low |
| RPS6KL1 | 2.66 | 1.24 | 3.19 | 3.46 | 4.8E-04 | GBM low |
| UTP11L | 6.40 | 6.04 | 6.14 | 5.59 | 4.8E-04 | IDH-O low |
| FAM19A4 | 1.05 | 0.00 | 0.05 | 0.11 | 4.8E-04 | K27M high |
| SH3D19 | 4.63 | 2.80 | 4.96 | 4.14 | 4.8E-04 | GBM low |
| MICU1 | 6.27 | 4.76 | 6.31 | 6.51 | 4.9E-04 | GBM low |
| ADORA1 | 3.58 | 3.56 | 1.33 | 3.65 | 4.9E-04 | IDH-A low |
| TUT1 | 4.50 | 4.51 | 5.11 | 5.61 | 4.9E-04 | IDH-O high |
| PIGB | 3.73 | 4.11 | 2.22 | 4.21 | 5.0E-04 | IDH-A low |
| PKIB | 4.21 | 6.12 | 1.35 | 0.86 | 5.0E-04 | IDH-WT high |
| EPHB4 | 0.95 | 3.39 | 0.82 | 1.11 | 5.0E-04 | GBM high |
| CDH6 | 3.37 | 6.52 | 1.67 | 2.38 | 5.1E-04 | GBM high |
| MCM3 | 5.82 | 6.78 | 5.07 | 4.87 | 5.1E-04 | GBM high |
| PEX16 | 4.62 | 4.92 | 4.77 | 5.67 | 5.1E-04 | IDH-O high |
| TMEM206 | 8.01 | 6.01 | 6.48 | 6.45 | 5.1E-04 | K27M high |
| MAML2 | 5.42 | 5.35 | 6.58 | 6.46 | 5.1E-04 | IDH-mut high |
| BEND7 | 2.61 | 1.48 | 3.48 | 2.59 | 5.1E-04 | IDH-A high & GBM low |
| FDPS | 7.93 | 7.14 | 7.43 | 8.68 | 5.1E-04 | IDH-O high |
| RAB11FIP1 | 1.99 | 0.72 | 1.06 | 1.08 | 5.1E-04 | K27M high |
| TPP2 | 5.69 | 4.16 | 6.37 | 5.66 | 5.1E-04 | GBM low |
| UNC5A | 1.62 | 0.88 | 2.80 | 3.06 | 5.1E-04 | IDH-mut high |
| ABCB4 | 2.29 | 0.29 | 0.13 | 0.06 | 5.1E-04 | K27M high |
| ANO4 | 3.33 | 0.16 | 2.27 | 3.99 | 5.1E-04 | GBM low |
| TMEM37 | 1.29 | 2.81 | 0.43 | 0.37 | 5.2E-04 | GBM high |
| CPPED1 | 2.99 | 1.95 | 1.81 | 1.77 | 5.2E-04 | K27M high |
| OMG | 8.09 | 3.55 | 8.23 | 8.62 | 5.2E-04 | GBM low |
| MYH14 | 1.86 | 0.05 | 1.39 | 1.51 | 5.3E-04 | GBM low |
| PCYT2 | 3.11 | 3.30 | 3.33 | 4.75 | 5.3E-04 | IDH-O high |
| SPTBN2 | 2.47 | 0.90 | 2.88 | 2.78 | 5.3E-04 | GBM low |
| DPP10 | 4.78 | 0.68 | 3.31 | 3.08 | 5.3E-04 | K27M high & GBM low |
| GABRA5 | 2.22 | 0.00 | 0.07 | 0.11 | 5.3E-04 | K27M high |
| CP | 1.07 | 2.61 | 0.18 | 0.29 | 5.3E-04 | GBM high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
| --- | --- | --- | --- | --- | --- | --- |
| FAM64A | 5.33 | 6.32 | 3.68 | 2.65 | 5.3E−04 | IDH-WT high |
| USP1 | 5.73 | 5.63 | 5.45 | 4.35 | 5.3E−04 | IDH-O low |
| CUTC | 5.61 | 4.40 | 5.70 | 5.94 | 5.3E−04 | GBM low |
| RLBP1 | 4.62 | 4.62 | 1.30 | 4.03 | 5.3E−04 | IDH-A low |
| ADAM22 | 4.46 | 4.11 | 5.62 | 5.96 | 5.3E−04 | IDH-mut high |
| LZTS1 | 2.90 | 5.19 | 1.12 | 2.11 | 5.3E−04 | GBM high |
| PCP4L1 | 4.06 | 0.11 | 0.79 | 1.33 | 5.3E−04 | K27M high |
| CAMSAP1 | 3.59 | 2.19 | 3.93 | 3.60 | 5.4E−04 | GBM low |
| CD44 | 3.68 | 7.28 | 1.90 | 0.93 | 5.4E−04 | GBM high |
| CDH20 | 3.04 | 1.75 | 4.31 | 4.35 | 5.4E−04 | IDH-mut high |
| STAR | 1.58 | 1.24 | 2.12 | 3.32 | 5.4E−04 | IDH-O high |
| TMEM194A | 3.77 | 4.99 | 3.16 | 3.31 | 5.4E−04 | GBM high |
| PDCD4 | 6.28 | 4.21 | 6.26 | 6.05 | 5.4E−04 | GBM low |
| AGAP5 | 3.83 | 1.98 | 3.97 | 4.02 | 5.4E−04 | GBM low |
| NUDT14 | 2.55 | 2.03 | 4.03 | 0.75 | 5.4E−04 | IDH-A high |
| COX6B1 | 8.11 | 8.67 | 7.90 | 7.28 | 5.4E−04 | IDH-O low |
| MARCKS | 8.27 | 6.93 | 8.42 | 9.15 | 5.4E−04 | IDH-O high & GBM low |
| TMEM63C | 2.25 | 0.47 | 2.03 | 3.60 | 5.4E−04 | IDH-O high & GBM low |
| MAL2 | 3.47 | 0.00 | 0.38 | 0.73 | 5.4E−04 | K27M high |
| DIAPH3 | 2.84 | 3.24 | 1.67 | 0.87 | 5.4E−04 | IDH-WT high |
| ATG16L2 | 3.16 | 1.63 | 4.21 | 4.35 | 5.4E−04 | GBM low |
| CCS | 5.84 | 5.75 | 6.59 | 7.05 | 5.5E−04 | IDH-mut high |
| ITGA5 | 2.48 | 3.46 | 0.50 | 0.18 | 5.5E−04 | IDH-WT high |
| CHML | 3.52 | 0.93 | 2.27 | 2.14 | 5.5E−04 | K27M high & GBM low |
| CDCA2 | 2.38 | 3.94 | 1.02 | 0.73 | 5.5E−04 | IDH-WT high |
| FILIP1L | 3.12 | 3.49 | 1.58 | 1.35 | 5.5E−04 | IDH-WT high |
| ZNF37A | 4.80 | 3.07 | 5.18 | 4.87 | 5.5E−04 | GBM low |
| WDR25 | 3.88 | 3.87 | 4.28 | 5.05 | 5.6E−04 | IDH-O high |
| SHC2 | 3.68 | 2.35 | 3.94 | 4.42 | 5.6E−04 | GBM low |
| TAF12 | 6.32 | 6.67 | 5.76 | 5.18 | 5.6E−04 | IDH-O low |
| ZNF32 | 7.52 | 6.43 | 7.51 | 7.79 | 5.6E−04 | GBM low |
| IGF2BP3 | 4.40 | 4.56 | 1.91 | 1.16 | 5.6E−04 | IDH-WT high |
| EIF4G3 | 5.19 | 4.60 | 5.85 | 4.54 | 5.6E−04 | IDH-A high |
| LGALS1 | 5.65 | 9.00 | 3.01 | 2.99 | 5.6E−04 | GBM high |
| LMAN2 | 6.89 | 7.87 | 6.49 | 7.00 | 5.6E−04 | GBM high |
| TROAP | 3.67 | 4.31 | 2.01 | 1.14 | 5.6E−04 | IDH-WT high |
| KANK2 | 2.00 | 4.58 | 1.55 | 1.59 | 5.6E−04 | GBM high |
| SORCS1 | 3.46 | 0.47 | 1.85 | 0.90 | 5.6E−04 | K27M high |
| ZDHHC23 | 1.60 | 2.27 | 0.15 | 0.28 | 5.6E−04 | IDH-WT high |
| FAH | 2.83 | 3.89 | 1.55 | 0.90 | 5.6E−04 | IDH-WT high |
| SRRM3 | 2.63 | 0.48 | 2.83 | 4.14 | 5.6E−04 | IDH-O high & GBM low |
| FAM117B | 4.36 | 2.42 | 4.46 | 4.48 | 5.6E−04 | GBM low |
| LMF1 | 7.53 | 6.04 | 8.81 | 8.56 | 5.7E−04 | GBM low |
| HRH1 | 1.96 | 4.92 | 1.17 | 1.75 | 5.7E−04 | GBM high |
| TPI1 | 9.31 | 10.65 | 9.60 | 9.15 | 5.7E−04 | GBM high |
| HMGCS1 | 5.95 | 5.30 | 5.32 | 7.19 | 5.7E−04 | IDH-O high |
| SLC25A45 | 2.06 | 3.33 | 1.16 | 1.01 | 5.7E−04 | GBM high |
| NMNAT3 | 4.26 | 4.36 | 1.61 | 1.07 | 5.7E−04 | IDH-WT high |
| PVRL3 | 4.23 | 0.93 | 3.21 | 3.66 | 5.8E−04 | GBM low |
| FAM45A | 5.49 | 4.53 | 5.56 | 5.85 | 5.8E−04 | GBM low |
| SCN9A | 2.88 | 0.10 | 0.17 | 0.34 | 5.8E−04 | K27M high |
| LACC1 | 2.48 | 0.68 | 0.64 | 0.30 | 5.8E−04 | K27M high |
| ZNF618 | 2.91 | 0.71 | 1.27 | 1.04 | 5.8E−04 | K27M high |
| AGMO | 1.09 | 5.09 | 2.87 | 3.21 | 5.9E−04 | GBM high & K27M low |
| PIPOX | 2.20 | 5.76 | 3.06 | 3.03 | 5.9E−04 | GBM high |
| BCL3 | 0.57 | 2.32 | 1.01 | 0.59 | 5.9E−04 | GBM high |
| NDST4 | 0.42 | 0.02 | 3.65 | 2.90 | 5.9E−04 | IDH-mut high |
| AK4 | 3.88 | 6.47 | 3.82 | 3.94 | 5.9E−04 | GBM high |
| SRC | 4.12 | 2.89 | 4.68 | 4.97 | 5.9E−04 | GBM low |
| FAM171A1 | 4.18 | 2.22 | 4.49 | 4.60 | 5.9E−04 | GBM low |
| AMPH | 4.89 | 1.25 | 3.87 | 5.27 | 6.0E−04 | GBM low |
| JMJD1C | 5.87 | 5.08 | 6.52 | 5.87 | 6.0E−04 | IDH-A high & GBM low |
| C21orf2 | 3.65 | 4.56 | 4.51 | 5.18 | 6.0E−04 | K27M low |
| MYL9 | 0.14 | 1.59 | 0.26 | 0.02 | 6.0E−04 | GBM high |
| YBX1 | 6.74 | 6.38 | 6.72 | 5.44 | 6.0E−04 | IDH-O low |
| FAXC | 2.94 | 0.86 | 3.02 | 3.16 | 6.0E−04 | GBM low |
| GRID1 | 3.45 | 1.24 | 3.20 | 4.17 | 6.0E−04 | GBM low |
| SUSD4 | 5.77 | 3.00 | 5.78 | 6.46 | 6.0E−04 | GBM low |
| BLM | 4.55 | 5.32 | 2.32 | 2.21 | 6.1E−04 | IDH-WT high |
| ZYX | 5.25 | 7.95 | 5.09 | 5.42 | 6.1E−04 | GBM high |
| BCL11A | 4.77 | 1.15 | 1.17 | 0.05 | 6.1E−04 | K27M high |
| NRD1 | 6.37 | 6.67 | 6.50 | 5.53 | 6.2E−04 | IDH-O low |
| AGAP6 | 4.19 | 3.20 | 4.67 | 4.63 | 6.2E−04 | GBM low |
| GDPD1 | 4.74 | 4.09 | 5.56 | 5.84 | 6.2E−04 | IDH-mut high |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| RAB11FIP4 | 2.53 | 0.48 | 2.51 | 2.23 | 6.3E−04 | GBM low |
| FERMT1 | 3.99 | 2.46 | 7.06 | 6.76 | 6.3E−04 | IDH-mut high |
| WASF1 | 6.28 | 4.09 | 6.30 | 6.36 | 6.3E−04 | GBM low |
| GLRX2 | 4.78 | 4.96 | 3.75 | 4.05 | 6.3E−04 | IDH-WT high |
| SDSL | 3.42 | 4.33 | 1.41 | 4.45 | 6.4E−04 | IDH-A low |
| HIST4H4 | 1.56 | 0.50 | 0.09 | 0.02 | 6.4E−04 | K27M high |
| PTPRN | 1.71 | 0.20 | 2.22 | 6.42 | 6.4E−04 | IDH-O high |
| TFB2M | 6.00 | 4.33 | 4.90 | 4.93 | 6.4E−04 | K27M high |
| ZNF146 | 6.95 | 7.16 | 7.08 | 5.86 | 6.4E−04 | IDH-O low |
| AIP | 6.61 | 6.15 | 7.34 | 7.22 | 6.4E−04 | IDH-mut high |
| DISP2 | 2.95 | 0.42 | 2.18 | 3.15 | 6.5E−04 | GBM low |
| CELF5 | 2.70 | 0.32 | 3.53 | 3.34 | 6.5E−04 | GBM low |
| ZNF488 | 5.20 | 0.64 | 5.45 | 4.92 | 6.5E−04 | GBM low |
| MYO18A | 3.10 | 2.71 | 4.34 | 4.41 | 6.5E−04 | IDH-mut high |
| GPR123 | 4.05 | 2.44 | 4.67 | 5.04 | 6.5E−04 | GBM low |
| CCNA1 | 2.04 | 0.20 | 0.23 | 0.14 | 6.5E−04 | K27M high |
| GTF2H2D | 5.16 | 5.43 | 4.36 | 4.51 | 6.5E−04 | IDH-WT high |
| ACSL3 | 6.59 | 7.78 | 5.60 | 6.55 | 6.6E−04 | GBM high & IDH-A low |
| TES | 3.22 | 0.94 | 1.51 | 1.21 | 6.6E−04 | K27M high |
| TMEM86A | 2.02 | 0.77 | 3.05 | 3.31 | 6.7E−04 | IDH-mut high |
| HSPG2 | 2.23 | 1.13 | 1.00 | 0.57 | 6.7E−04 | K27M high |
| PTGS1 | 0.40 | 2.29 | 0.15 | 0.13 | 6.7E−04 | GBM high |
| C7orf60 | 4.50 | 3.79 | 5.05 | 4.89 | 6.8E−04 | GBM low |
| DPYD | 3.19 | 4.81 | 1.17 | 2.79 | 6.8E−04 | IDH-A low |
| MEX3B | 3.13 | 0.41 | 2.85 | 2.64 | 6.8E−04 | GBM low |
| TPX2 | 4.87 | 5.86 | 3.34 | 2.76 | 6.8E−04 | IDH-WT high |
| SFRP4 | 3.62 | 4.45 | 0.74 | 0.89 | 6.8E−04 | IDH-WT high |
| CTAGE4 | 1.12 | 0.18 | 0.04 | 0.02 | 6.8E−04 | K27M high |
| STARD5 | 1.30 | 0.33 | 0.52 | 2.55 | 6.9E−04 | IDH-O high |
| LIF | 0.83 | 2.22 | 0.31 | 0.42 | 6.9E−04 | GBM high |
| MTF2 | 5.48 | 5.23 | 6.01 | 4.90 | 6.9E−04 | IDH-A high |
| C1R | 3.80 | 7.31 | 2.65 | 2.17 | 7.1E−04 | GBM high |
| CENPK | 4.51 | 5.87 | 2.92 | 2.54 | 7.1E−04 | IDH-WT high |
| PCBP3 | 3.04 | 0.17 | 3.87 | 5.12 | 7.1E−04 | GBM low |
| P4HA2 | 2.03 | 3.70 | 0.88 | 0.56 | 7.1E−04 | GBM high |
| VPS13A | 3.52 | 3.44 | 2.24 | 3.00 | 7.1E−04 | IDH-A low |
| KY | 2.48 | 0.09 | 0.65 | 0.79 | 7.1E−04 | K27M high |
| OSBPL10 | 1.39 | 2.16 | 0.19 | 0.16 | 7.2E−04 | IDH-WT high |
| COL4A2 | 2.54 | 4.29 | 1.10 | 0.90 | 7.3E−04 | IDH-WT high |
| CYP27A1 | 5.10 | 4.90 | 1.76 | 1.52 | 7.3E−04 | IDH-WT high |
| PLCXD2 | 2.86 | 0.32 | 2.98 | 2.54 | 7.3E−04 | GBM low |
| LAMC1 | 3.50 | 4.03 | 1.47 | 2.05 | 7.3E−04 | IDH-WT high |
| MYCBP | 4.27 | 4.53 | 3.70 | 2.96 | 7.3E−04 | IDH-O low |
| HAS2 | 4.78 | 5.16 | 4.15 | 1.35 | 7.4E−04 | IDH-O low |
| PTGR2 | 4.51 | 4.09 | 4.70 | 5.57 | 7.4E−04 | IDH-O high |
| PDLIM4 | 0.50 | 4.54 | 0.25 | 0.09 | 7.4E−04 | GBM high |
| COLQ | 2.28 | 0.68 | 3.05 | 3.06 | 7.4E−04 | GBM low |
| ERI3 | 6.43 | 6.22 | 6.51 | 5.55 | 7.4E−04 | IDH-O low |
| GABRG2 | 2.52 | 0.47 | 1.71 | 5.93 | 7.4E−04 | IDH-O high |
| MGAT1 | 4.50 | 5.66 | 4.53 | 4.87 | 7.4E−04 | GBM high |
| FAM21A | 3.74 | 2.32 | 4.03 | 4.27 | 7.4E−04 | GBM low |
| MKLN1 | 4.63 | 5.84 | 5.96 | 5.40 | 7.4E−04 | K27M low |
| SMC4 | 4.72 | 5.45 | 2.85 | 2.64 | 7.4E−04 | IDH-WT high |
| MOCOS | 0.62 | 2.48 | 0.05 | 0.10 | 7.4E−04 | GBM high |
| ASXL3 | 2.85 | 1.60 | 4.03 | 2.74 | 7.4E−04 | IDH-A high |
| BMI1 | 3.95 | 0.95 | 2.56 | 1.85 | 7.4E−04 | K27M high |
| CNN3 | 8.91 | 10.28 | 8.86 | 8.33 | 7.4E−04 | GBM high |
| DHX34 | 3.68 | 4.29 | 3.52 | 2.60 | 7.4E−04 | IDH-O low |
| ITGB3BP | 4.84 | 5.74 | 4.60 | 3.55 | 7.4E−04 | IDH-O low |
| MND1 | 3.92 | 4.36 | 2.04 | 1.31 | 7.4E−04 | IDH-WT high |
| C6orf226 | 4.37 | 6.27 | 4.45 | 4.90 | 7.4E−04 | GBM high |
| ZNF215 | 1.94 | 0.00 | 0.07 | 0.21 | 7.5E−04 | K27M high |
| FXYD6-FXYD2 | 1.87 | 0.90 | 2.77 | 2.80 | 7.5E−04 | IDH-mut high |
| ALG8 | 6.00 | 7.15 | 5.40 | 5.92 | 7.5E−04 | GBM high |
| RIPK1 | 2.99 | 3.90 | 2.57 | 3.07 | 7.5E−04 | GBM high |
| CEBPD | 1.98 | 4.50 | 1.97 | 1.09 | 7.6E−04 | GBM high |
| NPNT | 2.20 | 5.43 | 0.43 | 0.15 | 7.6E−04 | GBM high |
| PREX1 | 4.53 | 5.43 | 1.58 | 1.91 | 7.6E−04 | IDH-WT high |
| STARD10 | 4.50 | 3.39 | 5.63 | 5.94 | 7.6E−04 | IDH-mut high |
| TRIB1 | 3.64 | 3.38 | 1.78 | 1.40 | 7.6E−04 | IDH-WT high |
| SCUBE2 | 3.97 | 1.53 | 1.67 | 2.36 | 7.6E−04 | K27M high |
| ZNF776 | 4.67 | 5.23 | 4.44 | 3.45 | 7.6E−04 | IDH-O low |
| KIF1A | 5.77 | 2.39 | 5.46 | 6.26 | 7.6E−04 | GBM low |
| CDK11A | 3.46 | 4.13 | 3.82 | 2.42 | 7.7E−04 | IDH-O low |

TABLE S3-continued

Differentially expressed genes between glioma types
Columns indicate average gene expression per glioma
type (log2 TPM), and FDR-corrected P-value (ANOVA)

| Gene | K27M | GBM | IDH-A | IDH-O | Significance | Specificity |
|---|---|---|---|---|---|---|
| PLXDC2 | 3.71 | 0.09 | 1.25 | 0.43 | 7.7E−04 | K27M high |
| CLEC2B | 3.60 | 0.91 | 0.05 | 0.27 | 7.7E−04 | K27M high |
| PLSCR1 | 4.14 | 6.16 | 2.43 | 3.03 | 7.7E−04 | GBM high |
| UBE2D1 | 5.62 | 4.44 | 5.37 | 5.43 | 7.8E−04 | GBM low |
| ZNF662 | 4.92 | 4.79 | 4.43 | 1.99 | 7.8E−04 | IDH-O low |
| SLC22A3 | 5.01 | 0.20 | 2.70 | 1.23 | 7.8E−04 | K27M high |
| STBD1 | 2.55 | 4.19 | 1.55 | 1.32 | 7.8E−04 | GBM high |
| KIF15 | 3.16 | 3.59 | 1.84 | 1.79 | 7.9E−04 | IDH-WT high |
| FTL | 9.56 | 10.92 | 9.99 | 9.09 | 7.9E−04 | GBM high |
| CCNB2 | 5.28 | 5.74 | 3.42 | 2.34 | 7.9E−04 | IDH-WT high |
| SWI5 | 4.60 | 5.35 | 5.09 | 5.37 | 7.9E−04 | K27M low |
| THY1 | 7.74 | 5.37 | 7.66 | 8.27 | 7.9E−04 | GBM low |
| KCTD21 | 2.72 | 4.01 | 1.71 | 3.18 | 8.0E−04 | IDH-A low |
| RDH5 | 0.94 | 3.41 | 0.66 | 0.77 | 8.0E−04 | GBM high |
| SORT1 | 4.20 | 5.65 | 4.48 | 3.74 | 8.0E−04 | GBM high |
| ASPDH | 2.32 | 0.85 | 1.80 | 3.64 | 8.0E−04 | IDH-O high |
| C1orf52 | 5.55 | 5.39 | 5.36 | 4.61 | 8.0E−04 | IDH-O low |
| TMCO4 | 1.49 | 3.47 | 0.74 | 1.07 | 8.0E−04 | GBM high |
| ZDHHC2 | 4.86 | 1.75 | 3.83 | 3.56 | 8.0E−04 | GBM low |
| ELOVL7 | 2.35 | 0.88 | 1.05 | 1.19 | 8.1E−04 | K27M high |
| TMEM176A | 3.24 | 4.89 | 0.93 | 0.24 | 8.1E−04 | IDH-WT high |
| TTC13 | 5.33 | 3.55 | 4.42 | 4.86 | 8.1E−04 | GBM low |
| C19orf48 | 6.08 | 7.41 | 6.04 | 5.63 | 8.1E−04 | GBM high |
| AKR1E2 | 1.41 | 0.00 | 0.15 | 0.02 | 8.1E−04 | K27M high |
| TUBA1B | 10.12 | 11.39 | 9.79 | 8.99 | 8.2E−04 | GBM high |
| EIF2B3 | 5.50 | 6.27 | 5.69 | 5.07 | 8.2E−04 | GBM high |
| NEGR1 | 4.47 | 0.62 | 4.59 | 3.11 | 8.2E−04 | GBM low |
| AP2S1 | 6.74 | 7.40 | 6.07 | 5.67 | 8.2E−04 | IDH-WT high |
| OSBPL3 | 3.08 | 5.14 | 1.27 | 2.08 | 8.2E−04 | GBM high |
| CACNA1E | 3.52 | 0.17 | 2.27 | 3.42 | 8.3E−04 | GBM low |
| ARHGAP11A | 3.29 | 4.12 | 2.23 | 1.87 | 8.3E−04 | IDH-WT high |
| C1orf54 | 2.36 | 4.95 | 0.76 | 0.49 | 8.3E−04 | GBM high |
| CISH | 2.52 | 3.77 | 0.91 | 0.72 | 8.3E−04 | IDH-WT high |
| SPOCK3 | 6.48 | 0.51 | 2.33 | 2.63 | 8.3E−04 | K27M high |
| TGIF2 | 3.74 | 4.01 | 1.82 | 1.24 | 8.3E−04 | IDH-WT high |
| ETS1 | 3.35 | 1.79 | 3.69 | 3.87 | 8.3E−04 | GBM low |
| TNRC6C | 4.69 | 2.84 | 4.93 | 4.90 | 8.3E−04 | GBM low |
| RFFL | 3.28 | 4.99 | 3.75 | 3.39 | 8.4E−04 | GBM high |
| EFNA5 | 3.31 | 1.10 | 0.41 | 0.26 | 8.5E−04 | K27M high |
| CDH19 | 2.13 | 0.22 | 0.39 | 0.23 | 8.5E−04 | K27M high |
| TCEB3 | 4.99 | 5.11 | 5.31 | 4.22 | 8.5E−04 | IDH-O low |
| ELOVL4 | 4.75 | 2.53 | 3.90 | 4.82 | 8.5E−04 | GBM low |
| PCDH20 | 4.68 | 0.18 | 3.65 | 5.10 | 8.5E−04 | GBM low |
| ZNF804A | 3.19 | 0.18 | 3.72 | 2.50 | 8.5E−04 | GBM low |
| MXI1 | 5.23 | 3.22 | 5.72 | 5.70 | 8.5E−04 | GBM low |
| SCG3 | 7.89 | 6.23 | 8.56 | 9.24 | 8.5E−04 | GBM low |
| KCNN4 | 0.32 | 2.87 | 0.53 | 0.84 | 8.6E−04 | GBM high |
| OLFM1 | 5.45 | 2.43 | 5.39 | 6.69 | 8.6E−04 | GBM low |
| SYT12 | 0.79 | 0.53 | 0.38 | 1.52 | 8.6E−04 | IDH-O high |
| CYP26B1 | 2.50 | 0.14 | 0.46 | 0.32 | 8.6E−04 | K27M high |
| DGCR2 | 6.57 | 6.26 | 7.59 | 7.97 | 8.6E−04 | IDH-mut high |
| ZNF385D | 3.79 | 2.78 | 0.40 | 2.08 | 8.6E−04 | IDH-A low |
| SLIT2 | 4.45 | 0.08 | 0.28 | 1.53 | 8.6E−04 | K27M high |
| GABRA2 | 3.84 | 0.49 | 0.73 | 0.76 | 8.7E−04 | K27M high |
| POLQ | 2.00 | 2.77 | 0.81 | 0.72 | 8.7E−04 | IDH-WT high |
| MTSS1 | 6.67 | 4.26 | 6.24 | 6.70 | 8.7E−04 | GBM low |
| PRDX5 | 8.51 | 8.52 | 8.47 | 9.24 | 8.7E−04 | IDH-O high |
| KCNJ11 | 2.59 | 1.89 | 2.49 | 3.60 | 8.7E−04 | IDH-O high |
| GSTK1 | 6.47 | 7.99 | 6.20 | 6.77 | 8.9E−04 | GBM high |
| CHL1 | 5.26 | 5.38 | 1.22 | 4.58 | 8.9E−04 | IDH-A low |
| SCMH1 | 4.48 | 4.85 | 4.70 | 3.88 | 8.9E−04 | IDH-O low |
| GRB14 | 3.43 | 2.81 | 0.56 | 0.19 | 8.9E−04 | IDH-WT high |
| POPDC3 | 2.34 | 0.00 | 0.41 | 0.08 | 8.9E−04 | K27M high |
| SLMO2 | 6.97 | 7.20 | 5.50 | 6.70 | 9.0E−04 | IDH-A low |
| RPP25 | 2.55 | 0.02 | 0.36 | 0.35 | 9.1E−04 | K27M high |
| ZNF25 | 5.68 | 4.02 | 6.22 | 5.86 | 9.1E−04 | GBM low |
| TCIRG1 | 1.10 | 3.68 | 1.18 | 0.63 | 9.1E−04 | GBM high |
| TEAD4 | 2.26 | 0.59 | 0.70 | 0.04 | 9.1E−04 | K27M high |
| FAM160A1 | 1.58 | 0.06 | 0.31 | 0.18 | 9.1E−04 | K27M high |
| ZRANB1 | 3.54 | 1.78 | 3.41 | 3.27 | 9.2E−04 | GBM low |
| ACSL6 | 3.33 | 2.24 | 3.37 | 4.79 | 9.2E−04 | IDH-O high |
| LMO4 | 3.41 | 4.29 | 3.87 | 2.68 | 9.2E−04 | IDH-O low |
| RAP2A | 5.35 | 3.25 | 6.03 | 5.66 | 9.2E−04 | GBM low |
| INSIG1 | 6.44 | 5.89 | 6.42 | 8.14 | 9.2E−04 | IDH-O high |

TABLE S3-continued

Differentially expressed genes between glioma types
Columns indicate average gene expression per glioma type (log2 TPM), and FDR-corrected P-value (ANOVA)

| Gene | K27M | GBM | IDH-A | IDH-O | Significance | Specificity |
|---|---|---|---|---|---|---|
| CDH18 | 1.90 | 0.00 | 2.96 | 4.74 | 9.2E−04 | IDH-O high |
| EPS15 | 5.29 | 5.33 | 4.74 | 3.25 | 9.2E−04 | IDH-O low |
| PPM1M | 2.65 | 3.48 | 1.51 | 1.65 | 9.3E−04 | IDH-WT high |
| GLT25D2 | 4.37 | 5.06 | 5.68 | 6.79 | 9.3E−04 | IDH-O high |
| TOP2A | 5.00 | 6.24 | 3.30 | 2.32 | 9.3E−04 | IDH-WT high |
| CDK1 | 5.98 | 6.45 | 3.37 | 2.85 | 9.3E−04 | IDH-WT high |
| RASSF3 | 1.17 | 0.34 | 0.26 | 0.50 | 9.3E−04 | K27M high |
| SIGMAR1 | 7.16 | 6.17 | 7.09 | 7.75 | 9.3E−04 | GBM low |
| KIF21B | 4.54 | 1.27 | 3.92 | 3.96 | 9.4E−04 | GBM low |
| RREB1 | 1.14 | 2.75 | 0.62 | 0.69 | 9.4E−04 | GBM high |
| SAMD14 | 3.18 | 0.79 | 3.51 | 3.68 | 9.4E−04 | GBM low |
| JPH3 | 3.07 | 0.58 | 3.86 | 4.85 | 9.5E−04 | GBM low |
| RAB33B | 3.94 | 3.87 | 2.96 | 2.01 | 9.5E−04 | IDH-O low |
| EYA4 | 0.26 | 1.67 | 0.08 | 0.06 | 9.5E−04 | GBM high |
| SIKE1 | 5.21 | 5.10 | 4.87 | 4.17 | 9.5E−04 | IDH-O low |
| WDR77 | 5.90 | 5.87 | 5.75 | 4.64 | 9.5E−04 | IDH-O low |
| A2M | 2.63 | 5.56 | 1.40 | 0.76 | 9.6E−04 | GBM high |
| FAM208B | 3.76 | 2.37 | 4.19 | 3.71 | 9.6E−04 | GBM low |
| CRYZ | 5.68 | 6.18 | 4.65 | 3.91 | 9.7E−04 | IDH-WT high |
| RNF2 | 6.76 | 5.68 | 5.52 | 5.61 | 9.7E−04 | K27M high |
| C7orf49 | 5.10 | 6.76 | 5.78 | 6.01 | 9.8E−04 | K27M low |
| PTPRM | 3.87 | 0.76 | 3.48 | 4.13 | 9.8E−04 | GBM low |
| TSPAN19 | 1.45 | 0.00 | 0.01 | 0.03 | 9.9E−04 | K27M high |
| SLC13A5 | 2.05 | 0.70 | 0.08 | 0.31 | 9.9E−04 | K27M high |

TABLE S4

Supplementary patient annotations

GBM samples (unpublished) profiled by single-cell RNA-seq:

| Tumor | Sex | Age (years) | Location | Final Diagnosis | Primary or Recurrence | IDH | EGFR | MET | ATRX | MGMT | TP53 |
|---|---|---|---|---|---|---|---|---|---|---|---|
| MGH101 | M | 52 | Left frontal | GBM (IV) | Primary | WT | WT | WT | WT | NM | Some tumor cells stain strongly for p53 |
| MGH104 | F | 65 | Right parietal | GBM (IV) | Primary | WT | Positive | WT | WT | NM | Some tumor cells stain strongly for p53 |

Validation cohort of diffuse midline K27M tumors:

| Patient ID | Sex | Age (years) | Location |
|---|---|---|---|
| N626-88 B2 | F | 2.8 | Thalamus |
| N171-10 | M | 8.7 | Thalamus |
| N811-10 | F | 15 | Thalamus |
| N259-11 | M | 8.22 | Thalamus |
| N2240-13 | F | 5.3 | Pons |

TABLE S5

Gene expression signatures in H3K27M-Glioma

| Cell cycle | OC | AC | OPC-shared | OPC-variable |
|---|---|---|---|---|
| UBE2T | BCAS1 | AQP4 | PDGFRA | PDGFRA |
| HMGB2 | PLP1 | CLU | MEST | ITM2C |
| TYMS | PTGDS | AGT | CCND1 | SCG3 |
| MAD2L1 | GPR17 | SPARCL1 | KLRC2 | SERPINE2 |
| CDK1 | TUBB4A | VIM | ARC | CSPG4 |
| UBE2C | MBP | CRYAB | SEZ6L | CA10 |
| RRM2 | TF | GFAP | EGR1 | PTPRZ1 |
| PBK | SIRT2 | APOE | CD24 | CNTN1 |
| ZWINT | FYN | MLC1 | ASCL1 | NAV1 |
| NUSAP1 | MOG | EDNRB | FOS | TNR |
| PCNA | CNP | GJA1 | LINC00643 | LRP1 |
| BIRC5 | NFASC | SPON1 | ETV1 | TSPAN7 |
| H2AFZ | BMPER | PLTP | NNAT | SEMA5A |
| FAM64A | MPZL1 | ALDOC | EGR2 | CST3 |
| TOP2A | RGR | HSPB8 | PCP4 | GPM6A |
| KIAA0101 | CLDN11 | HEY1 | BTG2 | COL9A1 |
| PTTG1 | TNFRSF21 | DAAM2 | HES6 | APOD |
| GMNN | GNAI1 | TNC | IER2 | SLC1A2 |
| KPNA2 | TMEM206 | S1PR1 | MFNG | SPRY4 |
| TUBA1B | TMOD1 | TIMP3 | | NLGN3 |

TABLE S5-continued

Gene expression signatures in H3K27M-Glioma

| Cell cycle | OC | AC | OPC-shared | OPC-variable |
|---|---|---|---|---|
| NUF2 | RAB33A | EZR | | C3orf70 |
| TPX2 | SGK1 | SPARC | | CHAD |
| MLF1IP | TNR | SLC1A3 | | PSAP |
| HIST1H4C | TMTC4 | PON2 | | ZCCHC24 |
| KIF22 | FDFT1 | ATP1A2 | | EPN2 |
| TMPO | WASF1 | HLA-C | | DPYSL2 |
| CKS2 | ZNF488 | PSAT1 | | GPRC5B |
| CDCA5 | UGT8 | TGFBI | | TRIB2 |
| CENPM | BIN1 | CXCR4 | | BCAN |
| PRC1 | SEMA6D | CD99 | | ITM2B |
| MCM7 | APLP1 | EEPD1 | | ABHD2 |
| TMSB15A | EPB41L2 | SFRP2 | | LHFPL3 |
| CENPF | DYNLL1 | NID1 | | CHL1 |
| RNASEH2A | KANK1 | S100A16 | | GPM6B |
| RACGAP1 | TNS3 | C2orf40 | | MEG3 |
| DUT | SCRG1 | CCDC80 | | NXPH1 |
| CKS1B | DBNDD2 | ID4 | | PLEKHB1 |
| AURKB | CADM1 | B2M | | LNX1 |
| CCNB2 | IGSF11 | ITM2C | | HMP19 |
| DTL | PLXNB3 | KAL1 | | EDIL3 |
| FEN1 | PFN2 | HLA-B | | GRIA2 |
| FANCI | LRRN3 | F3 | | B3GNT7 |
| KIF11 | TSPAN15 | PBXIP1 | | HLA-C |
| RRM1 | SEMA5B | CDC42EP4 | | CD9 |
| MCM2 | APCDD1 | CST3 | | SYT11 |
| CDC20 | PSAT1 | GLUD1 | | ATP6AP2 |
| HMGN2 | E2F3 | CD44 | | XYLT1 |
| CCNA2 | ARHGAP5 | TTYH1 | | ACSL3 |
| TK1 | PKP4 | S100A10 | | GNG7 |
| PKMYT1 | KIF21A | BTBD17 | | EPAS1 |

TABLE S6 differentially expressed genes in H3K27M-gliomas vs normal cell types

| H3K27M-high | H3K27M-low |
|---|---|
| IER2 | FOXG1 |
| MIR4461 | |
| EIF3L | |
| PMP2 | |
| CCT3 | |
| PPA1 | |
| EIF3C | |
| HSBP1 | |
| MRPS21 | |
| CLNS1A | |
| PSMD4 | |
| TOMM20 | |
| TUFM | |
| SPCS1 | |
| C6orf48 | |
| RPL22 | |
| RSL24D1 | |
| IMPDH2 | |
| CCND1 | |
| SNHG8 | |
| TROVE2 | |

TABLE S6-continued differentially expressed genes in H3K27M-gliomas vs normal cell types

| H3K27M-high | H3K27M-low |
|---|---|
| NDUFS2 | |
| NCBP2 | |
| SNHG16 | |
| ATXN10 | |
| KLRC2 | |
| SNHG1 | |
| AASDHPPT | |
| KIFAP3 | |
| PCMTD2 | |
| BZW2 | |
| C4orf3 | |
| GRIA4 | |
| NFIA | |
| COX20 | |
| MKI67IP | |
| VPS45 | |
| RBM8A | |
| CCDC82 | |
| EPB41L4A-AS1 | |
| NUP35 | |
| B3GALNT1 | |
| LINC00643 | |
| TIPRL | |
| SRPRB | |
| RBM34 | |
| APBB2 | |
| NME7 | |
| KCND2 | |
| BRWD1 | |
| ARMCX6 | |
| ZNF883 | |
| FAM104A | |
| SETDB1 | |
| IMPACT | |
| ZNF300 | |
| TFB2M | |
| TIGD1 | |
| RCBTB2 | |
| CLDN12 | |
| TCF7L2 | |
| PPP3CA | |
| GLCCI1 | |
| TDRKH | |
| PSIMCT-1 | |
| LOC283174 | |
| CLGN | |
| NPPA | |
| KLRG1 | |
| OSR1 | |
| CARD8 | |
| FZD6 | |
| EPB41 | |
| TLE3 | |
| ZNF790-AS1 | |
| PINLYP | |
| TENM2 | |
| SLC30A3 | |
| IRX2 | |
| ZSCAN31 | |

TABLE S7

Differentially expressed genes between each pair of sample types Ordered as in FIG. 6F. Note that the same gene may appear twice, if it was found significant in two different comparisons.

| Patient > PDX | Patient > Cell lines | PDX > Patient | PDX > Cell lines | Cell lines > Patient | Cell lines > PDX | Undiff. > Diff. | Diff. > Undiff. |
|---|---|---|---|---|---|---|---|
| PILRB | HES6 | FOS | KLF6 | SEPT4 | TMSB10 | NNAT | PRPS1 |
| CALCRL | PCP4 | NR4A1 | MPZ | RLBP1 | C10orf90 | TACR1 | TSC22D3 |
| RORB | LINC00689 | KLF6 | TNS3 | FABP7 | SAT1 | NTRK2 | ARL6IP5 |

TABLE S7-continued

Differentially expressed genes between each pair of sample types
Ordered as in FIG. 6F. Note that the same gene may appear
twice, if it was found significant in two different comparisons.

| Patient > PDX | Patient > Cell lines | PDX > Patient | PDX > Cell lines | Cell lines > Patient | Cell lines > PDX | Undiff. > Diff. | Diff. > Undiff. |
|---|---|---|---|---|---|---|---|
| CCDC80 | CRABP1 | TENC1 | CDR1 | MIF | INPP4B | BCAN | GBA |
| NID1 | TMPRSS9 | TNS3 | NKAIN4 | GPC3 | CACNG5 | ACTG1 | GLT25D2 |
| GRIK1 | LINC00643 | MPZ | NLGN3 | HAS2 | KLHDC8A | CRMP1 | FBLN2 |
| DAPK1 | HMP19 | MYRF | SOX2-OT | SERINC2 | CD59 | H2AFY2 | DIO2 |
| KAL1 | NFIX | LIMD1 | B3GNT7 | C10orf90 | CD63 | CPXM1 | TRPM3 |
| KCNN3 | CRYBG3 | CPM | FGF12 | CPM | FTH1 | BEX1 | CHPF |
| ANKFN1 | MEST | COL11A2 | TMEM132B | COL11A2 | TPI1 | TUBB2B | POSTN |
| MSTN | EGFR | ACAN | HIP1R | ACAN | PKM | TUBA1A | CAV1 |
| PEA15 | SLC22A3 | GPC3 | LMF1 | HSPA12A | GAPDH | TUBB3 | HTRA1 |
| WNT5A | NMNAT2 | HAS2 | MAML2 | CAPN3 | ALDOA | STMN1 | CA2 |
| TACR1 | SMOC1 | SCRG1 | PELI1 | PPFIBP2 | LAPTM4A | TUBB | MVP |
| SLC17A8 | FXYD6 | FGF12 | LRP6 | CDK18 | PPIC | GNG4 | APOBEC3C |
| LOC145845 | DPYSL3 | LBH | RGMB | HSPB3 | STAT2 | TMEM97 | PYCR2 |
| C1orf61 | CD24 | RPL6 | PLK1S1 | EPHA3 | PLS3 | CA10 | PPIC |
| HEPN1 | NNAT | RPS8 | ARHGAP33 | CD9 | DPYD | CNTN1 | SYPL1 |
| PTPRS | MCL1 | RPS7 | ALKBH2 | SAT1 | NQO1 | CCND1 | SQSTM1 |
| MEG3 | DUSP1 | RPL31 | PPP1R15A | SLC25A5 | LGALS1 | MTSS1 | DPYD |
| ST6GAL2 | JUNB | RPS18 | BTG2 | GAPDH | SQSTM1 | APBB2 | TNFRSF1A |
| CRYBG3 | FOSB | | ARC | FTH1 | SHC1 | GRIK2 | LINC00152 |
| MEST | FOS | | EGR2 | CD63 | A2M | DCX | CARD16 |
| CRABP1 | EGR1 | | NR4A1 | PIR | IFI16 | SCG3 | NQO1 |
| | IER2 | | RHOB | MTRNR2L3 | LGALS3 | TAGLN3 | CLEC2B |
| | JUN | | JUN | MTRNR2L6 | S100A11 | SMOC1 | LAMA5 |
| | GRIA4 | | FOSB | MTRNR2L10 | GNG11 | FXYD6 | DDR2 |
| | GABBR1 | | JUNB | MTRNR2L8 | COL5A2 | CD24 | EFNA5 |
| | DPP6 | | FOS | MTRNR2L1 | SELENBP1 | CD200 | CD151 |
| | SCD5 | | EGR1 | MTRNR2L2 | NEAT1 | ANKRD36 | EEF2K |
| | PCDHGC3 | | IER2 | ENPP2 | ANXA2 | ANKRD36B | EPHA4 |
| | SLC1A2 | | DUSP1 | SERPINI1 | S100A16 | PCDH11X | KIRREL |
| | SLITRK3 | | MCL1 | LPL | LAMB2 | STMN1 | C1QTNF6 |
| | SPOCK3 | | LRRTM2 | LGALS3 | NID1 | NCKAP5 | FAM129A |
| | NDRG2 | | OLIG1 | S100A11 | | GPM6B | B4GALT1 |
| | ASTN1 | | AMOTL2 | SHC1 | | NKAIN4 | CALD1 |
| | SLC6A9 | | PCP4 | A2M | | IGFBPL1 | PROS1 |
| | DDR1 | | DPYSL3 | CACNG5 | | DLL3 | NRP1 |
| | JAM2 | | NNAT | KLHDC8A | | NXPH1 | CDC42EP3 |
| | CTNND2 | | HMP19 | CDKN1A | | PCSK2 | S100A13 |
| | PSD2 | | TMPRSS9 | | | ST3GAL5 | STAT2 |
| | TUBGCP6 | | REC8 | | | FGFBP3 | CTSD |
| | PILRB | | OMG | | | F5 | CDH6 |
| | LINC00461 | | NCAM1 | | | C10orf90 | LIMCH1 |
| | NFIA | | ILDR2 | | | SERINC2 | FAT1 |
| | LRRN3 | | UNC80 | | | MMP2 | STON1 |
| | WNT5A | | SCG5 | | | HAS2 | SLC40A1 |
| | BMPR1B | | FABP5 | | | NRIP3 | MYLK |
| | LUZP2 | | PCDH15 | | | E2F3 | IFI6 |
| | PEA15 | | LRRC4C | | | ENPP6 | TAGLN2 |
| | ADCYAP1R1 | | PCDHGC3 | | | GPC3 | HDAC9 |
| | UG0898H09 | | KIF21B | | | ACAN | PARP9 |
| | KCNN3 | | NRXN1 | | | COL11A2 | TENM2 |
| | KAL1 | | ST6GAL2 | | | CPM | OSMR |
| | CADPS | | LOC100216479 | | | P2RX7 | PAM |
| | ANKFN1 | | CACNA1E | | | ERBB3 | TPP1 |
| | MSTN | | NTRK2 | | | APOD | METTL7A |
| | C2orf88 | | LUZP2 | | | RNF144A | NOTCH2NL |
| | CDC42EP4 | | MARCKS | | | SLC1A1 | DKK3 |
| | TTYH1 | | TLE3 | | | SOX10 | MRC2 |
| | FAIM2 | | IRF1 | | | LINC00673 | ITGA7 |
| | PHGDH | | SULT1C4 | | | SCRG1 | SERPINH1 |
| | FHL1 | | CBR1 | | | AFAP1L2 | MGST1 |
| | MAGEH1 | | TPM2 | | | FGF12 | S100A16 |
| | NTRK2 | | CHST9 | | | CADM2 | LAMB2 |
| | HEPN1 | | | | | HIPK2 | C1QTNF3 |
| | HYDIN | | | | | SGCD | AHNAK |
| | ZBTB20 | | | | | CAPN3 | CYBRD1 |
| | HRNR | | | | | KCNS3 | NUPR1 |
| | RGMA | | | | | MYRF | ANXA2 |
| | RFX4 | | | | | LOC146481 | NEAT1 |
| | VIPR2 | | | | | BEST1 | SELENBP1 |
| | CCL5 | | | | | ANKS1B | COL5A2 |
| | KIF21B | | | | | LSAMP | LUM |
| | CACNA1E | | | | | RAP2A | CFH |
| | LOC100216479 | | | | | LRRTM1 | SERPINI1 |

TABLE S7-continued

Differentially expressed genes between each pair of sample types
Ordered as in FIG. 6F. Note that the same gene may appear
twice, if it was found significant in two different comparisons.

| Patient > PDX | Patient > Cell lines | PDX > Patient | PDX > Cell lines | Cell lines > Patient | Cell lines > PDX | Undiff. > Diff. | Diff. > Undiff. |
|---|---|---|---|---|---|---|---|
| | ST6GAL2 | | | | | PADI2 | SEPP1 |
| | NRXN1 | | | | | ARHGAP35 | FN1 |
| | LOC145845 | | | | | TSC22D1 | LEFTY2 |
| | SLC17A8 | | | | | PPP2R2B | CFI |
| | MARCKS | | | | | SOX6 | ANXA1 |
| | NFIB | | | | | DNM3 | NDP |
| | TLE3 | | | | | ATCAY | ENPP2 |
| | PTPRS | | | | | PHACTR3 | TMEM173 |
| | MEG3 | | | | | PCBP4 | ARPC1B |
| | SOX2-OT | | | | | TOMM20 | SHC1 |
| | CLK1 | | | | | SNHG16 | LOC541471 |
| | FABP5 | | | | | HNRNPA1 | LPL |
| | SCG5 | | | | | RPL15 | IFI16 |
| | LRRC4C | | | | | NPM1 | SP100 |
| | PCDH15 | | | | | GNB2L1 | S100A4 |
| | LRAT | | | | | EIF3L | IGFBP7 |
| | LOC254559 | | | | | HDAC2 | IFITM2 |
| | USP11 | | | | | LBH | ADAMTS9 |
| | RTN1 | | | | | COL9A3 | EMP1 |
| | GRIA3 | | | | | LDLRAD3 | CNIH3 |
| | SDC3 | | | | | LHFPL3 | TIMP1 |
| | TACR1 | | | | | SEMA5A | EMP3 |
| | NOTCH1 | | | | | CHAD | LGALS1 |
| | NCAM1 | | | | | TM4SF1 | LMNA |
| | PROM1 | | | | | SCARB1 | S100A10 |
| | LRRN1 | | | | | PARP1 | HSPB1 |
| | EPHB1 | | | | | FAM49B | C1orf54 |
| | PHACTR1 | | | | | MTHFD2 | GNG11 |
| | NPIP | | | | | ANP32B | S100A11 |
| | SPAG9 | | | | | MIF | LGALS3 |
| | AFF3 | | | | | PLEKHB1 | KLHDC8A |
| | MAT2A | | | | | WWP2 | LEMD1 |
| | TPM2 | | | | | EXTL1 | CA12 |
| | KCNE1L | | | | | TSPAN15 | SPOCK1 |
| | IGSF9 | | | | | DBC1 | LOC100506421 |
| | MFAP2 | | | | | DCC | FAM5C |
| | PAX3 | | | | | LPPR1 | CALCRL |
| | ZNF532 | | | | | GNG2 | RASA4 |
| | STARD4-AS1 | | | | | MND1 | ATP1B2 |
| | | | | | | TRIM2 | CCDC80 |
| | | | | | | GPR180 | SOX9 |
| | | | | | | TMEM163 | PBXIP1 |
| | | | | | | KHDRBS3 | PFKFB3 |
| | | | | | | RBM3 | ITPKB |
| | | | | | | PRKCZ | FAM107A |
| | | | | | | HSBP1 | ABCA1 |
| | | | | | | GPR19 | ARHGEF6 |
| | | | | | | PXDN | GDPD2 |
| | | | | | | PPAP2C | TFPI |
| | | | | | | FHL2 | ATP2B4 |
| | | | | | | ZNF652 | SPAG6 |
| | | | | | | LOC650226 | DAPK1 |
| | | | | | | OSR1 | RMST |
| | | | | | | B3GNT7 | LINC00478 |
| | | | | | | NLGN3 | IGFBP5 |
| | | | | | | PMP2 | SPDYE7P |
| | | | | | | TSPAN7 | ABLIM1 |
| | | | | | | SLC1A4 | PDE4DIP |
| | | | | | | SQLE | SETBP1 |
| | | | | | | ACAT2 | BOC |
| | | | | | | IDI1 | ELN |
| | | | | | | PDLIM3 | EFEMP2 |
| | | | | | | ITM2A | SDC4 |
| | | | | | | LYPD1 | C5orf15 |
| | | | | | | UGP2 | SULT1A1 |
| | | | | | | SEPT4 | GOLIM4 |
| | | | | | | RLBP1 | RASD1 |
| | | | | | | SLCO4A1 | MR1 |
| | | | | | | CTHRC1 | SULF1 |
| | | | | | | FANCI | TRPS1 |
| | | | | | | MELK | LMO3 |
| | | | | | | NCAPG | MEIS2 |
| | | | | | | CKAP2L | RORB |

TABLE S7-continued

Differentially expressed genes between each pair of sample types
Ordered as in FIG. 6F. Note that the same gene may appear
twice, if it was found significant in two different comparisons.

| Patient > PDX | Patient > Cell lines | PDX > Patient | PDX > Cell lines | Cell lines > Patient | Cell lines > PDX | Undiff. > Diff. | Diff. > Undiff. |
|---|---|---|---|---|---|---|---|
| | | | | | KIF2C | SESN3 | |
| | | | | | CCNA2 | TCTN1 | |
| | | | | | AURKB | AKR1C3 | |
| | | | | | NDC80 | STK17B | |
| | | | | | DEPDC1B | S100A6 | |
| | | | | | SGOL1 | CSRP1 | |
| | | | | | HMGN2 | RHBDD2 | |
| | | | | | | FAM171B | |
| | | | | | | C1orf85 | |
| | | | | | | SERPING1 | |
| | | | | | | ANGPTL1 | |
| | | | | | | THBS4 | |
| | | | | | | TRIM47 | |
| | | | | | | C1R | |
| | | | | | | PCDH9 | |
| | | | | | | CNN3 | |
| | | | | | | CIB1 | |
| | | | | | | NME3 | |
| | | | | | | ABI3BP | |
| | | | | | | CD44 | |
| | | | | | | MEF2C | |
| | | | | | | PGAM2 | |
| | | | | | | LETMD1 | |
| | | | | | | ANTXR1 | |
| | | | | | | PTPN14 | |
| | | | | | | SRI | |
| | | | | | | ID1 | |
| | | | | | | ID3 | |
| | | | | | | ZFP36L1 | |
| | | | | | | LINC00461 | |
| | | | | | | ZBTB20 | |
| | | | | | | RBP1 | |
| | | | | | | MDK | |
| | | | | | | PCDH10 | |
| | | | | | | CYP27A1 | |
| | | | | | | NFIA | |
| | | | | | | NCAN | |

REFERENCES

1. M. S. Lawrence et al., Discovery and saturation analysis of cancer genes across 21 tumour types in *Nature*. (2014), vol. 505, pp. 495-501 (10.1038/nature12912).
2. C. Jones et al., Pediatric high-grade glioma: biologically and clinically in need of new thinking. *Neuro-oncology* 19, 153-161 (2017) (10.1093/neuonc/now101).
3. J. Schwartzentruber et al., Driver mutations in histone H3.3 and chromatin remodelling genes in paediatric glioblastoma in *Nature*. (2012), vol. 482, pp. 226-231 (10.1038/nature10833).
4. D. Sturm et al., Hotspot mutations in H3F3A and IDH1 define distinct epigenetic and biological subgroups of glioblastoma. *Cancer cell* 22, 425-437 (2012) (10.1016/j.ccr.2012.08.024).
5. G. Wu et al., Somatic histone H3 alterations in pediatric diffuse intrinsic pontine gliomas and non-brainstem glioblastomas in *Nature genetics*. (2012), vol. 44, pp. 251-253 (10.1038/ng.1102).
6. K. Funato, T. Major, P. W. Lewis, C. D. Allis, V. Tabar, Use of human embryonic stem cells to model pediatric gliomas with H3.3K27M histone mutation. *Science* 346, 1529-1533 (2014) (10.1126/science.1253799).
7. K. M. Chan et al., The histone H3.3K27M mutation in pediatric glioma reprograms H3K27 methylation and gene expression in *Genes & development*. (2013), vol. 27, pp. 985-990 (10.1101/gad.217778.113).
8. H. M. Herz et al., Histone H3 lysine-to-methionine mutants as a paradigm to study chromatin signaling. *Science* 345, 1065-1070 (2014) (10.1126/science.1255104).
9. P. W. Lewis et al., Inhibition of PRC2 activity by a gain-of-function H3 mutation found in pediatric glioblastoma. *Science* 340, 857-861 (2013) (10.1126/science.1232245).
10. S. Venneti et al., Evaluation of Histone 3 Lysine 27 Trimethylation (H3K27me3) and Enhancer of Zest 2 (EZH2) in Pediatric Glial and Glioneuronal Tumors Shows Decreased H3K27me3 in H3F3A K27M Mutant Glioblastomas. *Brain pathology*, (2013) (10.1111/bpa.12042).
11. S. Muller et al., Single-cell sequencing maps gene expression to mutational phylogenies in PDGF- and EGF-driven gliomas. *Mol Syst Biol* 12, 889 (2016) (10.15252/msb.20166969).
12. A. P. Patel et al., Single-cell RNA-seq highlights intratumoral heterogeneity in primary glioblastoma. *Science* 344, 1396-1401 (2014) (10.1126/science.1254257).
13. I. Tirosh et al., Dissecting the multicellular ecosystem of metastatic melanoma by single-cell RNA-seq in *Science*. (2016), vol. 352, pp. 189-196 (10.1126/science.aad0501).
14. I. Tirosh et al., Single-cell RNA-seq supports a developmental hierarchy in human oligodendroglioma in *Nature*. (2016), vol. 539, pp. 309-313 (10.1038/nature20123).

15. A. S. Venteicher et al., Decoupling genetics, lineages, and microenvironment in IDH-mutant gliomas by single-cell RNA-seq. *Science* 355, (2017) (10.1126/science.aai8478).
16. S. Picelli et al., Full-length RNA-seq from single cells using Smart-seq2 in *Nat Protoc.* (2014), vol. 9, pp. 171-181 (10.1038/nprot.2014.006).
17. D. Sturm et al., Paediatric and adult glioblastoma: multiform (epi)genomic culprits emerge. *Nature reviews. Cancer* 14, 92-107 (2014) (10.1038/nrc3655).
18. H. Nikbakht et al., Spatial and temporal homogeneity of driver mutations in diffuse intrinsic pontine glioma. *Nat Commun* 7, 11185 (2016) (10.1038/ncomms11185).
19. B. B. Liau et al., Adaptive Chromatin Remodeling Drives Glioblastoma Stem Cell Plasticity and Drug Tolerance. *Cell stem cell* 20, 233-246 e237 (2017) (10.1016/j.stem.2016.11.003).
20. I. Ben-Porath et al., An embryonic stem cell-like gene expression signature in poorly differentiated aggressive human tumors. *Nature genetics* 40, 499-507 (2008) (10.1038/ng.127).
21. N. A. de Vries et al., Prolonged Ezh2 Depletion in Glioblastoma Causes a Robust Switch in Cell Fate Resulting in Tumor Progression. *Cell reports*, (2015) (10.1016/j.celrep.2014.12.028).
22. M. L. Suva et al., EZH2 is essential for glioblastoma cancer stem cell maintenance. *Cancer research* 69, 9211-9218 (2009) (10.1158/0008-5472.CAN-09-1622).
23. A. Kreso et al., Self-renewal as a therapeutic target in human colorectal cancer. *Nat Med* 20, 29-36 (2014) (10.1038/nm.3418).
24. G. La Manno et al., Molecular Diversity of Midbrain Development in Mouse, Human, and Stem Cells. *Cell* 167, 566-580 e519 (2016) (10.1016/j.cell.2016.09.027).
25. S. Marques et al., Oligodendrocyte heterogeneity in the mouse juvenile and adult central nervous system. *Science* 352, 1326-1329 (2016) (10.1126/science.aaf6463).
26. M. L. Suva et al., Reconstructing and reprogramming the tumor-propagating potential of glioblastoma stem-like cells. *Cell* 157, 580-594 (2014) (10.1016/j.cell.2014.02.030).
27. J. D. Lathia, S. C. Mack, E. E. Mulkearns-Hubert, C. L. Valentim, J. N. Rich, Cancer stem cells in glioblastoma. in *Genes & development*. (2015), vol. 29, pp. 1203-1217 (10.1101/gad.261982.115).
28. M. Monje et al., Hedgehog-responsive candidate cell of origin for diffuse intrinsic pontine glioma. *Proceedings of the National Academy of Sciences of the United States of America* 108, 4453-4458 (2011) (10.1073/pnas.1101657108).
29. F. Mohammad et al., EZH2 is a potential therapeutic target for H3K27M-mutant pediatric gliomas. *Nat Med* 23, 483-492 (2017) (10.1038/nm.4293).
30. M. L. Suva, N. Riggi, B. E. Bernstein, Epigenetic reprogramming in cancer. *Science* 339, 1567-1570 (2013) (10.1126/science.1230184).
31. A. Kreso, J. E. Dick, Evolution of the cancer stem cell model. *Cell stem cell* 14, 275-291 (2014) (10.1016/j.stem.2014.02.006).
32. A. Tanay, A. Regev, Scaling single-cell genomics from phenomenology to mechanism. *Nature* 541, 331-338 (2017) (10.1038/nature21350).
33. C. Liu et al., Mosaic analysis with double markers reveals tumor cell of origin in glioma in *Cell*. (2011), vol. 146, pp. 209-221 (10.1016/j.cell.2011.06.014).
34. M. C. Tate et al., Postnatal growth of the human pons: a morphometric and immunohistochemical analysis. *J Comp Neurol* 523, 449-462 (2015) (10.1002/cne.23690).
35. C. Lebel et al., Diffusion tensor imaging of white matter tract evolution over the lifespan. *Neuroimage* 60, 340-352 (2012) (10.1016/j.neuroimage.2011.11.094).
36. S. Nagaraja et al., Transcriptional Dependencies in Diffuse Intrinsic Pontine Glioma. *Cancer cell* 31, 635-652 e636 (2017) (10.1016/j.ccell.2017.03.011).
37. F. J. Cordero et al., Histone H3.3K27M Represses p16 to Accelerate Gliomagenesis in a Murine Model of DIPG. *Mol Cancer Res*, (2017) (10.1158/1541-7786.MCR-16-0389).
38. W. A. Flavahan et al., Insulator dysfunction and oncogene activation in IDH mutant gliomas in *Nature*. (2016), vol. 529, pp. 110-114 (10.1038/nature16490).
39. L. A. Johnson et al., Rational development and characterization of humanized anti-EGFR variant III chimeric antigen receptor T cells for glioblastoma in *Sci Transl Med*. (2015), vol. 7, pp. 275ra222 (10.1126/scitranslmed.aaa4963).
40. J. Godlewski et al., Targeting of the Bmi-1 oncogene/stem cell renewal factor by microRNA-128 inhibits glioma proliferation and self-renewal. *Cancer research* 68, 9125-9130 (2008) (10.1158/0008-5472.CAN-08-2629).
41. B. Li, C. N. Dewey, RSEM: accurate transcript quantification from RNA-Seq data with or without a reference genome in *BMC Bioinformatics*. (2011), vol. 12, pp. 323 (10.1186/1471-2105-12-323).
42. S. Fisher et al., A scalable, fully automated process for construction of sequence-ready human exome targeted capture libraries. *Genome biology* 12, R1 (2011) (10.1186/gb-2011-12-1-ri).
43. A. Gnirke et al., Solution hybrid selection with ultra-long oligonucleotides for massively parallel targeted sequencing. *Nature biotechnology* 27, 182-189 (2009) (10.1038/nbt.1523).
44. H. Li, R. Durbin, Fast and accurate short read alignment with Burrows-Wheeler transform. in *Bioinformatics*. (2009), vol. 25, pp. 1754-1760 (10.1093/bioinformatics/btp324).
45. A. McKenna et al., The Genome Analysis Toolkit: a MapReduce framework for analyzing next-generation DNA sequencing data in *Genome Res*. (2010), vol. 20, pp. 1297-1303 (10.1101/gr.107524.110).
46. K. Cibulskis et al., ContEst: estimating cross-contamination of human samples in next-generation sequencing data in *Bioinformatics*. (2011), vol. 27, pp. 2601-2602 (10.1093/bioinformatics/btr446).
47. K. Cibulskis et al., Sensitive detection of somatic point mutations in impure and heterogeneous cancer samples in *Nature biotechnology*. (2013), vol. 31, pp. 213-219 (10.1038/nbt.2514).
48. M. Costello et al., Discovery and characterization of artifactual mutations in deep coverage targeted capture sequencing data due to oxidative DNA damage during sample preparation in *Nucleic Acids Res*. (2013), vol. 41, pp. e67 (10.1093/nar/gks1443).
49. W. J. Kent, BLAT—the BLAST-like alignment tool. *Genome Res* 12, 656-664 (2002) (10.1101/gr.229202. Article published online before March 2002).
50. A. H. Ramos et al., Oncotator: cancer variant annotation tool. *Human mutation* 36, E2423-2429 (2015) (10.1002/humu.22771).
51. H. Wakimoto et al., Human glioblastoma-derived cancer stem cells: establishment of invasive glioma models and treatment with oncolytic herpes simplex virus vectors. *Cancer research* 69, 3472-3481 (2009) (10.1158/0008-5472.CAN-08-3886).

52. E. K. Brinkman, T. Chen, M. Amendola, B. van Steensel, Easy quantitative assessment of genome editing by sequence trace decomposition. *Nucleic Acids Res* 42, e168 (2014) (10.1093/nar/gku936).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A method of treating histone H3 lysine 27-to-methionine mutant glioma (H3K27M-glioma) in a subject, comprising: detecting an altered gene expression or activity of HENMT1 relative to a reference level in a gene signature of a plurality of H3K27M-glioma cells of the subject and administering to the subject either: 1) a small molecule inhibitor of BMI1 when the altered level of gene expression or activity of HENMT1 is increased or 2) a small molecule inhibitor that inhibits one or more PRC2 target genes when the altered level of gene expression or activity of HENMT1 is decreased.

2. The method of claim 1, wherein the gene signature further comprises one or more of CHAD, SEMA3E, PENK, C2orf40, CRYGD, RBP4, NMU, MEGF10, FAM162B, PLEKHG4, FBLN2 and RPL39L.

3. The method of claim 1, wherein the altered gene expression or activity of HENMT1 is downregulated relative to a reference level in the gene signature of the subject's H3K27M-glioma cells.

4. The method of claim 1, wherein the altered gene expression or activity of HENMT1 is upregulated relative to a reference level in the gene signature of the subject's H3K27M-glioma cells.

5. The method of claim 4, wherein the small molecule agent inhibits E3 ubiquitin ligase activity.

6. The method of claim 4, wherein the small molecule of BMI1 (PCGF4) comprises PTC-209 or PRT4165.

7. The method of claim 4, further comprising treating the subject with a kinase inhibitor.

8. The method of claim 7, wherein the kinase inhibitor comprises PDGFRA.

9. The method of claim 4, wherein the small molecule inhibitor of BMI1 comprises a small molecule degrader.

10. The method of claim 4, further comprising administering a histone demethylase inhibitor.

11. The method of claim 4, wherein the small molecule inhibitor of BMI1 is administered as an adjuvant or neoadjuvant therapy.

* * * * *